US009611262B2

(12) United States Patent
Shireman et al.

(10) Patent No.: US 9,611,262 B2
(45) Date of Patent: Apr. 4, 2017

(54) SUBSTITUTED 2-AZABICYCLES AND THEIR USE AS OREXIN RECEPTOR MODULATORS

(71) Applicant: JANSSEN PHARMACEUTICA NV, Beerse (BE)

(72) Inventors: Brock T. Shireman, Poway, CA (US); Terry P. Lebold, San Diego, CA (US); Curt A. Dvorak, Poway, CA (US); Heather R. Coate, San Diego, CA (US); Jeannie M. Ziff, San Diego, CA (US); Cathy Preville, La Jolla, CA (US); Christine Gelin, San Diego, CA (US); Gang Chen, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/851,909

(22) Filed: Sep. 11, 2015

(65) Prior Publication Data
US 2016/0075696 A1   Mar. 17, 2016

Related U.S. Application Data

(60) Provisional application No. 62/049,257, filed on Sep. 11, 2014.

(51) Int. Cl.
A61K 31/47      (2006.01)
C07D 413/14     (2006.01)
C07D 401/12     (2006.01)
C07D 401/14     (2006.01)
C07D 401/10     (2006.01)
C07D 471/08     (2006.01)
A61K 31/435     (2006.01)
A61K 31/444     (2006.01)
A61K 31/4436    (2006.01)

(52) U.S. Cl.
CPC ......... C07D 413/14 (2013.01); C07D 401/10 (2013.01); C07D 401/12 (2013.01); C07D 401/14 (2013.01); C07D 471/08 (2013.01); A61K 31/435 (2013.01); A61K 31/444 (2013.01); A61K 31/4436 (2013.01); A61K 31/47 (2013.01)

(58) Field of Classification Search
CPC .. C07D 401/12; C07D 401/14; C07D 413/14; C07D 401/10; C07D 471/08; A61K 31/47; A61K 31/4436; A61K 31/444; A61K 31/435
See application file for complete search history.

(56) References Cited

U.S. PATENT DOCUMENTS 3,674,793 A      7/1972   Bailey
8,957,074 B2 *   2/2015   Brain .................. C07D 487/04
                                                514/252.02
8,969,352 B2 *   3/2015   Gelin .................. C07D 413/14
                                                514/252.11
9,062,078 B2     6/2015   Coate et al.
9,309,252 B2 *   4/2016   Brain .................. C07D 487/04
2002/0148272 A1 10/2002   Jroski
2009/0005363 A1* 1/2009   Glatthar .............. C07D 213/82
                                                514/217.05
2009/0163485 A1  6/2009   Knust et al.
2011/0144150 A1  6/2011   Lampe et al.
2011/0172227 A1  7/2011   Conn et al.
2012/0202783 A1  8/2012   Branstetter et al.
2012/0208812 A1  8/2012   Chai et al.
2014/0275118 A1* 9/2014   Gelin .................. C07D 413/14
                                                514/255.05
2015/0174129 A1* 6/2015   Gelin .................. C07D 413/14
                                                514/255.05
2015/0218102 A1* 8/2015   Bogdan ............... C07D 215/48
                                                514/210.16
2015/0328224 A1 11/2015   Coate et al.
(Continued)

FOREIGN PATENT DOCUMENTS

CH   WO 2008031550 A2 *  3/2008  ............. A61K 31/00
WO       WO 02/094790 A1    11/2002
(Continued)

OTHER PUBLICATIONS

Ammoun et al, "Distinct Recognition of OX1 and OX2 Receptors by Orexin Peptides", Journal of Pharmacology and Experimental Therapeutics, Jan. 2003, 305(2):507-514.
Arendt et al, "Depressive Behavior and Activation of the Orexin/Hypocretin System", Behavioral Neuroscience, Feb. 2013, 127(1):86-94.
Borgland et al, "Orexin A in the VTA Is Critical for the Induction of Synaptic Plasticity and Behavioral Sensitization to Cocaine", Neuron, Feb. 2006, 49:589-601.
Brundin et al, "Reduced orexin levels in the cerebrospinal fluid of suicidal patients with major depressive disorder", European Neuropsychopharmacology, Jan. 2007, 17:573-579.
(Continued)

Primary Examiner — Alexander R Pagano
(74) Attorney, Agent, or Firm — Baker & Hostetler LLP

(57) ABSTRACT

The present invention is directed to compounds of Formula I:

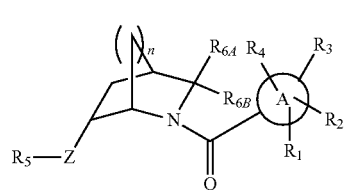

Methods of making the compounds of Formula I are also described. The invention also relates to pharmaceutical compositions comprising compounds of Formula I. Methods of using the compounds of the invention are also within the scope of the invention.

18 Claims, No Drawings

(56) References Cited

U.S. PATENT DOCUMENTS

2016/0052939 A1* 2/2016 Gelin ............... C07D 413/14
514/252.02

FOREIGN PATENT DOCUMENTS

| | | |
|---|---|---|
| WO | WO 2004/069816 A1 | 8/2004 |
| WO | WO 2004/074292 A1 | 9/2004 |
| WO | WO 2008/065626 A2 | 6/2008 |
| WO | WO 2008/081399 A2 | 7/2008 |
| WO | WO 2008/150364 A1 | 12/2008 |
| WO | WO 2009/012275 A1 | 1/2009 |
| WO | WO 2009/012277 A1 | 1/2009 |
| WO | WO 2009/104155 A1 | 8/2009 |
| WO | WO 2009/133522 A1 | 11/2009 |
| WO | WO 2010/009195 A1 | 1/2010 |
| WO | WO 2010/048012 A1 | 4/2010 |
| WO | WO 2010/048016 A1 | 4/2010 |
| WO | WO 2010/063663 A1 | 6/2010 |
| WO | WO 2010/114958 A1 | 10/2010 |
| WO | WO 2010/122151 A1 | 10/2010 |
| WO | WO 2011/050198 A1 | 4/2011 |
| WO | WO 2011/050200 A1 | 4/2011 |
| WO | WO 2011/050202 A1 | 4/2011 |
| WO | WO 2011/053688 A1 | 5/2011 |
| WO | WO 2011/066137 A1 | 6/2011 |
| WO | WO 2011/159657 A1 | 12/2011 |
| WO | WO 2012/089606 A1 | 7/2012 |
| WO | WO 2012/145581 A1 | 10/2012 |
| WO | WO 2013/059222 A1 | 4/2013 |
| WO | WO 2014/066196 A1 | 5/2014 |
| WO | WO 2014/075392 | 5/2014 |
| WO | WO 2014/165070 A1 | 10/2014 |

OTHER PUBLICATIONS

Carroll et al, "Synthesis and Muscarinic Receptor Activity of Ester Derivatives of 2-Substituted 2-Azabicyclo[2.2.1]heptan-5-ol and -6-01", Journal of Medicinal Chemistry, Jun. 1992, 35(12):2184-2191.
Chemelli et al, "Narcolepsy in orexin Knockout Mice: Molecular Genetics of Sleep Regulation", Cell, Aug. 1999, 98:437-451.
Chen et al, "Pressor effects of orexins injected intracisternally and to rostral ventrolateral medulla of anesthetized rats", American Journal of Physiology—Regulatory Integrative comparative Physiology, Mar. 2000, 278:R692-R697.
Chiu, "An improved procedure for the synthesis of chiral2-azabicyclo[2.2.1]heptane", Synthetic Communications, 1996, 26(3):577-584.
De Lecea, Chapter 3, "Hypocretins and the neurobiology of sleep-wake mechanisms", Progress in Brain Research, 2012, vol. 198, A. Shekhar (Ed.), pp. 15-24.
Fortuyn et al, "Anxiety and mood disorders in narcolepsy: a case-control study", General Hospital Psychiatry, Jan.-Feb. 2010, 32:49-56.
Hara et al, "Genetic Ablation of Orexin Neurons in Mice Results in Narcolepsy, Hypophagia, and Obesity", Neuron, May 2001, 30:345-354.
Harris et al, "A role for lateral hypothalamic orexin neurons in reward seeking", Nature Sep. 2005, 437:556-559.
Harris et al, "Lateral hypothalamic orexin neurons are critically involved in learning to associate an environment with morphine reward", Behavioural Brain Research, Nov. 2007, 183:43-51.
Hiebabecky et al, "Synthesis of novel azanorbornylpurine derivatives", Tetrahedron, Jan. 2012, 68:1286-1298.
Hollander et al, "Insular hypocretin transmission regulates nicotine reward", Proceedings of the National Academy of Sciences USA, Dec. 2008, 105(49):19480-19485.
International Patent Application No. PCT/US2014/024293: International Search Report dated May 22, 2014, 2 pages.
Johnson et al, "A key role for orexin in panic anxiety", Nature Medicine, Sep. 2010, 16(1):111-116.
Johnson et al, "Activation of the Orexin I Receptor is a Critical Component of C02-Medidated Anxiety and Hypertension but not Bradycardia", Neuropsychopharmacology, Mar. 2012, 37:1911-1922.
Johnson et al, Chapter 9, "Orexin, stress, and anxiety/panic states", Progress in Brain Research, 2012, vol. 198, A. Shekhar (Ed.), pp. 133-161.
Kapferer et al, "Electrophilic Bromination of N-Acylated Cyclohex-3-en-1-amines: Synthesis of 7-Azanorbornanes", Helvetica Chimica Acta, Nov. 2004, 87(11):2764-2789.
Kirchgessner et al, "Orexin Synthesis and Response in the Gut", Neuron, Dec. 1999, 24:941-951.
Kukkonen, "Physiology of the orexinergic/hypocretinergic system: a revisit in 2012", American Journal of Physiology—Cell Physiology, Jan. 2013, 304:C2-C32.
Langmead et al, "Characterisation of the binding of [3H]-SB-674042, a novel non peptide antagonist, to the human orexin-1 receptor", British Journal of Pharmacology, Oct. 2004, 141:340-346.
Larsen et al, "Aza Diels-Aider Reactions in Aqueous Solution: Cyclocondensation of Dienes with Simple Iminium Salts Generated under Mannich Conditions", Journal American Chemistry Society, Mar. 1985, 107:1769-1771.
Lawrence et al, "The orexin system regulates alcohol-seeking in rats", British Journal of Pharmacology, Jul. 2006, 148:752-759.
Leroy, "Preparation of 3-Bromopropiolic Esters: Methyl and tert-Butyl 3-Bromopropiolates (2-Propynoic acid, 3-bromo-, methyl and 1,1-dimethylethyl esters)", Organic Syntheses, Shinkai et al (Eds.), 1997, 74:212-216.
Lin et al, "The Sleep Disorder Canine Narcolepsy Is Caused by a Mutation in the Hypocretin (Orexin) Receptor 2 Gene", Cell, Aug. 1999, 98:365-376.
Mahler et al, Chapter 7, "Multiple roles for orexin/hypocretin in addiction", Progress in Brain Research (2012) vol. 198, A. Shekhar (Ed.), pp. 79-121.
Malherbe et al, "Biochemical and behavioural characterization of EMPA, a novel high affinity, selective antagonist for the OX2 receptor", British Journal of Pharmacology, Nov. 2009, 156:1326-1341.
Marcus et al, "Differential Expression of Orexin Receptors 1 and 2 in the Rat Brain", Journal of Comparative Neurology, Jun. 2001, 435:6-25.
Mignot et al, "Complex HLA-DR and -DQ Interactions Confer Risk of Narcolepsy-Cataplexy in Three Ethnic Groups", American Journal Human Genetics, Feb. 2001, 68:686-699.
Mignot et al, "Narcolepsy and the HLA System", New England Journal of Medicine, Mar. 2001, 344(9):692.
Nakamura et al, "Orexin-induced hyperlocomotion and stereotypy are mediated by the dopaminergic system", Brain Research, Jun. 2000, 873:181-187.
Narita et al, "Direct Involvement of Orexinergic Systems in the Activation of the Mesolimbic Dopamine Pathway and Related Behaviors Induced by Morphine", Journal of Neuroscience, Jan. 2006, 26(2):398-405.
Peyron et al, "A mutation in a case of early onset narcolepsy and a generalized absence of hypocretin peptides in human narcoleptic brains", Nature Medicine, Sep. 2000, 6(9):991-997.
Peyron et al, "Neurons Containing Hypocretin (Orexin) Project to Multiple Neuronal Systems", Journal of Neuroscience, Dec. 1998, 18(23):9996-10015.
Piper et al, "The novel brain neuropeptide, orexin-A, modulates the sleep-wake cycle of rats", European Journal of Neuroscience, Feb. 2000, 12:726-730.
Sakurai et al, "Orexins and Orexin Receptors: A Family of Hypothalamic Neuropeptides and G Protein-Coupled Receptors that Regulate Feeding Behavior", Cell, Feb. 1998, 92:573-585.
Salomon et al, "Diurnal Variation of Cerebrospinal Fluid Hypocretin-1-(Orexin-A) Levels in Control and Depressed Subjects", Biological Psychiatry, Jul. 2003, 54:96-104.
Samson et al, "Cardiovascular Regulatory Actions of the Hypocretins in Brain", Brain Research, Jun. 1999, 831:248-253.

(56) References Cited

OTHER PUBLICATIONS

Sharf et al, "Orexin Mediates the Expression of Precipitated Morphine Withdrawal and Concurrent Activation of the Nucleus Accumbens Shell", Biological Psychiatry, Jan. 2008, 64:175-183.
Shirasaka et al, "Sympathetic and cardiovascular actions of orexins in conscious rats", American Journal of Physiology (Regulatory Integrative Camp. Physiol. 46), Dec. 1999, 277: R1780-R1785.
Shoblock et al, "Selective blockade of the orexin-2 receptor attenuates ethanol self-administration, place preference, and reinstatement", Psychopharmacology, Sep.-Oct. 2011, 215:191-203.
Singh et al, "Efficient Synthesis of (+)-N-BOC-exo-2-(methoxycarbonyl)-7-Azabicyclo [2.2.1]heptane, A Versatile Intermediate for the Synthesis of Epibatidine and Epiboxidine", Tetrahedron Letters, Sep. 1997, 38(39):6829-6830.
Strawn et al, "Low cerebrospinal fluid and plasma orexin-A (hypocretin-1) concentrations in combat-related posttraumatic stress disorder", Psychoneuroendocrinology, Aug. 2010, 35:1001-1007.
Takahashi et al, "Stimulation of Gastric Acid Secretion by Centrally Administered Orexin-A in Conscious Rats", Biochemical and Biophysical Research Communications, Jan. 1999, 254:623-627.
Trivedi et al, "Distribution of orexin receptor mRNA in the rat brain", FEBS Letters, Oct. 1998, 438:71-75.
Van Den Pol, "Hypothalamic Hypocretin (Orexin): Robust Innervation of the Spinal Cord", Journal of Neuroscience, Apr. 1999, 19(8):3171-3182.
Walker et al, "Design, synthesis, structure-activity relationship, and in vivo activity of azabicyclic aryl amides as α7 nicotinic acetylcholine receptor agonists", Bioorganic & Medicinal Chemistry, Sep. 2006, 14:8219-8248.
Yamanaka et al, "Orexins Activate Histaminergic Neurons via the Orexin 2 Receptor", Biochemical and Biophysical Research Communications, Feb. 2002, 290:1237-1245.
Aissaoui et al., "N-Glycine-sulfonamides as potent dual orexin 1/orexin 2 receptor antagonists", Bioorganic & Medicinal Chemistry Letters, Nov. 2008, 18, 5729-5733.
Baxter et al., "The First Large-Scale Synthesis of MK-4305: A Dual Orexin Receptor Antagonist for the Treatment of Sleep Disorder", Organic Process Research & Development, Mar. 2011, 15, 367-375.
Bergman et al., "Proline bis-amides as potent dual orexin receptor antagonists", Bioorganic & Medicinal Chemistry Letters, Feb. 2008, 18, 1425-1430.
Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.
Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.
Bettica et al., "The Orexin Antagonist SB-649868 Promotes and Maintains Sleep in Men with Primary Insomnia", SLEEP, Aug. 2012, 35(8), 1097-1104.
Brisbare-Roch et al., "Promotion of sleep by targeting the orexin system in rats, dogs and humans", Nature Medicine, Feb. 2007, 13(2), 150-155.
Coleman et al., "Design and synthesis of conformationally constrained N,N-disubstituted 1,4-diazepanes as potent orexin receptor antagonists", Bioorganic & Medicinal Chemistry Letters, Apr. 2010, 20, 2311-2315.
Coleman et al., "Discovery of [(2R,5R)-5-{[(5-Fluoropyridin-2-yl)oxy]methyl}- 2methylpiperidin-1-yl][5-methyl-2-(pyrimidin-2-yl)phenyl]methanone (MK-6096): A Dual Orexin Receptor Antagonist with Potent Sleep-Promoting Properties", Chem Med Chem, Mar. 2012, 7, 415-424.
Coleman et al., "Discovery of 3,9-diazabicyclo[4.2.1]nonanes as potent dual orexin receptor antagonists with sleep-promoting activity in the rat", Bioorganic & Medicinal Chemistry Letters, Jul. 2010, 20, 4201-4205.

Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.
Cox et al., "Discovery of the Dual Orexin Receptor Antagonist [(7R)-4-(5-Chloro-1,3-benzoxazol-2-yl)-7-methyl-1,4-diazepan-1-yl][5-methyl-2-(2H-1,2,3-triazol-2-yl)phenyl]methanone (MK-4305) for the Treatment of Insomnia", Journal of Medicinal Chemistry, Jul. 2010, 53, 5320-5332.
De Lecea et al., "The hypocretins: Hypothalamus-specific peptides with neuroexcitatory activity", Proc. Natl. Acad. Sci., Jan. 1998, 95, 322-327.
DiFabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.
Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.
Dugovic et al., "Orexin-1 receptor blockade dysregulates REM sleep in the presence of orexin-2 receptor antagonism", Frontiers in Neuroscience, Feb. 2014, vol. 8, Article 29, 1-8.
Fujimoto et al., "Discovery of potent, selective, orally active benzoxazepine-based Orexin-2 receptor antagonists", Bioorganic & Medicinal Chemistry Letters, Nov. 2011, 21, 6414-6416.
Fujimoto et al., "Discovery of spiropiperidine-based potent and selective Orexin-2 receptor antagonists", Nov. 2011, 21, 6409-6413.
Gatfield et al., "Orexin Receptor Antagonists: A New Concept in CNS Disorders?", Chem Med Chem, Aug. 2010, 5, 1197-1214.
Girardin et al., "Convergent Kilogram-Scale Synthesis of Dual Orexin Receptor Antagonist", Organic Process Research & Development, Jan. 2013, 17, 61-68.
Gotter et al., "International Union of Basic and Clinical Pharmacology. LXXXVI. Orexin Receptor Function, Nomenclature and Pharmacology", Pharmacological Reviews, Jul. 2012, 64(3), 389-420.
Gotter et al., "Orexin receptors as therapeutic drug targets", Progress in Brain Research, 2012, 198, 163-188.
Gozzi et al., "Functional Magnetic Resonance Imaging Reveals Different Neural Substrates for the Effects of Orexin-1 and Orexin-2 Receptor Antagonists", PLoS ONE, Jan. 2011, 6(1), e16406, 12 pages.
Hirose et al., "N-Acyl 6,7-Dimethoxy-1,2,3,4-tetrahydroisoquinoline: The First Orexin-2 Receptor Selective Nonpeptidic Antagonist", Bioorganic & Medicinal Chemistry Letters, Dec. 2003, 13, 4497-4499.
Jiang et al., "Disubstituted piperidines as potent orexin (hypocretin) receptor antagonists", Bioorganic & Medicinal Chemistry Letters, Jun. 2012, 22, 3890-3894.
King, "Bioisosteres, Conformational Restriction, and Pro-drugs—Case History: An Example of a Conformational Restriction Approach", Med. Chem.: Principle and Practice, 1994, 206-208.
Kuduk et al., "Synthesis and evaluation of carbon-linked analogs of dual orexin receptor antagonist filorexant", Bioorganic & Medicinal Chemistry Letters, Apr. 2014, 24, 1784-1789.
Lebold et al., "Selective orexin receptor antagonists", Bioorganic & Medicinal Chemistry Letters, Sep. 2013, 23, 4761-4769.
Mang et al., "The Dual Orexin Receptor Antagonist Almorexant Induces Sleep and Decreases Orexin-Induced Locomotion by Blocking Orexin 2 Receptors", SLEEP, Dec. 2012, 35(12), 1625-1635.
McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.
McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.
Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.

(56) References Cited

OTHER PUBLICATIONS

Micheli et al., "2-Methyl-3-furanyl-4H-1,2,4-triazol-3-ylthioamides: A new class of selective orexin 2 antagonists", Bioorganic & Medicinal Chemistry Letters, Nov. 2010, 20, 6405-6407.

Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.

Nambu et al., "Distribution of orexin neurons in the adult rat brain", Brain Research, May 1999, 827, 243-260.

Oi et al., "Synthesis and Evaluation of Novel Radioligands for Positron Emission Tomography Imaging of the Orexin-2 Receptor", Journal of Medicinal Chemistry, Jul. 2013, 56, 6371-6385.

Perrey et al., "Diary! urea analogues of SB-334867 as orexin-1 receptor antagonists", Bioorganic & Medicinal Chemistry Letters, May 2011, 21, 2980-2985.

Perrey et al., "Substituted Tetrahydroisoquinolines as Selective Antagonists for the Orexin 1 Receptor", Journal of Medicinal Chemistry, Sep. 2013, 56, 6901-6916.

Porter et al., "1,3-Biarylureas as Selective Non-peptide Antagonists of the Orexin-1 Receptor", Bioorganic & Medicinal Chemistry Letters, Jul. 2001, 11, 1907-1910.

Renzulli et al., "Disposition and Metabolism of [$^{14}$C]SB-649868, an Orexin 1 and 2 Receptor Antagonist, in Humans", Drug Metabolism and Disposition, 2011, 39(2), 215-227.

Roecker et al., "Discovery of 5″-Chloro-N-[(5,6-dimethoxypyridin-2-yl)methyl]-2,2′:5′,3″- terpyridine-3′-carboxamide (MK-1064): A Selective Orexin 2 Receptor Antagonist (2-SORA) for the Treatment of Insomnia", Chem Med Chem, Feb. 2014, 9, 311-322.

Sakurai, "The neural circuit of orexin (hypocretin): maintaining sleep and wakefulness", Nature Reviews, Mar. 2007, 8, 171-181.

Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, 24, Feb. 2014, 1201-1208.

Sifferlen et al., "Novel pyrazolo-tetrahydropyridines as potent orexin receptor antagonists", Bioorganic & Medicinal Chemistry Letters, Mar. 2010, 20, 1539-1542.

Sifferlen et al., "Structure-activity relationship studies and sleep-promoting activity of novel 1-chloro-5,6,7,8-tetrahydroimidazo[1,5-a]pyrazine derivatives as dual orexin receptor antagonists. Part 2", Bioorganic & Medicinal Chemistry Letters, Jul. 2013, 23, 3857-3863.

Sifferlen et al., "Synthesis, structure-activity relationship studies, and identification of novel 5,6,7,8-tetrahydroimidazo[1,5-a]pyrazine derivatives as dual orexin receptor antagonists. Part 1", Bioorganic & Medicinal Chemistry Letters, Apr. 2013, 23, 2212-2216.

Smart et al., "SB-334867-A: the first selective orexin-1 receptor antagonist", British Journal of Pharmacology, Mar. 2001, 132, 1179-1182.

Stasi et al., "Discovery, synthesis, selectivity modulation and DMPK characterization of 5-azaspiro[2.4]heptanes as potent orexin receptor antagonists", Bioorganic & Medicinal Chemistry Letters, May 2013, 23, 2653-2658.

Steiner et al. "Discovery and Characterization of ACT-335827, an Orally Available, Brain Penetrant Orexin Receptor Type 1 Selective Antagonist", Chem Med Chem, Jun. 2013, 8, 898-903.

Steiner et al., "The brain orexin system and almorexant in fear-conditioned startle reactions in the rat", Psychopharmacology, Oct. 2012, 223, 465-475.

Whitman et al., "Discovery of a Potent, CNS-Penetrant Orexin Receptor Antagonist Based on an N,N-Disubstituted-1, 4-diazepane Scaffold that Promotes Sleep in Rats", Chem Med Chem, Jul. 2009, 4, 1069-1074.

Winrow et al., "Discovery and development of orexin receptor antagonists as therapeutics for insomnia", British Journal of Pharmacology, Jan. 2014, 171, 283-293.

* cited by examiner

SUBSTITUTED 2-AZABICYCLES AND THEIR USE AS OREXIN RECEPTOR MODULATORS

CROSS-REFERENCE TO RELATED APPLICATIONS

This application claims the benefit of U.S. Provisional Patent Application No. 62/049,257, filed Sep. 11, 2014, the entirety of which is incorporated herein by reference.

TECHNICAL FIELD

The present invention is directed to substituted 2-azabicyclic compounds, pharmaceutical compositions comprising them, methods of making them, and methods of using them for the modulation of the orexin receptor for the treatment of disease states, disorders, and conditions mediated by orexin receptor activity.

BACKGROUND

Orexin/hypocretin signaling is mediated by two receptors and two peptide agonists. The peptides (orexin-A and orexin-B) are cleavage products of the same gene, pre-pro orexin. In the central nervous system, neurons producing pre-pro orexin are found solely in the perifornical nucleus, the dorsal hypothalamus, and the lateral hypothalamus (Peyron et al., 1998, *J. Neurosci.* 18: 9996-10015). Orexigenic cells in these regions project to many areas of the brain, extending rostrally to the olfactory bulbs and caudally to the spinal cord (Van den Pol, 1999, *J. Neurosci.* 19: 3171-3182).

The orexins bind to two high affinity receptors, referred to as orexin-1 and orexin-2 receptors. Orexin-1 and orexin-2 receptors are G-protein-coupled, seven transmembrane receptors that share over 64% amino acid sequence identity with one another. Both receptors are generally excitatory, the common cellular response to orexin-induced receptor activation being increases in intracellular calcium. Homology between the species orthologs is high. Orexin-A and -B are usually considered equal ligands for orexin-2 receptor but orexin-B is reported to be 5- to 100-fold weaker ligand than orexin-A at the orexin-1 receptor (Sakurai et al., 1998, *Cell* 92: 573-585; Ammoun et al., 2003, *J. Pharmacol. Exp. Ther.* 305: 507-514).

Many regions of the brain have fairly selective expression of the orexin-1 or orexin-2 receptors (Marcus et al., 2001, *J. Comp Neurology* 435, 6-25; Trivedi et al., 1998, *FEBS Letters*, 438, 71-75). Orexin-1 receptors are relatively selective for the limbic system (bed nucleus of the stria terminalis and amygdala), cingulate cortex and noradrenergic neurons in the locus coeruleus. Conversely, the orexin-2 receptor is almost the exclusive orexin receptor in the histaminergic neurons in the tuberomammilary nucleus which play a critical role in wake promotion; in paraventricular neurons and the parabrachial nucleus. In other brain regions like the dorsal raphe, the ventral tegmental area or the prefontal cortex both receptors are coexpressed.

The broad CNS distribution of cells producing orexin, as well as cells expressing the orexin receptors, suggests involvement of orexin in a number of physiological functions, including feeding and metabolism, regulation of wakefulness and sleep, sympathetic activation and stress response (de Lecea, 2012, *Progress in Brain Research*, 198, 15-24; Kukkonen, 2013, *Am J. Physiol. Cell Physiol.*, 304, C2-C32). Orexin also plays a key role regulating motivation and reward associated with food intake and with drugs of abuse (Mahler et al., 2012, *Progress in Brain Research*, 198, 79-121).

Several lines of evidence indicate that the orexin system is an important modulator of arousal. Rodents administered orexin intracerebroventricularly spend more time awake (Piper et al., 2000, *J. Neurosci.* 12: 726-730. Orexin-mediated effects on arousal have been linked to orexin neuronal projections to histaminergic neurons in the tuberomammillary nucleus (Yamanaka et al., 2002, *Biochem. Biophys. Res. Comm.* 290: 1237-1245). Rodents whose pre-pro orexin gene has been knocked out, or whose orexigenic neurons have been ablated, display altered sleep/wake cycles similar to narcolepsy (Chemelli et al., 1999, *Cell* 98: 437-451; Hara et al., 2001, *Neuron* 30: 345-354). Dog models of narcolepsy have been shown to have mutant or non-functional orexin-2 receptors (Lin et al., 1999, *Cell* 98: 365-376). Orexin signaling as a target for sleep-promoting therapies was further validated clinically by findings of attenuated orexin levels and loss of orexinergic neurons in human narcoleptic patients (Mignot et al., 2001, *Am. J. Hum. Genet.* 68: 686-699; Minot & Thorsby, 2001, *New England J. Med.* 344: 692) (Peyron et al., 2000, *Nature Med.* 6: 991-997). Disorders of the sleep-wake cycle are therefore likely targets for orexin-2 receptor modulator activity. Examples of sleep-wake disorders that may be treated by agonists or other modulators that up-regulate orexin-2 receptor-mediated processes include narcolepsy, jet lag (sleepiness) and sleep disorders secondary to neurological disorders such as depression. Examples of disorders that may be treated by antagonists or other modulators that down-regulate orexin-2 receptor-mediated processes include insomnia, restless leg syndrome, jet lag (wakefulness) and sleep disorders secondary to neurological disorders such as mania, schizophrenia, pain syndromes, depression and the like.

Evidence has accumulated to demonstrate a clear involvement of orexin signaling in reward pathways associated with drug dependence (Mahler et al., 2012, *Progress in Brain Research*, 198, 79-121). Orexinergic neurons send projections to the ventral tegmental area and other brain regions involved in reward processing. Orexin ligands mediate reward behavior, and antagonizing these effects with a selective orexin-1 receptor antagonist in various preclinical model of addiction has suggested that these actions are mediated through orexin-1 receptor. Specifically, a selective orexin-1 antagonist attenuates morphine conditioned place preference and reinstatement (Harris et al., 2005, *Nature*, 437, 556-5599; Narita et al., 2006, *J Neurosci.*, 26, 398-405; Harris et al., 2007, *Behav Brain Res*, 183, 43-51), stress-induced cocaine reinstatement, cocaine-induced behavioral and synaptic plasticity (Borgland et al., 2006, *Neuron*, 49, 589-601), and intake and cue and stress-induced reinstatement of ethanol (Lawrence et al., 2006, *Br J Pharmacol*, 148, 752-759), in addition to attenuating precipitated morphine withdrawal (Sharf et al., 2008, *Biol Psychiatry*, 64, 175-183) and nicotine self-administration (Hollander et al., 2008, *Proc Natl Acad Sci USA.*, 105, 19480-19485). Another recent study has also suggested a role for the orexin-2 receptor OX2R (Shoblock et al., 2011, *Psychopharmacology*, 215, 191-203).

Orexin's role in more complex emotional behavior is also emerging (Johnson et al., 2012, *Progress in Brain Research*, 198, 133-161). Changes in orexin levels in patients with panic and posttraumatic stress disorders have been noted (Johnson et al., 2010, *Nature Medicine*, 16, 111-115; Fortuyn et al., 2010, *General Hospital Psychiatry*, 32, 49-56; Strawn et al., 2010, *Psychoneuroendocrinology*, 35, 1001-

1007). Lactate infusion or acute hypercapnia, which causes panic in humans, and are used as an animal model of panic, activates orexin neurons in the perifornical hypothalamus. This activation correlates with anxiety in the social interaction test or open field test. Blocking orexin signaling with either siRNA or selective orexin-1 receptor antagonists attenuates panic-like responses to lactate or $CO_2$ (Johnson et al., 2010, *Nature Medicine*, 16, 111-115; Johnson et al., 2012, *Neuropsychopharmacology*, 37, 1911, 1922). There was no significant side effect of selective orexin-1 receptor antagonist sedation as assessed by monitoring baseline locomotion, or autonomic activity. Thus orexin-1 antagonism represents a novel therapeutic strategy for the treatment of various psychiatric disorders with a stress induced hyperarousal state component.

Cerebral spinal fluid (CSF) levels of orexin are lower in depressed or suicidal patients, and the level of orexin inversely correlates with illness severity (Brundin et al., 2007, *European Neuropsychopharmacology*, 17, 573-579; Salomon et al., 2003, *Biol Psychiatry*, 54, 96-104). A positive correlation between orexin-1 receptor mRNA in the amygdala and depressive behavior in the forced swim test in mice has been reported (Arendt, 2013, *Behavioral Neuroscience*, 127, 86-94).

The orexin system also interacts with brain dopamine systems. Intracerebroventricular injections of orexin in mice increase locomotor activity, grooming and stereotypy; these behavioral effects are reversed by administration of D2 dopamine receptor antagonists (Nakamura et al., 2000, *Brain Res.* 873: 181-187). Therefore, orexin receptor modulators may be useful to treat various neurological disorders; e.g., agonists or up-regulators to treat catatonia, antagonists or down-regulators to treat Parkinson's disease, Tourette's syndrome, anxiety, delirium and dementias.

Orexins and their receptors have been found in both the myenteric and submucosal plexus of the enteric nervous system, where orexins have been shown to increase motility in vitro (Kirchgessner & Liu, 1999, *Neuron* 24: 941-951) and to stimulate gastric acid secretion in vitro (Takahashi et al., 1999, *Biochem. Biophys. Res. Comm.* 254: 623-627). Orexin effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism. Some effects of orexin on metabolism and appetite may be mediated in the gut, where, as mentioned, orexins alter gastric motility and gastric acid secretion. Orexin antagonists therefore are likely to be useful in treatment of overweight or obesity and conditions related to overweight or obesity (such as insulin resistance/type II diabetes, hyperlipidemia), gallstones, angina, hypertension, breathlessness, tachycardia, infertility, sleep apnea, back and joint pain, varicose veins and osteoarthritis. Conversely, orexin agonists are likely to be useful in treatment of underweight and related conditions such as hypotension, bradycardia, ammenorrhea and related infertility, and eating disorders such as anorexia and bulimia.

Intracerebroventricularly administered orexins have been shown to increase mean arterial pressure and heart rate in freely moving (awake) animals (Samson et al., 1999, *Brain Res.* 831: 248-253; Shirasaka et al., 1999, *Am. J. Physiol.* 277: R1780-R1785) and in urethane-anesthetized animals (Chen et al., 2000, *Am. J. Physiol.* 278: R692-R697), with similar results. Orexin receptor agonists may therefore be candidates for treatment of hypotension, bradycardia and heart failure related thereto, while orexin receptor antagonists may be useful for treatment of arrhythmias (e.g., hypertension, tachycardia and the like), angina pectoris and acute heart failure.

From the foregoing discussion, it can be seen that the identification of orexin receptor modulators, will be of great advantage in the development of therapeutic agents for the treatment of a wide variety of disorders that are mediated through these receptor systems.

SUMMARY

The present invention is directed to compounds of Formula I:

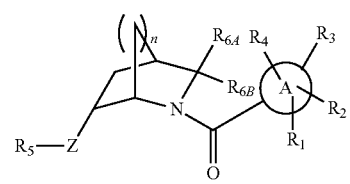

wherein
ring A is phenyl, or a heteroaryl ring selected from pyridinyl and thiazolyl; wherein when ring A is thiazolyl, ring A is optionally substituted with up to 3 substituents selected from $R_1$, $R_2$, $R_3$ and $R_4$, and wherein when ring A is phenyl or pyridinyl, ring A is optionally substituted with up to 4 substituents selected from $R_1$, $R_2$, $R_3$ and $R_4$;

$R_1$ is H, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo and alkyl;

$R_2$ is H, alkyl, alkoxy, or halo;

Z is NH, N—$CH_3$, N—$CH_2CH_3$, N—$CH_2$-cyclopropyl, N—C(=O)$CH_3$, N—$CH_2CH_2OCH_3$ or O;

$R_3$ is H, alkyl, alkoxy, halo, triazolyl, thiazolyl, pyridazinyl, pyrimidinyl, pyrazinyl, oxazolyl, isoxazolyl, oxadiazolyl, pyridyl, phenyl, or pyrazolyl, wherein triazolyl, thiazolyl, pyridazinyl, pyrimidinyl, pyrazinyl, oxazolyl, isoxazolyl, oxadiazolyl, pyridyl, phenyl or pyrazolyl is optionally substituted with up to two substituents selected from halo, alkyl, $NO_2$, and hydroxy-alkoxy;

$R_4$ is H or alkyl;

or $R_3$ and $R_4$, together with the atoms to which they are attached, form a 6-membered aryl ring or a 5- or 6-membered heteroaryl ring;

$R_5$ is pyridyl, pyrazinyl, benzoxazolyl, pyridazinyl, naphthyridinyl, pyrimidinyl, quinoxalinyl, quinolinyl, or phenyl, wherein the pyridyl, pyrazinyl, benzoxazolyl, pyridazinyl, naphthyridinyl pyrimidinyl, quinoxalinyl, quinolinyl, or phenyl is optionally substituted with up to two substituents selected from halo, alkoxy, hydroxymethyl and alkyl;

$R_{6A}$ and $R_{6B}$ are independently selected from H, alkyl, hydroxyalkyl, alkyl-alkoxy, alkyl-alkoxy-alkoxy, or —$CO_2$-alkyl; and n is 1 or 2. Enantiomers and diastereomers of the compounds of Formula I are also described, as well as the pharmaceutically acceptable salts.

Methods of making the compounds of Formula I are also described. The invention also relates to pharmaceutical compositions comprising therapeutically effective amounts of compounds of Formula I. Methods of using the compounds of the invention are also within the scope of the invention.

DETAILED DESCRIPTION OF ILLUSTRATIVE EMBODIMENTS

The invention may be more fully appreciated by reference to the following description, including the following glossary of terms and the concluding examples.

The term "alkyl" refers to a straight- or branched-chain alkyl group having from 1 to 12 carbon atoms in the chain. In some embodiments, an alkyl group is a $C_1$-$C_6$ alkyl group. In some embodiments, an alkyl group is a $C_1$-$C_4$ alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups of the invention can be substituted with, for example, halogen atoms. One exemplary substitutent is fluoro. Thus the term "alkyl" includes substituted alkyl groups such as mono, di and trihalogenated alkyl groups e.g., $CF_3$, $CHF_2$, $CH_2F$ groups and the like.

The term "alkoxy" includes a straight chain or branched alkyl group with a terminal oxygen linking the alkyl group to the rest of the molecule. In some embodiments, an alkoxy group is a $C_1$-$C_6$ alkoxy group. In some embodiments, an alkoxy group is a $C_1$-$C_4$ alkoxy group. Alkoxy includes methoxy, ethoxy, propoxy, isopropoxy, butoxy, t-butoxy, pentoxy and so on. Alkoxy groups of the invention can be substituted with, for example, halogen atoms. One exemplary substitutent is fluoro. Thus the term "alkoxy" includes substituted alkoxy groups such as mono, di and trihalogenated alkoxy groups e.g., trifluoromethoxy groups and the like.

The term "aryl ring" represents" a mono- or bi-cyclic aromatic, hydrocarbon ring structure. Aryl rings can have 6 or 10 carbon atoms in the ring.

The term "halogen" represents chlorine, fluorine, bromine, or iodine. The term "halo" represents chloro, fluoro, bromo, or iodo.

The term "heteroaryl ring" represents a mono- or bicyclic aromatic ring structure including carbon atoms as well as up to four heteroatoms selected from nitrogen, oxygen, and sulfur. Heteroaryl rings can include a total of 5, 6, 9, or 10 ring atoms. Examples of heteroaryl rings include, and are not limited to pyridinyl, pyrimidinyl, pyridazinyl, pyrazinyl, triazolyl, pyrazolyl, thiazolyl, oxazolyl, isoxazolyl, benzoxazolyl, and the like.

The term "hydroxyalkyl" refers to an alkyl group with a hydroxyl (—OH) moiety, where alkyl is as define above. The term "alkyl-alkoxy-alkoxy" refers to an alkyl group substituted with an alkoxy substituent wherein said alkoxy substituent is further substituted with an additional alkoxy group; for example

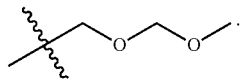 [SMILES: *COCOC]

The term "isoxazolyl" represents the following moiety:

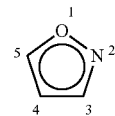

The isoxazolyl moiety can be attached through any one of the 3-, 4-, or 5-position carbon atoms. Isoxazolyl groups of the invention can be optionally substituted with, for example, one or two alkyl groups, for example, one or two methyl groups.

The term "oxazolyl" represents the following moiety:

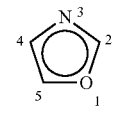

The oxazolyl moiety can be attached through any one of the carbon atoms.

The term "oxadiazolyl" represents a 1,2,3-oxadiazole, 1,2,4-oxadiazole, 1,2,5-oxadiazole, or 1,3,4-oxadiazole moiety:

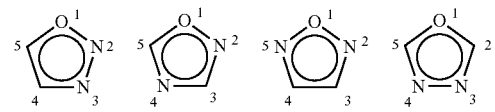

The oxadiazolyl moieties can be attached through any one of the carbon or nitrogen atoms. Within the scope of the invention, "oxadiazolyl" groups can be substituted with an alkyl or halo group, preferably a methyl group.

The term "pyridyl" represents the following moiety:

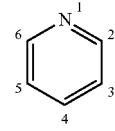

The pyridyl moiety can be attached through any one of the 2-, 3-, 4-, 5-, or 6-position carbon atoms.

The term "pyrimidinyl" represents the following moiety:

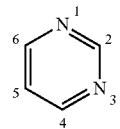

The pyrimidinyl moiety can be attached through any one of the 2-, 4-, 5-, or 6-position carbon atoms. Within the scope of the invention, "pyrimidinyl" groups of the invention can be substituted with halogen, for example fluoro, or alkyl, for example methyl.

The term "pyrazinyl" represents the following moiety:

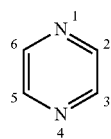

The pyrazinyl moiety can be attached through any one of the 2-, 3-, 5-, or 6-position carbon atoms.

The term "pyridazinyl" represents the following moiety:

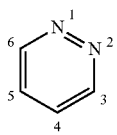

The pyridazinyl moiety can be attached through any one of the 3-, 4-, 5-, or 6-position carbon atoms.

The term "pyrazolyl" represents the following moiety:

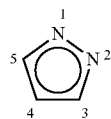

The pyrazolyl moiety can be attached through any one of the 1-, 2-, 3-, 4-, or 5-position carbon atoms. Pyrazolyl groups of the invention can be optionally substituted with, for example, one or two alkyl groups, for example, one or two methyl groups.

The term "triazolyl" represents a 1,2,3-triazole or a 1,2,4-triazole moiety:

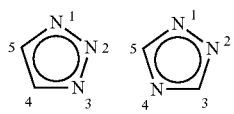

The triazolyl moieties can be attached through any one of their atoms.

The term "imidazolyl" represents the following moiety:

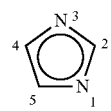

The imidazolyl moiety can be attached through any one of the 2-, 4-, or 5-position carbon atoms, or via the N-1 nitrogen atom. Imidazolyl groups of the invention can be optionally substituted with, for example, one or two alkyl groups, for example, one or two methyl groups.

The term "thiazolyl" represents the following moiety:

The thiazolyl moiety can be attached through any one of the carbon atoms. Thiazolyl groups of the invention can be optionally substituted with, for example, one or two alkyl groups, for example, one or two methyl groups.

The term "naphthyridinyl" represents the following moiety:

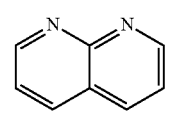

The naphthyridinyl moiety can be attached through any one of the carbon atoms. Naphthyridinyl groups of the invention can be optionally substituted with, for example, one or two alkyl groups, for example, one or two methyl groups, or halo groups.

The term "quinoxalinyl" represents the following moiety:

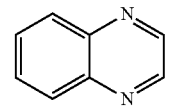

The quinoxalinyl moiety can be attached through any one of the carbon atoms. Quinoxalinyl groups of the invention can be optionally substituted as described in the claims.

The term "quinolinyl" represents the following moiety:

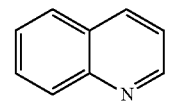

The quinolinyl moiety can be attached through any one of the carbon atoms. Quinolinyl groups of the invention can be optionally substituted as described in the claims.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like.

"Pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

As used herein, the term "isotopic variant" refers to a compound that contains unnatural proportions of isotopes at one or more of the atoms that constitute such compound. For example, an "isotopic variant" of a compound can be radiolabeled, that is, contain one or more non-radioactive or radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. Radiolabeled compounds of the invention can be used in diagnostic methods such as Single-photon emission computed tomography (SPECT). The radioactive isotopes tritium, i.e. $^3$H, and carbon-14, i.e. $^{14}$C, are particularly useful for their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds of the invention, radioactive or not, are intended to be encompassed within the scope of the invention. In one aspect, provided herein are deuterated analogs of compounds of Formula I and Formula II. In one embodiment, deuterated analogs of compounds of Formula I and Formula II comprise deuterium atoms attached to one or more positions on the 2-azabicyclic ring, such as bridgehead carbons, or non-bridgehead carbons of the 2-azabicyclic ring, and preferably comprise one or more deuterium atoms attached to non-bridgehead carbons of the 2-azabicyclic ring. Also contemplated within the scope of embodiments described herein are compounds in which a single proton in compounds of Formula I and Formula II is replaced with a deuterium, or 2 protons in compounds of Formula I and Formula II are replaced with deuterium, or more than 2 protons in compounds of Formula I and Formula II are replaced with deuterium. Deuteration of a compound of Formula I and Formula II may also be effected on one or more substituents (such as e.g., ring A, $R_1$, $R_2$, $R_5$, $R_{6A}$ or $R_{6B}$) present on the 2-azabicyclic ring. In one group of embodiments, one of $R_{6A}$ or $R_{6B}$ is deuterium. In another group of embodiments, $R_{6A}$ is selected from alkyl, hydroxyalkyl, and alkyl-alkoxy, wherein one or more hydrogen atoms are replaced with deuterium, and $R_{6B}$ is hydrogen or deuterium.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In one aspect, the present invention is directed to compounds of Formula I:

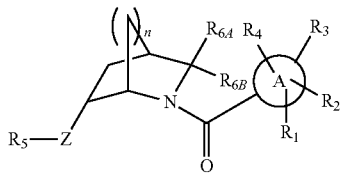

and enantiomers or diastereomers thereof;
and pharmaceutically acceptable salts thereof;
wherein
ring A is phenyl, or a heteroaryl ring selected from pyridinyl thiazolyl, and isoquinolinyl; wherein when ring A is thiazolyl, ring A is optionally substituted with up to 3 substituents selected from $R_1$, $R_2$, $R_3$ and $R_4$, and wherein when ring A is phenyl, pyridinyl, or isoquinolinyl, ring A is optionally substituted with up to 4 substituents selected from $R_1$, $R_2$, $R_3$ and $R_4$;

$R_1$ is H, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo and alkyl;

$R_2$ is H, alkyl, alkoxy, or halo;

Z is NH, N—$CH_3$, N—$CH_2CH_3$, N—$CH_2$-cyclopropyl, N—C(=O)$CH_3$, N—$CH_2CH_2OCH_3$ or O;

$R_3$ is H, alkyl, alkoxy, halo, triazolyl, thiazolyl, pyridazinyl, pyrimidinyl, pyrazinyl, oxazolyl, isoxazolyl, oxadiazolyl, pyridyl, phenyl, or pyrazolyl, wherein triazolyl, thiazolyl, pyridazinyl, pyrimidinyl, pyrazinyl, oxazolyl, isoxazolyl, oxadiazolyl, pyridyl, phenyl or pyrazolyl is optionally substituted with up to two substituents selected from halo, alkyl, $NO_2$, and hydroxy-alkoxy;

$R_4$ is H or alkyl;

or $R_3$ and $R_4$, together with the atoms to which they are attached, form a 6-membered aryl ring or a 5- or 6-membered heteroaryl ring;

$R_5$ is pyridyl, pyrazinyl, benzoxazolyl, pyridazinyl, naphthyridinyl, pyrimidinyl, quinoxalinyl, quinolinyl, or phenyl, wherein the pyridyl, pyrazinyl, benzoxazolyl, pyridazinyl, naphthyridinyl pyrimidinyl, quinoxalinyl, quinolinyl, or phenyl is optionally substituted with up to two substituents selected from halo, alkoxy, hydroxymethyl and alkyl;

$R_{6A}$ and $R_{6B}$ are independently selected from H, alkyl, hydroxyalkyl, alkyl-alkoxy, alkyl-alkoxy-alkoxy, or —$CO_2$-alkyl; and n is 1 or 2.

In another embodiment of the invention:
ring A is phenyl, or a heteroaryl ring selected from pyridinyl and thiazolyl; wherein when ring A is thiazolyl, ring A is optionally substituted with up to 3 substituents selected from $R_1$, $R_2$, $R_3$ and $R_4$, and wherein when ring A is phenyl or pyridinyl, ring A is optionally substituted with up to 4 substituents selected from $R_1$, $R_2$, $R_3$ and $R_4$;

$R_1$ is H, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo and alkyl;

$R_2$ is H, alkyl, alkoxy, or halo;

Z is NH, N—$CH_3$, N—$CH_2CH_3$, N—$CH_2$-cyclopropyl, N—C(=O)$CH_3$, N—$CH_2CH_2OCH_3$ or O;

$R_3$ is H, alkyl, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo and alkyl;

$R_4$ is H or alkyl;

or $R_3$ and $R_4$, together with the atoms to which they are attached, form a 6-membered aryl ring or a 5- or 6-membered heteroaryl ring;

$R_5$ is pyridyl, pyrazinyl, benzoxazolyl, pyridazinyl, naphthyridinyl or pyrimidinyl, wherein the pyridyl, pyrazinyl, benzoxazolyl, pyridazinyl, naphthyridinyl or pyrimidinyl is optionally substituted with up to two substituents selected from halo, alkoxy, hydroxymethyl and alkyl;

$R_{6A}$ and $R_{6B}$ are independently selected from H, alkyl, hydroxyalkyl, alkyl-alkoxy, and alkyl-alkoxy-alkoxy; and n is 1 or 2.

In some cases, ring A is a phenyl ring. In further cases, ring A is a pyridinyl ring. In other cases, ring A is a thiazolyl ring. In some embodiments, ring A is

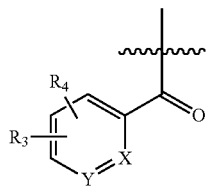

where X, Y, $R_3$ and $R_4$ are as defined herein.

In one aspect, provided herein are compounds of Formula II:

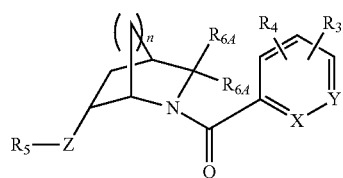

wherein
X is N or $CR_1$;
Y is N or $CR_2$; provided that X and Y are not both N;
$R_1$ is H, halo, triazolyl, pyridazinyl, pyrimidinyl, oxazolyl, or pyridyl, wherein triazolyl, pyridazinyl, pyrimidinyl, oxazolyl, or pyridyl is optionally substituted with up to two substituents selected from halo and alkyl;
$R_2$ is H, alkyl, alkoxy, or halo;
Z is NH, or O;
$R_3$ is H, alkyl, alkoxy, halo, triazolyl, pyrimidinyl, pyridyl, or phenyl, wherein triazolyl, pyrimidinyl, pyridyl, or phenyl is optionally substituted with up to two substituents selected from halo and alkyl;
$R_4$ is H or alkyl;
$R_5$ is pyridyl, pyrazinyl, or benzoxazolyl, wherein the pyridyl, pyrazinyl, or benzoxazolyl is optionally substituted with up to two groups selected from halo, alkoxy, hydroxymethyl and alkyl;
$R_{6A}$ and $R_{6B}$ are independently selected from H, alkyl, hydroxyalkyl, alkyl-alkoxy and alkyl-alkoxy-alkoxy; and
n is 1 or 2.

Enantiomers and diastereomers of the compounds of Formula I and Formula II are also within the scope of the invention. Also within the scope of the invention are the pharmaceutically acceptable salts of the compounds of Formula I and Formula II, as well as the pharmaceutically acceptable salts of the enantiomers and diastereomers of the compounds of Formula I and Formula II. Also within the scope of the invention are isotopic variations of compounds of Formula I and Formula II, such as, e.g., deuterated compounds of Formula I and Formula II.

In preferred embodiments, Z is NH. In other embodiments, Z is O. In yet other embodiments, Z is NH, N—$CH_3$, N—$CH_2CH_3$, N—$CH_2$-cyclopropyl, N—C(=O)$CH_3$, or N—$CH_2CH_2OCH_3$.

In preferred embodiments, X is $CR_1$ and Y is $CR_2$.
In other embodiments, X is $CR_1$ and Y is N.
In yet other embodiments, X is N and Y is $CR_2$.
In those embodiments wherein X is $CR_1$, for example, where X is $CR_1$ and Y is $CR_2$ or X is $CR_1$ and Y is N, $R_1$ is H. In other embodiments, $R_1$ is alkoxy, for example, $C_{1-6}$alkoxy such as methoxy or ethoxy.

In those embodiments wherein X is $CR_1$, for example, where X is $CR_1$ and Y is $CR_2$ or X is $CR_1$ and Y is N, $R_1$ is halo, preferably F, Cl, or Br.

In those embodiments wherein X is $CR_1$, for example, where X is $CR_1$ and Y is $CR_2$ or X is $CR_1$ and Y is N, $R_1$ is triazolyl, optionally substituted with up to two substituents selected from halo and alkyl, with 1,2,3-triazolyl being preferred. In preferred embodiments, the 1,2,3-triazolyl is attached through the 2-position nitrogen atom. In other embodiments, the 1,2,3-triazolyl is attached through the 1-position nitrogen atom.

In those embodiments wherein X is $CR_1$, for example, where X is $CR_1$ and Y is $CR_2$ or X is $CR_1$ and Y is N, $R_1$ is pyrimidinyl, optionally substituted with up to two substituents selected from halo and alkyl, which can be attached through any available atom.

In those embodiments wherein X is $CR_1$, for example, where X is $CR_1$ and Y is $CR_2$ or X is $CR_1$ and Y is N, $R_1$ is oxazolyl, optionally substituted with up to two substituents selected from halo and alkyl, which can be attached through any available atom.

In those embodiments wherein X is $CR_1$, for example, where X is $CR_1$ and Y is $CR_2$ or X is $CR_1$ and Y is N, $R_1$ is isoxazolyl, optionally substituted with up to two substituents selected from halo and alkyl, which can be attached through any available atom.

In those embodiments wherein X is $CR_1$, for example, where X is $CR_1$ and Y is $CR_2$ or X is $CR_1$ and Y is N, $R_1$ is oxadiazolyl, optionally substituted with up to two substituents selected from halo and alkyl, which can be attached through any available atom. The oxadiazolyl group can optionally be substituted with alkyl, for example methyl. In exemplary embodiments, the substituted oxadiazolyl moiety is 1,2,4-oxadiazolyl substituted with methyl.

In those embodiments wherein X is $CR_1$, for example, where X is $CR_1$ and Y is $CR_2$ or X is $CR_1$ and Y is N, $R_1$ is pyridyl, optionally substituted with up to two substituents selected from halo and alkyl, which can be attached through any available atom. The pyridyl group can optionally be substituted with alkyl, for example methyl or halo.

In those embodiments wherein X is $CR_1$, for example, where X is $CR_1$ and Y is $CR_2$ or X is $CR_1$ and Y is N, $R_1$ is imidazolyl, optionally substituted with up to two substituents selected from halo and alkyl, which can be attached through any available atom. The imidazolyl group can optionally be substituted with alkyl, for example methyl or halo.

In those embodiments wherein X is $CR_1$, for example, where X is $CR_1$ and Y is $CR_2$ or X is $CR_1$ and Y is N, $R_1$ is phenyl, optionally substituted with up to two substituents selected from halo and alkyl, which can be attached through any available atom. The phenyl group can optionally be substituted with alkyl, for example methyl or halo.

In those embodiments wherein X is $CR_1$, for example, where X is $CR_1$ and Y is $CR_2$ or X is $CR_1$ and Y is N, $R_1$ is pyrazolyl, optionally substituted with up to two substituents selected from halo and alkyl, which can be attached through any available atom. The pyrazolyl group can optionally be substituted with one or two $C_{1-6}$alkyl, for example methyl.

In those embodiments wherein X is $CR_1$, for example, where X is $CR_1$ and Y is $CR_2$ or X is $CR_1$ and Y is N, $R_1$ is thiazolyl, optionally substituted with up to two substituents selected from halo and alkyl, which can be attached through any available atom.

In those embodiments wherein X is $CR_1$, for example, where X is $CR_1$ and Y is $CR_2$ or X is $CR_1$ and Y is N, $R_1$ is pyridazinyl, optionally substituted with up to two substituents selected from halo and alkyl, which can be attached through any available atom.

In preferred embodiments wherein Y is $CR_2$, for example, X is $CR_1$ and Y is $CR_2$ or X is N and Y is $CR_2$, $R_2$ is H. In other embodiments, $R_2$ is alkyl, for example $C_{1-6}$alkyl such as methyl.

In those embodiments wherein Y is $CR_2$, for example, X is $CR_1$ and Y is $CR_2$ or X is N and Y is $CR_2$, $R_2$ is alkoxy, for example, $C_{1-6}$alkoxy such as methoxy or ethoxy.

In those embodiments wherein Y is $CR_2$, for example, X is $CR_1$ and Y is $CR_2$ or X is N and Y is $CR_2$, $R_2$ is halo, preferably one of F, Cl, or Br.

In preferred embodiments, $R_3$ is H. In other embodiments, $R_3$ is alkyl, for example, $C_{1-6}$alkyl such as methyl.

In yet other embodiments, $R_3$ is alkoxy, for example, $C_{1-6}$alkoxy such as methoxy or ethoxy.

In still other embodiments, $R_3$ is halo, preferably F, Cl, or Br.

In other embodiments, $R_3$ is triazolyl, with 1,2,3-triazolyl being preferred. In preferred embodiments, the 1,2,3-triazolyl is attached through the 2-position nitrogen atom. In other embodiments, the 1,2,3-triazolyl is attached through the 1-position nitrogen atom.

In preferred embodiments, $R_4$ is H. In other embodiments, $R_3$ is alkyl, for example $C_{1-6}$alkyl such as methyl.

In alternative embodiments, $R_3$ and $R_4$, together with the atoms to which they are attached, form a 6-membered aryl ring.

In other embodiments, $R_3$ and $R_4$, together with the atoms to which they are attached, form a 5-membered heteroaryl ring. Preferably, the 5-membered heteroaryl ring includes one nitrogen atom.

In other embodiments, $R_3$ and $R_4$, together with the atoms to which they are attached, form a 6-membered heteroaryl ring. Preferably, the 6-membered heteroaryl ring includes one nitrogen atom.

In some embodiments of the invention, $R_5$ is a phenyl ring optionally substituted with a one or two substituents independently selected from the group consisting of alkyl, cyano, alkoxy, and halo, or from the group consisting of alkyl and halo. In some embodiments of the invention, $R_5$ is a heteroaryl ring. In some of such embodiments, $R_5$ is a heteroaryl optionally substituted with a one or two substituents independently selected from the group consisting of alkyl, cyano, alkoxy, and halo, or from the group consisting of alkyl and halo. In preferred embodiments, $R_5$ is pyridyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Other substituted alkyl groups include difluoromethyl or monofluoromethyl. Preferably, $R_5$ is pyridyl substituted at any available position with trifluoromethyl.

In preferred embodiments, $R_5$ is pyrazinyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Other substituted alkyl groups include difluoromethyl or monofluoromethyl. Preferably, $R_5$ is pyrazinyl substituted at any available position with trifluoromethyl.

In preferred embodiments, $R_5$ is pyrimidinyl, which can be attached through any available atom, optionally substituted with halo (preferably F, Cl, or Br) or alkyl. In some embodiments, the alkyl is substituted with one or more halogen atoms. A preferred substituted alkyl group is trihaloalkyl such as trifluoromethyl. Other substituted alkyl groups include difluoromethyl or monofluoromethyl. Preferably, $R_5$ is pyrimidinyl substituted at any available position with trifluoromethyl.

In other embodiments, $R_5$ is benzoxazolyl which can be attached through any available atom, optionally substituted with halo (preferably F, Cl, or Br) or alkyl. In some embodiments, the alkyl is substituted with one or more halogen atoms. A preferred substituted alkyl group is trifluoromethyl. Other substituted alkyl groups include difluoromethyl or monofluoromethyl. Preferably, $R_5$ is benzoxazolyl, pyridazinyl, or naphthyridinyl substituted at any available position with trifluoromethyl.

In other embodiments, $R_5$ is pyridazinyl which can be attached through any available atom, optionally substituted with halo (preferably F, Cl, or Br) or alkyl. In some embodiments, the alkyl is substituted with one or more halogen atoms. A preferred substituted alkyl group is trifluoromethyl. Other substituted alkyl groups include difluoromethyl or monofluoromethyl. Preferably, $R_5$ is benzoxazolyl, pyridazinyl, or naphthyridinyl substituted at any available position with trifluoromethyl.

In other embodiments, $R_5$ is naphthyridinyl which can be attached through any available atom, optionally substituted with halo (preferably F, Cl, or Br) or alkyl. In some embodiments, the alkyl is substituted with one or more halogen atoms. A preferred substituted alkyl group is trifluoromethyl. Other substituted alkyl groups include difluoromethyl or monofluoromethyl. Preferably, $R_5$ is benzoxazolyl, pyridazinyl, or naphthyridinyl substituted at any available position with trifluoromethyl.

In preferred embodiments, n is 1. In other embodiments, n is 2.

In some embodiments of Formula I, where the compounds have the structure of Formula II, X is C, $R_1$ is H and $R_3$ is as defined above for Formula II, preferably $R_3$ is triazolyl, oxazolyl, pyridyl or pyrimidinyl. In other embodiments of Formula I, where the compounds have the structure of Formula II, $R_3$ is H and $R_1$ is as defined above for Formula II, preferably $R_1$ is triazolyl, oxazolyl, isoxazolyl, oxadiazolyl, pyridyl or pyrimidinyl.

In some embodiments of Formula I, where the compounds have the structure of Formula II, the group

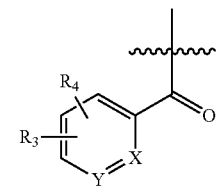

comprises a pyridyl group, preferably X is N, Y is C—$R_2$, $R_3$ is a ring selected from triazolyl, thiazolyl, pyridazinyl, pyrimidinyl, oxazolyl, isoxazolyl, oxadiazolyl, pyridyl, phenyl or pyrazolyl; preferably triazolyl or pyridyl or pyrimidinyl; $R_4$ is H or alkyl, preferably methyl; Z is NH or O, preferably O; preferably NH, $R_5$ is a heteroaryl, preferably pyridyl or pyrazinyl. In some of such embodiments, $R_3$ is a ring at the ortho position relative to the carbonyl group in Formula II, and $R_4$ is at the ortho, meta or para position on the relative to the carbonyl group in Formula II, preferably $R_4$ is at the meta position adjacent to $R_3$. In some other such embodiments, $R_3$ is a ring at the ortho position relative to the carbonyl group in Formula II, and $R_4$ is at the ortho, meta or para position relative to the carbonyl group in Formula II, preferably $R_4$ is at the meta position not adjacent to $R_3$. $R_3$ and $R_5$ are optionally substituted as described above.

In some embodiments of Formula I, where the compounds have the structure of Formula II, the group

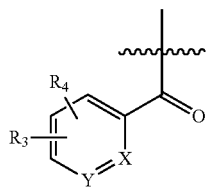

comprises a pyridyl group, preferably Y is N, X is C—$R_1$, $R_1$ is a ring selected from triazolyl, thiazolyl, pyridazinyl, pyrimidinyl, oxazolyl, isoxazolyl, oxadiazolyl, pyridyl, phenyl or pyrazolyl; preferably triazolyl or pyridyl or pyrimidinyl; $R_4$ is H or alkyl, preferably methyl; Z is NH or O, preferably O; preferably NH, $R_5$ is a heteroaryl, preferably pyridyl or pyrazinyl. In some of such embodiments, $R_1$ is a ring at the ortho position relative to the carbonyl group in Formula II, and $R_4$ is at the ortho, meta or para position on the relative to the carbonyl group in Formula II, preferably $R_4$ is at the meta position adjacent to $R_1$. In some other such embodiments, $R_1$ is a ring at the ortho position relative to the carbonyl group in Formula II, and $R_4$ is at the ortho, meta or para position relative to the carbonyl group in Formula II, preferably $R_4$ is at the meta position not adjacent to $R_1$. $R_1$ and $R_5$ are optionally substituted as described above.

In some embodiments of Formula I, where the compounds have the structure of Formula II, the group

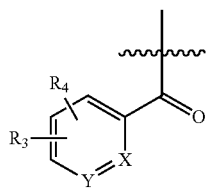

comprises a phenyl group, i.e., X and Y are C—$R_1$ and C—$R_2$, $R_3$ is a ring selected from triazolyl, thiazolyl, pyridazinyl, pyrimidinyl, oxazolyl, isoxazolyl, oxadiazolyl, pyridyl, phenyl or pyrazolyl; preferably triazolyl or pyridyl or pyrimidinyl at the ortho position; $R_4$ is H or alkyl, preferably methyl; Z is NH or O, preferably O; preferably NH, $R_5$ is a heteroaryl, preferably pyridyl or pyrazinyl. In some of such embodiments, $R_3$ is a ring at the ortho position relative to the carbonyl group in Formula II, and $R_4$ is at the ortho, meta or para position on the relative to the carbonyl group in Formula II, preferably $R_4$ is at the meta position adjacent to $R_3$. In some other such embodiments, $R_3$ is a ring at the ortho position relative to the carbonyl group in Formula II, and $R_4$ is at the ortho, meta or para position relative to the carbonyl group in Formula II, preferably $R_4$ is at the meta position not adjacent to $R_3$. $R_3$ and $R_5$ are optionally substituted as described above.

For any embodiments described above for Formula I and Formula II, in one case, $R_{6A}$ is H and $R_{6B}$ is selected from alkyl, $CH_2$-halo, $CH_2$—OH, and $CH_2$-alkoxy, or $R_{6B}$ is selected from methyl, ethyl, $CH_2$—F, $CH_2$—OH, and $CH_2$—$OCH_3$. In another case, $R_{6B}$ is H and $R_{6A}$ is selected from alkyl, $CH_2$-halo, $CH_2$—OH, and $CH_2$-alkoxy, or $R_{6B}$ is selected from methyl, ethyl, $CH_2$—F, $CH_2$—OH, and $CH_2$—$OCH_3$. In another instance, $R_{6A}$ and $R_{6B}$ are independently selected from H, $CH_3$, $CH_2$—$CH_3$, $CH_2$—$CH(CH_3)_2$, $CH_2$—F, $CH_2$—OH, $CH_2$—$OCH_3$, and $CH_2$—$OCH_2$—$OCH_3$. In yet another instance, $R_{6A}$ and $R_{6B}$ are independently selected from H, $CH_3$, $CH_2$—F, $CH_2$—OH, and $CH_2$—$OCH_3$. In some of such embodiments, one or more hydrogen atoms in $R_{6A}$ and/or $R_{6B}$ is/are replaced with deuterium.

For any embodiments described above for Formula I and Formula II, in one group of embodiments,

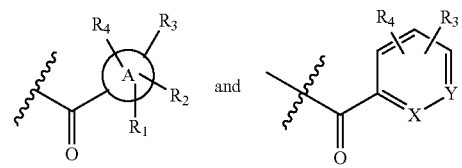

are selected from moieties of Examples 1-155, or Examples 1-80. For any embodiments described above for Formula I and Formula II, in one group of embodiments, —Z—$R_5$ is selected from moieties of Examples 1-155, or Examples 1-80. For any embodiments described above for Formula I and Formula II, in one group of embodiments, ring A, $R_1$, $R_2$, $R_3$ and $R_4$ are selected from moieties of Examples 1-155, or Examples 1-80. In one aspect provided herein is a compound selected from Examples 1-80. In one aspect provided herein is a compound selected from Examples 81-155. In one aspect provided herein is a compound selected from:

| Ex. No. | Chemical Name |
|---|---|
| 1 | (R/S)-(3-fluoro-2-(pyrimidin-2-yl)phenyl)(-3-methyl-6-((5-(trifluoromethyl)pyridin-2-yl)oxy)-2-azabicyclo[2.2.1]heptan-2-yl)methanone; |
| 2 | (R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone; |
| 2A | (2-(2H-1,2,3-triazol-2-yl)phenyl)((1R*,3R*,4S*,6S*)-3-methyl-6-((5-(trifluoromethyl)pyridin-2-yl)oxy)-2-azabicyclo[2.2.1]heptan-2-yl)methanone; |
| 2B | (2-(2H-1,2,3-triazol-2-yl)phenyl)((1S*,3S*,4R*,6R*)-3-methyl-6-((5-(trifluoromethyl)pyridin-2-yl)oxy)-2-azabicyclo[2.2.1]heptan-2-yl)methanone; |
| 3 | (R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone; |
| 3A | (6-methyl-3-(2H-1,2,3-triazol-2-yl)pyridin-2-yl)((1R*,3R*,4S*,6S*)-3-methyl-6-((5-(trifluoromethyl)pyridin-2-yl)oxy)-2-azabicyclo[2.2.1]heptan-2-yl)methanone; |
| 3B | (6-methyl-3-(2H-1,2,3-triazol-2-yl)pyridin-2-yl)((1S*,3S*,4R*,6R*)-3-methyl-6-((5-(trifluoromethyl)pyridin-2-yl)oxy)-2-azabicyclo[2.2.1]heptan-2-yl)methanone; |

| Ex. No. | Chemical Name |
|---|---|
| 4 | (R/S)-(3-fluoro-2-(pyrimidin-2-yl)phenyl)(3-methyl-6-((5-(trifluoromethyl)pyrazin-2-yl)amino)-2-azabicyclo[2.2.1]heptan-2-yl)methanone; |
| 5 | (R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone; |
| 5A | (2-(2H-1,2,3-triazol-2-yl)phenyl)((1R*,3R*,4R*,6S*)-3-methyl-6-((5-(trifluoromethyl)pyrazin-2-yl)amino)-2-azabicyclo[2.2.1]heptan-2-yl)methanone; |
| 5B | (2-(2H-1,2,3-triazol-2-yl)phenyl)((1S*,3S*,4S*,6R*)-3-methyl-6-((5-(trifluoromethyl)pyrazin-2-yl)amino)-2-azabicyclo[2.2.1]heptan-2-yl)methanone; |
| 6 | (R/S)-(6-methyl-3-(2H-1,2,3-triazol-2-yl)pyridin-2-yl)(3-methyl-6-((5-(trifluoromethyl)pyrazin-2-yl)amino)-2-azabicyclo[2.2.1]heptan-2-yl)methanone; |
| 6A | (6-methyl-3-(2H-1,2,3-triazol-2-yl)pyridin-2-yl)((1R*,3R*,4R*,6S*)-3-methyl-6-((5-(trifluoromethyl)pyrazin-2-yl)amino)-2-azabicyclo[2.2.1]heptan-2-yl)methanone; |
| 6B | (6-methyl-3-(2H-1,2,3-triazol-2-yl)pyridin-2-yl)((1S*,3S*,4S*,6R*)-3-methyl-6-((5-(trifluoromethyl)pyrazin-2-yl)amino)-2-azabicyclo[2.2.1]heptan-2-yl)methanone; |
| 7 | (R/S)-(3-bromo-6-methylpyridin-2-yl)(3-methyl-6-((5-(trifluoromethyl)pyrazin-2-yl)amino)-2-azabicyclo[2.2.1]heptan-2-yl)methanone; |
| 8 | (R/S)-(3-fluoro-2-(pyrimidin-2-yl)phenyl)(3-methyl-6-((5-(trifluoromethyl)pyridin-2-yl)oxy)-2-azabicyclo[2.2.1]heptan-2-yl)methanone; |
| 9 | (R/S)-(3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone; |
| 10 | (R/S)-(6-methyl-2-(2H-1,2,3-triazol-2-yl)pyridin-3-yl)(3-methyl-6-((5-(trifluoromethyl)pyridin-2-yl)oxy)-2-azabicyclo[2.2.1]heptan-2-yl)methanone; |
| 11 | (R/S)-(5-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone; |
| 12 | (R/S)-(3-fluoro-2-(oxazol-2-yl)phenyl)(3-methyl-6-((5-(trifluoromethyl)pyridin-2-yl)oxy)-2-azabicyclo[2.2.1]heptan-2-yl)methanone; |
| 13 | (R/S)-(3-ethoxy-6-methylpyridin-2-yl)(3-methyl-6-((5-(trifluoromethyl)pyridin-2-yl)oxy)-2-azabicyclo[2.2.1]heptan-2-yl)methanone; |
| 14 | (R/S)-3-methyl-6-((5 -(trifluoromethyl)pyridin-2-yl)oxy)-2-azabicyclo[2.2.1]heptan-2-yl)(3-(pyrimidin-2-yl)pyridin-2-yl)methanone; |
| 15 | (R/S)-3-methyl-6-((5-(trifluoromethyl)pyridin-2-yl)oxy)-2-azabicyclo[2.2.1]heptan-2-yl)(2-(pyrimidin-2-yl)phenyl)methanone; |
| 16 | (R/S)-(6-methyl-3-(pyrimidin-2-yl)pyridin-2-yl)(3-methyl-6-((5-(trifluoromethyl)pyridin-2-yl)oxy)-2-azabicyclo[2.2.1]heptan-2-yl)methanone; |
| 16A | (6-methyl-3-(pyrimidin-2-yl)pyridin-2-yl)((1R*,3S*,4S*,6S*)-3-methyl-6-((5-(trifluoromethyl)pyridin-2-yl)oxy)-2-azabicyclo[2.2.1]heptan-2-yl)methanone; |
| 16B | (6-methyl-3-(pyrimidin-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 17 | (R/S)-(4-fluoro-2-(pyrimidin-2-yl)phenyl)(-3-methyl-6-((5-(trifluoromethyl)pyridin-2-yl)oxy)-2-azabicyclo[2.2.1]heptan-2-yl)methanone; |
| 17A | (4-fluoro-2-(pyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone; |
| 17B | (4-fluoro-2-(pyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 18 | (R/S)-(5-fluoro-2-(pyrimidin-2-yl)phenyl)(-3-methyl-6-((5-(trifluoromethyl)pyridin-2-yl)oxy)-2-azabicyclo[2.2.1]heptan-2-yl)methanone; |
| 18A | (5-fluoro-2-(pyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone; |
| 18B | (5-fluoro-2-(pyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 19 | (R/S)-(2-(5-fluoropyrimidin-2-yl)phenyl)(3-methyl-6-((5-(trifluoromethyl)pyridin-2-yl)oxy)-2-azabicyclo[2.2.1]heptan-2-yl)methanone; |
| 19A | (2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone; |
| 19B | (2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 20 | (R/S)-(3-fluoro-2-(5-fluoropyrimidin-2-yl)phenyl)(3-methyl-6-((5-(trifluoromethyl)pyridin-2-yl)oxy)-2-azabicyclo[2.2.1]heptan-2-yl)methanone; |
| 20A | (3-fluoro-2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone; |
| 20B | (3-fluoro-2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 21 | (R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone; |
| 21A | (2-(2H-1,2,3-triazol-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone; |
| 21B | (2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 22 | (R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone; |
| 22A | (6-methyl-3-(2H-1,2,3-triazol-2-yl)pyridin-2-yl)((1R*,3S*,4S*,6S*)-3-methyl-6-((5-(trifluoromethyl)pyridin-2-yl)oxy)-2-azabicyclo[2.2.1]heptan-2-yl)methanone; |
| 22B | (6-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 23 | (3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone; |

| Ex. No. | Chemical Name |
|---|---|
| 24 | (5-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 25 | (6-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 26 | (5-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 27 | (3-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 28 | (4-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 29 | (5-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 30 | (2-fluoro-6-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 31 | (4-methoxy-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone; |
| 32 | ((1S*,3R*,4R*,6R*)-3-methyl-6-((5-(trifluoromethyl)pyridin-2-yl)oxy)-2-azabicyclo[2.2.1]heptan-2-yl)(3-(pyrimidin-2-yl)pyridin-2-yl)methanone; |
| 33 | ((1S*,3R*,4R*,6R*)-3-methyl-6-((5-(trifluoromethyl)pyridin-2-yl)oxy)-2-azabicyclo[2.2.1]heptan-2-yl)(2-(pyrimidin-2-yl)phenyl)methanone; |
| 34 | (3-fluoro-5'-methyl-[2,3'-bipyridin]-2'-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 35 | (5-methyl-3-(pyrimidin-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone; |
| 36 | (4'-fluoro-[1,1'-biphenyl]-3-yl)((1S,3R,4R,6R)-3-methyl-6-((5-(trifluoromethyl)pyridin-2-yl)oxy)-2-azabicyclo[2.2.1]heptan-2-yl)methanone; |
| 37 | (3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone; |
| 38 | (3-fluoro-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone; |
| 39 | (3-methyl-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone; |
| 40 | (6-methyl-3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone; |
| 41 | (2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone; |
| 42 | (R/S)-(6-methyl-3-(2H-1,2,3-triazol-2-yl)pyridin-2-yl)(3-methyl-6-((5-(trifluoromethyl)pyrazin-2-yl)oxy)-2-azabicyclo[2.2.1]heptan-2-yl)methanone; |
| 43 | (R/S)-(2-(2H-1,2,3-triazol-2-yl)phenyl)(3-methyl-6-((5-(trifluoromethyl)pyrazin-2-yl)oxy)-2-azabicyclo[2.2.1]heptan-2-yl)methanone; |
| 44 | (R/S)-(6-methyl-3-(pyrimidin-2-yl)pyridin-2-yl)(3-methyl-6-((5-(trifluoromethyl)pyrazin-2-yl)oxy)-2-azabicyclo[2.2.1]heptan-2-yl)methanone; |
| 45 | (R/S)-3-methyl-6-((5-(trifluoromethyl)pyrazin-2-yl)oxy)-2-azabicyclo[2.2.1]heptan-2-yl)(2-(pyrimidin-2-yl)phenyl)methanone; |
| 46 | (6-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 47 | (3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 48 | (5-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 49 | (6-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 50 | (5-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 51 | (2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 52 | (3-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 53 | (4-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 54 | 5-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 55 | (2-fluoro-6-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 56 | (3-ethoxy-6-methylpyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone; |
| 57 | 4-methoxy-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone; |
| 58 | (R/S)-(6-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone; |
| 59 | R/S)-(5-methyl-3-(pyrimidin-2-yl)pyridin-2-yl)(3-methyl-6-((5-(trifluoromethyl)pyridin-2-yl)amino)-2-azabicyclo[2.2.1]heptan-2-yl)methanone;. |
| 60 | (6-methyl-3-(pyrimidin-2-yl)pyridin-2-yl)((1S,3R,4S,6R)-3-methyl-6-((5-(trifluoromethyl)pyridin-2-yl)amino)-2-azabicyclo[2.2.1]heptan-2-yl)methanone; |
| 61 | (R/S)-(5-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone; |

| Ex. No. | Chemical Name |
|---|---|
| 62 | ((1S*,3R*,4S*,6R*)-3-methyl-6-((5-(trifluoromethyl)pyridin-2-yl)amino)-2-azabicyclo[2.2.1]heptan-2-yl)(3-(pyrimidin-2-yl)pyridin-2-yl)methanone; |
| 63 | (6-methyl-3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone; |
| 64 | (3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone; |
| 65 | (3-fluoro-2-(2H-1,2,3-triazol-2-yl)phenyl)((1S*,3R*,4S*,6R*)-3-methyl-6-((5-(trifluoromethyl)pyridin-2-yl)amino)-2-azabicyclo[2.2.1]heptan-2-yl)methanone; |
| 66 | (5-methyl-3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone; |
| 67 | (R/S)-(3-fluoro-2-(pyrimidin-2-yl)phenyl)(3-methyl-6-((5-(trifluoromethyl)pyrazin-2-yl)amino)-2-azabicyclo[2.2.1]heptan-2-yl)methanone;. |
| 68 | (R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone; |
| 68A | (2-(2H-1,2,3-triazol-2-yl)phenyl)((1R*,3S*,4R*,6S*)-3-methyl-6-((5-(trifluoromethyl)pyrazin-2-yl)amino)-2-azabicyclo[2.2.1]heptan-2-yl)methanone; |
| 68B | (2-(2H-1,2,3-triazol-2-yl)phenyl)((1S*,3R*,4S*,6R*)-3-methyl-6-((5-(trifluoromethyl)pyrazin-2-yl)amino)-2-azabicyclo[2.2.1]heptan-2-yl)methanone; |
| 69 | (R/S)-(6-methyl-3-(2H-1,2,3-triazol-2-yl)pyridin-2-yl)(3-methyl-6-((5-(trifluoromethyl)pyrazin-2-yl)amino)-2-azabicyclo[2.2.1]heptan-2-yl)methanone; |
| 69A | (6-methyl-3-(2H-1,2,3-triazol-2-yl)pyridin-2-yl)((1R*,3S*,4R*,6S*)-3-methyl-6-((5-(trifluoromethyl)pyrazin-2-yl)amino)-2-azabicyclo[2.2.1]heptan-2-yl)methanone; |
| 69B | (6-methyl-3-(2H-1,2,3-triazol-2-yl)pyridin-2-yl)((1S*,3R*,4S*,6R*)-3-methyl-6-((5-(trifluoromethyl)pyrazin-2-yl)amino)-2-azabicyclo[2.2.1]heptan-2-yl)methanone; |
| 70 | (R/S)-3-(fluoromethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 71 | (R/S)-(2-fluoro-6-(oxazol-2-yl)phenyl)-3-(fluoromethyl)-6-((5-(trifluoromethyl)pyridin-2-yl)oxy)-2-azabicyclo[2.2.1]heptan-2-yl)methanone; |
| 72 | (R/S)-3-(fluoromethyl)-6-((5-(trifluoromethyl)pyridin-2-yl)oxy)-2-azabicyclo[2.2.1]heptan-2-yl)(5-methyl-2-(2H-1,2,3-triazol-2-yl)pyridin-3-yl)methanone; |
| 73 | (R/S)-(2-(2H-1,2,3-triazol-2-yl)phenyl)(3-(fluoromethyl)-6-((5-(trifluoromethyl)pyridin-2-yl)oxy)-2-azabicyclo[2.2.1]heptan-2-yl)methanone; |
| 74 | ((1S,3S,4R,6R)-3-(fluoromethyl)-6-((5-(trifluoromethyl)pyridin-2-yl)oxy)-2-azabicyclo[2.2.2]octan-2-yl)(6-methyl-3-(pyrimidin-2-yl)pyridin-2-yl)methanone; |
| 75 | ((1S,3S,4R,6R)-3-(fluoromethyl)-6-((5-(trifluoromethyl)pyridin-2-yl)oxy)-2-azabicyclo[2.2.2]octan-2-yl)(2-(pyrimidin-2-yl)phenyl)methanone; |
| 76 | (5-fluoro-2-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; |
| 77 | ((1S,3S,4R,6R)-3-(fluoromethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone; |
| 78 | (5-fluoro-2-(2H-1,2,3-triazol-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; |
| 79 | (3-fluoro-2-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; and |
| 80 | (5-fluoro-2-(5-fluoropyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; and pharmaceutically acceptable salts thereof. |

In another aspect provided herein is a compound selected from:

| Ex. No. | Chemical Name |
|---|---|
| 81 | ((1S,3R,4R,6R)-3-ethyl-6-((5-(trifluoromethyl)pyridin-2-yl)oxy)-2-azabicyclo[2.2.1]heptan-2-yl)(2-(pyrimidin-2-yl)phenyl)methanone; |
| 82 | ((1S,3R,4R,6R)-3-ethyl-6-((5-(trifluoromethyl)pyridin-2-yl)oxy)-2-azabicyclo[2.2.1]heptan-2-yl)(3-fluoro-2-(pyrimidin-2-yl)phenyl)methanone; |
| 83 | ((1S,3R,4R,6R)-3-ethyl-6-((5-(trifluoromethyl)pyridin-2-yl)oxy)-2-azabicyclo[2.2.1]heptan-2-yl)(2-(5-fluoropyrimidin-2-yl)phenyl)methanone; |
| 84 | ((1S,3R,4S,6R)-3-ethyl-6-((5-(trifluoromethyl)pyridin-2-yl)amino)-2-azabicyclo[2.2.1]heptan-2-yl)(2-(pyrimidin-2-yl)phenyl)methanone; |
| 85 | (2-(2H-1,2,3-triazol-2-yl)phenyl)((1S,3R,4S,6R)-3-ethyl-6-((5-(trifluoromethyl)pyridin-2-yl)amino)-2-azabicyclo[2.2.1]heptan-2-yl)methanone; |
| 86 | ((1S,3R,4S,6R)-3-ethyl-6-((5-(trifluoromethyl)pyridin-2-yl)amino)-2-azabicyclo[2.2.1]heptan-2-yl)(6-methyl-3-(2H-1,2,3-triazol-2-yl)pyridin-2-yl)methanone; |
| 87 | ((1S,3R,4S,6R)-3-ethyl-6-((5-(trifluoromethyl)pyridin-2-yl)amino)-2-azabicyclo[2.2.1]heptan-2-yl)(6-methyl-3-(2H-1,2,3-triazol-2-yl)pyridin-2-yl)methanone; |
| 88 | (2-(2H-1,2,3-triazol-2-yl)phenyl)((1S,3R,4R,6R)-3-ethyl-6-((5-(trifluoromethyl)pyridin-2-yl)oxy)-2-azabicyclo[2.2.1]heptan-2-yl)methanone; |
| 89 | ((1S,3R,4R,6R)-3-ethyl-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 90 | ((1S,3R,4R,6R)-3-ethyl-6-((5-(trifluoromethyl)pyridin-2-yl)oxy)-2-azabicyclo[2.2.1]heptan-2-yl)(5-methyl-3-(2H-1,2,3-triazol-2-yl)pyridin-2-yl)methanone; |

| Ex. No. | Chemical Name |
|---|---|
| 91 | ((1S,3R,4S,6R)-3-ethyl-6-((5-(trifluoromethyl)pyrazin-2-yl)amino)-2-azabicyclo[2.2.1]heptan-2-yl)(2-(pyrimidin-2-yl)phenyl)methanone; |
| 92 | (2-(2H-1,2,3-triazol-2-yl)phenyl)((1S,3R,4S,6R)-3-ethyl-6-((5-(trifluoromethyl)pyrazin-2-yl)amino)-2-azabicyclo[2.2.1]heptan-2-yl)methanone; |
| 93 | ((1S,3R,4S,6R)-3-ethyl-6-((5-(trifluoromethyl)pyrazin-2-yl)amino)-2-azabicyclo[2.2.1]heptan-2-yl)(6-methyl-3-(2H-1,2,3-triazol-2-yl)pyridin-2-yl)methanone; |
| 94 | ((1S,3R,4R,6R)-3-isobutyl-6-((5-(trifluoromethyl)pyridin-2-yl)oxy)-2-azabicyclo[2.2.1]heptan-2-yl)(2-(pyrimidin-2-yl)phenyl)methanone; |
| 95 | (3-fluoro-2-(pyrimidin-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone; |
| 96 | (2-(5-fluoropyrimidin-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone; |
| 97 | ((1S,3R,4R,6R)-6-((5-(fluoromethyl)pyridin-2-yl)oxy)-3-methyl-2-azabicyclo[2.2.1]heptan-2-yl)(2-(pyrimidin-2-yl)phenyl)methanone; |
| 98 | (2-(2H-1,2,3-triazol-2-yl)phenyl)((1S,3R,4R,6R)-6-((5-(fluoromethyl)pyridin-2-yl)oxy)-3-methyl-2-azabicyclo[2.2.1]heptan-2-yl)methanone; |
| 99 | ((1S,3R,4R,6R)-6-((5-(fluoromethyl)pyridin-2-yl)oxy)-3-methyl-2-azabicyclo[2.2.1]heptan-2-yl)(6-methyl-3-(2H-1,2,3-triazol-2-yl)pyridin-2-yl)methanone; |
| 100 | (2-(2H-1,2,3-triazol-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone; |
| 101 | ((1S,3R,4R,6R)-3-isobutyl-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 102 | ((1S,3R,4R,6R)-3-isobutyl-6-((5-(trifluoromethyl)pyridin-2-yl)oxy)-2-azabicyclo[2.2.1]heptan-2-yl)(5-methyl-3-(2H-1,2,3-triazol-2-yl)pyridin-2-yl)methanone; |
| 103 | ((1S,3S,4R,6R)-3-(methoxymethyl)-6-((5-(trifluoromethyl)pyridin-2-yl)oxy)-2-azabicyclo[2.2.1]heptan-2-yl)(2-(pyrimidin-2-yl)phenyl)methanone; |
| 104 | (2-(2H-1,2,3-triazol-2-yl)phenyl)((1S,3S,4R,6R)-3-(methoxymethyl)-6-((5-(trifluoromethyl)pyridin-2-yl)oxy)-2-azabicyclo[2.2.1]heptan-2-yl)methanone; |
| 105 | ((1S,3S,4R,6R)-3-(methoxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 106 | ((1S,3R,4R,6R)-3-methyl-6-((5-(trifluoromethyl)pyridin-2-yl)oxy)-2-azabicyclo[2.2.1]heptan-2-yl)(2-(pyridazin-3-yl)phenyl)methanone; |
| 107 | (5-(4-fluorophenyl)-2-methylthiazol-4-yl)((1S,3R,4R,6R)-3-methyl-6-((5-(trifluoromethyl)pyridin-2-yl)oxy)-2-azabicyclo[2.2.1]heptan-2-yl)methanone; |
| 108 | ((1S,3R,4R,6R)-6-((5-(difluoromethyl)pyridin-2-yl)oxy)-3-methyl-2-azabicyclo[2.2.1]heptan-2-yl)(2-(pyrimidin-2-yl)phenyl)methanone; |
| 109 | (2-(2H-1,2,3-triazol-2-yl)phenyl)((1S,3R,4R,6R)-6-((5-(difluoromethyl)pyridin-2-yl)oxy)-3-methyl-2-azabicyclo[2.2.1]heptan-2-yl)methanone; |
| 110 | ((1S,3R,4R,6R)-6-((5-(difluoromethyl)pyridin-2-yl)oxy)-3-methyl-2-azabicyclo[2.2.1]heptan-2-yl)(6-methyl-3-(2H-1,2,3-triazol-2-yl)pyridin-2-yl)methanone; |
| 111 | ((1S,3S,4R,6R)-3-(1-methoxyethyl)-6-((5-(trifluoromethyl)pyridin-2-yl)oxy)-2-azabicyclo[2.2.1]heptan-2-yl)(2-(pyrimidin-2-yl)phenyl)methanone; |
| 112 | (2-(2H-1,2,3-triazol-2-yl)phenyl)((1S,3S,4R,6R)-3-(1-methoxyethyl)-6-((5-(trifluoromethyl)pyridin-2-yl)oxy)-2-azabicyclo[2.2.1]heptan-2-yl)methanone; |
| 113 | ((1S,3S,4R,6R)-3-(1-methoxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 114 | ((1S,3R,4R,6R)-3-methyl-6-((5-methylpyridin-2-yl)oxy)-2-azabicyclo[2.2.1]heptan-2-yl)(2-(pyrimidin-2-yl)phenyl)methanone; |
| 115 | (2-(2H-1,2,3-triazol-2-yl)phenyl)((1S,3R,4R,6R)-3-methyl-6-((5-methylpyridin-2-yl)oxy)-2-azabicyclo[2.2.1]heptan-2-yl)methanone; |
| 116 | (6-methyl-3-(2H-1,2,3-triazol-2-yl)pyridin-2-yl)((1S,3R,4R,6R)-3-methyl-6-((5-methylpyridin-2-yl)oxy)-2-azabicyclo[2.2.1]heptan-2-yl)methanone; |
| 117 | ((1S,3S,4R,6R)-3-(hydroxymethyl)-6-((5-(trifluoromethyl)pyridin-2-yl)oxy)-2-azabicyclo[2.2.1]heptan-2-yl)(2-(pyrimidin-2-yl)phenyl)methanone; |
| 118 | (2-(2H-1,2,3-triazol-2-yl)phenyl)((1S,3S,4R,6R)-3-(hydroxymethyl)-6-((5-(trifluoromethyl)pyridin-2-yl)oxy)-2-azabicyclo[2.2.1]heptan-2-yl)methanone; |
| 119 | ((1S,3S,4R,6R)-3-(hydroxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 120 | ((1S,3R,4R,6R)-6-((5-chloropyridin-2-yl)oxy)-3-methyl-2-azabicyclo[2.2.1]heptan-2-yl)(2-(pyrimidin-2-yl)phenyl)methanone; |
| 121 | (2-(2H-1,2,3-triazol-2-yl)phenyl)((1S,3R,4R,6R)-6-((5-chloropyridin-2-yl)oxy)-3-methyl-2-azabicyclo[2.2.1]heptan-2-yl)methanone; |
| 122 | ((1S,3R,4R,6R)-6-((5-chloropyridin-2-yl)oxy)-3-methyl-2-azabicyclo[2.2.1]heptan-2-yl)(6-methyl-3-(2H-1,2,3-triazol-2-yl)pyridin-2-yl)methanone; |
| 123 | ((1S,3S,4R,6R)-3-(1-hydroxyethyl)-6-((5-(trifluoromethyl)pyridin-2-yl)oxy)-2-azabicyclo[2.2.1]heptan-2-yl)(2-(pyrimidin-2-yl)phenyl)methanone; |
| 124 | (2-(2H-1,2,3-triazol-2-yl)phenyl)((1S,3S,4R,6R)-3-(1-hydroxyethyl)-6-((5-(trifluoromethyl)pyridin-2-yl)oxy)-2-azabicyclo[2.2.1]heptan-2-yl)methanone; |
| 125 | ((1S,3S,4R,6R)-3-(1-hydroxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone; |
| 126 | ((1S,3R,4S,6R)-6-((3-fluoro-5-(trifluoromethyl)pyridin-2-yl)amino)-3-methyl-2-azabicyclo[2.2.1]heptan-2-yl)(2-(pyrimidin-2-yl)phenyl)methanone; |
| 127 | (2-(2H-1,2,3-triazol-2-yl)phenyl)((1S,3R,4S,6R)-6-((3-fluoro-5-(trifluoromethyl)pyridin-2-yl)amino)-3-methyl-2-azabicyclo[2.2.1]heptan-2-yl)methanone; |
| 128 | ((1S,3R,4S,6R)-6-((3-fluoro-5-(trifluoromethyl)pyridin-2-yl)amino)-3-methyl-2-azabicyclo[2.2.1]heptan-2-yl)(6-methyl-3-(2H-1,2,3-triazol-2-yl)pyridin-2-yl)methanone; |

| Ex. No. | Chemical Name |
|---|---|
| 129 | ((1S,3R,4S,6R)-6-(benzo[d]oxazol-2-ylamino)-3-methyl-2-azabicyclo[2.2.1]heptan-2-yl)(2-(pyrimidin-2-yl)phenyl)methanone; |
| 130 | (2-(2H-1,2,3-triazol-2-yl)phenyl)((1S,3R,4S,6R)-6-(benzo[d]oxazol-2-ylamino)-3-methyl-2-azabicyclo[2.2.1]heptan-2-yl)methanone; |
| 131 | ((1S,3R,4S,6R)-6-(benzo[d]oxazol-2-ylamino)-3-methyl-2-azabicyclo[2.2.1]heptan-2-yl)(6-methyl-3-(2H-1,2,3-triazol-2-yl)pyridin-2-yl)methanone; |
| 132 | ((1S,3R,4S,6R)-3-methyl-6-((5-(trifluoromethyl)pyrimidin-2-yl)amino)-2-azabicyclo[2.2.1]heptan-2-yl)(2-(pyrimidin-2-yl)phenyl)methanone; |
| 133 | (2-(2H-1,2,3-triazol-2-yl)phenyl)((1S,3R,4S,6R)-3-methyl-6-((5-(trifluoromethyl)pyrimidin-2-yl)amino)-2-azabicyclo[2.2.1]heptan-2-yl)methanone; |
| 134 | (6-methyl-3-(2H-1,2,3-triazol-2-yl)pyridin-2-yl)((1S,3R,4S,6R)-3-methyl-6-((5-(trifluoromethyl)pyrimidin-2-yl)amino)-2-azabicyclo[2.2.1]heptan-2-yl)methanone; |
| 135 | ((1S,3R,4R,6R)-6-((5-bromopyridin-2-yl)oxy)-3-methyl-2-azabicyclo[2.2.1]heptan-2-yl)(2-(pyrimidin-2-yl)phenyl)methanone; |
| 136 | (2-(2H-1,2,3-triazol-2-yl)phenyl)((1S,3R,4R,6R)-6-((5-bromopyridin-2-yl)oxy)-3-methyl-2-azabicyclo[2.2.1]heptan-2-yl)methanone; |
| 137 | ((1S,3R,4R,6R)-6-((5-bromopyridin-2-yl)oxy)-3-methyl-2-azabicyclo[2.2.1]heptan-2-yl)(6-methyl-3-(2H-1,2,3-triazol-2-yl)pyridin-2-yl)methanone; |
| 138 | ((1S,3S,4R,6R)-3-(fluoromethyl)-6-((5-(trifluoromethyl)pyridin-2-yl)oxy)-2-azabicyclo[2.2.2]octan-2-yl)(2-methoxy-6-(pyrimidin-2-yl)phenyl)methanone; |
| 139 | ((1S,3S,4R,6R)-3-(fluoromethyl)-6-((5-(trifluoromethyl)pyridin-2-yl)oxy)-2-azabicyclo[2.2.2]octan-2-yl)(4-methyl-2-(2H-1,2,3-triazol-2-yl)phenyl)methanone; |
| 140 | ((1S,3S,4R,6R)-3-(fluoromethyl)-6-((5-(trifluoromethyl)pyridin-2-yl)oxy)-2-azabicyclo[2.2.2]octan-2-yl)(2-methyl-6-(2H-1,2,3-triazol-2-yl)phenyl)methanone; |
| 141 | (2-fluoro-6-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; |
| 142 | (2-(2H-1,2,3-triazol-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone; |
| 143 | ((1S,3S,4R,6R)-3-(fluoromethyl)-6-((5-(trifluoromethyl)pyridin-2-yl)oxy)-2-azabicyclo[2.2.2]octan-2-yl)(3-methyl-2-(oxazol-2-yl)phenyl)methanone; |
| 144 | ((1S,3S,4R,6R)-3-(fluoromethyl)-6-((5-(trifluoromethyl)pyridin-2-yl)oxy)-2-azabicyclo[2.2.2]octan-2-yl)(3-methyl-2-(pyridin-2-yl)phenyl)methanone; |
| 145 | ((1S,3S,4R,6R)-3-(fluoromethyl)-6-((5-(trifluoromethyl)pyridin-2-yl)oxy)-2-azabicyclo[2.2.2]octan-2-yl)(2-(5-fluoropyrimidin-2-yl)phenyl)methanone; |
| 146 | ((1S,3S,4R,6R)-3-(fluoromethyl)-6-((5-(trifluoromethyl)pyridin-2-yl)oxy)-2-azabicyclo[2.2.2]octan-2-yl)(5-methyl-3-(2H-1,2,3-triazol-2-yl)pyridin-2-yl)methanone; |
| 147 | (2-bromo-3-fluorophenyl)((1S,3S,4R,6R)-3-(fluoromethyl)-6-((5-(trifluoromethyl)pyridin-2-yl)oxy)-2-azabicyclo[2.2.2]octan-2-yl)methanone; |
| 148 | (3-fluoro-2-(pyrimidin-2-yl)phenyl)((1S,3R,4R,6R)-3-methyl-6-((5-(trifluoromethyl)pyridin-2-yl)oxy)-2-azabicyclo[2.2.2]octan-2-yl)methanone; |
| 149 | (3-fluoro-2-(pyrimidin-2-yl)phenyl)((1S,3S,4R,6R)-3-(hydroxymethyl)-6-((5-(trifluoromethyl)pyridin-2-yl)oxy)-2-azabicyclo[2.2.2]octan-2-yl)methanone; |
| 150 | (3-fluoro-2-(pyrimidin-2-yl)phenyl)((1S,3S,4R,6R)-3-(methoxymethyl)-6-((5-(trifluoromethyl)pyridin-2-yl)oxy)-2-azabicyclo[2.2.2]octan-2-yl)methanone; |
| 151 | (3-fluoro-2-(2H-1,2,3-triazol-2-yl)phenyl)((1S,3R,4R,6R)-3-methyl-6-((5-(trifluoromethyl)pyridin-2-yl)oxy)-2-azabicyclo[2.2.2]octan-2-yl)methanone; |
| 152 | (3-fluoro-2-(2H-1,2,3-triazol-2-yl)phenyl)((1S,3S,4R,6R)-3-(hydroxymethyl)-6-((5-(trifluoromethyl)pyridin-2-yl)oxy)-2-azabicyclo[2.2.2]octan-2-yl)methanone; |
| 153 | (3-fluoro-2-(2H-1,2,3-triazol-2-yl)phenyl)((1S,3S,4R,6R)-3-(methoxymethyl)-6-((5-(trifluoromethyl)pyridin-2-yl)oxy)-2-azabicyclo[2.2.2]octan-2-yl)methanone; |
| 154 | (3-fluoro-2-(pyrimidin-2-yl)phenyl)((1S,3S,4R,6R)-3-((methoxymethoxy)methyl)-6-((5-(trifluoromethyl)pyridin-2-yl)oxy)-2-azabicyclo[2.2.2]octan-2-yl)methanone; and |
| 155 | (3-fluoro-2-(2H-1,2,3-triazol-2-yl)phenyl)((1S,3S,4R,6R)-3-((methoxymethoxy)methyl)-6-((5-(trifluoromethyl)pyridin-2-yl)oxy)-2-azabicyclo[2.2.2]octan-2-yl)methanone; and pharmaceutically acceptable salts thereof. |

In another aspect provided herein is a compound selected from:

| Ex. No. | Chemical Name |
|---|---|
| 77 | ((1S,3S,4R,6R)-3-(fluoromethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone; |
| 110 | [(1R,2R,4S,5R)-5-[[5-(difluoromethyl)-2-pyridyl]oxy]-2-methyl-3-azabicyclo[2.2.1]heptan-3-yl]-[6-methyl-3-(triazol-2-yl)-2-pyridyl]methanone; |
| 121 | [(1R,2R,4S,5R)-5-[(5-chloro-2-pyridyl)oxy]-2-methyl-3-azabicyclo[2.2.1]heptan-3-yl]-[2-(triazol-2-yl)phenyl]methanone; |
| 122 | [(1R,2R,4S,5R)-5-[(5-chloro-2-pyridyl)oxy]-2-methyl-3-azabicyclo[2.2.1]heptan-3-yl]-[6-methyl-3-(triazol-2-yl)-2-pyridyl]methanone; |
| 148 | (3-fluoro-2-pyrimidin-2-yl-phenyl)-[(1R,2R,4S,5R)-2-methyl-5-[[5-(trifluoromethyl)-2-pyridyl]oxy]-3-azabicyclo[2.2.2]octan-3-yl]methanone; |
| 156 | [6-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone; |

| Ex. No. | Chemical Name |
|---|---|
| 157 | [(1R,2R,4S,5R)-2-methyl-5-[[5-(trifluoromethyl)-2-pyridyl]oxy]-3-azabicyclo[2.2.2]octan-3-yl]-[2-(triazol-2-yl)phenyl]methanone; |
| 158 | (6-methyl-3-pyrimidin-2-yl-2-pyridyl)-[(1R,2R,4S,5R)-2-methyl-5-[[5-(trifluoromethyl)-2-pyridyl]oxy]-3-azabicyclo[2.2.2]octan-3-yl]methanone; |
| 159 | [(1R,2R,4S,5R)-2-methyl-5-[[5-(trifluoromethyl)-2-pyridyl]oxy]-3-azabicyclo[2.2.2]octan-3-yl]-[3-(triazol-2-yl)-2-pyridyl]methanone; |
| 160 | [5-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone; |
| 161 | (5-methyl-3-pyrimidin-2-yl-2-pyridyl)-[(1R,2R,4S,5R)-2-methyl-5-[[5-(trifluoromethyl)-2-pyridyl]oxy]-3-azabicyclo[2.2.2]octan-3-yl]methanone; |
| 162 | (3-fluoro-2-pyrimidin-2-yl-phenyl)-[(1R,2R,4S,5S)-2-methyl-5-[[5-(trifluoromethyl)-2-pyridyl]oxy]-3-azabicyclo[2.2.2]octan-3-yl]methanone; |
| 163 | [(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[2-(triazol-2-yl)phenyl]methanone; |
| 164 | [(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[3-fluoro-2-(triazol-2-yl)phenyl]methanone; |
| 165 | [(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[6-methyl-3-(triazol-2-yl)-2-pyridyl]methanone; |
| 166 | [(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[5-methyl-3-(triazol-2-yl)-2-pyridyl]methanone; |
| 167 | [(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-(5-fluoro-2-pyrimidin-2-yl-phenyl)methanone; |
| 168 | [2-[4-(3-fluoropropyl)triazol-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone; |
| 169 | [2-[5-(2-fluoroethoxy)pyrimidin-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone; |
| 170 | [2-(5-fluoropyrazin-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 171 | [2-(6-fluoro-3-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 172 | [2-(2-fluoro-4-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 173 | [2-(6-fluoro-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 174 | [(1R,2R,4S,5R)-2-methyl-5-[[5-(trifluoromethyl)-2-pyridyl]oxy]-3-azabicyclo[2.2.1]heptan-3-yl]-[2-(6-nitro-2-pyridyl)phenyl]methanone; |
| 175 | [2-(6-bromo-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 176 | [(1R,2S,4S,5R)-2-(hydroxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone; |
| 177 | [2-fluoro-6-(triazol-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone; |
| 178 | [5-fluoro-2-(5-fluoropyrimidin-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone; |
| 179 | [(1R,2S,4S,5R)-2-(methoxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone; |
| 180 | [(1R,2S,4S,5R)-2-(methoxymethyl)-5-[[5-(trifluoromethyl)-2-pyridyl]oxy]-3-azabicyclo[2.2.2]octan-3-yl]-(6-methyl-3-pyrimidin-2-yl-2-pyridyl)methanone; |
| 181 | [(1R,2S,4S,5R)-2-(methoxymethyl)-5-[[5-(trifluoromethyl)-2-pyridyl]oxy]-3-azabicyclo[2.2.2]octan-3-yl]-(2-pyrimidin-2-ylphenyl)methanone; |
| 182 | [(1R,2R,4S,5R)-5-[[5-(difluoromethyl)-2-pyridyl]oxy]-2-methyl-3-azabicyclo[2.2.1]heptan-3-yl]-(6-methyl-3-pyrimidin-2-yl-2-pyridyl)methanone; |
| 183 | (6-methyl-3-(2H-1,2,3-triazol-2-yl)pyridin-2-yl)((1S*,3R*,4R*,6R*)-3-methyl-6-(quinoxalin-2-yloxy)-2-azabicyclo[2.2.1]heptan-2-yl)methanone; |
| 184 | (3-fluoro-2-(2H-1,2,3-triazol-2-yl)phenyl)((1S*,3R*,4R*,6R*)-3-methyl-6-(quinoxalin-2-yloxy)-2-azabicyclo[2.2.1]heptan-2-yl)methanone; |
| 185 | (6-methyl-3-(2H-1,2,3-triazol-2-yl)pyridin-2-yl)((1S*,3R*,4R*,6R*)-3-methyl-6-(quinolin-3-yloxy)-2-azabicyclo[2.2.1]heptan-2-yl)methanone; |
| 186 | ((1S*,3R*,4R*,6R*)-6-((6-fluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone; |
| 187 | (3-fluoro-2-(2H-1,2,3-triazol-2-yl)phenyl)((1S*,3R*,4R*,6R*)-6-((6-fluoroquinoxalin-2-yl)oxy)-3-methyl-2-azabicyclo[2.2.1]heptan-2-yl)methanone; |
| 188 | (2-(2H-1,2,3-triazol-2-yl)phenyl)((1S*,3R*,4R*,6R*)-6-((6-fluoroquinoxalin-2-yl)oxy)-3-methyl-2-azabicyclo[2.2.1]heptan-2-yl)methanone; |
| 189 | ((1S*,3R*,4R*,6R*)-6-((6,7-difluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone; |
| 190 | ((1S*,3R*,4R*,6R*)-6-((6,7-difluoroquinoxalin-2-yl)oxy)-3-methyl-2-azabicyclo[2.2.1]heptan-2-yl)(3-fluoro-2-(2H-1,2,3-triazol-2-yl)phenyl)methanone; |
| 191 | (2-(2H-1,2,3-triazol-2-yl)phenyl)((1S*,3R*,4R*,6R*)-6-((6,7-difluoroquinoxalin-2-yl)oxy)-3-methyl-2-azabicyclo[2.2.1]heptan-2-yl)methanone; |
| 192 | ethyl (1R,2S,4S,5R)-3-[6-methyl-3-(triazol-2-yl)pyridine-2-carbonyl]-5-[[5-(trifluoromethyl)-2-pyridyl]oxy]-3-azabicyclo[2.2.1]heptane-2-carboxylate; |
| 193 | [(1R,2R,4S,5R)-5-[(5-chloro-2-pyridyl)oxy]-2-methyl-3-azabicyclo[2.2.1]heptan-3-yl]-[6-methyl-2-(triazol-2-yl)-3-pyridyl]methanone; |
| 194 | [(1R,2R,4S,5R)-5-[(5-chloro-2-pyridyl)oxy]-2-methyl-3-azabicyclo[2.2.1]heptan-3-yl]-[5-methyl-2-(triazol-2-yl)-3-pyridyl]methanone; |

-continued

| Ex. No. | Chemical Name |
|---|---|
| 195 | [(1R,3R,4S,6R)-3-[(5-chloro-2-pyridyl)oxy]-2,2-dideuterio-6-methyl-5-azabicyclo[2.2.1]heptan-5-yl]-[2-(triazol-2-yl)phenyl]methanone; |
| 196 | [(1R,3R,4S,6R)-3-[(5-chloro-2-pyridyl)oxy]-2,2-dideuterio-6-methyl-5-azabicyclo[2.2.1]heptan-5-yl]-[6-methyl-3-(triazol-2-yl)-2-pyridyl]methanone; |
| 197 | [(1R,3R,4S,6R)-3-[(5-chloro-2-pyridyl)oxy]-2,2-dideuterio-6-methyl-5-azabicyclo[2.2.1]heptan-5-yl]-[3-fluoro-2-(triazol-2-yl)phenyl]methanone; |
| 198 | [(1R,3R,4S,6R)-2,2-dideuterio-6-methyl-3-[[5-(trifluoromethyl)-2-pyridyl]oxy]-5-azabicyclo[2.2.1]heptan-5-yl]-[6-methyl-3-(triazol-2-yl)-2-pyridyl]methanone; |
| 199 | [(1R,3R,4S,6R)-2,2-dideuterio-6-methyl-3-[[5-(trifluoromethyl)-2-pyridyl]oxy]-5-azabicyclo[2.2.1]heptan-5-yl]-[3-fluoro-2-(triazol-2-yl)phenyl]methanone; |
| 200 | [(1R,3R,4S,6R)-2,2-dideuterio-6-methyl-3-[[5-(trifluoromethyl)-2-pyridyl]oxy]-5-azabicyclo[2.2.1]heptan-5-yl]-[5-methyl-3-(triazol-2-yl)-2-pyridyl]methanone; |
| 201 | [(1R,3R,4S,6R)-2,2-dideuterio-6-methyl-3-[[5-(trifluoromethyl)-2-pyridyl]oxy]-5-azabicyclo[2.2.1]heptan-5-yl]-[2-(triazol-2-yl)phenyl]methanone; |
| 202 | [4-(2-fluoroethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 203 | [2-(2-hydroxyethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone; |
| 204 | [5-(2-bromoethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone; |
| 205 | [2-(2-fluoroethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone; |
| 206 | (7-(2-fluoroethoxy)quinolin-8-yl)((1S,3R,4R,6R)-3-methyl-6-((5-(trifluoromethyl)pyridin-2-yl)oxy)-2-azabicyclo[2.2.1]heptan-2-yl)methanone; |
| 207 | (R/S)-[2-isobutyl-5-[[5-(trifluoromethyl)-2-pyridyl]oxy]-3-azabicyclo[2.2.1]heptan-3-yl]-[2-(triazol-2-yl)phenyl]methanone; |
| 208 | (R/S)-[2-isobutyl-5-[[5-(trifluoromethyl)-2-pyridyl]oxy]-3-azabicyclo[2.2.1]heptan-3-yl]-[5-methyl-3-(triazol-2-yl)-2-pyridyl]methanone; |
| 209 | (R/S)-[2-isobutyl-5-[[5-(trifluoromethyl)-2-pyridyl]oxy]-3-azabicyclo[2.2.1]heptan-3-yl]-(2-pyrimidin-2-ylphenyl)methanone; |
| 210 | (R/S)-[2-isobutyl-5-[[5-(trifluoromethyl)-2-pyridyl]oxy]-3-azabicyclo[2.2.1]heptan-3-yl]-[6-methyl-3-(triazol-2-yl)-2-pyridyl]methanone; |
| 211 | (R/S)-(3-fluoro-2-pyrimidin-2-yl-phenyl)-[2-isobutyl-5-[[5-(trifluoromethyl)-2-pyridyl]oxy]-3-azabicyclo[2.2.1]heptan-3-yl]methanone; |
| 212 | (R/S)-[2-(5-fluoropyrimidin-2-yl)phenyl]-[2-isobutyl-5-[[5-(trifluoromethyl)-2-pyridyl]oxy]-3-azabicyclo[2.2.1]heptan-3-yl]methanone; |
| 213 | (R/S)-[2-ethyl-5-[[5-(trifluoromethyl)-2-pyridyl]oxy]-3-azabicyclo[2.2.1]heptan-3-yl]-[2-(triazol-2-yl)phenyl]methanone; |
| 214 | (R/S)-[2-ethyl-5-[[5-(trifluoromethyl)-2-pyridyl]oxy]-3-azabicyclo[2.2.1]heptan-3-yl]-(2-pyrimidin-2-ylphenyl)methanone; |
| 215 | (R/S)-[2-ethyl-5-[[5-(trifluoromethyl)-2-pyridyl]oxy]-3-azabicyclo[2.2.1]heptan-3-yl]-[6-methyl-3-(triazol-2-yl)-2-pyridyl]methanone; |
| 216 | (R/S)-[2-ethyl-5-[[5-(trifluoromethyl)-2-pyridyl]oxy]-3-azabicyclo[2.2.1]heptan-3-yl]-[5-methyl-3-(triazol-2-yl)-2-pyridyl]methanone; |
| 217 | (R/S)-[2-ethyl-5-[[5-(trifluoromethyl)-2-pyridyl]oxy]-3-azabicyclo[2.2.1]heptan-3-yl]-(3-fluoro-2-pyrimidin-2-yl-phenyl)methanone; |
| 218 | (R/S)-[2-ethyl-5-[[5-(trifluoromethyl)-2-pyridyl]oxy]-3-azabicyclo[2.2.1]heptan-3-yl]-[2-(5-fluoropyrimidin-2-yl)phenyl]methanone; and |
| 219 | (2-(pyrimidin-2-yl)phenyl)((1S,3R,4R,6R)-3-methyl-6-((6-fluoro-5-(trifluoromethyl)pyridin-2-yl)oxy)-2-azabicyclo[2.2.1]heptan-2-yl)methanone; and pharmaceutically acceptable salts thereof. |

In another aspect provided herein is a compound selected from:

| Ex. No. | Chemical Name |
|---|---|
| 220 | ((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone; |
| 221 | ((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone; |
| 222 | (5-fluoro-2-(5-fluoropyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; |
| 223 | (5-fluoro-2-(pyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; |
| 224 | ((1S,3R,4R,6R)-6-((6-fluoro-5-(trifluoromethyl)pyridin-2-yl)oxy)-3-methyl-2-azabicyclo[2.2.1]heptan-2-yl)(2-(pyrimidin-2-yl)phenyl)methanone; |
| 225 | (3-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; |
| 226 | (3-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; |
| 227 | (4-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; |

| Ex. No. | Chemical Name |
|---|---|
| 228 | (5-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone; and |
| 229 | (3-(2-fluoroethoxy)isoquinolin-4-yl)((1S,3R,4R,6R)-3-methyl-6-((5-(trifluoromethyl)pyridin-2-yl)oxy)-2-azabicyclo[2.2.1]heptan-2-yl)methanone; and pharmaceutically acceptable salts thereof. |

Any combination of the groups described above for the various variables is contemplated herein. Throughout the specification, groups and substituents thereof are chosen by one skilled in the field to provide stable moieties and compounds.

The invention relates to methods of using the compounds described herein to treat subjects diagnosed with or suffering from a disease, disorder, or condition mediated by orexin receptor activity. These methods are accomplished by administering to the subject a compound of the invention. In some embodiments, the compounds described herein are selective for orexin-1 receptor activity. In some embodiments, the compounds described herein are selective for orexin-1 receptor activity over orexin-2 receptor activity.

Diseases, disorders, and conditions mediated by orexin receptor activity include disorders of the sleep-wake cycle (e.g., insomnia, restless legs syndrome, jet-lag, disturbed sleep, sleep disorders secondary to neurological disorders, and the like), narcolepsy, schizophrenia, pain syndromes, (e.g., fibromyalgia, neuropathic pain, back and joint pain and the like), neurological conditions (e.g., catatonia, Parkinson's disease, Tourette's syndrome), delirium, dementia, overweight, obesity, or conditions related to overweight or obesity (e.g., insulin resistance, type II diabetes, hyperlipidemia, gallstones, breathlessness), underweight and related conditions (such as ammenorrhea and related infertility, and eating disorders such as anorexia and bulimia), sleep apnea, varicose veins, osteoarthritis, hypotension, bradycardia and heart failure related thereto, arrhythmias (e.g., hypertension, tachycardia), angina pectoris, acute heart failure, ulcers, irritable bowel syndrome, diarrhea gastroesophageal reflux, mood disorders (e.g., panic disorders, anxiety, anxious depression, mania, depression, manic depression, and the like), post-traumatic stress disorder, attention deficit disorders, cognitive deficiencies, delirium, dementias, substance abuse, or psychiatric disorders with a stress induced hyperarousal state component.

Compounds of the invention are particularly suited for the treatment of mood disorders, stress-related disorders (e.g., post-traumatic stress disorder), attention deficit disorders, cognitive deficiencies, or substance abuse.

In one aspect, compounds of the invention are particularly suited for the treatment of mood disorders. Non-limiting examples of mood disorders include anxiety-related mood disorders, depression, panic-related mood disorders, stress related mood disorders and the like. In another aspect, compounds of the invention are suitable for the treatment of post-traumatic stress disorder, panic disorders, attention deficit disorders, cognitive deficiencies, or substance abuse (e.g., morphine abuse, cocaine abuse, alcohol abuse and the like). It will be understood that certain disorders such as, for example, depression and/or schizophrenia and/or substance abuse and/or cognitive impairments also have elements of anxiety and/or panic and/or stress associated with them and the treatment of such conditions and/or combinations of conditions are also contemplated within the scope of embodiments presented herein. In some embodiments, advantageously, compounds of the invention treat a mood disorder (e.g., anxiety) with reduced concomitant sedation and/or with reduced effect on sleep (e.g., attenuated arousal effects). In one embodiment, compounds of the invention are particularly suited for the treatment of anxious depression. In another embodiment, compounds of the invention are particularly suited for the treatment of panic, schizophrenia, and substance abuse. In an additional embodiment, the compounds described herein are suitable for treatment of psychiatric disorders with a stress induced hyperarousal state component.

Sleep disorders include, but are not limited to, sleep-wake transition disorders, restless legs syndrome, insomnia, jet-lag, disturbed sleep, and sleep disorders secondary to neurological disorders and/or mood disorders (e.g., anxiety, depression, narcolepsy, schizophrenia), and pain syndromes (e.g., fibromyalgia, neuropathic).

Metabolic disorders include, but are not limited to, overweight or obesity and conditions related to overweight or obesity, (such as insulin resistance, type II diabetes, or hyperlipidemia). In some embodiments provided herein are methods for treatment of gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, and the like.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula I. Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

The synthesis of exemplary intermediates having the structure

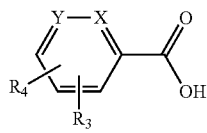

is described in Schemes 1-5 below and in the Examples section below (Intermediates A-1 to A-32).

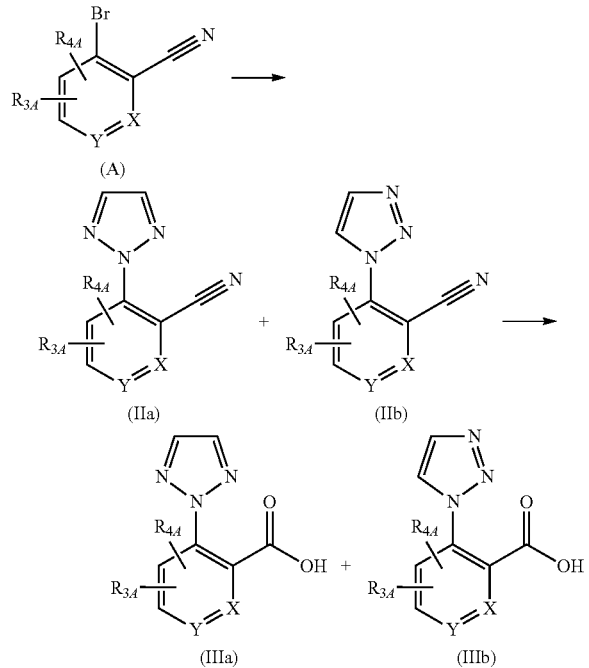

Intermediate compounds of formula (IIIa) and (IIIb) can be prepared as outlined in Scheme 1 from commercially available or synthetically accessible compounds of formula (A) where $R_{3A}$, $R_{4A}$ are —H, halo, —$C_{1-4}$alkyl, —$C_{1-4}$alkoxy or $R_{3A}$ and $R_{4A}$ together with the atoms to which they are attached form a 6-membered aryl or 6 membered heteroaryl ring and X and Y are as defined in Formula I as above. Compounds of formula (IIa) and (IIb), are obtained by reacting a compound of formula (A), with commercially available 1,2,3-triazole, in the presence $K_2CO_3$ in DMF or dioxane, at temperatures ranging from about 60° C. to about 100° C. Compounds of formula (IIIa) and (IIIb) are obtained by reacting compounds of formula (IIa) or (IIb) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus accounting for the formation of (IIIa) and (IIIb). One skilled in the art will recognize that compounds of formula (IIIa) and (IIIb) can be separated (e.g., via column chromatography or preparative HPLC).

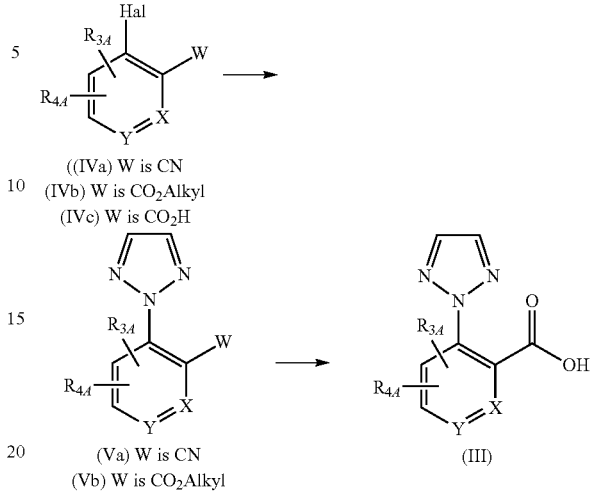

Intermediate compounds of formula (III) can be prepared as outlined in Scheme 2 from commercially available or synthetically accessible compounds of formula (IVa-c). Compounds of formula (Va) and (Vb) are obtained by reacting compounds of formula (IVa), (IVb) and (IVc) where Hal is —Br, or —I; W is $CO_2H$, $CO_2$Alkyl, or CN and $R_{3A}$ and $R_{4A}$ are —H, halo, —$C_{1-4}$alkyl, —$C_{1-4}$alkoxy or $R_{3A}$ and $R_{4A}$ together with the atoms to which they are attached form a 6-membered aryl or 6 membered heteroaryl ring, and X and Y are as defined in Formula I above, with commercially available 1,2,3-triazole, in the presence of, for example, copper(I)iodide, $Cs_2CO_3$ and trans-N,N'-dimethyl-1,2-cyclohexanediamine in, for example, DMF or dioxane, at temperatures ranging from about 60° C. to about 120° C. Compounds of formula (IVc) can be converted to the corresponding esters (Vb) by treatment with, for example, alkyl iodide in the presence of a base such as $K_2CO_3$ in a solvent such as DMF. Compounds of formula (III) are obtained by reacting a compound of formula (Va) and (Vb) in the presence of a base such as NaOH in a solvent such as EtOH at temperatures ranging from about 80° C. to about 100° C. One skilled in the art will recognize that 1,2,3-triazole can exist in two tautomeric forms defined as 2H-[1,2,3]triazole and 1H-[1,2,3]triazole thus compounds of formula (Va), (Vb), and (III) can also exist as the N1 linked variant (structure not shown). It will be understood that the heterocycle in (Va) and (Vb) is not limited to triazole and may be any other suitable heterocycle.

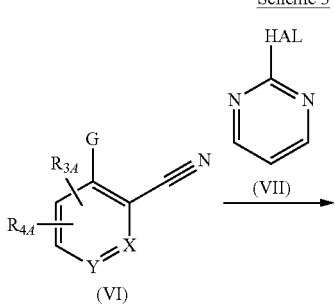

-continued

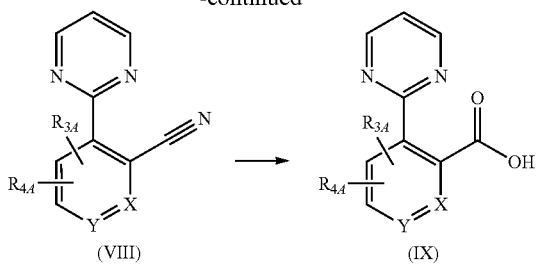

Intermediate compounds of formula (IX) can be prepared as outlined in Scheme 3 from commercially available or synthetically accessible compounds of formula (VI) where $R_{3A}$, $R_{4A}$ are —H, halo, —$C_{1-4}$alkyl, —$C_{1-4}$alkoxy or $R_{3A}$ and $R_{4A}$ together with the atoms to which they are attached form a 6-membered aryl or 6 membered heteroaryl ring, and X and Y are as defined in Formula I as above, G is SnBu$_3$, or 4,4,5,5 tetramethyl-1,dioxaboralane, and HAL is Cl, or Br, preferably Br. Compounds of formula (VIII) are obtained by reacting a compound of formula (VI) with commercially available (VII) in the presence of a catalyst such as 1,1′-Bis (di-tert-butylphosphino)ferrocene palladium dichloride and a base such as Na$_2$CO$_3$ in a solvent such as 2-MeTHF or THF at temperatures ranging from about 60° C. to about 90° C. Compounds of formula (IX) are obtained by reacting a compound of formula (VIII) in the presence of a base such as NaOH in a solvent such as MeOH at temperatures ranging from about 80° C. to about 100° C. or acids such as H$_2$SO$_4$ in solvents such as H$_2$O at temperatures ranging from about 80° C. to about 100° C. It will be understood that the heterocycle in (VII) is not limited to pyrimidine and may be any other suitable heterocycle.

Scheme 4

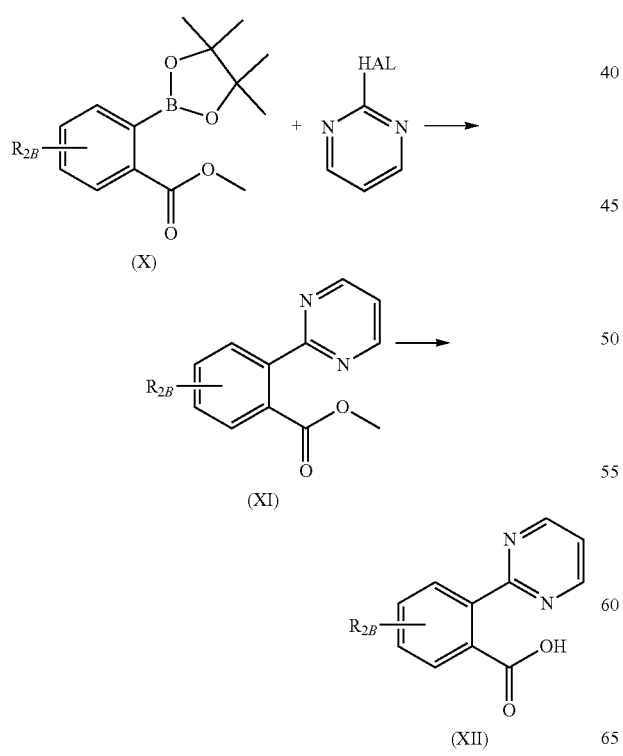

Intermediate compounds of formula (XII) are prepared as outlined in Scheme 4 from commercially available or synthetically accessible compounds of formula (X) where $R_{2B}$ is —H, —$C_{1-4}$alkyl, or —$C_{1-4}$alkoxy, or $R_{2B}$ is —H, halo, —$C_{1-4}$alkyl, or —$C_{1-4}$alkoxy, and HAL is halo, preferably Cl, or Br. Compounds of formula (XI) are obtained by reacting a compound of formula (X) with commercially available (VII) in the presence of a catalyst such as Pd(dppf)Cl$_2$ and a base such as Na$_2$CO$_3$ in a solvent such as 2-MeTHF at temperatures ranging from about 75° C. to about 150° C. Compounds of formula (XII) are obtained by reacting a compound of formula (XI) in the presence of a base such as NaOH in a solvent such as MeOH at temperatures ranging from about 80° C. to about 100° C. It will be understood that the heterocycle in (XI) is not limited to pyrimidine and may be any other suitable heterocycle.

Scheme 5

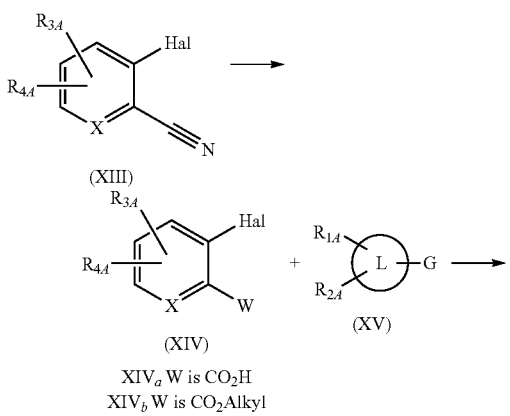

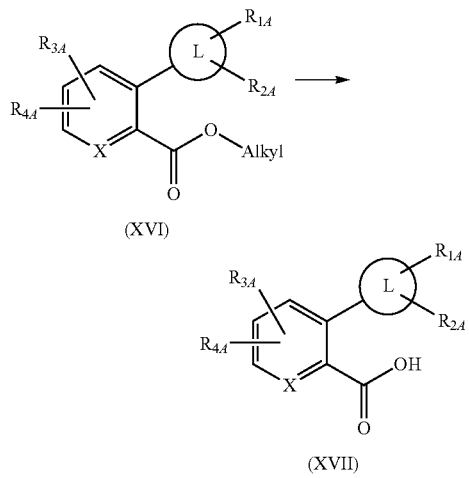

Intermediate compounds of formula (XVII) can be prepared as outlined in Scheme 5 from commercially available or synthetically accessible compounds of formula (XIII) where Hal is Br or I; and where $R_{3A}$ and $R_{4A}$ are —H, halo, —$C_{1-4}$alkyl, —$C_{1-4}$alkoxy, or $R_{3A}$ and $R_{4A}$ together with the atoms to which they are attached form a 6-membered aryl or 6 membered heteroaryl ring; and X is defined in Formula I as above. Compounds of formula (XIVa) can be converted to the corresponding ester (XIVb) by treatment with, for example, thionyl chloride in a solvent such as MeOH. Compounds of the formula (XVI) are obtained by reacting compounds of formula (XIVb) with commercially available compounds of the formula (XV) where L is a heterocycle such as pyrazole, pyridyl, or oxazole or any other heterocycle described herein; G is $SnBu_3$ or 4,4,5,5 tetramethyl-1,dioxaboralane and $R_{1A}$ and $R_{2A}$ are —H, —$C_{1-4}$alkyl, or —$C_{1-4}$alkoxy, or $R_{1A}$ and $R_{2A}$ are —H, halo, —$C_{1-4}$alkyl, or —$C_{1-4}$alkoxy; in the presence of a catalyst such as $Pd(Ph_3P)_4$ and a base such as $Na_2CO_3$ in a mixture of solvents such as DME and $H_2O$ at temperatures ranging from about 100° C. to about 150° C. Compounds of formula (XVII) are obtained by reacting a compound of formula (XVI) in the presence of a base such as NaOH in a solvent such as MeOH at temperatures ranging from about 80° C. to about 100° C.

oxidized with, for example, IBX at 85° C., in a solvent such as, EtOAc to afford a compound of formula (XX). Enantio-enriched compounds of formula (+)-(XX) and (−)-(XX), where $PG_2$ is Boc, were obtained from (XX) using SFC chromatography, where the mobile phase was typically a mixture of $CO_2$/iPrOH.

A compound of formula (XXI) where Z is OH, is obtained from reduction ([R]) of the ketone in a compound of formula (XX), with a reducing agent such as L-Selectride, $NaBH_4$ and the like, in a solvent such as THF, MeOH, DCM, and the like at temperatures ranging from about −78° C. to room temperature (about 23° C.). Compounds of formula (XXI) were resolved into individual enantiomers of formula (+)-

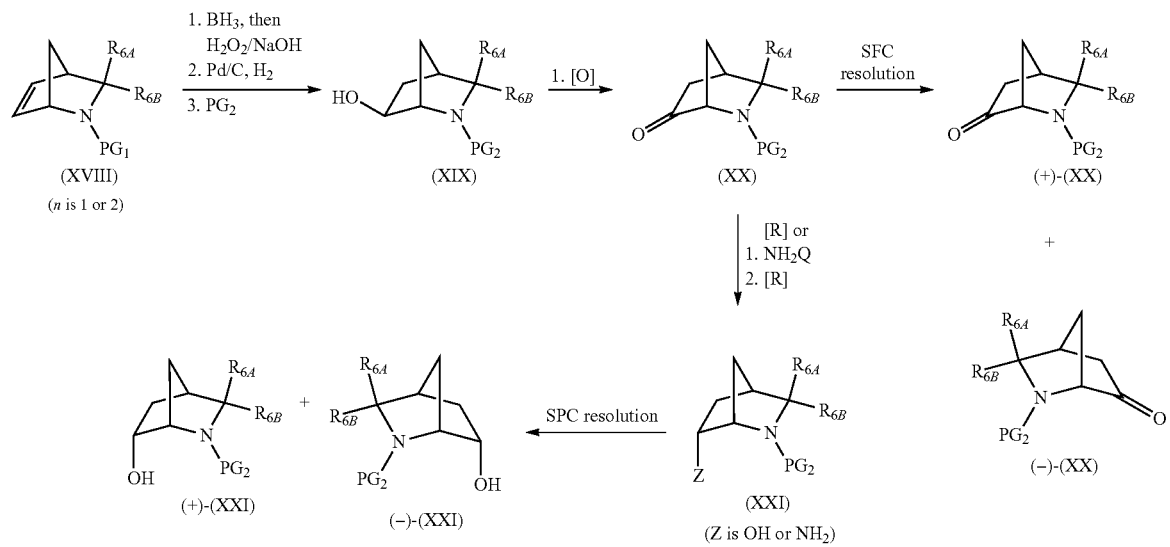

Scheme 6

Intermediate compounds of formula (XVIII) in Scheme 6, where $PG_1$ is H, benzyl (Bn), and the like, and $R_{6A}$ and $R_{6B}$ are as defined for Formula I, are readily prepared as described in S. Larsen et al. *J. Am. Chem. Soc.* 1985, 107, 1768-1769. Compound (XIX) is obtained from (XVIII) through a hydroboration/oxidation sequence of the olefin to install the hydroxyl group; followed by, for example, a palladium-mediated hydrogenolysis to remove $PG_1$; and subsequent protection of the amine salt, where $PG_2$ is an amine protecting group such as a Boc group, and the like. Alternatively, the free amine intermediate of compound (XVIII) can be protected to give a compound of formula (XIX), where $PG_2$ is Boc, and the like. Oxidation of the hydroxyl group of compound (XIX) using an oxidant such as IBX, $SO_3$-pyridine, Swern conditions [$(COCl)_2$, DMSO, $Et_3N$], and the like, in a solvent such as EtOAc, DMSO, DCM, and the like, at temperatures ranging from about −78° C. to room temperature (about 23° C.), provides a compound of formula (XX). In a preferred embodiment, a compound of formula (XX) where $PG_1$ is benzyl, is treated with, for example, $BH_3$-$Me_2S$ followed by $H_2O_2$ and NaOH to install the hydroxyl group, and, for example, a palladium mediated hydrogenolysis using hydrogen gas (1 atm) and Pd/C in MeOH at 60° C. to give the amine salt. The amine salt intermediate is then protected with, for example, $Boc_2O$ to afford a compound of formula (XIX). Compound (XIX) is (XXI) and (−)-(XXI) using SFC chromatography, where the mobile phase was typically a mixture of $CO_2$/iPrOH. Alternatively, the enantiopure compounds of formula (+)-(XXI) and (−)-(XXI) can come from reaction of (+)-(XX) and (−)-(XX), respectively, under the conditions described above for a compound of formula (XXI) where Z is OH.

A compound of formula (XXI) where Z is $NH_2$, is obtained by reacting a compound of formula (XX) with an amine $NH_2$-Q, where Q is OH or Bn, followed by reduction of the corresponding oxime or imine with a suitable reducing agent such as $NaBH_4$ (with or without a metal salt additive such as $NiCl_2$ and the like), Raney Ni ($H_2$ atm), $Zn(BH_4)_2$, and the like in a solvent such as MeOH and the like. In a particular embodiment, the oxime intermediate from reaction of a compound of formula (XX) with an amine $NH_2$-Q, where Q is OH, is obtained by reacting a compound of formula (XX) with commercially available hydroxylamine hydrochloride and triethylamine in EtOH at temperatures ranging from room temperature (about 23° C.) to reflux. The oxime intermediate is reduced with $NaBH_4$ in combination with $NiCl_2$ in MeOH to give a compound of formula (XXI) where Z is $NH_2$. The enantiopure compounds of formula (+)-(XXI) and (−)-(XXI) can come from reaction of (+)-(XXI) and (−)-(XXI), respectively, under the conditions described above for a compound of formula (XXI) where Z is $NH_2$.

Scheme 7

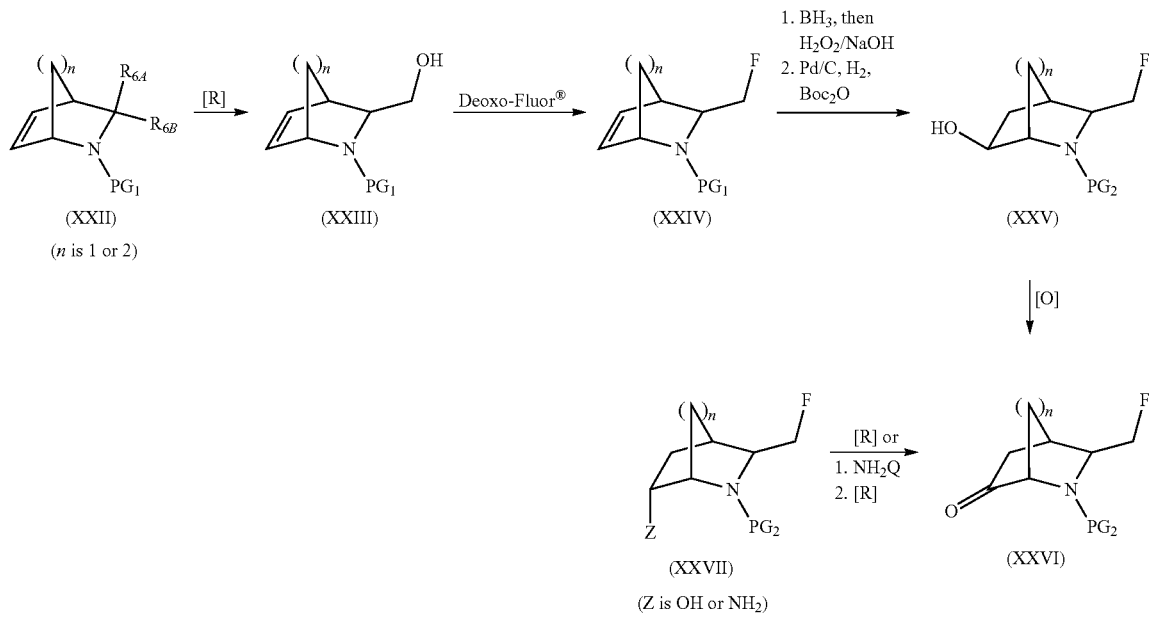

Intermediate compounds of formula (XXII) in Scheme 7, where PG$_1$ is H, benzyl (Bn), methyl benzyl, and the like, and R$_{6A}$ and R$_{6B}$ are as defined for Formula I, are readily prepared as described in P. Bailey et al. *Tet. Asymm.* 1991, 2, 1263-1282. A compound of formula (XXIII), where n is 1 or 2, PG$_1$ is H, benzyl (Bn), methyl benzyl, and the like, are obtained from a compound of formula (XXII), where R$_{6A}$ is CO$_2$Et and R$_{6B}$ is H, or R$_{6A}$ is H and R$_{6B}$ is CO$_2$Et, by reduction of the ester using a reducing agent such as LAH, Dibal-H, or LiBH$_4$, and the like, in a solvent such as Et$_2$O, THF, DCM, and the like, at temperatures ranging from 0° C. to 70° C. Compound (XXIV) is readily prepared from compound (XXIII) by treatment with a nucleophilic fluorinating agent, such as Deoxo-fluor®, and the like, in a solvent such as DCM, DMF, and the like, at temperatures ranging from 0° C. to room temperature (about 23° C.). Alternatively, activation of the hydroxyl group in a compound of formula (XXIII) can be followed by nucleophilic displacement using a nucleophile such as H, alkyl, halo, and the like. Compound (XXV) is obtained from (XXIV) through a hydroboration/oxidation sequence of the olefin to install the hydroxyl group; followed by, for example, a one-pot palladium-mediated hydrogenolysis and protecting group "swap" (e.g., benzyl to Boc). Oxidation of the hydroxyl group of a compound of formula (XXV) using an oxidant such as IBX, SO$_3$-pyridine, Swern conditions [(COCl)$_2$, DMSO, Et$_3$N], and the like, in a solvent such as EtOAc, DMSO, DCM, and the like, at temperatures ranging from about −78° C. to room temperature (about 23° C.) affords a compound of formula (XXVI). In a preferred embodiment, a compound of formula (XXIV) where PG$_1$ is benzyl, is treated with, for example, BH$_3$ followed by H$_2$O$_2$ and NaOH to install the hydroxyl group, and, for example, a one-pot palladium mediated hydrogenolysis using hydrogen gas (1 atm) and Pd/C, and Boc$_2$O, in EtOH at room temperature (about 23° C.) exchanges the benzyl for a Boc group to give a compound of formula (XXV). Compound (XXV) is oxidized with, for example, IBX at 85° C., in a solvent such as, EtOAc to afford a compound of formula (XXVI).

A compound of formula (XXVII) where Z is OH, is obtained from reduction ([R]) of the ketone in a compound of formula (XXVI), with a reducing agent such as L-Selectride, NaBH$_4$ and the like, in a solvent such as THF, MeOH and the like at temperatures ranging from about −78° C. to room temperature (about 23° C.).

A compound of formula (XXVII) where Z is NH$_2$, is obtained by reacting a compound of formula (XXVI) with an amine NH-Q, where Q is OH or Bn, followed by reduction of the corresponding oxime or imine with a suitable reducing agent such as NaBH$_4$ (with or without a metal salt additive such as NiCl$_2$ and the like), Raney Ni (H$_2$ atm), Zn(BH$_4$)$_2$, and the like in a solvent such as MeOH and the like. In a particular embodiment, the oxime intermediate from reaction of a compound of formula (XXVI) with an amine NH$_2$-Q, where Q is OH, is obtained by reacting a compound of formula (XXVI) with commercially available hydroxylamine hydrochloride and triethylamine in EtOH at temperatures ranging from room temperature (about 23° C.) to reflux. The oxime intermediate is reduced with NaBH$_4$ in combination with NiCl$_2$ in MeOH to give a compound of formula (XXVII) where Z is NH$_2$.

Scheme 8

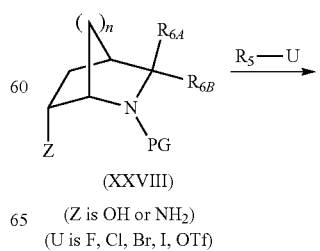

(Z is OH or NH$_2$)
(U is F, Cl, Br, I, OTf)

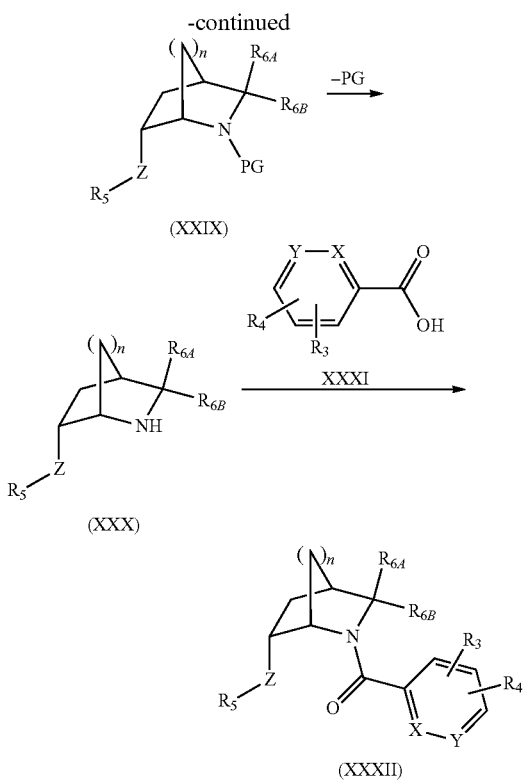

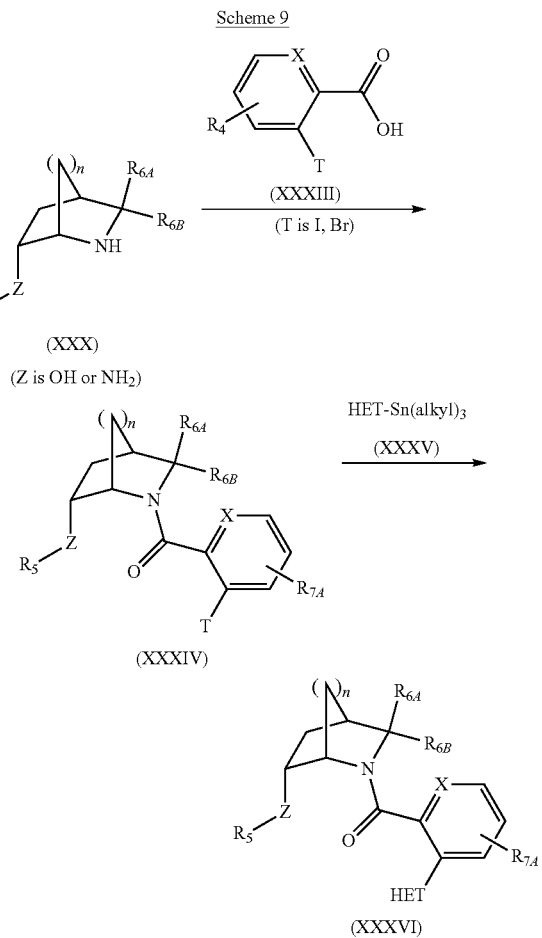

According to Scheme 8, a compound of formula (XXIX), where Z is O or NH, and $R_{6A}$ and $R_{6B}$ are as defined for Formula I, is obtained from a compound of formula (XXVIII), by a $S_NAr$ reaction or metal mediated cross-coupling reaction with a compound $R_5$-U; where $R_5$-U is a suitable commercially available or synthetically accessible halogen-substituted heteroaryl compound, where $R_5$ is defined in Formula I as above and U is F, Cl, Br, I, or OTf. A compound of formula (XXIX) where Z is O, is obtained from a compound of formula (XXVIII), where Z is OH, by $S_NAr$ coupling with a compound $R_5$-U as described above, in the presence of a base, such as NaH, $K_2CO_3$ and the like, in a solvent such as DMF at temperatures ranging from room temperature (about 23° C.) to about 90° C. In a preferred embodiment the base is NaH and the solvent is DMF. A compound of formula (XXIX), where Z is NH, is obtained from a compound of formula (XXVIII), where Z is $NH_2$, by metal mediated cross-coupling with a compound $R_5$-U as described above, in the presence of a palladium catalyst, a phosphine ligand such as BINAP and the like, a base such as NaOtBu and the like, in a solvent such as toluene, DME, and DMF, at temperatures ranging from room temperature (about 23° C.) to about 100° C. In a preferred embodiment the palladium catalyst is $Pd(OAc)_2$, the ligand is BINAP, the base is NaOtBu, and the solvent is toluene. Alternatively, a compound of formula (XXIX) where Z is NH, is obtained from a compound of formula (XXVIII), where Z is $NH_2$, by $S_NAr$ coupling with a compound $R_5$-U as described above, in the presence of a base, such as NaH, $K_2CO_3$ in a solvent such as DMF at temperatures ranging from room temperature (about 23° C.) to about 90° C. In a preferred embodiment the base is $K_2CO_3$ and the solvent is DMF. Removal of PG (where PG is Boc, Bn, methyl benzyl, and the like) in compounds of formula (XXIX) is accomplished using methods known to one skilled in the art to give compounds of formula (XXX). In a preferred embodiment, where PG is Boc in a compound of formula (XXIX) and Z is O or NH, is treated with, for example, HCl in dioxane to afford a compound of formula (XXX).

A compound of formula (XXXII) is obtained from a compound of formula (XXX), by reaction of a compound of formula (XXX) with a compound of formula (XXXI), under amide bond formation conditions. Compounds of formula (XXXI), where X, Y, $R_3$, and $R_4$ are as defined in Formula I, are commercially available, as described, or synthetically accessible appropriately substituted aryl or heteroaryl carboxylic acids or acid salts. A compound of formula (XXX), either as a free base or as an acid salt, is reacted with a compound of formula (XXXI) in the presence of a dehydrating agent such as HOBt/EDAC, CDI, HATU, HOAT, $T_3P$; a suitably selected base such as DIPEA, TEA; in an organic solvent or mixture thereof, such as toluene, ACN, EtOAc, DMF, THF, DCM to afford a compound of formula (XXXII). In a particularly preferred embodiment, a compound of formula (XXXII) is obtained using, for example, the dehydrating agent HATU, the base DIPEA, and the solvent DMF; or the dehydrating agent $T_3P$, the base $Et_3N$, and the solvent mixture of DCM/DMF. Alternatively, one skilled in the art can transform a compound of formula (XXXI) to the corresponding acid chloride or an activated ester before amide formation with a compound of formula (XXX).

According to Scheme 9, compounds of formula (XXXIV) where Z is O or NH; X, $R_{6A}$, $R_{6B}$ and $R_5$ are as defined in Formula I, T is I or Br, and $R_{7A}$ is —H, halo, —$C_{1-4}$alkyl, or —$C_{1-4}$alkoxy are obtained from a compound of formula (XXX), by reaction of a compound of formula (XXX) with a compound of formula (XXXIII), under amide bond formation conditions. Compounds of formula (XXXIII), where X, is as defined in Formula I, T is I or Br, and $R_{7A}$ is —H, halo, —$C_{1-4}$alkyl, or —$C_{1-4}$alkoxy are commercially available, as described, or synthetically accessible appropriately substituted aryl or heteroaryl carboxylic acids or acid salts. It will be understood that in certain embodiments, $R_{7A}$ corresponds to $R_2$, or $R_3$, or $R_4$ as defined for Formula I. A compound of formula (XXX), either as a free base or as an acid salt, is reacted with a compound of formula (XXXIII) in the presence of a dehydrating agent such as HOBt/EDAC, CDI, HATU, HOAT, $T_3P$; a suitably selected base such as DIPEA, TEA; in an organic solvent or mixture thereof, such as toluene, ACN, EtOAc, DMF, THF, DCM to afford a compound of formula (XXXIV). In a particularly preferred embodiment, a compound of formula (XXXIV) is obtained using, for example, the dehydrating agent HATU, the base DIPEA, and the solvent DMF; or the dehydrating agent $T_3P$, the base $Et_3N$, and the solvent mixture of DCM/DMF. Compounds of formula (XXXVI) were obtained through coupling of compounds of formula (XXXIV) with compounds of formula (XXXV) in a solvent such as DME or toluene in the presence of a Pd catalyst such as $Pd(PPh_3)_4$, an additive or catalyst such as copper iodide under microwave heating conditions. For schemes 8 and 9 described above, compounds of formula (XXIX), (XXX), (XXXII), (XXXIV) or (XXXVI) may be N-alkylated to provide additional compounds of formula I, wherein Z is N—$CH_3$, N—$CH_2CH_3$, N—$CH_2$-cyclopropyl, N—C(=O)$CH_3$, N—$CH_2CH_2OCH_3$ and the like.

Referring to Schemes 7-9, the synthesis of compounds wherein n is 2 is described in the Examples section, for instance in Examples 74-80.

In one group of embodiments, provided herein is a compound of Formula I of Examples 1-80 with structures and names as set forth in the Examples section. In another group of embodiments, provided herein is a compound of Formula I of Examples 181-155 with structures and names as set forth in the Examples section below. In yet another embodiment, provided herein is a compound of Formula I of Examples 1-155 with structures and names as set forth in the Examples section below.

EXAMPLES

Abbreviations

| Term | Abbreviation |
|---|---|
| Acetic Acid | HOAc |
| Acetonitrile | ACN |
| Apparent | app |
| Aqueous | Aq |
| Atmosphere | atm |
| 1-Ethyl-3-(3-dimethylaminopropyl)carbodiimide | EDCI |
| 2-(1H-9-Azobenzotriazole-1-yl)-1,1,3,3-tetramethyl-aminium hexafluorophosphate | HATU |
| O-Benzotriazole-N,N,N',N'-tetramethyl-uronium-hexafluoro-phosphate | HBTU |
| 1-Hydroxy-7-azabenzotriazole | HOAT |
| Benzyl | Bn |
| 2,2'-bis(diphenylphosphino)-1,1'-binaphthalene | BINAP |
| [1,1'-Bis(di-tert-butylphosphino)ferrocene]-dichloropalladium(II) | $PdCl_2$(dtbpf) |

-continued

| Term | Abbreviation |
|---|---|
| Broad | Br |
| tert-Butylcarbamoyl | Boc/Boc |
| Dichloromethane | DCM |
| Diisopropylethylamine | DIPEA |
| 1,2-Dimethoxyethane | DME |
| N,N-Dimethylformamide | DMF |
| Dimethylsulfoxide | DMSO |
| Doublet | D |
| Electrospray ionization | ESI |
| Enantiomeric excess | Ee |
| Ethanol | EtOH |
| Ethyl Acetate | EtOAc, or EA |
| Grams | G |
| Hertz | Hz |
| High-pressure liquid chromatography | HPLC |
| Hours | H |
| Liquid chromatography and mass spectrometry | LCMS |
| Mass spectrometry | MS |
| Mass to charge ratio | m/z |
| Melting Point | MP |
| Methanol | MeOH |
| Microliter | μL |
| Milligrams | mg |
| Milliliter | mL |
| Millimoles | mmol |
| Minute | min |
| Molar | M |
| Multiplet | M |
| Normal | N |
| Nuclear magnetic resonance | NMR |
| Palladium on carbon | Pd/C |
| Palladium hydroxide on carbon | $Pd(OH)_2$/C |
| Parts per million | ppm |
| Phenyl | Ph |
| Propylphosphonic anhydride | $T_3P$ |
| Retention time | $R_t$ |
| Room temperature | Rt |
| Quartet | Q |
| Singlet | S |
| Supercritical Fluid Chromatography | SFC |
| Temperature | T |
| Thin layer chromatography | TLC |
| Times | X |
| Triethylamine | TEA |
| Trifluoroacetic acid | TFA |
| propylphosphonic anhydride | $T_3P$ |
| Triplet | T |
| Diisopropyl ether | DIPE |

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or a CEM Corporation Discover instrument.

Where compounds were "purified via silica gel chromatography" normal-phase flash column chromatography was performed on silica gel ($SiO_2$) using prepackaged cartridges, eluting with the indicated solvents.

Where compounds were purified by "Agilent Prep Method X" the method employed was either:

Preparative reverse-phase high performance liquid chromatography (HPLC) was performed on a Agilent 1100 Series HPLC with an XBridge C18 OBD column (5 μm, 30×100 mm), mobile phase of 5% ACN in 20 mM NH₄OH was held for 2 min, then a gradient of 5-99% ACN over 15 min, then held at 99% ACN for 5 min, with a flow rate of 40 mL/min.

or

Preparative reverse-phase high performance liquid chromatography (HPLC) was performed on a Agilent 1100 Series HPLC with an XBridge C18 OBD column (5 μm, 50×100 mm), mobile phase of 5% ACN in 20 mM NH₄OH was held for 2 min, then a gradient of 5-99% ACN over 15 min, then held at 99% ACN for 5 min, with a flow rate of 80 mL/min.

One of skill in the art will recognize that depending on the reaction and/or work up of a reaction, a combination of one or more methods maybe required for purification of compounds, e.g., silica gel column chromatography followed by preparative reverse-phase high performance liquid chromatography. On of skill in the art will recognize that purity data provided herein is within the detection limits of the instrument employed. Thus a purity of 100%, for example, means that within the detection limits of the instrument, no other components were detected.

Mass spectra (MS) were obtained on an Agilent series 1100 MSD using electrospray ionization (ESI) in positive mode unless otherwise indicated. Calculated (calcd.) mass corresponds to the exact mass.

Where acids are employed for amide bond coupling the free acid or acid salt may be used interchangeably. Where amines are employed for amide bond coupling, the free base or the amine salt may be used interchangeably. It will be understood that amide coupling reagents may be interchangeably (e.g., HBTU instead of HATU).

Nuclear magnetic resonance (NMR) spectra were obtained on Bruker model DRX spectrometers. The format of the ¹H NMR data below is: chemical shift in ppm downfield of the tetramethylsilane reference (multiplicity, coupling constant J in Hz, integration). Definitions for multiplicity are as follows: s=singlet, d=doublet, t=triplet, q=quartet, m=multiplet, br=broad. For compounds that are present as a mixture of rotamers the ratio is represented so that the total is 1, e.g. 0.80:0.20. Alternatively, ¹H NMR data may be reported for only the major rotamer as indicated, or the data may be reported for one or more rotamers such that the total is less than 1. It will be understood that for compounds comprising an exchangeable proton, said proton may or may not be visible on an NMR spectrum depending on the choice of solvent used for running the NMR spectrum and the concentration of the compound in the solution. Similarly, for HPLC assays, data is reported for the major rotamer unless indicated otherwise.

Chemical names were generated using ChemDraw Ultra 12.0 (CambridgeSoft Corp., Cambridge, Mass.) or ACD/Name Version 10.01 (Advanced Chemistry).

A notation of (±) or R/S indicates that the product is a racemic mixture of enantiomers and/or diastereomers. A notation of, for example, (2S,3R) indicates that product stereochemistry depicted is based on the known stereochemistry of similar compounds and/or reactions. A notation of, for example, (2S*, 3R*) indicates that the product is a pure and single diastereomer but the absolute stereochemistry is not established and relative stereochemistry is shown.

Examples 1-155 are suitable for preparation using methods described in the synthetic schemes and in the Examples section.

| INTERMEDIATES | | | |
|---|---|---|---|
| Intermediate | Name | Structure | Reference |
| A-1 | 2-(2H-1,2,3-triazol-2-yl)benzoic acid | | Prepared according to WO 2011/050198 Intermediate 2 |
| A-2 | 3-fluoro-2-(pyrimidin-2-yl)benzoic acid | | Prepared according to WO 2011/050198 Intermediate 50 |
| A-3 | 6-methyl-2-(2H-1,2,3-triazol-2-yl)nicotinic acid | | Prepared according to WO 2011/050198 Intermediate 70 |

-continued

| | | INTERMEDIATES | |
|---|---|---|---|
| Intermediate | Name | Structure | Reference |
| A-4 | 2-iodobenzoic acid | | Commercially available, CAS 88-67-5 |
| A-5 | 4-methoxy-2-(2H-1,2,3-triazol-2-yl)benzoic acid | | Prepared according to WO 2011/050198 Intermediate 54 |
| A-6 | 5-fluoro-2-iodobenzoic acid | | Commercially available, CAS 52548-63-7 |
| A-7 | 5-fluoro-2-(pyrimidin-2-yl)benzoic acid | | Prepared according to WO 2011/050198 Intermediate 13 |
| A-8 | 3-ethoxy-6-methylpicolinic acid | | WO 2010/063663 Description 39 |
| A-9 | 3-fluoro-2-iodobenzoic acid | | Commercially available, CAS 387-48-4 |
| A-10 | 5-fluoro-2-(2H-1,2,3-triazol-2-yl)benzoic acid | | Prepared according to WO 2011/050198 Intermediate 1 |

-continued

| Intermediate | Name | Structure | Reference |
|---|---|---|---|
| A-11 | 2-fluoro-6-(2H-1,2,3-triazol-2-yl)benzoic acid | 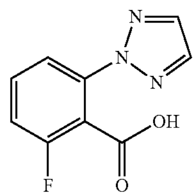 [SMILES: O=C(O)c1c(F)cccc1-n1nccn1] | Prepared according to WO 2011/050198 Intermediate 12 |
| A-12 | 4-fluoro-2-(2H-1,2,3-triazol-2-yl)benzoic acid | 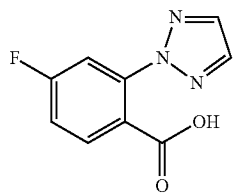 [SMILES: O=C(O)c1ccc(F)cc1-n1nccn1] | Prepared according to WO 2011/050198 Intermediate 4 |
| A-13 | 3-bromo-6-methylpicolinic acid | 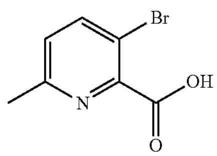 | Commercially available, CAS 1033201-61-4 |
| A-14 | 4-fluoro-2-(pyrimidin-2-yl)benzoic acid | 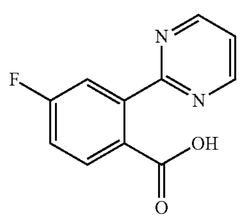 [SMILES: O=C(O)c1ccc(F)cc1-c1ncccn1] | Prepared according to WO 2011/050198 Intermediate 87 |
| A-15 | 3-(2H-1,2,3-triazol-2-yl)picolinic acid | 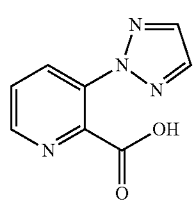 [SMILES: O=C(O)c1ncccc1-n1nccn1] | Prepared according to WO 2011/050198 Intermediate 72 |
| A-16 | 3-fluoro-2-(2H-1,2,3-triazol-2-yl)benzoic acid | 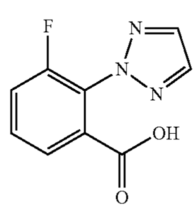 [SMILES: O=C(O)c1cccc(F)c1-n1nccn1] | Prepared according to WO 2011/050198 Intermediate 5 |
| A-17 | 3-methyl-2-(2H-1,2,3-triazol-2-yl)benzoic acid | 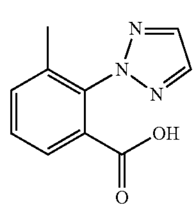 | Prepared according to WO 2011/050198 Intermediate 82 |

| INTERMEDIATES | | | |
|---|---|---|---|
| Intermediate | Name | Structure | Reference |
| A-18 | 4'-fluoro-[1,1'-biphenyl]-3-carboxylic acid | 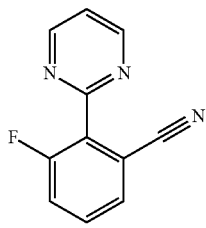 [SMILES: N#Cc1cccc(F)c1-c1ncccn1] | Commercially available, CAS 10540-39-3 |

Synthesis of 3-fluoro-2-(pyrimidin-2-yl)benzonitrile
(Intermediate in the Synthesis of Intermediate A-2)

To a solution of 3-fluoro-2-(4,4,5,5-tetramethyl-1,3,2-dioxaborolan-2-yl)benzonitrile (4.98 g, 19.1 mmol) and 2-bromopyrimidine (3.85 g, 23 mmol) in THF (96 mL) was added $Na_2CO_3$ (6 g, 57.4 mmol) followed by water (43 mL). The reaction mixture was degassed with $N_2$ for 10 minutes. $PdCl_2$(dtbpf) (374 mg, 0.57 mmol) was added and the reaction mixture was stirred at 80° C. for 5 h. The solution was cooled to room temperature and a mixture of EtOAc and water was added. The aqueous was extracted twice with EtOAc and the combined organic layers were dried over $MgSO4$, filtered and evaporated. The title compound was precipitated by dissolving the residue in a minimum amount of EtOAc and then adding hexanes. The solid was filtered, washed with hexanes and dried to afford the title compound (2.46 g, 64%). MS (ESI) mass calcd. for $C_{11}H_6FN_3$, 199.1. m/z found 200.1 [M+H]$^+$. $^1$H NMR (400 MHz, Chloroform-d) δ 9.02-8.91 (m, 2H), 7.65 (dt, J=7.7, 1.0 Hz, 1H), 7.60-7.52 (m, 1H), 7.51-7.43 (m, 1H), 7.41 (t, J=4.9 Hz, 1H).

Intermediate A-19:
5-methyl-3-(2H-1,2,3-triazol-2-yl)picolinic acid

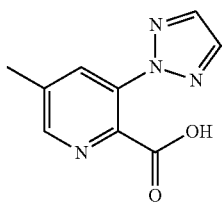

Step A: 5-methyl-3-(2H-1,2,3-triazol-2-yl)picolinonitrile. To 3-bromo-5-methylpicolinic acid (1.5 g, 7.6 mmol) in DMF (19 mL) was added $K_2CO_3$ (1.2 g, 8.4 mmol) and 2H-1,2,3-triazole (440 µL, 7.6 mmol). The mixture was heated to 100° C. for 16 h, cooled to room temperature and extracted with EtOAc (2×). The combined organics were dried ($Na_2SO_4$) and concentrated. Purification via silica gel chromatography (5-60% EtOAc in hexanes) gave the title compound (490 mg, 35%) $^1$H NMR (500 MHz, Chloroform-d) 8.58-8.53 (m, 1H), 8.29-8.24 (m, 1H), 7.98 (s, 2H), 2.54 (s, 3H) and 5-methyl-3-(1H-1,2,3-triazol-1-yl)picolinonitrile (387 mg, 27%).

Step B: (sodium 5-methyl-3-(2H-1,2,3-triazol-2-yl)picolinate). To a solution of the title compound of Step A (489 mg, 2.6 mmol) in EtOH (7 mL) was added 4 N NaOH (660 µL, 2.6 mmol). The mixture was heated at 100° C. for 24 h. The reaction mixture was concentrated in vacuo to a white solid which was used without further purification in subsequent steps. MS (ESI) mass calcd. for $C_9H_8N_4O_2$, 204.1. m/z found 205.0 [M+H]$^+$.

Intermediate A-20:
2-(5-fluoropyrimidin-2-yl)benzoic acid

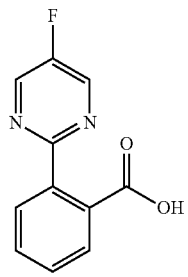 [SMILES: O=C(O)c1ccccc1-c1ncc(F)cn1]

Step A: 5-fluoro-2-iodopyrimidine. To a solution of 2-chloro-5-fluoropyrimidine (4 mL, 32 mmol) in propionitrile (33 mL) was added chlorotrimethylsilane (12 mL, 97 mmol) and sodium iodide (15 g, 97 mmol), and the reaction mixture was heated to 150° C. for 1 h. Upon completion of the reaction, the reaction mixture was cooled to room temperature and the solvent removed. The residue was taken up in EtOAc and a solution of saturated $NaHCO_3$. The organic layer was dried over $MgSO_4$, filtered and evaporated. Purification via silica gel chromatography (0-20% EtOAc in hexanes) gave the title compound (2.82 g, 39%).

Step B: 2-(5-fluoropyrimidin-2-yl)benzonitrile. In a microwave vial was dissolved 2-cyanophenylboronic acid (500 mg, 3.40 mmol) in THF (15 mL), and the reaction mixture was degassed with $N_2$. Then, the title compound of step A (915 mg, 4.08 mmol), $Na_2CO_3$ (1.08 g, 10.2 mmol), water (5 mL), and $PdCl_2$(dtbpf) (CAS 95408-45-0) (89 mg, 0.14 mmol) were added, and the reaction mixture was stirred at room temperature for 1 h and then heated via microwave heating to 75° C. for 2 h. The mixture was cooled to room temperature and water and EtOAc added. The reaction mixture was extracted with EtOAc. The combined organic layers were dried over MgSO$_4$, filtered and concentrated. The crude was purified via silica gel chromatography (0-30% EtOAc in hexanes) to afford the title compound (280 mg, 41%). MS (ESI) mass calcd. for $C_{11}H_6FN_3$, 199.1. m/z found 200.0 [M+H]$^+$.

Step C: 2-(5-fluoropyrimidin-2-yl)benzoic acid. A solution of the title compound of step B (1.24 g, 6.22 mmol) in H$_2$SO$_4$ (6 mL) and water (6 mL) was stirred at 80° C. for 1 h. Then, the reaction mixture was cooled to 0° C. and the aqueous phase extracted with DCM (2×). A solution of 20 M NaOH (11 mL) was added to the aqueous layer until pH ~3-4. The aqueous layer was extracted again with EtOAc and DCM. The combined organic layers were dried over MgSO$_4$, filtered and concentrated to afford the title compound (672 mg, 50%). MS (ESI) mass calcd. for $C_{11}H_7FN_2O_2$, 218.1. m/z found 219.1 [M+H]$^+$.

Intermediate A-21:
3-fluoro-2-(5-fluoropyrimidin-2-yl)benzoic acid

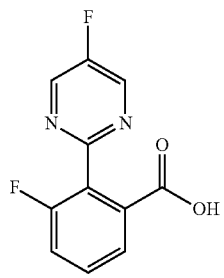 [SMILES: O=C(O)c1cccc(F)c1-c1ncc(F)cn1]

Prepared analogous to Intermediate A-20, substituting 2-cyanophenylboronic acid with (2-cyano-6-fluorophenyl) boronic acid (CAS 656235-44-8). MS (ESI) mass calcd. for $C_{11}H_6F_2N_2O_2$, 236.0. m/z found 237.1 [M+H]$^+$.

Intermediate A-22:
5-fluoro-2-(5-fluoropyrimidin-2-yl)benzoic acid

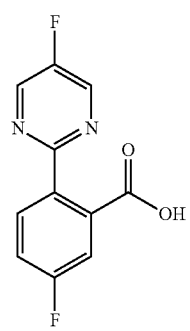 [SMILES: O=C(O)c1cc(F)ccc1-c1ncc(F)cn1]

Prepared analogous to Intermediate A-20, substituting 2-cyanophenylboronic acid with 5-fluoro-2-(4,4,5,5-tetramethyl-1,3-dioxolan-2-yl)benzonitrile. MS (ESI) mass calcd. for $C_{11}H_6F_2N_2O_2$, 236.0. m/z found 237.1 [M+H]$^+$. $^1$H NMR (400 MHz, Chloroform-d) δ 8.68 (s, 2H), 8.02-7.95 (m, 1H), 7.65-7.59 (m, 1H), 7.36-7.29 (m, 1H).

Intermediate A-23: 3-fluoro-5'-methyl-[2,3'-bipyridine]-2'-carboxylic acid

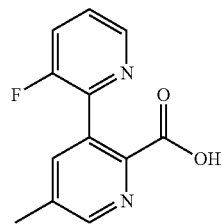

Step A: Methyl 3-fluoro-5'-methyl-[2,3'-bipyridine]-2'-carboxylate. In a sealed tube 3-fluoro-2-(tributylstannyl) pyridine (2.87 g, 6.9 mmol) was added to a stirred solution of methyl 3-bromo-5-methylpicolinate (1.46 g, 6.3 mmol), Pd(PPh$_3$)$_4$ (367 mg, 0.3 mmol), copper(I) iodide (60 mg, 0.3 mmol) and lithium chloride (267 mg, 6.3 mmol) in toluene (19 mL) while the solution was bubbled with nitrogen. The reaction mixture was stirred at 120° C. overnight and then diluted with water and extracted with ethyl acetate. The organic layers were dried over MgSO$_4$, filtered and concentrated. The crude was purified via silica gel chromatography (0-4% MeOH in DCM) to afford the title compound (1.24 g, 79%). MS (ESI) mass calcd. for $C_{13}H_{11}FN_2O_2$, 246.1. m/z found 247.0 [M+H]$^+$.

Step B: 3-fluoro-5'-methyl-[2,3'-bipyridine]-2'-carboxylic acid. To a suspension of the title compound of step A (1.24 g, 5 mmol) in MeOH (15 mL) was added 1M NaOH (7.5 mL, 7.5 mmol). The reaction mixture was stirred overnight at 50° C. and then the solvent was evaporated. 6 N HCl was added until pH=3-4. The product was extracted with a mixture of DCM/MeOH (9:1). The organic layer was dried over MgSO$_4$, filtered and evaporated. The crude was purified via silica gel chromatography (0-10% MeOH in DCM) to afford the title compound (504 mg, 42%). MS (ESI) mass calcd. for $C_{12}H_9FN_2O_2$, 232.1. m/z found 233.0 [M+H]$^+$.

| Intermediate | Name | Structure | Reference |
|---|---|---|---|
| A-24 | 2-(pyrimidin-2-yl)benzoic acid | 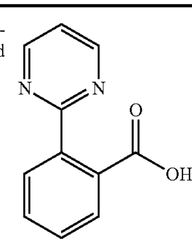 | Commercially available, CAS 400892-62-8 |
| A-25 | 5-methyl-2-(2H-1,2,3-triazol-2-yl)nicotinic acid | 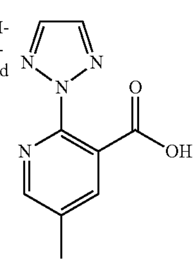 | Prepared analogous to WO 2011/050200 Intermediate 47, Example 160 |

-continued

| Intermediate | Name | Structure | Reference |
|---|---|---|---|
| A-26 | 6-methyl-3-(2H-1,2,3-triazol-2-yl)picolinic acid | 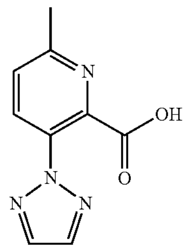 | WO 2012/089606 Intermediate D40. |
| A-27 | 6-methyl-3-(pyrimidin-2-yl)picolinic acid | 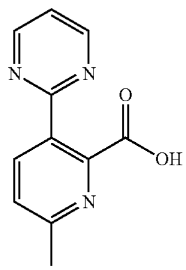 [SMILES: Cc1ccc(-c2ncccn2)c(C(=O)O)n1] | WO 2010/122151 Intermediate D28 |
| A-28 | 3-(pyrimidin-2-yl)picolinic acid | 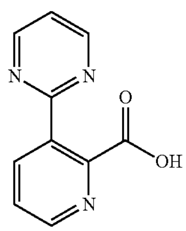 [SMILES: O=C(O)c1ncccc1-c1ncccn1] | WO 2010/122151 Intermediate D105 |

Intermediate A-29: Lithium 5-methyl-3-(pyrimidin-2-yl)picolinate

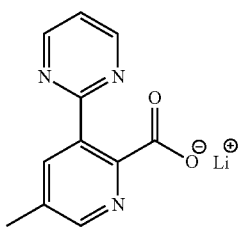 [SMILES: Cc1cnc(C(=O)[O-])c(-c2ncccn2)c1 ; [Li+]]

Step A: Methyl 5-methyl-3-(pyrimidin-2-yl)picolinate. To a sealed tube containing 3-bromo-5-methylpicolinate (1.5 g, 6.5 mmol), CuI (62 mg, 0.33 mmol), LiCl (274 mg, 6.5 mmol), and Pd(PPh$_3$)$_4$ (377 mg, 0.33 mmol) in toluene (10 mL) was added 2-(tributylstannyl)pyrimidine (2.4 mL, 7.17 mmol), and the reaction mixture was heated at 120° C. overnight. The reaction mixture was diluted with water and extracted with DCM. The combined organic layers were dried over MgSO$_4$, filtered and evaporated. Purification via silica gel chromatography (0-80% EtOAc in hexanes) gave the title compound (1.02 g, 68%). MS (ESI) mass calcd. for C$_{12}$H$_{11}$N$_3$O$_2$, 229.1. m/z found 230.0 [M+H]$^+$.

Step B: Lithium 5-methyl-3-(pyrimidin-2-yl)picolinate. To a solution of the title compound of step A (592 mg, 2.58 mmol) in THF (5 mL) was added 4 M LiOH (0.8 mL) and water (1.5 mL), and the reaction mixture was stirred at room temperature for 2.5 h. The solvent was removed and the crude reaction mixture placed under vacuum overnight to give the title compound (591 mg), which was used in the next step without further purification. MS (ESI) mass calcd. for C$_{11}$H$_9$N$_3$O$_2$, 215.1. m/z found 216.1 [M+H]$^+$. $^1$H NMR (500 MHz, Methanol-d$_4$) δ 8.83 (d, J=4.9 Hz, 2H), 8.39 (br. s, 1H), 8.23-8.18 (m, 1H), 7.38 (t, J=4.9 Hz, 1H), 2.44 (s, 3H).

Intermediate A-30: 3-fluoro-2-(oxazol-2-yl)benzoic acid

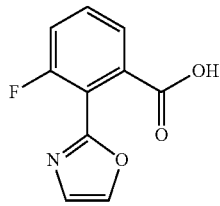

Step A: 2-bromo-N-(2,2-dimethoxyethyl)-6-fluorobenzamide. To a solution of 2-bromo-6-fluorobenzoic acid (2 g, 9.1 mmol) in DMF (27 mL) was added HBTU (5.20 g, 13.7 mmol) and DIPEA (4.7 mL, 27 mmol), and the reaction mixture was stirred for 10 min. Then, 2,2-dimethoxyethylamine (1.3 mL, 11.9 mmol) was added and the reaction mixture stirred at room temperature for 12 h. The reaction mixture was diluted with EtOAc and washed with saturated aqueous NaHCO$_3$. The combined organic layers were dried over MgSO$_4$, filtered and concentrated. Purification via silica gel chromatography (0-25% EtOAc in hexanes) gave the title compound (2.3 g, 82%).

Step B: 2-(2-bromo-6-fluorophenyl)oxazole. To P$_2$O$_5$ (6.4 g, 22.6 mmol) was added methanesulfonic acid (52 mL, 801 mmol), and the reaction mixture was stirred at room temperature for 1 h. Then, the title compound of step A (2.3 g, 7.54 mmol) was added to the reaction mixture, and the mixture heated to 140° C. for 2 h. DCM was added and the mixture was slowly poured into a saturated solution of aqueous NaHCO$_3$ on ice. The mixture was extracted with DCM. The combined organic layers were dried over MgSO$_4$, filtered and concentrated. Purification via silica gel chromatography (0-10% EtOAc in hexanes) gave the title compound (1.5 g, 82%). MS (ESI) mass calcd. for C$_9$H$_5$BrFNO, 240.95. m/z found 242.0 [M+H]$^+$.

Step C: Methyl 3-fluoro-2-(oxazol-2-yl)benzoate. A solution of the title compound of step B (2.18 g, 8.99 mmol), Pd(OAc)$_2$ (40 mg, 0.18 mmol), 1,1'-bis(diphenylphosphino)ferrocene (199 mg, 0.36 mmol), and Et$_3$N (3.7 mL, 27 mmol) in 1:1 MeOH/1,4-dioxane (36 mL) was degassed with N$_2$ for 15 min. Then, the mixture was stirred at 95° C. under an atmosphere of carbon monoxide overnight. The reaction mixture was diluted with EtOAc and washed with a solution of NaHCO$_3$. The organic layer was separated, dried over MgSO$_4$, filtered, and concentrated. Purification via silica gel chromatography (0-12% EtOAc in hexanes) gave the title compound (1.7 g, 83%). MS (ESI) mass calcd. for C$_{11}$H$_8$FNO$_3$, 221.1. m/z found 222.0 [M+H]$^+$.

Step D: 3-fluoro-2-(oxazol-2-yl)benzoic acid. To a solution of the title compound of step C (1.65 g, 7.46 mmol) in MeOH (22 mL) was added 2 M NaOH (7.5 mL), and the reaction mixture was stirred at room temperature overnight. The reaction mixture was acidified with 1 M HCl$_{(aq)}$ and the solvents evaporated in vacuo. The mixture was diluted with water and extracted with DCM. The combined organic were dried over MgSO₄, filtered and concentrated to afford the title compound (905 mg, 58%). MS (ESI) mass calcd. for C₁₀H₆FNO₃, 207.0. m/z found 208.0 [M+H]⁺. MP=182° C.

Intermediate A-31: 2-fluoro-6-(oxazol-2-yl)benzoic acid

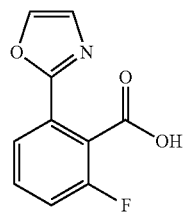 [SMILES: O=C(O)c1c(F)cccc1-c1ncco1]

Prepared analogous to intermediate 30, substituting 2-bromo-6-fluorobenzoic acid with 2-bromo-3-fluorobenzoic acid. MS (ESI) mass calcd. for C₁₀H₆FNO₃, 207.0. m/z found 208.0 [M+H]⁺.

| Intermediate | Name | Structure | Reference |
|---|---|---|---|
| A-32 | 4-fluoro-2-iodobenzoic acid | 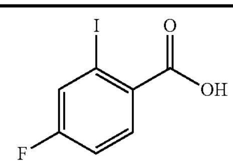 | Commercially available, CAS 56096-89-0 |

Intermediate A-33: 4-(2-fluoroethoxy)-2-(2H-1,2,3-triazol-2-yl)benzoic acid

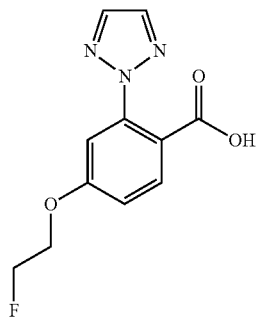 [SMILES: O=C(O)c1ccc(OCCF)cc1-n1nccn1]

Step A: 2-bromo-4-(2-fluoroethoxy)benzonitrile. To 2-bromo-4-hydroxybenzonitrile (1.5 g, 7.6 mmol) in DMF (5 mL) was added Cs₂CO₃ (3.7 g, 11.4 mmol) and 1-iodo-2-fluoroethane (1.23 mL, 15.1 mmol) and the mixture was left to stir at room temperature. Upon completion the reaction mixture was diluted with H₂O and the aqueous layer extracted with EtOAc (3×). The combined organics were washed with 5% LiCl solution, brine, dried with MgSO₄, filtered and concentrated. Purification via silica gel chromatography (0-20% EtOAc in hexanes) gave the title compound (1.576 g) as a light yellow oil. MS (ESI) mass calcd. for C₉H₇BrFNO, 243.0. m/z found 205.0 [M+H]⁺. ¹H NMR (500 MHz, Chloroform-d) δ 7.58 (d, J=8.7 Hz, 1H), 7.22 (d, J=2.5 Hz, 1H), 6.95 (dd, J=8.7, 2.5 Hz, 1H), 4.83-4.79 (m, 1H), 4.74-4.70 (m, 1H), 4.31-4.27 (m, 1H), 4.25-4.21 (m, 1H).

Step B: 4-(2-fluoroethoxy)-2-(2H-1,2,3-triazol-2-yl)benzonitrile. To a solution of the title compound of Step A (1.53 g, 6.27 mmol) in 1,4-dioxane (8 mL) in a 20 mL microwave vial was added H₂O (34 µL, 1.9 mmol), Cs₂CO₃ (4.1 g, 12.6 mmol), CuI (95 mg, 0.50 mmol), (1R,2R)—N1,N2-dimethylcyclohexane-1,2-diamine (0.21 mL, 1.5 mmol), and 2H-1,2,3-triazole (0.73 mL, 12.5 mmol). The vial was capped and the mixture was heated at 120° C. for 22 h under microwave irradiation. The reaction mixture was diluted with EtOAc/H₂O and the aqueous layer extracted with extracted with EtOAc (3×). The combined organics were washed with brine, dried with MgSO₄, filtered and concentrated. Purification via silica gel chromatography (0-50% EtOAc in hexanes) gave the title compound (100 mg) as an off-white solid. MS (ESI): mass calcd. for C₁₁H₉FN₄O, 232.1. m/z found, 233.0 [M+H]⁺. ¹H NMR (400 MHz, Chloroform-d) δ 7.92 (s, 2H), 7.74 (d, J=8.8 Hz, 1H), 7.64 (d, J=2.5 Hz, 1H), 7.01 (dd, J=8.7, 2.5 Hz, 1H), 4.88-4.84 (m, 1H), 4.76-4.72 (m, 1H), 4.41-4.37 (m, 1H), 4.34-4.30 (m, 1H).

Step C: 4-(2-fluoroethoxy)-2-(2H-1,2,3-triazol-2-yl)benzoic acid. To a solution of the title compound of Step B (100 mg, 0.43 mmol) in EtOH (5 mL) was added 4 N NaOH (0.32 mL, 1.3 mmol). The mixture was heated at 100° C. for 24 h after which the reaction went dry. Additional EtOH (5 mL) and 4 N NaOH (4 mL, 16 mmol) were added and the reaction was heated at 100° C. After 27 h the reaction mixture was concentrated to remove the EtOH and the aqueous layer acidified with 6N HCl. The aqueous layer was extracted with EtOAc (3×). The combined organics were washed with brine, dried with MgSO₄, filtered and concentrated to produce a light yellow solid (106 mg) which was used without further purification in subsequent steps. MS (ESI): mass calcd. for C₁₁H₁₀FN₃O₃, 251.1. m/z found, 252.0 [M+H]⁺. ¹H NMR (400 MHz, Chloroform-d) δ 7.96 (d, J=8.8 Hz, 1H), 7.84 (s, 2H), 7.28-7.24 (m, 1H), 7.07 (dd, J=8.7, 2.6 Hz, 1H), 4.86-4.82 (m, 1H), 4.75-4.70 (m, 1H), 4.38-4.33 (m, 1H), 4.31-4.26 (m, 1H). Note: Acidic proton is not observed.

Intermediate A-34: 2-(2-hydroxyethoxy)quinoline-3-carboxylic acid

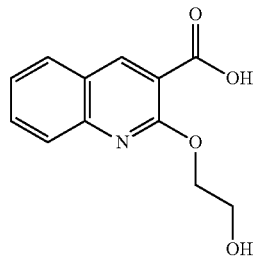 [SMILES: O=C(O)c1cc2ccccc2nc1OCCO]

Step A: 2-fluoroethyl 2-(2-fluoroethoxy)quinoline-3-carboxylate. To 2-hydroxyquinoline-3-carboxylic acid (306 mg, 1.62 mmol) suspended in THF (5 mL) was added PPh$_3$ (1.27 g, 4.84 mmol), EtOH (295 mL, 4.85 mmol), and (E)-diisopropyl diazene-1,2-dicarboxylate (955 mL, 4.85 mmol). The sides of flask were washed with additional THF (2 mL) and the reaction stirred at room temperature. After 1.25 h the reaction was diluted with H$_2$O and 1 M NaOH solution and the aqueous layer extracted with DCM (3×). The combined organics were dried with MgSO$_4$, filtered, and concentrated. Purification via silica gel chromatography (0-50% EtOAc in hexanes) gave the title compound (220 mg) as an off-white solid. MS (ESI) mass calcd. for C$_{14}$H$_{13}$F$_2$NO$_3$, 281.1. m/z found 282.0 [M+H]$^+$. $^1$H NMR (400 MHz, Chloroform-d) δ 8.69 (s, 1H), 7.85-7.80 (m, 2H), 7.72 (ddd, J=8.4, 6.9, 1.5 Hz, 1H), 7.44 (ddd, J=8.1, 6.9, 1.2 Hz, 1H), 4.94-4.90 (m, 1H), 4.88-4.82 (m, 2H), 4.81-4.78 (m, 2H), 4.73-4.69 (m, 1H), 4.66-4.63 (m, 1H), 4.59-4.56 (m, 1H).

Step B: 2-(2-hydroxyethoxy)quinoline-3-carboxylic acid. To a solution of the title compound of Step A (217 mg, 0.77 mmol) in MeOH (5 mL) was added 4 N LiOH (0.4 mL, 1.6 mmol) and the mixture was heated at 50° C. After 16.25 h the reaction mixture was concentrated to remove the MeOH and the aqueous layer acidified with 6N HCl. The mixture was then further concentrated to produce a light yellow solid (254 mg) which was used without further purification in subsequent steps. MS (ESI): mass calcd. for C$_{12}$H$_{11}$NO$_4$, 233.1. m/z found, 234.0 [M+H]$^+$.

Intermediate A-35:
7-(2-fluoroethoxy)quinoline-8-carboxylic acid

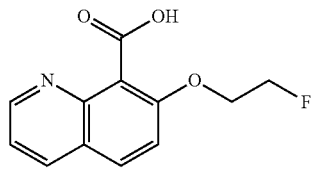 [SMILES: O=C(O)c1c(OCCF)ccc2cccnc12]

Step A: 8-bromo-7-(2-fluoroethoxy)quinoline. To 8-bromoquinolin-7-ol (1.7 g, 7.6 mmol) dissolved in DMF (5 mL) was added Cs$_2$CO$_3$ (2.1 g, 15.2 mmol) and 1-bromo-2-fluoroethane (623 µL, 8.35 mmol) and the mixture was heated to 60° C. After 4 h the reaction mixture was diluted with H$_2$O and the aqueous layer extracted with EtOAc (3×). The combined organics were dried with MgSO$_4$, filtered, and concentrated. Purification via silica gel chromatography (5-30% EtOAc in heptane) gave the title compound (1.140 g) as a colourless solid.

Step B: methyl 7-(2-fluoroethoxy)quinoline-8-carboxylate. To a solution of the title compound of Step A (1.43 g, 5.29 mmol) in MeOH (15 mL) and 1,4-dioxane (15 mL) was added Pd(OAc)$_2$ (48 mg, 0.21 mmol), 1,1'-bis(diphenylphosphino)ferrocene (235 mg, 0.424 mmol) and NEt$_3$ (2.2 mL, 15.9 mmol). The mixture was placed under a CO atmosphere (6 atmosphere) and heated to 50° C. After 18 h the reaction mixture was diluted with saturated NaHCO$_3$ solution/EtOAc and the aqueous layer extracted with EtOAc (2×). The combined organics were dried with MgSO$_4$, filtered, and concentrated. Purification via silica gel chromatography (5-30% EtOAc in heptane) gave the title compound (370 mg) as a beige coloured solid.

Step C: 7-(2-fluoroethoxy)quinoline-8-carboxylic acid. To a solution of the title compound of Step B (365 mg, 1.46 mmol) in MeOH (5 mL), THF (8 mL), and H$_2$O (2 mL) at 0° C. was added LiOH (184 mg, 4.38 mmol). The reaction mixture was heated at 70° C. for 18 h after which additional LiOH (61 mg, 1.46 mmol) was added. After an additional 18 h the reaction mixture was acidified with 1N HCl until a pH of 3-4 was reached. The mixture was then concentrated and purified by reverse phase chromatography (5-100% [95% H$_2$O (25 mM NH$_4$HCO$_3$)] in MeCN) to produce the title compound (370 mg). MS (ESI): mass calcd. for C$_{12}$H$_{10}$FNO$_3$, 235.1. m/z found, 236.0 [M+H]$^+$.

Intermediate A-26: 5-(2-bromoethoxy)-2-(2H-1,2,3-triazol-2-yl)benzoic acid

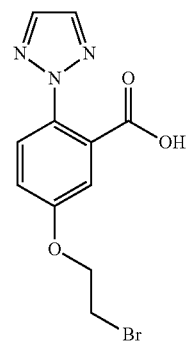 [SMILES: O=C(O)c1cc(OCCBr)ccc1-n1nccn1]

Step A: 2-bromo-5-(2-fluoroethoxy)benzonitrile. To 2-bromo-5-hydroxybenzonitrile (1.5 g, 7.6 mmol) in DMF (5 mL) was added Cs$_2$CO$_3$ (3.7 g, 11.4 mmol) and 1-iodo-2-fluoroethane (1.23 mL, 15.1 mmol) and the mixture was left to stir at room temperature. Upon completion the reaction mixture was diluted with H$_2$O and the aqueous layer extracted with EtOAc (3×). The combined organics were washed with 5% LiCl solution, brine, dried with MgSO$_4$, filtered and concentrated. Purification via silica gel chromatography (0-30% EtOAc in hexanes) gave the title compound (1.69 g) as a light yellow oil. 1H NMR (500 MHz, Chloroform-d) δ 7.56 (d, J=8.9 Hz, 1H), 7.18 (d, J=3.0 Hz, 1H), 7.05 (dd, J=8.9, 3.0 Hz, 1H), 4.87-4.63 (m, 2H), 4.30-4.14 (m, 2H).

Step B: 5-(2-bromoethoxy)-2-(2H-1,2,3-triazol-2-yl)benzonitrile. To a solution of the title compound of Step A (300 mg, 1.23 mmol) and 2H-1,2,3-triazole (86 µL, 1.5 mmol) in DMF (4 mL) was added K$_2$CO$_3$ (340 mg, 2.46 mmol) and the reaction mixture heated to 120° C. After 24 h the reaction mixture was diluted with H$_2$O and the aqueous layer extracted with EtOAc (3×). The combined organics were washed with 5% LiCl solution, brine, dried with Na$_2$SO$_4$, filtered and concentrated. Purification via silica gel chromatography (0-40% EtOAc in hexanes) gave the title compound (58 mg). MS (ESI): mass calcd. for C$_{11}$H$_9$BrN$_4$O, 292.0. m/z found, 293.0 [M+H]$^+$. $^1$H NMR (400 MHz, Chloroform-d) δ 7.63 (s, 2H), 7.52 (d, J=9.0 Hz, 1H), 7.11 (d, J=3.0 Hz, 1H), 6.97 (dd, J=9.0, 3.0 Hz, 1H), 4.84 (t, J=5.5 Hz, 2H), 4.50 (t, J=5.5 Hz, 2H).

Step C: 5-(2-bromoethoxy)-2-(2H-1,2,3-triazol-2-yl)benzoic acid. To a solution of the title compound of Step B (58 mg, 0.25 mmol) in EtOH (2.9 mL) was added 4 N NaOH (1.25 mL, 5.0 mmol). The mixture was heated at 60° C. overnight and then concentrated to remove the EtOH. The aqueous layer was then acidified with 4N HCl and extracted with 20% iPrOH/CHCl$_3$ (3×). The combined organics were dried with Na$_2$SO$_4$, filtered and concentrated to produce a yellow/orange film which was used without further purification in subsequent steps. MS (ESI): mass calcd. for C$_{11}$H$_{10}$BrN$_3$O$_3$, 311.0. m/z found, 311.9 [M+H]$^+$.

Intermediate B-1: (R/S)-2-benzyl-3-methyl-2-azabicyclo[2.2.1]hept-5-ene

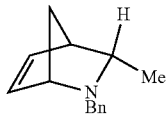 [SMILES: CC1C2C=CC(C2)N1Cc1ccccc1]

Intermediate B-1 was prepared according to the procedure of S. D. Larsen and P. A. Grieco [*J. Am. Chem. Soc.* 1985, 107, 1768-1769]. MS (ESI) mass calcd. for C$_{14}$H$_{17}$N, 199.1. m/z found, 200 [M+H]$^+$.

Intermediate B-2: (R/S)-2-benzyl-3-methyl-2-azabicyclo[2.2.1]heptan-6-ol.HCl

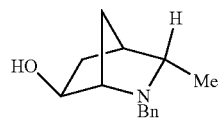

A 2 M solution of BH$_3$-Me$_2$S (2 M BH$_3$-Me$_2$S in THF, 109 mL, 217 mmol) was added dropwise over 15 minutes to a stirred solution of intermediate B-1 (14 g, 72 mmol) in THF (210 mL) at 0° C. Upon complete addition of BH$_3$-Me$_2$S, the reaction mixture was stirred at 0° C. for 0.5 h and then room temperature for an additional 1.5 h. Then, excess BH$_3$ was carefully quenched with a solution of THF—H$_2$O (1:1, 72 mL). A 4 M NaOH (23.5 mL) solution was added followed by the dropwise addition of H$_2$O$_2$ (50% w/w in H$_2$O, 23.0 mL), and the reaction mixture was warmed to 45° C. and stirred for 2 h. The biphasic mixture was then cooled to room temperature and K$_2$CO$_3$ (13 g) added. The resulting mixture was partially concentrated under reduced pressure to remove most of the THF, diluted further with H$_2$O, and then extracted with DCM. The combined organics were then dried with MgSO$_4$, filtered, and concentrated to give the crude reaction product, which was further purified by silica gel chromatography (0-15% EtOAc in heptane), to yield the free base of intermediate B-2 as a yellow oil (6.1 g). The oil was dissolved in DIPE and converted to the HCl salt which was then filtered off as a solid (7.1 g, 28 mmol, 38%). MS (ESI) mass calcd. for C$_{14}$H$_{19}$NO, 217.1. m/z found, 218 [M+H]$^+$.

Intermediate B-3:
(R/S)-3-methyl-2-azabicyclo[2.2.1]heptan-6-ol.HCl

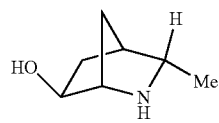

To a solution of intermediate B-2 (17.4 g, 68.7 mmol) in MeOH (240 mL) was added 10 wt % Pd/C wet Degussa (1.7 g). The reaction mixture was stirred under an atmosphere of H$_2$ (balloon) at 60° C. overnight. Then, the reaction mixture was filtered through a pad of Celite and concentrated to give the title compound (11.2 g), which was used without further purification. MS (ESI) mass calcd. for C$_7$H$_{13}$NO, 127.1. m/z found 128 [M+H]$^+$.

Intermediate B-4: (R/S)-tert-butyl 6-hydroxy-3-methyl-2-azabicyclo[2.2.1]heptane-2-carboxylate

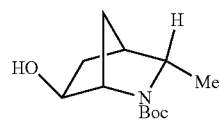 [SMILES: CC1C2CC(O)C(C2)N1C(=O)OC(C)(C)C]

To a solution of intermediate B-3 (11.2 g) in THF (240 mL) and H$_2$O (24 mL) was added NaHCO$_3$ (16.8 g, 200 mmol) and Boc$_2$O (27.6 g, 120 mmol) and the mixture was stirred at room temperature for 3 h. The reaction was then diluted with H$_2$O and the aqueous layer extracted with EtOAc. The combined organics were then dried with MgSO$_4$, filtered, and concentrated to give the crude reaction product, which was further purified by silica gel chromatography (0-30% EtOAc in heptane), to give the title compound as a colourless oil (9.4 g, 41 mmol, 60% over two steps). MS (ESI) mass calcd. for C$_{12}$H$_{21}$NO$_3$, 227.2. m/z found 172 [M+2H-tBu]$^+$.

Intermediate B-5: (R/S)-tert-butyl 3-methyl-6-oxo-2-azabicyclo[2.2.1]heptane-2-carboxylate

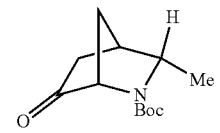 [SMILES: CC1C2CC(=O)C(C2)N1C(=O)OC(C)(C)C]

To a solution of intermediate B-4 (9.4 g, 41 mmol) in EtOAc (266 mL) was added IBX (13.9 g, 50 mmol), and the heterogeneous reaction mixture was stirred at 85° C. for 3 h. Additional IBX (5.8 g, 21 mmol) was added and the reaction mixture stirred for another 3 h at 85° C. before it was cooled to room temperature, filtered through a pad of Celite, and concentrated. The resulting solid was dissolved in EtOAc and washed with a 5% aqueous Na$_2$CO$_3$ solution. The aqueous layer was further extracted with EtOAc and the combined organics were washed with brine, dried with MgSO$_4$, filtered, and concentrated to provide the crude reaction product, which was further purified by silica gel chromatography (0-15% EtOAc in heptane), to give the title compound (7.9 g, 35 mmol, 85%). MS (ESI) mass calcd. for C$_{12}$H$_{19}$NO$_3$, 225.1. m/z found, 170 [M+2H-tBu]$^+$.

Intermediate B-6: (R/S)-tert-butyl 6-hydroxy-3-methyl-2-azabicyclo[2.2.1]heptane-2-carboxylate

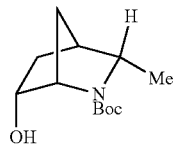

A 1 M solution of L-Selectride (1 M in THF, 285 mL, 285 mmol) was added to a solution of intermediate B-5 (25.4 g, 113 mmol) in dry THF (563 mL) at −78° C., and the reaction mixture was stirred at that temperature for 2 h. Then, the reaction mixture was warmed to 0° C. and a 3 M NaOH (118 mL) solution was added followed by a solution of $H_2O_2$ (35% w/w in $H_2O$, 56.4 mL). The resulting mixture was warmed to room temperature and stirred for 2 h. The biphasic mixture was then concentrated in vacuo to remove THF and the aqueous layer extracted with DCM. The combined organics were dried with $MgSO_4$, filtered, and concentrated to provide the crude reaction product, which was further purified by silica gel chromatography (0-20% EtOAc in heptanes), to give the title compound (24.7 g). MS (ESI) mass calcd. for $C_{12}H_{21}NO_3$, 227.2. m/z found 172 [M+2H-tBu]$^+$.

Intermediate B-6 was subjected to Chiral SFC purification [Stationary phase: Chiralpak AD-H (5 μm 250×30 mm), Mobile phase of 15% MeOH: 85% $CO_2$] to provide the corresponding single enantiomers (Intermediate B-6A and Intermediate B-6B) were the absolute stereochemistry was not determined Intermediate B-6A was subjected to a second Chiral SFC purification [Stationary phase: Chiralpak AD-H (5 μm 250×30 mm), Mobile phase of 7% MeOH: 93% $CO_2$] to improve the enantiopurity. The enantiomeric purity was confirmed by analytical SFC using a Chiralpak AD-H column (5 μm 150×4.6 mm), mobile phase of 10% MeOH: 90% $CO_2$, and a flow rate of 3 mL/min over 7 minutes (Temperature=35° C.). Elution was monitored following absorbance at 210 nm.

Intermediate B-6A: (1S*,3S*,4R*,6R*)-tert-butyl 6-hydroxy-3-methyl-2-azabicyclo[2.2.1]heptane-2-carboxylate

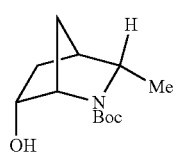 [SMILES: CC1C2CC(O)C(C2)N1C(=O)OC(C)(C)C]

Enantiomeric purity (SFC/Chiralpak AD): 100%. R$_t$: 1.39 min. MS (ESI) mass calcd. for $C_{12}H_{21}NO_3$, 227.2. m/z found, 172.1 [M+2H-tBu]$^+$. $^1$H NMR is in agreement with intermediate B-6B.

Intermediate B-6B: (1R*,3R*,4S*,6S*)-tert-butyl 6-hydroxy-3-methyl-2-azabicyclo[2.2.1]heptane-2-carboxylate

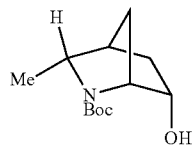

Enantiomeric purity (SFC/Chiralpak AD): 100%. R$_t$: 3.93 min MS (ESI) mass calcd. for $C_{12}H_{21}NO_3$, 227.2. m/z found, 172.1 [M+2H-tBu]$^+$. $^1$H NMR (500 MHz, Chloroform-d) δ 4.29-4.20 (m, 1H), 4.20-4.12 (m, 1H), 3.88-3.67 (m, 1H), 2.37-2.19 (m, 1H), 1.84-1.74 (m, 1H), 1.68-1.59 (m, 1H), 1.52-1.41 (m, 11H), 1.31 (dd, J=6.4, 2.2 Hz, 3H).

Intermediate B-7: (R/S)-tert-butyl 6-(hydroxyimino)-3-methyl-2-azabicyclo[2.2.1]heptane-2-carboxylate

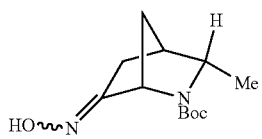 [SMILES: CC1C2CC(=NO)C(C2)N1C(=O)OC(C)(C)C]

To a flask containing Intermediate B-5 (644 mg, 2.86 mmol) dissolved in EtOH (6 mL) was added NEt$_3$ (0.64 ml, 4.8 mmol), and hydroxylamine hydrochloride (397 mg, 5.72 mmol) and the reaction mixture was brought to reflux. Upon completion, the reaction mixture was concentrated, triturated with $H_2O$, and the solids filtered off to give the title compound as a white solid (608 mg, 2.53 mmol, 88%) which was used without further purification. MS (ESI) mass calcd. for $C_{12}H_{20}N_2O_3$, 240.1. m/z found 185 [M+2H-tBu]$^+$.

Intermediate B-8: (R/S)-tert-butyl 6-amino-3-methyl-2-azabicyclo[2.2.1]heptane-2-carboxylate

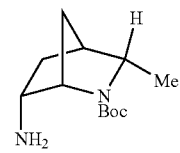

A mixture of NiCl$_2$ (656 mg, 5.06 mmol) and intermediate B-7 (608 mg, 2.53 mmol) in MeOH (18 mL) was cooled to −60° C. and NaBH$_4$ (287 mg, 7.59 mmol) was cautiously added portion wise to the reaction mixture over 60 min. Upon complete addition of NaBH$_4$, the reaction mixture was warmed to −30° C. and stirred for an additional 4 hours before additional NaBH$_4$ (96 mg, 2.53 mmol) was added portionwise. The reaction was stirred at −30° C. for an additional 1 hour before it was allowed to warm to room temperature overnight. The reaction mixture was then diluted with aqueous NH$_3$ (2.9 mL) and H$_2$O (9 mL) and the aqueous layer extracted with Et$_2$O. The combined organics were then dried with MgSO$_4$, filtered, and concentrated to give the crude reaction product, which was further purified by silica gel chromatography [0-100% DCM-MeOH (10:1, v/v)], to give the title compound (306 mg, 1.352 mmol, 53%). MS (ESI) mass calcd. for $C_{12}H_{22}N_2O_2$, 226.2. m/z found 227. [M+H]$^+$.

Intermediate B-9: (R/S)-2-benzyl-3-methyl-2-azabicyclo[2.2.1]hept-5-ene

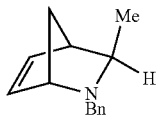 [SMILES: CC1C2C=CC(C2)N1Cc1ccccc1]

Intermediate B-9 was prepared according to the procedure of S. D. Larsen and P. A. Grieco [*J. Am. Chem. Soc.* 1985, 107, 1768-1769]. MS (ESI) mass calcd. for $C_{14}H_{17}N$, 199.1. m/z found, 200 [M+H]$^+$.

Intermediate B-10: (R/S)-2-benzyl-3-methyl-2-azabicyclo[2.2.1]heptan-6-ol.HCl

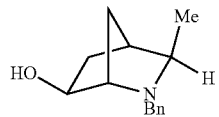

A 2 M solution of BH$_3$-Me$_2$S (2 M BH$_3$-Me$_2$S in THF, 62.5 mL, 125 mmol) was added dropwise over 15 minutes to a stirred solution of intermediate B-9 (8.3 g, 42 mmol) in THF (121 mL) at 0° C. Upon complete addition of BH$_3$-Me$_2$S, the reaction mixture was stirred at 0° C. for 0.5 h and then room temperature for an additional 1.5 h. Then, excess BH$_3$ was carefully quenched with a solution of THF—H$_2$O (1:1, 42 mL). A 4 M NaOH (14 mL) solution was added followed by the dropwise addition of H$_2$O$_2$ (50% w/w in H$_2$O, 13 mL), and the reaction mixture was warmed to 45° C. and stirred for 2 h. The biphasic mixture was then cooled to room temperature and K$_2$CO$_3$ (7 g) added. The resulting mixture was partially concentrated under reduced pressure to remove most of the THF, diluted further with H$_2$O, and then extracted with DCM. The combined organics were then dried with MgSO$_4$, filtered, and concentrated to give the crude reaction product, which was further purified by silica gel chromatography (0-15% EtOAc in heptane), to give intermediate B-10 as a yellow oil (3.66 g). The oil was dissolved in DIPE and converted to the HCl salt which was then filtered off as a solid (4.3 g, 17 mmol, 40%). MS (ESI) mass calcd. for $C_{14}H_{19}NO$, 217.1. m/z found, 218 [M+H]$^+$.

Intermediate B-11: (R/S)-3-methyl-2-azabicyclo[2.2.1]heptan-6-ol.HCl

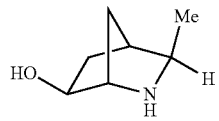

To a solution of intermediate B-10 (11.8 g, 46.6 mmol) in MeOH was added 10 wt % Pd/C wet Degussa (1.2 g). The reaction mixture was stirred under an atmosphere of H$_2$ (balloon) at 60° C. overnight. Then, the reaction mixture was filtered through a pad of Celite and concentrated to give the title compound (7.6 g), which was used without further purification. MS (ESI) mass calcd. for $C_7H_{13}NO$, 127.1. m/z found 128 [M+H]$^+$.

Intermediate B-12: (R/S)-tert-butyl 6-hydroxy-3-methyl-2-azabicyclo[2.2.1]heptane-2-carboxylate

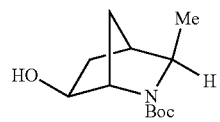

To a solution of intermediate B-11 (25.1 g, 154 mmol) in THF (460 mL) and H$_2$O (46 mL) was added NaHCO$_3$ (32.2 g, 384 mmol) and Boc$_2$O (5.5 g, 25 mmol) and the mixture was stirred at room temperature overnight. The reaction was then diluted with H$_2$O and EtOAc and the layers separated. The combined organics were then dried with MgSO$_4$, filtered, and concentrated to give the crude reaction product, which was further purified by silica gel chromatography (0-20% EtOAc in heptanes), to give the title compound as a colourless oil (25.3 g, 112 mmol, 73%). MS (ESI) mass calcd. for $C_{12}H_{21}NO_3$, 227.2. m/z found 172 [M+2H-tBu]$^+$.

Intermediate B-13: (R/S)-tert-butyl 3-methyl-6-oxo-2-azabicyclo[2.2.1]heptane-2-carboxylate

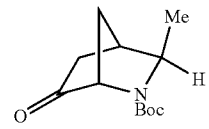

To a solution of intermediate B-12 (3.1 g, 13.8 mmol) in EtOAc (89 mL) was added IBX (4.6 g, 16.5 mmol), and the heterogeneous reaction mixture was stirred at 80° C. for 3 h. Additional IBX (1.927 g, 6.881 mmol) was added and the reaction mixture stirred for another 6 h at 80° C. before it was cooled to room temperature, filtered through a pad of Celite, and concentrated. The resulting solid was dissolved in EtOAc and washed with a 5% aqueous Na$_2$CO$_3$ solution. The aqueous layer was further extracted with EtOAc and the combined organics were washed with brine, dried with MgSO$_4$, filtered, and concentrated to provide the crude reaction product, which was further purified by silica gel chromatography (0-12% EtOAc in heptane), to give the title compound as a colourless oil (2.4 g, 10.6 mmol, 76%). MS (ESI) mass calcd. for $C_{12}H_{19}NO_3$, 225.1. m/z found, 170 [M+2H-tBu]$^+$.

Intermediate B-13 was subjected to Chiral SFC purification [Stationary phase: Chiralpak AD-H (5 μm 250×30 mm), Mobile phase of 5% iPrOH: 95% CO$_2$] to provide the corresponding single enantiomers (Intermediate B-13A and Intermediate B-13B) were the absolute stereochemistry was not determined. The enantiomeric purity was confirmed by analytical SFC using a Chiralpak IC-H column (5 μm 150×4.6 mm), mobile phase of 5% iPrOH: 95% CO$_2$, and a flow rate of 3 mL/min over 12 minutes (Temperature=35° C.). Elution was monitored following absorbance at 210 nm.

Intermediate B-13A: (1S*,3R*,4R*)-tert-butyl 3-methyl-6-oxo-2-azabicyclo[2.2.1]heptane-2-carboxylate

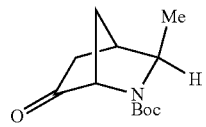 [SMILES: CC1C2CC(=O)C(C2)N1C(=O)OC(C)(C)C]

Enantiomeric purity (SFC/Chiralpak IC-H): 100%. $R_t$: 6.43 min. MS (ESI) mass calcd. for $C_{12}H_{19}NO_3$, 225.1. m/z found, 170.1 [M+2H-tBu]$^+$. $^1$H NMR (500 MHz, Chloroform-d) δ 4.25-3.94 (m, 1H), 3.60-3.32 (m, 1H), 2.51-2.38 (m, 1H), 2.24-2.14 (m, 1H), 2.13-2.02 (m, 1H), 2.03-1.90 (m, 1H), 1.61-1.53 (m, 1H), 1.43 (s, 9H), 1.30 (d, J=6.2 Hz, 3H).

Intermediate B-13B: (1R*,3S*,4S*)-tert-butyl 3-methyl-6-oxo-2-azabicyclo[2.2.1]heptane-2-carboxylate

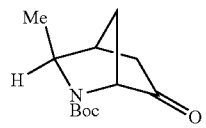

Enantiomeric purity (SFC/Chiralpak IC-H): 100%. $R_t$: 6.43 min. MS (ESI) mass calcd. for $C_{12}H_{19}NO_3$, 225.1. m/z found, 170.1 [M+2H-tBu]$^+$. $^1$H NMR is in agreement with intermediate B-13A.

Intermediate B-14: (R/S)-tert-butyl 6-hydroxy-3-methyl-2-azabicyclo[2.2.1]heptane-2-carboxylate

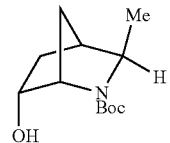 [SMILES: CC1C2CC(O)C(C2)N1C(=O)OC(C)(C)C]

A 1 M solution of L-Selectride (1 M in THF, 118.5 mL, 118.5 mmol) was added to a solution of intermediate B-13 (10.5 g, 46.8 mmol) in dry THF (234 mL) at −78° C., and the reaction mixture was stirred at that temperature for 2 h. Then, the reaction mixture was warmed to 0° C. and a 3 M NaOH (49 mL) solution was added followed by a solution of $H_2O_2$ (35% w/w in $H_2O$, 23.4 mL). The resulting mixture was warmed to room temperature and stirred for 2 h. The biphasic mixture was then concentrated in vacuo to remove THF and the aqueous layer extracted with DCM. The combined organics were dried with $MgSO_4$, filtered, and concentrated to provide the crude reaction product, which was further purified by silica gel chromatography (0-20% EtOAc in heptanes), to give the title compound (9.2 g, 40.4 mmol, 86%). MS (ESI) mass calcd. for $C_{12}H_{21}NO_3$, 227.2. m/z found 172.1 [M+2H-tBu]$^+$.

Intermediate B-14 was subjected to Chiral SFC purification [Stationary phase: Chiralpak IC (5 μm 250×30 mm), Mobile phase of 13% iPrOH: 87% $CO_2$] to provide the corresponding single enantiomers (Intermediate B-14A and Intermediate B-14B) were the absolute stereochemistry was not determined. The enantiomeric purity was confirmed by analytical SFC using a Chiralpak IC column (5 μm 150×4.6 mm), mobile phase of 10% iPrOH: 90% $CO_2$, and a flow rate of 3 mL/min over 7 minutes (Temperature=35° C.). Elution was monitored following absorbance at 210 nm.

Intermediate B-14A: (1S*,3R*,4R*,6R*)-tert-butyl 6-hydroxy-3-methyl-2-azabicyclo[2.2.1]heptane-2-carboxylate

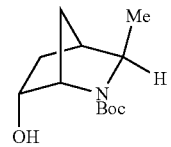

Enantiomeric purity (SFC/Chiralpak IC): 100%. $R_t$: 2.12 min. MS (ESI) mass calcd. for $C_{12}H_{21}NO_3$, 227.2. m/z found, 172.1 [M+2H-tBu]$^+$. $^1$H NMR (500 MHz, Chloroform-d) δ 4.36-4.28 (m, 1H), 4.20-4.14 (m, 1H), 3.45-3.35 (m, 1H), 2.67-2.55 (m, 1H), 2.12-2.08 (m, 1H), 2.03-1.96 (m, 1H), 1.78-1.71 (m, 1H), 1.45 (s, 9H), 1.37-1.31 (m, 1H), 1.16 (d, J=6.2 Hz, 3H).

Intermediate B-14B: (1R*,3S*,4S*,6S*)-tert-butyl 6-hydroxy-3-methyl-2-azabicyclo[2.2.1]heptane-2-carboxylate

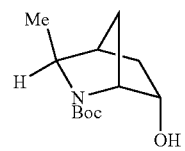

Enantiomeric purity (SFC/Chiralpak IC): 100%. $R_t$: 2.99 min MS (ESI) mass calcd. for $C_{12}H_{21}NO_3$, 227.2. m/z found, 172.1 [M+2H-tBu]$^+$. $^1$H NMR is in agreement with intermediate B-14A.

Intermediate B-15: (R/S)-tert-butyl 6-(hydroxyimino)-3-methyl-2-azabicyclo[2.2.1]heptane-2-carboxylate

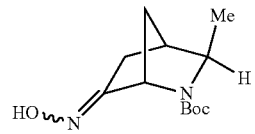 [SMILES: CC1C2CC(=NO)C(C2)N1C(=O)OC(C)(C)C]

Prepared analogous to intermediate B-7, substituting intermediate B-5 with intermediate B-13. MS (ESI) mass calcd. for $C_{12}H_{20}N_2O_3$, 240.1. m/z found 185 [M+2H-tBu]$^+$.

Intermediate B-15A: (1S*,3R*,4R*)-tert-butyl 6-(hydroxyimino)-3-methyl-2-azabicyclo[2.2.1]heptane-2-carboxylate

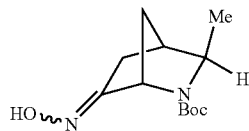 [SMILES: CC1C2CC(=NO)C(C2)N1C(=O)OC(C)(C)C]

To a flask containing intermediate B-13A (1.0 g, 4.4 mmol) dissolved in EtOH (40 mL) was added NEt$_3$ (1.8 ml, 13 mmol), and hydroxylamine hydrochloride (617 mg, 8.9 mmol) and the reaction mixture was brought to reflux. Upon completion, the reaction mixture was concentrated, diluted with H$_2$O, and the aqueous layer extracted with EtOAc (3×). The combined organics were then washed with H$_2$O, brine, dried with MgSO$_4$, filtered, and concentrated to provide the title compound as an off-white solid (1.1 g) which was used without further purification. MS (ESI) mass calcd. for C$_{12}$H$_{20}$N$_2$O$_3$, 240.1. m/z found 185.1 [M+2H-tBu]$^+$.

Intermediate B-16: (R/S)-tert-butyl 6-amino-3-methyl-2-azabicyclo[2.2.1]heptane-2-carboxylate

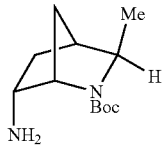

Prepared analogous to intermediate B-8, substituting intermediate B-7 with intermediate B-15. MS (ESI) mass calcd. for C$_{12}$H$_{22}$N$_2$O$_2$, 226.2. m/z found 227 [M+H]$^+$.

Intermediate B-16A: (1S*,3R*,4S*,6R*)-tert-butyl 6-amino-3-methyl-2-azabicyclo[2.2.1]heptane-2-carboxylate

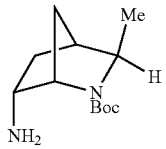

A mixture of NiCl$_2$ (1.19 g, 9.15 mmol) and intermediate B-15A (1.1 g, 4.6 mmol) in MeOH (30 mL) was cooled to −35° C. and NaBH$_4$ (3.46 g, 91.5 mmol) was added portion wise to the reaction mixture over 30 min. Upon complete addition of NaBH$_4$, the reaction mixture was stirred for an additional 25 min and then warmed to room temperature. After 30 min at room temperature the reaction mixture was quenched with H$_2$O and concentrated under reduced pressure to a dark brown residue, which was re-dissolved in a mixture of DCM and 15% aqueous NaOH solution and filtered through Celite. The aqueous layer extracted with DCM (3×). The combined organics were washed with brine, dried with MgSO$_4$, filtered, and concentrated to provide the title compound (890 mg) as a brown oil which was used without further purification. MS (ESI) mass calcd. for C$_{12}$H$_{22}$N$_2$O$_2$, 226.2. m/z found 227.2 [M+H]$^+$.

Intermediate B-17: ((1S,3S,4R)-2-benzyl-2-azabicyclo[2.2.1]hept-5-en-3-yl)methanol

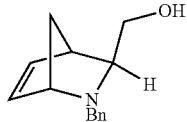 [SMILES: OCC1C2C=CC(C2)N1Cc1ccccc1]

Literature compound [F. Fernandez et al. *Synlett* 2005, 2, 319-321]. MS (ESI) mass calcd. for: C$_{14}$H$_{17}$NO, 215.1. m/z found 216.1 [M+H]$^+$.

Intermediate B-18: (R/S)-2-benzyl-3-(fluoromethyl)-2-azabicyclo[2.2.1]hept-5-ene

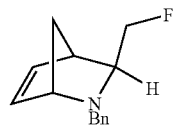 [SMILES: FCC1C2C=CC(C2)N1Cc1ccccc1]

Intermediate B-17 (400 mg, 1.86 mmol) was dissolved in DCM (20 mL) and cooled to 0° C. Deoxo-Fluor® (0.43 mL, 2.3 mmol) was then added dropwise and the ice bath was allowed to slowly expire. Upon completion, the reaction was quenched by dropwise addition of the reaction mixture into a solution of saturated NaHCO$_3$ cooled to 0° C. Upon complete addition the reaction was stirred for an additional 5 min and then the layers separated. The aqueous layer was extracted with DCM (2×) and the combined organics were washed with brine, dried with MgSO$_4$, filtered, and concentrated to provide the crude reaction product, which was further purified by silica gel chromatography (0-20% EtOAc in hexane), to give the title compound as a light yellow oil (263 mg, 1.21 mmol, 65%). MS (ESI) mass calcd. for: C$_{14}$H$_{16}$FN, 217.1. m/z found 218.1 [M+H]$^+$. $^1$H NMR (400 MHz, Chloroform-d) δ 7.36-7.28 (m, 4H), 7.31-7.20 (m, 1H), 6.52-6.42 (m, 1H), 6.19 (dd, J=5.7, 2.0 Hz, 1H), 4.30-4.00 (m, 2H), 3.80-3.70 (m, 1H), 3.56-3.47 (m, 1H), 3.42-3.32 (m, 1H), 2.94-2.86 (m, 1H), 2.05-1.95 (m, 1H), 1.72-1.62 (m, 1H), 1.43-1.32 (m, 1H).

Intermediate B-19: (R/S)-2-benzyl-3-(fluoromethyl)-2-azabicyclo[2.2.1]heptan-6-ol

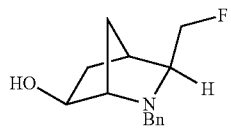 [SMILES: OC1CC2CC1N(Cc1ccccc1)C2CF]

A 1 M solution of BH$_3$-THF (1 M BH$_3$-THF in THF, 4.3 mL, 4.3 mmol) was added dropwise over 10 minutes to a stirred solution of intermediate B-18 (313 mg, 1.44 mmol) in THF (10 mL) at 0° C. After 40 min the excess BH$_3$-THF was carefully quenched with H$_2$O (0.4 mL), followed by a 4 M NaOH solution (1.0 mL), and dropwise addition of H$_2$O$_2$ (30% w/w in H$_2$O, 1.0 mL). The reaction mixture was removed from the ice bath and warmed between 35-40° for 3.5 h. The biphasic mixture was then cooled to room temperature and K$_2$CO$_3$ added. The resulting mixture was partially concentrated under reduced pressure to remove most of the THF, NaCl was added, and the aqueous layer extracted with EtOAc (3×). The combined organics were washed with H$_2$O, brine, dried with Na$_2$SO$_4$, filtered, and concentrated to give the crude reaction product, which was further purified by silica gel chromatography (0-50% EtOAc in hexane), to provide the title compound along with some of the undesired regioisomer (245 mg). This material was carried on to the next step without further purification. MS (ESI) mass calcd. for: C$_{14}$H$_{18}$FN, 235.1; m/z found 236.2 [M+H]$^+$.

Intermediate B-20: (R/S)-tert-butyl 3-(fluoromethyl)-6-hydroxy-2-azabicyclo[2.2.1]heptane-2-carboxylate

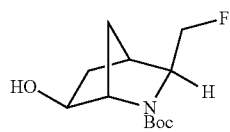 [SMILES: CC(C)(C)OC(=O)N1C2CC(CC2O)C1CF]

To crude intermediate B-19 (245 mg) and Boc$_2$O (228 mg, 1.05 mmol) dissolved in EtOH (20 mL) was added 10% Pd/C (100 mg). The resulting mixture was placed under a H$_2$ atmosphere (balloon) and stirred at room temperature overnight. Upon completion the reaction was filtered through a pad of Celite, washed with EtOAc, and concentrated under reduced pressure to provide the title compound as a light brown oil along with some of the undesired regioisomer (449 mg). This material was carried on to the next step without further purification. MS (ESI) mass calcd. for: C$_{12}$H$_{20}$FNO$_3$, 245.1. m/z found 190.1 [M+2H-tBu]$^+$.

Intermediate B-21: (R/S)-tert-butyl 3-(fluoromethyl)-6-oxo-2-azabicyclo[2.2.1]heptane-2-carboxylate

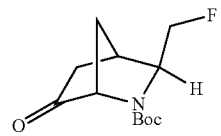 [SMILES: CC(C)(C)OC(=O)N1C2CC(CC2=O)C1CF]

To crude intermediate B-20 (449 mg) dissolved in EtOAc (20 mL) was added IBX (877 mg, 3.13 mmol) and the resulting mixture was brought to reflux for 3.5 h before additional IBX (877 mg, 3.13 mmol) was added. Upon completion the reaction was cooled to room temperature, filtered through a pad of Celite, washed with EtOAc, and concentrated under reduced pressure to provide the crude reaction product, which was further purified by silica gel chromatography (0-25% EtOAc in hexane), to give the title compound as a colourless solid (182 mg, 0.748 mmol, 52% over 3 steps). MS (ESI) mass calcd. for: C$_{12}$H$_{18}$FNO$_3$, 243.1. m/z found 188.1 [M+2H-tBu]$^+$.

Intermediate B-22: (R/S)-tert-butyl 3-(fluoromethyl)-6-hydroxy-2-azabicyclo[2.2.1]heptane-2-carboxylate

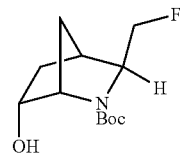 [SMILES: CC(C)(C)OC(=O)N1C2CC(CC2O)C1CF]

Intermediate B-21 (182 mg, 0.748 mmol) was dissolved in DCM (15 mL) and MeOH (1 mL) and cooled to 0° C. NaBH$_4$ (85 mg, 2.2 mmol) was then added in a single portion. Upon completion, the reaction was quenched by H$_2$O and the aqueous layer extracted with DCM (3×). The combined organics were dried with MgSO$_4$, filtered, and concentrated to provide the crude reaction product, along with some of the undesired diastereomer, as a colourless viscous oil (170 mg). This material was carried on to the next step without further purification. MS (ESI) mass calcd. for: C$_{12}$H$_{20}$FNO$_3$, 245.1. m/z found 190.1 [M+2H-tBu]$^+$.

Intermediate B-23: (1S,3S,4R)-ethyl 2-((R)-1-phenylethyl)-2-azabicyclo[2.2.2]oct-5-ene-3-carboxylate

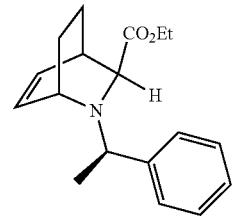 [SMILES: CCOC(=O)C1C2C=CC(CC2)N1[C@H](C)c1ccccc1]

Intermediate B-23 was prepared according to the procedure of P. Bailey et al. [*Tet. Asymm.* 1991, 2, 1263-1282]. MS (ESI) mass calcd. for C$_{18}$H$_{23}$NO$_2$, 285.2. m/z found, 286.2 [M+H]$^+$. $^1$H NMR (400 MHz, Chloroform-d) δ 7.45-7.39 (m, 2H), 7.29-7.23 (m, 2H), 7.21-7.15 (m, 1H), 6.43-6.37 (m, 1H), 6.30-6.24 (m, 1H), 3.98 (q, J=7.1 Hz, 2H), 3.69-3.57 (m, 1H), 3.50-3.39 (m, 1H), 2.95-2.85 (m, 1H), 2.80-2.68 (m, 1H), 2.11-1.98 (m, 1H), 1.68-1.55 (m, 1H), 1.36-1.24 (m, 4H), 1.13 (t, J=7.1 Hz, 3H), 1.09-1.00 (m, 1H).

Intermediate B-24: ((1S,3S,4R)-2-((R)-1-phenylethyl)-2-azabicyclo[2.2.2]oct-5-en-3-yl)methanol

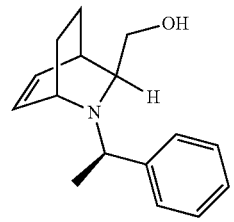 [SMILES: C[C@H](c1ccccc1)N1C2C=CC(CC2)C1CO]

Intermediate B-23 (4.97 g, 17.4 mmol) was dissolved in THF (100 mL) and cooled to 0° C. Then, a solution of LAH (1M in THF, 20 mL, 20 mmol) was added and the reaction mixture was stirred for 90 min. The mixture was then quenched with $H_2O$ (15 mL) followed by a 15% NaOH (aq.) solution (50 mL). The mixture was extracted with EtOAc (3×). The combined organics were dried with $Na_2SO_4$ and concentrated under reduced pressure to afford the title compound (4.5 g, 100%). MS (ESI) mass calcd. for: $C_{16}H_{21}NO$, 243.2. m/z found 244.2 $[M+H]^+$.

Intermediate B-25: (1S,3S,4R)-3-(fluoromethyl)-2-((R)-1-phenylethyl)-2-azabicyclo[2.2.2]oct-5-ene

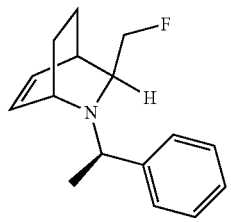 [SMILES: C[C@H](c1ccccc1)N1C2C=CC(CC2)C1CF]

To a solution of intermediate B-24 (1.13 g, 4.64 mmol) in DCM (20 mL) at 0° C. was added Deoxo-Fluor® (1.0 mL, 5.8 mmol) drop-wise, and the reaction mixture was allowed to slowly warm to rt over 2 h. The reaction mixture was quenched with $NaHCO_3$ (aq.) and stirred for 5 min. The reaction mixture was extracted with DCM (2×), dried with $Na_2SO_4$, filtered, and concentrated under reduced pressure. The concentrate was purified via silica gel chromatography (0-10% EtOAc in hexanes) to give intermediate B-25 (780 mg, 68%). MS (ESI) mass calcd. for: $C_{16}H_{20}FN$, 245.2. m/z found 246.2 $[M+H]^+$.

Intermediate B-26: (1S,3S,4R,6S)-3-(fluoromethyl)-2-((R)-1-phenylethyl)-2-azabicyclo[2.2.2]octan-6-ol

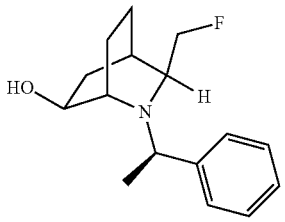 [SMILES: C[C@H](c1ccccc1)N1C2CCC(CC2O)C1CF]

Intermediate B-25 (1.98 g, 8.07 mmol) was dissolved in THF (50 mL) and the reaction mixture was cooled to 0° C. A solution of $BH_3$-THF (1 M $BH_3$-THF in THF, 18 mL, 18 mmol) was added drop-wise, and the resulting solution was stirred at 0° C. for 90 min. The excess borane was quenched with $H_2O$ (6 mL), followed by 4M NaOH (aq.) (6 mL), and the drop-wise addition of $H_2O_2$ (50% w/w, 6 mL). After complete addition of $H_2O_2$, the ice bath was removed and the reaction mixture heated to 40° C. for 3 h. Then, the reaction mixture was cooled to rt and solid $K_2CO_3$ (1 g) was added. The resulting mixture was concentrated under reduced pressure to remove. A solution of NaCl (aq.) was added and the mixture was extracted with DCM (3×). The combine organics were washed with $H_2O$, dried ($MgSO_4$), filtered and concentrated under reduced pressure to provide the title compound along with some of the undesired regioisomer (2.1 g). This material was carried on to the next step without further purification. MS (ESI) mass calcd. for: $C_{16}H_{22}FNO$, 263.2. m/z found 264.1 $[M+H]^+$.

Intermediate B-27: (1S,3S,4R,6S)-tert-butyl 3-(fluoromethyl)-6-hydroxy-2-azabicyclo[2.2.2]octane-2-carboxylate

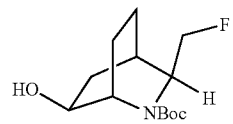

A solution of crude intermediate B-26 (2.1 g), $Boc_2O$ (1.74 g, 7.97 mmol) and 10% Pd/C (763 mg, 0.717 mmol) in EtOH (30 mL) was flushed with $N_2$. The resulting mixture was stirred at rt overnight under an atmosphere of $H_2$ (balloon). The completed reaction was filtered through a bed of celite, washed with EtOAc and concentrated under reduced pressure to provide the title compound as a clear oil along with some of the undesired regioisomer (2.1 g), which was carried on to the next step without further purification. MS (ESI) mass calcd. for: $C_{13}H_{22}FNO_3$, 259.2. m/z found 204.1 $[M+2H-tBu]^+$.

Intermediate B-28: (1S,3S,4R)-tert-butyl 3-(fluoromethyl)-6-oxo-2-azabicyclo[2.2.2]octane-2-carboxylate

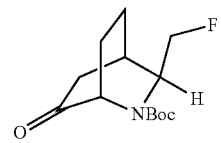 [SMILES: CC(C)(C)OC(=O)N1C2CCC(CC2=O)C1CF]

To a solution of crude intermediate B-27 (2.1 g) in EtOAc (50 mL) was added IBX (6.8 g, 24 mmol) and the mixture was heated to reflux for 1.5 h. Upon completion, the reaction mixture was cooled to rt and filtered through a plug of Celite. The plug was washed with EtOAc and the filtrate concentrated under reduced pressure. Purification via silica gel chromatography (0-25% EtOAc in hexanes) provided the title compound (710 mg, 34% over three steps). MS (ESI) mass calcd. for: $C_{13}H_{20}FNO_3$, 257.1. m/z found 158.1 $[M+2H-CO_2tBu]^+$.

Intermediate B-29: (1S,3S,4R,6R)-tert-butyl 3-(fluoromethyl)-6-hydroxy-2-azabicyclo[2.2.2]octane-2-carboxylate

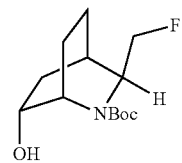 [SMILES: CC(C)(C)OC(=O)N1C2CCC(CC2O)C1CF]

To a solution of intermediate B-28 (710 mg, 2.8 mmol) in DCM (20 mL)/MeOH (2 mL) at 0° C. was added NaBH₄ (313 mg, 8.28 mmol) in a single portion, and the resulting reaction mixture was stirred for 3 h at 0° C. The completed reaction was quenched with H₂O (30 mL) and extract with DCM (2×), dried with Na₂SO₄, filtered, and concentrated under reduced pressure to provide the title compound along with some of the undesired regioisomer (710 mg). This material was carried on to the next step without further purification. MS (ESI) mass calcd. for: $C_{13}H_{22}FNO_3$, 259.2. m/z found 204.1 [M+2H-tBu]⁺.

Intermediate B-30: (1S,3R,4R)-3-methyl-2-((R)-1-phenylethyl)-2-azabicyclo[2.2.2]oct-5-ene

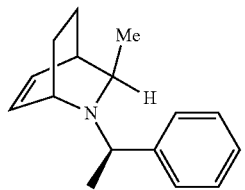 [SMILES: CC1C2C=CC(CC2)N1[C@H](C)c1ccccc1]

Intermediate B-24 (1.52 g, 6.25 mmol) and Et₃N (1.7 mL, 12.5 mmol) were dissolved in THF (42 mL) and cooled to 0° C. Methanesulfonyl chloride (0.7 mL, 9.4 mmol) was then added dropwise and the reaction mixture warmed to room temperature and stirred overnight. Upon completion, the reaction was diluted with EtOAc and quenched with a solution of saturated NaHCO₃. The aqueous layer was extracted with EtOAc (2×) and the combined organics were dried with Na₂SO₄, filtered and concentrated to give (1S,3S,4R)-3-(chloromethyl)-2-((R)-1-phenylethyl)-2-azabicyclo[2.2.2]oct-5-ene as a light yellow oil, which was used in the next step without further purification.

(1S,3S,4R)-3-(chloromethyl)-2-((R)-1-phenylethyl)-2-azabicyclo[2.2.2]oct-5-ene (1.64 g, 6.25 mmol) was dissolved in THF (62 mL), and a solution of LAH (1 M in THF, 12.5 mL, 12.5 mmol) was added dropwise. Upon complete addition of LAH, the reaction mixture was refluxed for 2 h. The mixture was then quenched with H₂O (1.7 mL) followed by a 15% NaOH (aq.) solution (1.7 mL), and additional H₂O (4.5 mL). Then, Et₂O and solid Na₂SO₄ were added, and the crude reaction mixture stirred at room temperature for 15 min. The reaction mixture was filtered and the solids rinsed with Et₂O. The filtrate was concentrated under reduced pressure to provide the crude product, which was further purified by silica gel chromatography (5-10% MeOH (with 10% 2 N NH₃) in DCM), to give the title compound (1.3 g, 5.7 mmol, 92% over 2 steps). MS (ESI) mass calcd. for: $C_{16}H_{21}N$, 227.1. m/z found 228.1 [M+H]⁺.

Intermediate B-31: tert-butyl (1S,3R,4R,6R)-6-hydroxy-3-methyl-2-azabicyclo[2.2.2]octane-2-carboxylate

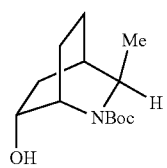 [SMILES: CC1C2CCC(C(O)C2)N1C(=O)OC(C)(C)C]

Intermediate B-31 was prepared analogous to intermediate B-29, starting from intermediate B-30. MS (ESI) mass calcd. for: $C_{13}H_{23}NO_3$, 241.2. m/z found 186.1 [M+2H-tBu]⁺.

Intermediate B-32: (1S,3S,4R)-3-((methoxymethoxy)methyl)-2-((R)-1-phenylethyl)-2-azabicyclo[2.2.2]oct-5-ene

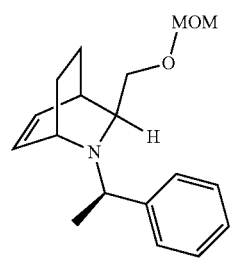

To a solution of intermediate B-24 (1.0 g, 3.9 mmol) and DIEA (1.5 mL, 8.6 mmol) in DCM (20 mL) was added MOMCl (0.6 mL, 7.1 mmol), the reaction mixture was stirred at rt for 1.5 h. The reaction mixture was extracted with DCM (2×), dried with Na₂SO₄, filtered, and concentrated under reduced pressure to give intermediate B-32 (1S,3S,4R)-3-((methoxymethoxy)methyl)-2-((R)-1-phenylethyl)-2-azabicyclo[2.2.2]oct-5-ene (1.1 g, 98%). This material was carried on to the next step without further purification. MS (ESI) mass calcd. for: $C_{18}H_{25}NO_2$, 287.4. m/z found 288.3 [M+H]. ¹H NMR (400 MHz, Chloroform-d) δ 7.41-7.35 (m, 2H), 7.31-7.24 (m, 2H), 7.24-7.16 (m, 1H), 6.47-6.39 (m, 1H), 6.26-6.19 (m, 1H), 4.49-4.45 (m, 1H), 4.45-4.40 (m, 1H), 3.49 (q, J=6.8 Hz, 1H), 3.41-3.33 (m, 2H), 3.23 (s, 3H), 3.17 (dd, J=9.9, 4.7 Hz, 1H), 2.65-2.58 (m, 1H), 2.51-2.38 (m, 1H), 1.81-1.67 (m, 2H), 1.25 (d, J=6.7 Hz, 3H), 1.07-0.96 (m, 2H).

Intermediate B-33: (1S,3S,4R,6S)-3-((methoxymethoxy)methyl)-2-((R)-1-phenylethyl)-2-azabicyclo[2.2.2]octan-6-ol

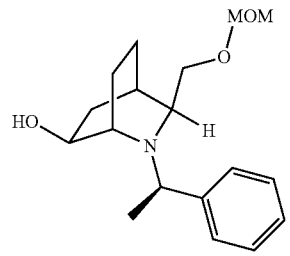

(1S,3S,4R)-3-((methoxymethoxy)methyl)-2-((R)-1-phenylethyl)-2-azabicyclo[2.2.2]oct-5-ene (1.1 g, 3.8 mmol) was dissolved in THF (15 mL) and the reaction mixture was cooled to 0° C. A solution of BH₃-THF (1 M BH₃-THF in THF, 6 mL, 6 mmol) was added drop-wise, and the resulting solution was stirred at 0° C. for 90 min. The excess borane was quenched with H₂O (0.5 mL), followed by 6M NaOH (aq.) (4 mL), and the drop-wise addition of H₂O₂ (50% w/w, 3 mL). After complete addition of H₂O₂, the reaction mixture was stirred overnight. Then, solid K₂CO₃ (1 g) was added. The resulting mixture was concentrated under reduced pressure. A solution of NaCl (aq.) was added and the mixture was extracted with DCM (3×). The combine organics were washed with $H_2O$, dried ($MgSO_4$), filtered and concentrated under reduced pressure to provide the title compound along with some of the undesired regioisomer (1.2 g). This material was carried on to the next step without further purification. MS (ESI) mass calcd. for: $C_{18}H_{27}NO_3$, 305.4. m/z found 306.2 $[M+H]^+$.

Intermediate B-34: (1S,3S,4R,6S)-tert-butyl 6-hydroxy-3-((methoxymethoxy)methyl)-2-azabicyclo[2.2.2]octane-2-carboxylate

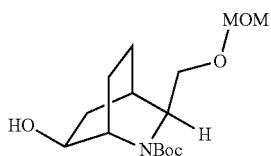

A solution of crude intermediate B-33 (1S,3S,4R,6S)-3-((methoxymethoxy)methyl)-2-((R)-1-phenylethyl)-2-azabicyclo[2.2.2]octan-6-ol (1.2 g), $Boc_2O$ (0.84 g, 3.8 mmol) and 10% Pd/C (366 mg, 0.34 mmol) in EtOH (30 mL) was flushed with $N_2$. The resulting mixture was stirred at rt overnight under an atmosphere of $H_2$ (balloon). The completed reaction was filtered through a bed of celite, washed with EtOAc and concentrated under reduced pressure to provide the title compound as a clear oil along with some of the undesired regioisomer (1.38 g), which was carried on to the next step without further purification. MS (ESI) mass calcd. for: $C_{15}H_{27}NO_5$, 301.38. m/z found 202.2 $[M+2H-CO_2tBu]^+$.

Intermediate B-35: (1S,3S,4R)-tert-butyl 3-((methoxymethoxy)methyl)-6-oxo-2-azabicyclo[2.2.2]octane-2-carboxylate

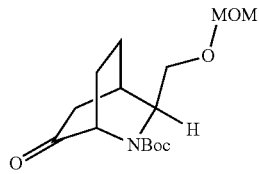

To a solution of crude intermediate B-34 (1S,3S,4R,6S)-tert-butyl 6-hydroxy-3-((methoxymethoxy)methyl)-2-azabicyclo[2.2.2]octane-2-carboxylate (1.16 g) in EtOAc (50 mL) was added IBX (3.2 g, 12 mmol) and the mixture was heated to reflux for 1.5 h. Upon completion, the reaction mixture was cooled to rt and filtered through a plug of Celite. The plug was washed with EtOAc and the filtrate was concentrated under reduced pressure. Purification via silica gel chromatography (0-25% EtOAc in hexanes) provided the title compound (550 mg, 48% over three steps). MS (ESI) mass calcd. for: $C_{15}H_{25}NO_5$, 299.4. m/z found 200.1 $[M+2H-CO_2tBu]^+$. $^1H$ NMR (400 MHz, $CDCl_3$) δ 4.76-4.57 (m, 2H), 4.57-4.34 (m, 1H), 4.19-3.82 (m, 2H), 3.60-3.45 (dd, J=16.7, 9.5 Hz, 1H), 3.43-3.33 (m, 3H), 2.84-2.69 (s, 1H), 2.63-2.43 (d, J=14.0 Hz, 1H), 2.42-2.28 (m, 1H), 2.27-2.14 (m, 1H), 2.08-1.90 (s, 1H), 1.89-1.64 (m, 2H), 1.50-1.39 (m, 9H).

Intermediate B-36: (1S,3S,4R,6R)-tert-butyl 6-hydroxy-3-((methoxymethoxy)methyl)-2-azabicyclo[2.2.2]octane-2-carboxylate

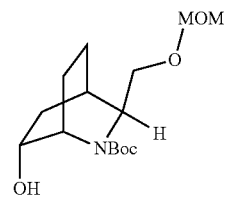

To a solution of intermediate B-35 (1S,3S,4R)-tert-butyl 3-((methoxymethoxy)methyl)-6-oxo-2-azabicyclo[2.2.2]octane-2-carboxylate (130 mg, 0.43 mmol) in DCM (9 mL)/MeOH (0.6 mL) at 0° C. was added $NaBH_4$ (49 mg, 1.3 mmol) in a single portion, the resulting reaction mixture was stirred for 3 h at 0° C. The completed reaction was quenched with $H_2O$ (10 mL) and extract with DCM (2×), dried with $Na_2SO_4$, filtered, and concentrated under reduced pressure to provide the title compound along with some of the undesired regioisomer (130 mg). This material was carried on to the next step without further purification. MS (ESI) mass calcd. for: $C_{15}H_{27}NO_5$, 301.38. m/z found 202.2 $[M+2H-tBu]^+$.

Intermediate C-1: 2-(tributylstannyl)pyrimidine

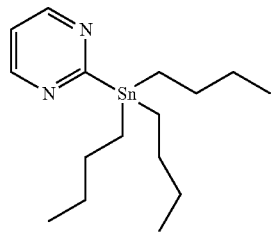 [SMILES: CCC[CH2][Sn]([CH2]CCC)([CH2]CCC)[c]1ncccn1]

Commercially available [CAS: 153435-63-3].

Intermediate C-2: 5-fluoro-2-(tributylstannyl)pyrimidine

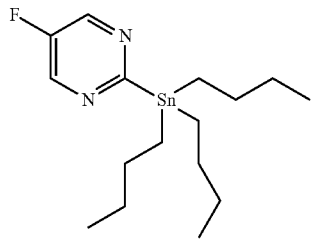 [SMILES: CCC[CH2][Sn]([CH2]CCC)([CH2]CCC)[c]1ncc(F)cn1]

Step A: In a sealable vessel 2-chloro-5-fluoropyrimidine (5.0 mL, 40 mmol) was dissolved in propionitrile (40 mL). TMSCl (15.4 mL, 121.5 mmol) and NaI (18.2 g, 121.5 mmol) were then added, the vessel sealed, and the reaction mixture was heated to 150° C. overnight. The solvent was removed under reduced pressure and the remaining residue was partitioned between EtOAc and saturated $NaHCO_3$ solution. The layers were separated and the organic layer dried with MgSO₄, filtered, and concentrated under reduced pressure. Purification via silica gel chromatography (0-20% EtOAc in heptane) gave the title compound (4.14 g).

Step B: To the title compound of step A (100 mg, 0.446 mmol) and 1,1,1,2,2,2-hexabutyldistannane (818 mg, 1.34 mmol) dissolved in dioxane (5 mL) was bubbled N₂ for 5 min. Pd(PPh₃)₂Cl₂ was then added and the mixture heated at 105° C. overnight before the reaction was diluted with H₂O and EtOAc. The layers were separated and the organic layer dried with MgSO₄, filtered, and concentrated under reduced pressure. Purification via Prep HPLC (MeCN/NH₄OAc (aq)) gave the title compound (97 mg).

Examples 1-7 describe exemplary methods for the synthesis of certain compounds of Formula I wherein $R_{6A}$ is H and $R_{6B}$ is as described herein (endo adducts of compounds of Formula I).

Example 1

(R/S)-(3-fluoro-2-(pyrimidin-2-yl)phenyl)(3-methyl-6-((5-(trifluoromethyl)pyridin-2-yl)oxy)-2-azabicyclo[2.2.1]heptan-2-yl)methanone

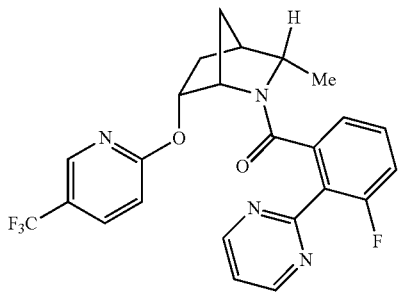

The title compound was prepared analogous to Example 18 substituting intermediate A-6 with intermediate A-2 and intermediate B-14 with B-6. MS (ESI): mass calcd. for C₂₄H₂₀F₄N₄O₂, 472.2. m/z found, 473 [M+H]⁺.

Example 2

(R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone

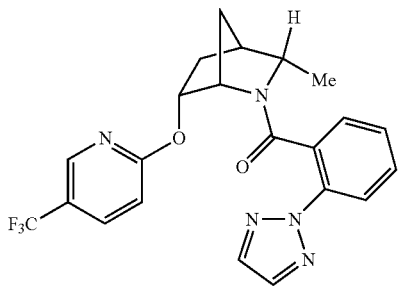

The title compound was prepared analogous to Example 12 substituting intermediate A-30 with intermediate A-1 and intermediate B-14 with B-6. MS (ESI): mass calcd. for C₂₂H₂₀F₃N₅O₂, 443.2. m/z found, 444.2 [M+H]⁺. MP=221.6° C. ¹H NMR (400 MHz, Chloroform-d) δ 8.07-8.01 (m, 1H), 7.90 (d, J=8.1 Hz, 1H), 7.83-7.81 (m, 1H), 7.80 (s, 2H), 7.35-7.27 (m, 1H), 6.95-6.90 (m, 1H), 6.90-6.83 (m, 1H), 6.77 (t, J=7.5 Hz, 1H), 5.04 (dt, J=10.1, 3.2 Hz, 1H), 4.20-4.05 (m, 2H), 2.58-2.41 (m, 1H), 2.10-1.95 (m, 1H), 1.87 (dt, J=13.9, 3.5 Hz, 1H), 1.69-1.62 (m, 1H), 1.55 (d, J=6.3 Hz, 3H), 1.45 (d, J=10.2 Hz, 1H).

Example 2 was subjected to Chiral SFC purification [Stationary phase: CHIRALCEL AD-H (5 μm 250×20 mm), Mobile phase of 15% MeOH: 85% CO₂] to provide the corresponding single enantiomers (Example 2A and Example 2B) were the absolute stereochemistry was not determined. The enantiomeric purity was confirmed by analytical SFC using a Chiralcel AD-H column (5 μm 150×4.6 mm), mobile phase of 10% MeOH: 90% CO₂, and a flow rate of 3 mL/min over 7 minutes (Temperature=35° C.).

Example 2A (2-(2H-1,2,3-triazol-2-yl)phenyl)((1R*,3R*,4S*,6S*)-3-methyl-6-((5-(trifluoromethyl)pyridin-2-yl)oxy)-2-azabicyclo[2.2.1]heptan-2-yl)methanone

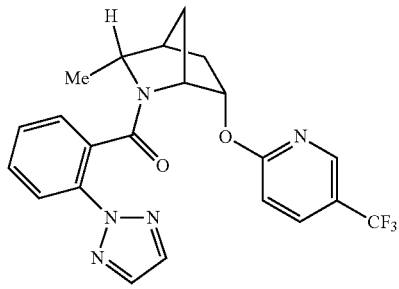 [SMILES: CC1C2CC(Oc3ccc(C(F)(F)F)cn3)C(C2)N1C(=O)c1ccccc1-n1nccn1]

Enantiomeric purity (SFC/Chiralcel AD-H): 100%. R_t: 2.02 min. MS (ESI): mass calcd. for C₂₂H₂₀F₃N₅O₂, 443.2. m/z found, 444.2 [M+H]⁺. ¹H NMR (400 MHz, Chloroform-d) δ 8.04 (s, 1H), 7.90 (d, J=8.2 Hz, 1H), 7.87-7.76 (m, 3H), 7.35-7.27 (m, 1H), 6.92 (d, J=7.8 Hz, 1H), 6.90-6.83 (m, 1H), 6.77 (t, J=7.3 Hz, 1H), 5.04 (dt, J=10.1, 3.2 Hz, 1H), 4.25-4.05 (m, 2H), 2.51-2.43 (m, 1H), 2.09-1.96 (m, 1H), 1.87 (dt, J=14.0, 3.5 Hz, 1H), 1.69-1.62 (m, 1H), 1.56 (d, J=6.6 Hz, 3H), 1.46 (d, J=10.2 Hz, 1H).

Example 2B (2-(2H-1,2,3-triazol-2-yl)phenyl)((1S*,3S*,4R*,6R*)-3-methyl-6-((5-(trifluoromethyl)pyridin-2-yl)oxy)-2-azabicyclo[2.2.1]heptan-2-yl)methanone

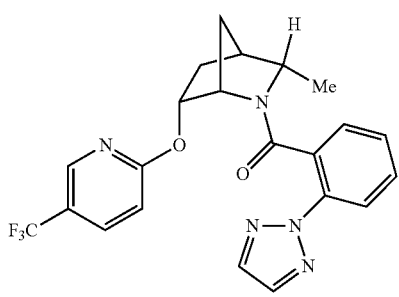

Enantiomeric purity (SFC/Chiralcel AD-H): 96.7%. R_t: 4.53 min. MS (ESI): mass calcd. for C₂₂H₂₀F₃N₅O₂, 443.2. m/z found, 444.2 [M+H]⁺. ¹H NMR (400 MHz, Chloroform-d) δ 8.04 (s, 1H), 7.90 (d, J=8.3 Hz, 1H), 7.82-7.76 (m, 3H), 7.35-7.27 (m, 1H), 6.96-6.89 (m, 1H), 6.90-6.83 (m, 1H), 6.77 (t, J=7.6 Hz, 1H), 5.04 (dt, J=10.1, 3.2 Hz, 1H), 4.20-4.04 (m, 2H), 2.53-2.41 (m, 1H), 2.10-1.97 (m, 1H), 1.87 (dt, J=14.0, 3.5 Hz, 1H), 1.70-1.62 (m, 1H), 1.56 (d, J=6.2 Hz, 3H), 1.46 (d, J=10.2 Hz, 1H).

Example 3

(R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone

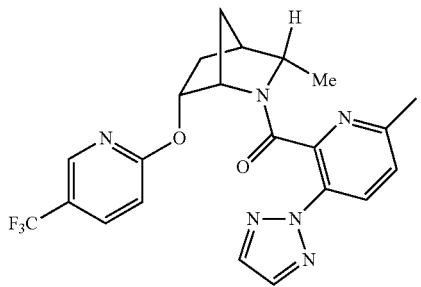 [SMILES: Cc1ccc(-n2nccn2)c(C(=O)N2C(C)C3CC(Oc4ccc(C(F)(F)F)cn4)C2C3)n1]

The title compound was prepared analogous to Example 12 substituting intermediate A-30 with intermediate A-26 and intermediate B-14 with B-6. MS (ESI): mass calcd. for $C_{22}H_{21}F_3N_6O_2$, 458.2. m/z found, 459.2 [M+H]$^+$. $^1$H NMR (400 MHz, Chloroform-d) δ 8.05 (d, J=8.4 Hz, 1H), 8.00-7.95 (m, 1H), 7.81 (s, 2H), 7.68 (dd, J=8.7, 2.5 Hz, 1H), 7.06 (d, J=8.5 Hz, 1H), 6.79-6.73 (m, 1H), 4.96 (dt, J=10.0, 3.3 Hz, 1H), 4.33-4.24 (m, 1H), 4.24-4.14 (m, 1H), 2.56-2.42 (m, 1H), 2.18 (s, 3H), 2.03-1.94 (m, 1H), 1.95-1.87 (m, 1H), 1.73-1.65 (m, 1H), 1.62 (d, J=6.4 Hz, 3H), 1.53-1.47 (m, 1H).

Example 3 was subjected to Chiral SFC purification [Stationary phase: Chiralcel OD-H (5 μm 250×20 mm), Mobile phase of 10% iPrOH: 90% $CO_2$] to provide the corresponding single enantiomers (Example 3A and Example 3B) were the absolute stereochemistry was not determined. The enantiomeric purity was confirmed by analytical SFC using a Chiralcel OD-H column (5 μm 150×4.6 mm), mobile phase of 10% iPrOH: 90% $CO_2$, and a flow rate of 3 mL/min over 7 minutes (Temperature=35° C.).

Example 3A (6-methyl-3-(2H-1,2,3-triazol-2-yl)pyridin-2-yl)((1R*,3R*,4S*,6S*)-3-methyl-6-((5-(trifluoromethyl)pyridin-2-yl)oxy)-2-azabicyclo[2.2.1]heptan-2-yl)methanone

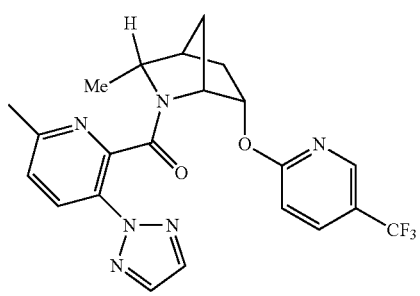 [SMILES: Cc1ccc(-n2nccn2)c(C(=O)N2C(C)C3CC(Oc4ccc(C(F)(F)F)cn4)C2C3)n1]

Enantiomeric purity (SFC/Chiralcel OD-H): 100%. R$_t$: 4.97 min. MS (ESI): mass calcd. for $C_{22}H_{21}F_3N_6O_2$, 458.2. m/z found, 459.2 [M+H]$^+$. $^1$H NMR (400 MHz, Chloroform-d) δ 8.05 (d, J=8.4 Hz, 1H), 7.99-7.93 (m, 1H), 7.81 (s, 2H), 7.68 (dd, J=8.8, 2.5 Hz, 1H), 7.06 (d, J=8.5 Hz, 1H), 6.76 (d, J=8.7 Hz, 1H), 4.96 (dt, J=10.0, 3.3 Hz, 1H), 4.31-4.24 (m, 1H), 4.24-4.14 (m, 1H), 2.54-2.46 (m, 1H), 2.18 (s, 3H), 2.05-1.96 (m, 1H), 1.95-1.88 (m, 1H), 1.73-1.65 (m, 1H), 1.62 (d, J=6.3 Hz, 3H), 1.53-1.45 (m, 1H).

Example 3B (6-methyl-3-(2H-1,2,3-triazol-2-yl)pyridin-2-yl)((1S*,3S*,4R*,6R*)-3-methyl-6-((5-(trifluoromethyl)pyridin-2-yl)oxy)-2-azabicyclo[2.2.1]heptan-2-yl)methanone

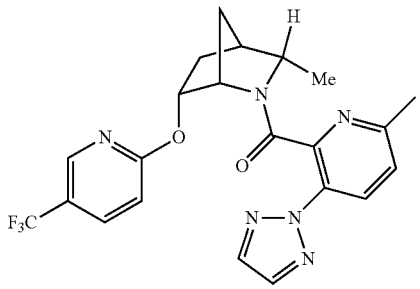 [SMILES: Cc1ccc(-n2nccn2)c(C(=O)N2C(C)C3CC(Oc4ccc(C(F)(F)F)cn4)C2C3)n1]

Enantiomeric purity (SFC/Chiralcel OD-H): 98.9%. R$_t$: 6.39 min. MS (ESI): mass calcd. for $C_{22}H_{21}F_3N_6O_2$, 458.2. m/z found, 459.2 [M+H]$^+$. $^1$H NMR (400 MHz, Chloroform-d) δ 8.05 (d, J=8.4 Hz, 1H), 7.99-7.94 (m, 1H), 7.80 (s, 2H), 7.67 (dd, J=8.7, 2.5 Hz, 1H), 7.06 (d, J=8.4 Hz, 1H), 6.76 (d, J=8.7 Hz, 1H), 4.96 (dt, J=10.0, 3.3 Hz, 1H), 4.32-4.25 (m, 1H), 4.25-4.12 (m, 1H), 2.51-2.41 (m, 1H), 2.18 (s, 3H), 2.06-1.96 (m, 1H), 1.92 (dt, J=13.9, 3.6 Hz, 1H), 1.72-1.65 (m, 1H), 1.61 (d, J=6.3 Hz, 3H), 1.52-1.46 (m, 1H).

Example 4

(R/S)-(3-fluoro-2-(pyrimidin-2-yl)phenyl)(3-methyl-6-((5-(trifluoromethyl)pyrazin-2-yl)amino)-2-azabicyclo[2.2.1]heptan-2-yl)methanone

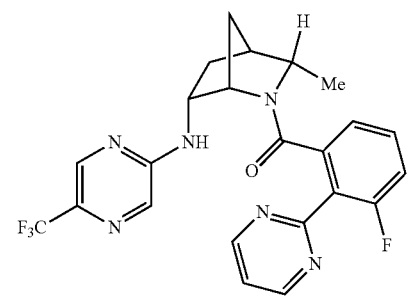

The title compound was prepared analogous to Example 5 substituting intermediate A-1 with intermediate A-9 and carrying out an additional cross coupling step (Step D).

Step D: To a sealable tube containing (R/S)-(3-fluoro-2-iodophenyl)(3-methyl-6-((5-(trifluoromethyl)pyrazin-2-yl)

amino)-2-azabicyclo[2.2.1]heptan-2-yl)methanone (100 mg, 0.177 mmol) and CuI (2.5 mg, 0.013 mmol) in DME (2 mL) was bubbled $N_2$ gas for 5 minutes. 2-(tributylstannyl) pyrimidine (98 mg, 0.27 mmol), LiCl (7.5 mg, 0.18 mmol), and $Pd(PPh_3)_4$ (15.5 mg, 0.0134 mmol) were then added, the vessel sealed, and heated to 120° C. After 3 hours the reaction was concentrated and the residual purified using Agilent Prep Method X to give the title compound (10 mg). MS (ESI): mass calcd. for $C_{23}H_{20}F_4N_6O$, 472.2. m/z found, 473 [M+H]$^+$.

Example 5

(R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone

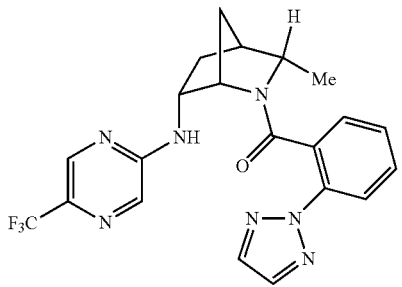

Step A: (R/S)-tert-butyl 3-methyl-6-((5-(trifluoromethyl)pyrazin-2-yl)amino)-2-azabicyclo[2.2.1]heptane-2-carboxylate. To intermediate B-8 (303 mg, 1.399 mmol) and 2-chloro-5-(trifluoromethyl)pyrazine (0.165 mL, 1.34 mmol) dissolved in DMSO (4 mL) was added $K_2CO_3$ (315 mg, 2.28 mmol) and the reaction mixture was heated at 120° C. in the microwave for 5 min. Saturated $NaHCO_3$ solution was then added and the aqueous layer extracted with DCM (3×). The combined organics were washed with brine, dried with $MgSO_4$, filtered and concentrated. Purification via silica gel chromatography (0-20% EtOAc in heptane) gave the title compound (283 mg, 0.760 mmol, 57%). MS (ESI) mass calcd. for $C_{17}H_{23}F_3N_4O_2$, 372.2. m/z found 273 [M+2H-tBu]$^+$.

Step B: (R/S)-3-methyl-N-(5-(trifluoromethyl)pyrazin-2-yl)-2-azabicyclo[2.2.1]heptan-6-amine.xHCl. To the title compound of step A (283 mg, 0.760 mmol) in dioxane (2 mL) was added 6M HCl in 2-propanol (0.76 mL) and the reaction was heated at 60° C. overnight after which the reaction was concentrated to give the title compound of step B (263 mg), which was used without further purification. MS (ESI) mass calcd. for $C_{12}H_{15}F_3N_4$, 272.1. m/z found 273 [M+H]$^+$.

Step C: (R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone. To intermediate A-1 (79 mg, 0.42 mmol) in DMF (2 mL) was added DIPEA (0.24 mL, 1.4 mmol) and HBTU (198 mg, 0.42 mmol). After 10 minutes the title compound of step B (120 mg) was added and the reaction was left to stir overnight. Upon completion, the reaction was diluted with a saturated aqueous $NaHCO_3$ solution and the aqueous layer extracted with EtOAc (3×). The combined organics were dried with $MgSO_4$, filtered and concentrated. Purification via silica gel chromatography (0-50% EtOAc in heptanes) and trituration with DIPE gave the title compound (134 mg). MS (ESI): mass calcd. for $C_{21}H_{20}F_3N_7O$, 443.2. m/z found, 444.2 [M+H]$^+$. MP=163.8° C. Analytical HPLC was obtained on a Agilent 1100 Series using a XBridge C18 column (5 μm, 100×4 6 mm), mobile phase of 10-100% ACN in 20 mM $NH_4OH$ over 8 min and then hold at 100% ACN for 3 min, at a flow rate of 1 mL/min (Temperature=45° C.). $R_t$=5.54 min at 254 nm.

Example 5 was subjected to Chiral SFC purification [Stationary phase: Chiralcel AD-H (5 μm 250×30 mm), Mobile phase of 30% MeOH: 70% $CO_2$] to provide the corresponding single enantiomers (Example 5A and Example 5B) were the absolute stereochemistry was not determined. The enantiomeric purity was confirmed by analytical SFC using a Chiralpak AD-H column (5 μm 150×4.6 mm), mobile phase of 25% MeOH: 75% $CO_2$, and a flow rate of 3 mL/min over 7 minutes (Temperature=35° C.).

Example 5A (2-(2H-1,2,3-triazol-2-yl)phenyl)((1R*,3R*,4R*,6S*)-3-methyl-6-((5-(trifluoromethyl)pyrazin-2-yl)amino)-2-azabicyclo[2.2.1]heptan-2-yl)methanone

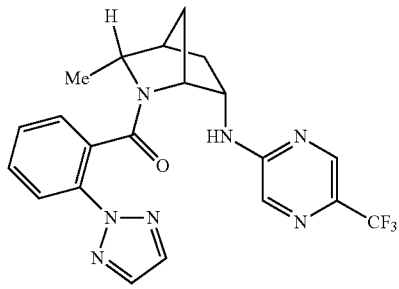 [SMILES: CC1C2CC(Nc3cnc(C(F)(F)F)cn3)C(C2)N1C(=O)c1ccccc1-n1nccn1]

Enantiomeric purity (SFC/Chiralcel AD-H): 100%. $R_t$: 1.11 min. MS (ESI): mass calcd. for $C_{21}H_{20}F_3N_7O$, 443.2. m/z found, 444.2 [M+H]$^+$. Analytical HPLC was obtained on a Agilent 1100 Series using a XBridge C18 column (5 μm, 100×4 6 mm), mobile phase of 10-100% ACN in 20 mM $NH_4OH$ over 8 min and then hold at 100% ACN for 3 min, at a flow rate of 1 mL/min (Temperature=45° C.). $R_t$=6.59 min at 254 nm.

Example 5B (2-(2H-1,2,3-triazol-2-yl)phenyl)((1S*,3S*,4S*,6R*)-3-methyl-6-((5-(trifluoromethyl)pyrazin-2-yl)amino)-2-azabicyclo[2.2.1]heptan-2-yl)methanone

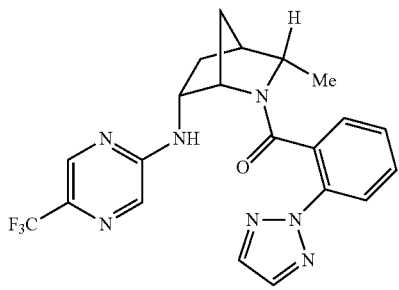

Enantiomeric purity (SFC/Chiralcel AD-H): 100%. $R_t$: 4.90 min. MS (ESI): mass calcd. for $C_{21}H_{20}F_3N_7O$, 443.2. m/z found, 444.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). $R_t$=6.60 min at 254 nm.

Example 6

(R/S)-(6-methyl-3-(2H-1,2,3-triazol-2-yl)pyridin-2-yl)(3-methyl-6-((5-(trifluoromethyl)pyrazin-2-yl)amino)-2-azabicyclo[2.2.1]heptan-2-yl)methanone

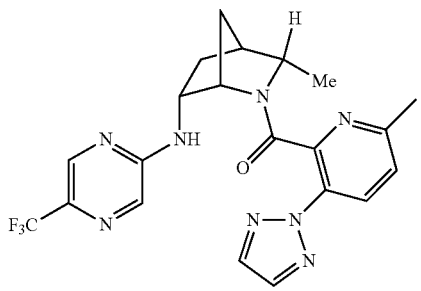 [SMILES: Cc1ccc(-n2nccn2)c(C(=O)N2C(C)C3CC(Nc4cnc(C(F)(F)F)cn4)C2C3)n1]

The title compound was prepared analogous to Example 5 substituting intermediate A-1 with intermediate A-26. MS (ESI): mass calcd. for $C_{21}H_{21}F_3N_8O$, 458.2. m/z found, 459.2 [M+H]$^+$. MP=212.8° C.

Example 6 was subjected to Chiral SFC purification [Stationary phase: Whelk O1 (S,S) (5 μm, 250×21.1 mm), Mobile phase of 40% iPrOH: 60% CO$_2$] to provide the corresponding single enantiomers (Example 6A and Example 6B) were the absolute stereochemistry was not determined. The enantiomeric purity was confirmed by analytical SFC using a Whelk-O1 column (5 μm 250×4.6 mm), mobile phase of 40% iPrOH: 60% CO$_2$, and a flow rate of 3 mL/min over 7 minutes (Temperature=35° C.).

Example 6A (6-methyl-3-(2H-1,2,3-triazol-2-yl)pyridin-2-yl)((1R*,3R*,4R*,6S*)-3-methyl-6-((5-(trifluoromethyl)pyrazin-2-yl)amino)-2-azabicyclo[2.2.1]heptan-2-yl)methanone

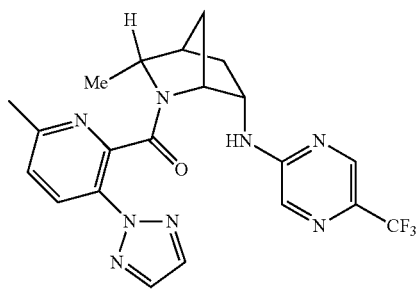 [SMILES: Cc1ccc(-n2nccn2)c(C(=O)N2C(C)C3CC(Nc4cnc(C(F)(F)F)cn4)C2C3)n1]

Enantiomeric purity (SFC/Whelk-O1): 100%. $R_t$: 3.50 min. MS (ESI): mass calcd. for $C_{21}H_{21}F_3N_8O$, 458.2. m/z found, 459.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). $R_t$=6.55 min at 254 nm.

Example 6B (6-methyl-3-(2H-1,2,3-triazol-2-yl)pyridin-2-yl)((1S*,3S*,4S*,6R*)-3-methyl-6-((5-(trifluoromethyl)pyrazin-2-yl)amino)-2-azabicyclo[2.2.1]heptan-2-yl)methanone

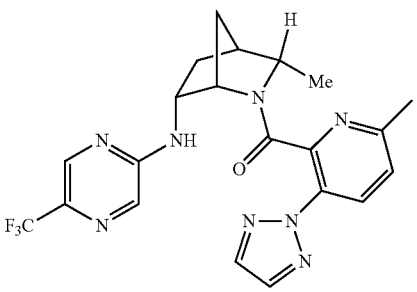 [SMILES: Cc1ccc(-n2nccn2)c(C(=O)N2C(C)C3CC(Nc4cnc(C(F)(F)F)cn4)C2C3)n1]

Enantiomeric purity (SFC/Whelk-O1): 100%. $R_t$: 4.79 min. MS (ESI): mass calcd. for $C_{21}H_{21}F_3N_8O$, 458.2. m/z found, 459.2 [M+H]$^+$. Analytical HPLC was obtained on a Agilent 1100 Series using a XBridge C18 column (5 μm, 100×4.6 mm), mobile phase of 10-100% ACN in 20 mM NH$_4$OH over 8 min and then hold at 100% ACN for 3 min, at a flow rate of 1 mL/min (Temperature=45° C.). $R_t$=6.56 min at 254 nm.

Example 7

(R/S)-(3-bromo-6-methylpyridin-2-yl)(3-methyl-6-((5-(trifluoromethyl)pyrazin-2-yl)amino)-2-azabicyclo[2.2.1]heptan-2-yl)methanone

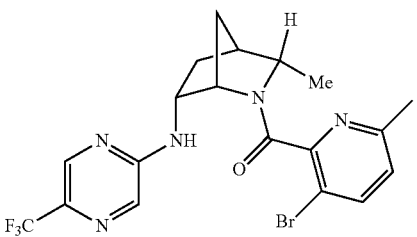 [SMILES: Cc1ccc(Br)c(C(=O)N2C(C)C3CC(Nc4cnc(C(F)(F)F)cn4)C2C3)n1]

The title compound was prepared analogous to Example 5 substituting intermediate A-1 with intermediate A-13. MS (ESI): mass calcd. for $C_{19}H_{19}BrF_3N_5O$, 469.1. m/z found, 470.1 [M+H]$^+$.

Examples 8-80 describe exemplary methods for the synthesis of certain compounds of Formula I wherein $R_{6B}$ is H and $R_{6A}$ is as described herein (exo adducts of compounds of Formula I).

Example 8

(R/S)-(3-fluoro-2-(pyrimidin-2-yl)phenyl)(3-methyl-6-((5-(trifluoromethyl)pyridin-2-yl)oxy)-2-azabicyclo[2.2.1]heptan-2-yl)methanone

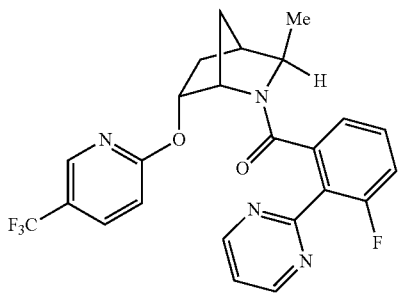 [SMILES: CC1C2CC(Oc3ccc(C(F)(F)F)cn3)C(C2)N1C(=O)c1cccc(F)c1-c1ncccn1]

The title compound was prepared analogous to Example 18 substituting intermediate A-6 with intermediate A-9. MS (ESI): mass calcd. for $C_{24}H_{20}F_4N_4O_2$, 472.2. m/z found, 473 [M+H]$^+$.

Example 9

(R/S)-(3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone

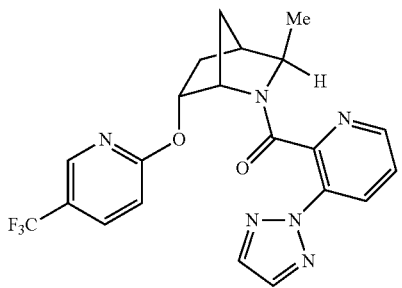 [SMILES: CC1C2CC(Oc3ccc(C(F)(F)F)cn3)C(C2)N1C(=O)c1ncccc1-n1nccn1]

The title compound was prepared analogous to Example 12 substituting intermediate A-30 with intermediate A-15. MS (ESI): mass calcd. for $C_{21}H_{19}F_3N_6O_2$, 444.2. m/z found, 445 [M+H]$^+$.

Example 10

(R/S)-(6-methyl-2-(2H-1,2,3-triazol-2-yl)pyridin-3-yl)(3-methyl-6-((5-(trifluoromethyl)pyridin-2-yl)oxy)-2-azabicyclo[2.2.1]heptan-2-yl)methanone

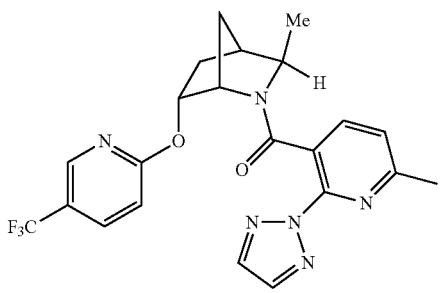 [SMILES: Cc1ccc(C(=O)N2C(C)C3CC(Oc4ccc(C(F)(F)F)cn4)C2C3)c(-n2nccn2)n1]

The title compound was prepared analogous to Example 12 substituting intermediate A-30 with intermediate A-3. MS (ESI): mass calcd. for $C_{22}H_{21}F_3N_6O_2$, 458.2. m/z found, 459 [M+H]$^+$. MP=267.4° C.

Example 11

(R/S)-(5-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone

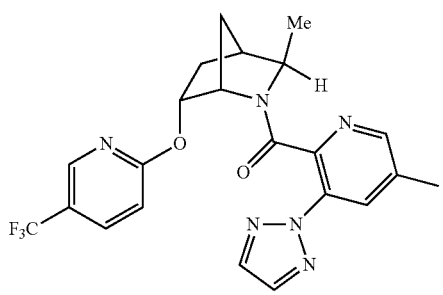 [SMILES: Cc1cnc(C(=O)N2C(C)C3CC(Oc4ccc(C(F)(F)F)cn4)C2C3)c(-n2nccn2)c1]

The title compound was prepared analogous to Example 12 substituting intermediate A-30 with intermediate A-19. MS (ESI): mass calcd. for $C_{22}H_{21}F_3N_6O_2$, 458.2. m/z found, 459 [M+H]$^+$. MP=189.7° C.

Example 12

(R/S)-(3-fluoro-2-(oxazol-2-yl)phenyl)(3-methyl-6-((5-(trifluoromethyl)pyridin-2-yl)oxy)-2-azabicyclo[2.2.1]heptan-2-yl)methanone

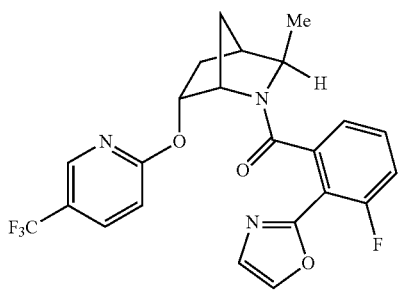 [SMILES: CC1C2CC(Oc3ccc(C(F)(F)F)cn3)C(C2)N1C(=O)c1cccc(F)c1-c1ncco1]

Step A: (R/S)-tert-butyl 3-methyl-6-((5-(trifluoromethyl)pyridin-2-yl)oxy)-2-azabicyclo[2.2.1]heptane-2-carboxylate. To a solution of intermediate B-14 (994 mg, 4.37 mmol) in THF (13 mL) at 0° C. was added NaH (262 mg, 6.56 mmol, 60% dispersion in mineral oil). After 30 min, 2-fluoro-5-(trifluoromethyl)pyridine (866 mg, 5.248 mmol) was added and the reaction was allowed to stir at rt overnight. The mixture was carefully quenched with H$_2$O, and the aqueous layer extracted with EtOAc. The combined organics were dried with MgSO$_4$, filtered and concentrated. Purification via silica gel chromatography (0-6% EtOAc in heptanes) gave the title compound (1.09 g, 2.94 mmol, 66%). MS (ESI) mass calcd. for $C_{18}H_{23}F_3N_2O_3$, 372.2. m/z found 373 [M+H]$^+$.

Step B: (R/S)-3-methyl-6-((5-(trifluoromethyl)pyridin-2-yl)oxy)-2-azabicyclo[2.2.1]heptane.xHCl. To the title compound of step A (1.09 g, 2.94 mmol) in dioxane (9 mL) was added 6M HCl in 2-propanol (2.9 mL) and the reaction was heated at 60° C. overnight after which the reaction was concentrated to give the title compound of step B (859 mg) which was used without further purification. MS (ESI) mass calcd. for $C_{13}H_{15}F_3N_2O$, 272.1. m/z found 273 [M+H]$^+$.

Step C: (R/S)-(3-fluoro-2-(oxazol-2-yl)phenyl)(3-methyl-6-((5-(trifluoromethyl)pyridin-2-yl)oxy)-2-azabicyclo[2.2.1]heptan-2-yl)methanone. To intermediate A-30 (64 mg, 0.31 mmol) in DMF (2 mL) was added DIPEA (0.13 mL, 0.75 mmol) and HATU (148 mg, 0.388 mmol). After 10 minutes the title compound of step B (80 mg) was added and the reaction was left to stir at rt overnight. Upon completion, the reaction was diluted with a saturated aqueous NaHCO$_3$ solution and the aqueous layer extracted with EtOAc (3×). The combined organics were dried with MgSO$_4$, filtered and concentrated. Purification via silica gel chromatography (0-60% EtOAc in heptanes) followed by trituration with DIPE gave the title compound. MS (ESI): mass calcd. for $C_{23}H_{19}F_4N_3O_3$, 461.1. m/z found, 462 [M+H]$^+$. MP=192.8° C.

Example 13

(R/S)-(3-ethoxy-6-methylpyridin-2-yl)(3-methyl-6-((5-(trifluoromethyl)pyridin-2-yl)oxy)-2-azabicyclo[2.2.1]heptan-2-yl)methanone

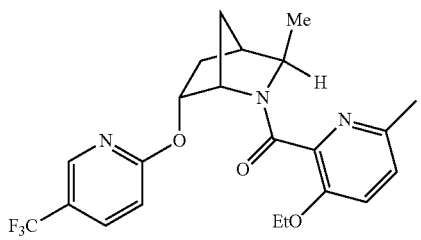

The title compound was prepared analogous to Example 12 substituting intermediate A-30 with intermediate A-8. MS (ESI): mass calcd. for $C_{22}H_{24}F_3N_3O_3$, 435.2. m/z found, 436 [M+H]$^+$.

Example 14

(R/S)-3-methyl-6-((5-(trifluoromethyl)pyridin-2-yl)oxy)-2-azabicyclo[2.2.1]heptan-2-yl)(3-(pyrimidin-2-yl)pyridin-2-yl)methanone

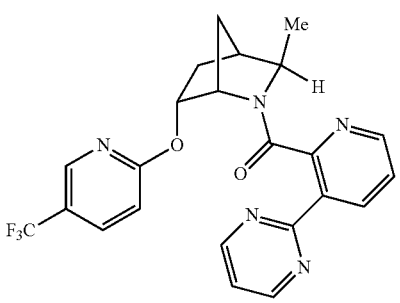 [SMILES: CC1C2CC(Oc3ccc(C(F)(F)F)cn3)C(C2)N1C(=O)c1ncccc1-c1ncccn1]

The title compound was prepared analogous to Example 12 substituting intermediate A-30 with intermediate A-28. MS (ESI): mass calcd. for $C_{23}H_{20}F_3N_5O_2$, 455.2. m/z found, 456 [M+H]$^+$.

Example 15

(R/S)-(3-methyl-6-((5-(trifluoromethyl)pyridin-2-yl)oxy)-2-azabicyclo[2.2.1]heptan-2-yl)(2-(pyrimidin-2-yl)phenyl)methanone

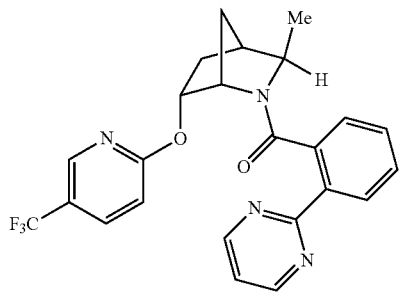 [SMILES: CC1C2CC(Oc3ccc(C(F)(F)F)cn3)C(C2)N1C(=O)c1ccccc1-c1ncccn1]

The title compound was prepared analogous to Example 18 substituting intermediate A-6 with intermediate A-4. MS (ESI): mass calcd. for $C_{24}H_{21}F_3N_4O_2$, 454.2. m/z found, 455 [M+H]$^+$.

Example 16

(R/S)-(6-methyl-3-(pyrimidin-2-yl)pyridin-2-yl)(3-methyl-6-((5-(trifluoromethyl)pyridin-2-yl)oxy)-2-azabicyclo[2.2.1]heptan-2-yl)methanone

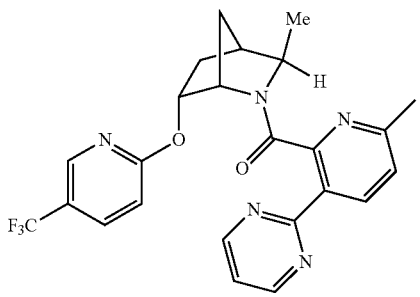

The title compound was prepared analogous to Example 12 substituting intermediate A-30 with intermediate A-27. MS (ESI): mass calcd. for $C_{24}H_{22}F_3N_5O_2$, 469.2. m/z found, 470.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.35 min at 280 nm.

Example 16 was subjected to Chiral SFC purification [Stationary phase: Chiralpak AD-H (5 μm 250×20 mm), Mobile phase of 20% EtOH: 80% CO$_2$] to provide the corresponding single enantiomers (Example 16A and Example 16B) were the absolute stereochemistry was not determined. The enantiomeric purity was confirmed by analytical SFC using a Chiralpak AD-H column (5 μm 150×4.6 mm), mobile phase of 20% EtOH (0.3% iPrNH$_2$): 80% CO$_2$, and a flow rate of 3 mL/min over 7 minutes (Temperature=35° C.).

Example 16A (6-methyl-3-(pyrimidin-2-yl)pyridin-2-yl)((1R*,3S*, 4S*,6S*)-3-methyl-6-((5-(trifluoromethyl)pyridin-2-yl)oxy)-2-azabicyclo[2.2.1]heptan-2-yl)methanone

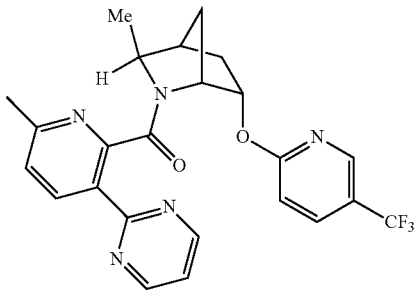 [SMILES: Cc1ccc(-c2ncccn2)c(C(=O)N2C(C)C3CC(Oc4ccc(C(F)(F)F)cn4)C2C3)n1]

Enantiomeric purity (SFC/Chiralpak AD-H): 100%. R$_t$: 1.80 min. MS (ESI): mass calcd. for C$_{24}$H$_{22}$F$_3$N$_5$O$_2$, 469.2. m/z found, 470.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.37 min at 280 nm. $^1$H NMR (500 MHz, Chloroform-d) δ 8.93-8.78 (m, 2H), 8.20-8.11 (m, 1H), 8.11-8.00 (m, 1H), 7.76-7.64 (m, 1H), 7.12-7.01 (m, 1H), 7.01-6.92 (m, 1H), 5.01-4.84 (m, 1H), 4.28-4.17 (m, 1H), 4.10-3.92 (m, 1H), 2.29 (s, 3H), 2.24-2.12 (m, 2H), 1.49-1.20 (m, 6H). *1H buried under solvent peak.

Example 16B (6-methyl-3-(pyrimidin-2-yl)pyridin-2-yl)((1S*,3R*, 4R*,6R*)-3-methyl-6-((5-(trifluoromethyl)pyridin-2-yl)oxy)-2-azabicyclo[2.2.1]heptan-2-yl)methanone

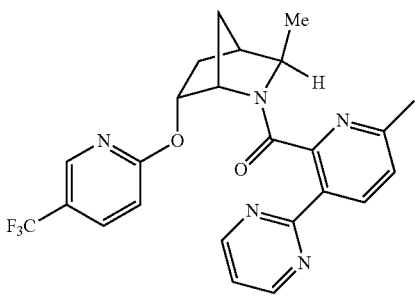 [SMILES: Cc1ccc(-c2ncccn2)c(C(=O)N2C(C)C3CC(Oc4ccc(C(F)(F)F)cn4)C2C3)n1]

Enantiomeric purity (SFC/Chiralpak AD-H): 100%. R$_t$: 4.11 min. MS (ESI mass calcd. for C$_{24}$H$_{22}$F$_3$N$_5$O$_2$, 469.2. m/z found, 470.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.43 min at 280 nm. $^1$H NMR (500 MHz, Chloroform-d) δ 8.81 (d, J=4.8 Hz, 2H), 8.14 (d, J=8.0 Hz, 1H), 8.07-8.02 (m, 1H), 7.68 (dd, J=8.7, 2.6 Hz, 1H), 7.26-7.23 (m, 1H), 7.03 (d, J=8.1 Hz, 1H), 7.00-6.93 (m, 1H), 5.02-4.85 (m, 1H), 4.26-4.17 (m, 1H), 4.05-3.91 (m, 1H), 2.28 (s, 3H), 2.24-2.13 (m, 2H), 1.40-1.38 (m, 3H), 1.37-1.23 (m, 3H).

Example 17

(R/S)-(4-fluoro-2-(pyrimidin-2-yl)phenyl)(-3-methyl-6-((5-(trifluoromethyl)pyridin-2-yl)oxy)-2-azabicyclo[2.2.1]heptan-2-yl)methanone

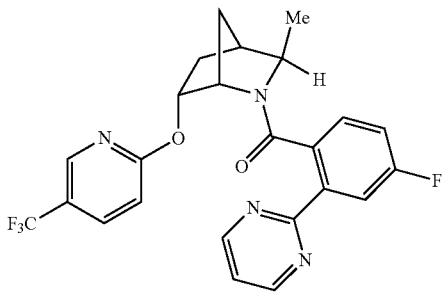 [SMILES: CC1C2CC(Oc3ccc(C(F)(F)F)cn3)C(C2)N1C(=O)c1ccc(F)cc1-c1ncccn1]

The title compound was prepared analogous to Example 18 substituting intermediate A-6 with intermediate A-32. MS (ESI): mass calcd. for C$_{24}$H$_{20}$F$_4$N$_4$O$_2$, 472.2. m/z found, 473.2 [M+H]$^+$. MP=163° C.

Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.04 min at 280 nm.

Example 17 was subjected to Chiral SFC purification [Stationary phase: Chiralpak AD-H (5 μm 250×20 mm), Mobile phase of 30% EtOH: 70% CO$_2$] to provide the corresponding single enantiomers (Example 17A and Example 17B) were the absolute stereochemistry was not determined. The enantiomeric purity was confirmed by analytical SFC using a Chiralpak AD-H column (5 μm 150×4.6 mm), mobile phase of 30% EtOH (0.3% iPrNH$_2$): 70% CO$_2$, and a flow rate of 3 mL/min over 7 minutes (Temperature=35° C.).

Example 17A (4-fluoro-2-(pyrimidin-2-yl)phenyl)((1R*,3S*,4S*, 6S*)-3-methyl-6-((5-(trifluoromethyl)pyridin-2-yl) oxy)-2-azabicyclo[2.2.1]heptan-2-yl)methanone

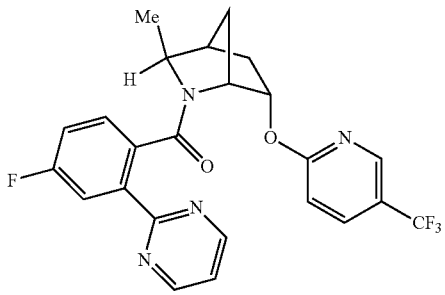 [SMILES: CC1C2CC(Oc3ccc(C(F)(F)F)cn3)C(C2)N1C(=O)c1ccc(F)cc1-c1ncccn1]

Enantiomeric purity (SFC/Chiralpak AD-H): 100%. R$_t$: 1.52 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 nm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.10 min at 280 nm. $^1$HNMR is in agreement with Example 17B.

Example 17B (4-fluoro-2-(pyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

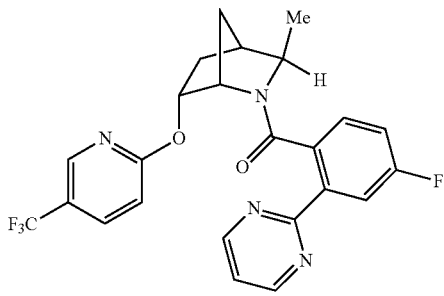 [SMILES: CC1C2CC(Oc3ccc(C(F)(F)F)cn3)C(C2)N1C(=O)c1ccc(F)cc1-c1ncccn1]

Enantiomeric purity (SFC/Chiralpak AD-H): 100%. R$_t$: 3.11 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 nm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.10 min at 280 nm. $^1$H NMR (500 MHz, Chloroform-d) δ 8.93-8.80 (m, 2H), 8.17-8.00 (m, 1H), 7.77 (dd, J=8.7, 2.6 Hz, 1H), 7.69 (dd, J=9.6, 2.7 Hz, 1H), 7.33-7.27 (m, 1H), 7.24-7.12 (m, 1H), 6.80 (d, J=8.7 Hz, 1H), 6.66-6.55 (m, 1H), 5.03-4.89 (m, 1H), 4.06-3.85 (m, 2H), 2.23-2.10 (m, 2H), 1.44-1.29 (m, 4H), 1.24-1.06 (m, 2H).

Example 18

(R/S)-(5-fluoro-2-(pyrimidin-2-yl)phenyl)(–3-methyl-6-((5-(trifluoromethyl)pyridin-2-yl)oxy)-2-azabicyclo[2.2.1]heptan-2-yl)methanone

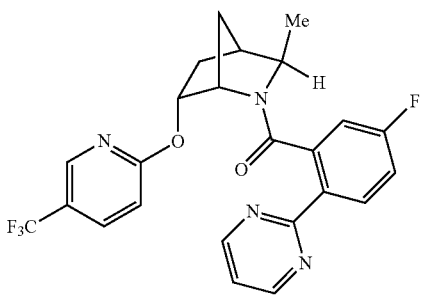 [SMILES: CC1C2CC(Oc3ccc(C(F)(F)F)cn3)C(C2)N1C(=O)c1cc(F)ccc1-c1ncccn1]

The title compound was prepared analogous to Example 12 substituting intermediate A-30 with intermediate A-6 and carrying out an additional cross coupling step (Step D).

Step D: To a sealable tube containing (R/S)-(5-fluoro-2-iodophenyl)(3-methyl-6-((5-(trifluoromethyl)pyridin-2-yl)oxy)-2-azabicyclo[2.2.1]heptan-2-yl)methanone (70 mg, 0.135 mmol) and CuI (1.9 mg, 0.01 mmol) in DME (2 mL) was bubbled N$_2$ gas for 5 minutes. Intermediate C-1 (70 mg, 0.19 mmol), and Pd(PPh$_3$)$_4$ (12 mg, 0.01 mmol) were then added, the vessel sealed, and heated to 120° C. After 6 hours the reaction was concentrated and the residual purified via silica gel chromatography (0-40% EtOAc in heptane) to give the title compound (24 mg). MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.98 min at 280 nm.

Example 18 was subjected to Chiral SFC purification [Stationary phase: Chiralpak AD-H (5 μm 250×20 mm), Mobile phase of 25% MeOH: 75% CO$_2$] to provide the corresponding single enantiomers (Example 18A and Example 18B) were the absolute stereochemistry was not determined. The enantiomeric purity was confirmed by analytical SFC using a Chiralpak AD-H column (5 μm 150×4.6 mm), mobile phase of 25% MeOH (0.3% iPrNH$_2$): 75% CO$_2$, and a flow rate of 3 mL/min over 7 minutes (Temperature=35° C.).

Example 18A (5-fluoro-2-(pyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone

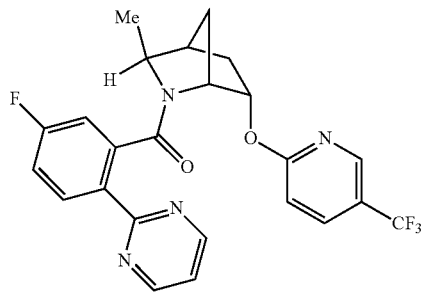 [SMILES: CC1C2CC(Oc3ccc(C(F)(F)F)cn3)C(C2)N1C(=O)c1cc(F)ccc1-c1ncccn1]

Enantiomeric purity (SFC/Chiralpak AD-H): 100%. R$_t$: 1.22 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.04 min at 280 nm. $^1$H NMR is in agreement with Example 18B.

Example 18B (5-fluoro-2-(pyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

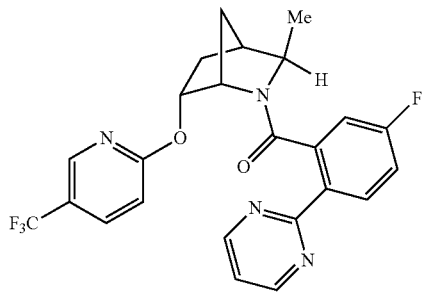 [SMILES: CC1C2CC(Oc3ccc(C(F)(F)F)cn3)C(C2)N1C(=O)c1cc(F)ccc1-c1ncccn1]

Enantiomeric purity (SFC/Chiralpak AD-H): 100%. R$_t$: 4.47 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.04 min at 280 nm. $^1$H NMR (500 MHz, Chloroform-d) δ 8.84-8.76 (m, 2H), 8.09-8.03 (m, 1H), 7.99 (dd, J=8.9, 5.7 Hz, 1H), 7.79 (dd, J=8.6, 2.6 Hz, 1H), 7.25-7.20 (m, 1H), 6.97-6.86 (m, 2H), 6.80 (d, J=8.7 Hz, 1H), 5.01-4.84 (m, 1H), 3.99-3.89 (m, 2H), 2.22-2.11 (m, 2H), 1.41-1.31 (m, 4H), 1.28-1.12 (m, 2H).

Example 19

(R/S)-(2-(5-fluoropyrimidin-2-yl)phenyl)(3-methyl-6-((5-(trifluoromethyl)pyridin-2-yl)oxy)-2-azabicyclo[2.2.1]heptan-2-yl)methanone

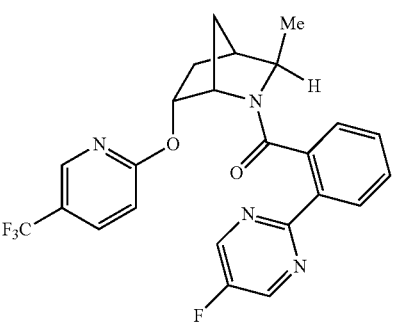 [SMILES: CC1C2CC(Oc3ccc(C(F)(F)F)cn3)C(C2)N1C(=O)c1ccccc1-c1ncc(F)cn1]

The title compound was prepared analogous to Example 18 substituting intermediate A-6 with intermediate A-4 and intermediate C-1 with intermediate C-2. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.31 min at 280 nm.

Example 19 was subjected to Chiral SFC purification [Stationary phase: Chiralpak AD-H (5 μm 250×20 mm), Mobile phase of 30% EtOH: 70% CO$_2$] to provide the corresponding single enantiomers (Example 19A and Example 19B) were the absolute stereochemistry was not determined. The enantiomeric purity was confirmed by analytical SFC using a Chiralpak AD-H column (5 μm 150×4.6 mm), mobile phase of 30% EtOH (0.3% iPrNH$_2$): 70% CO$_2$, and a flow rate of 3 mL/min over 7 minutes (Temperature=35° C.).

Example 19A (2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone

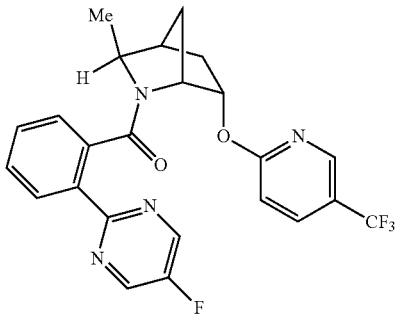 [SMILES: CC1C2CC(Oc3ccc(C(F)(F)F)cn3)C(C2)N1C(=O)c1ccccc1-c1ncc(F)cn1]

Enantiomeric purity (SFC/Chiralpak AD-H): 100%. R$_t$: 1.30 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.36 min at 280 nm. $^1$H NMR (500 MHz, Chloroform-d) δ 8.67 (d, J=1.2 Hz, 2H), 8.04-7.97 (m, 1H), 7.93-7.86 (m, 1H), 7.78-7.71 (m, 1H), 7.30-7.23 (m, 1H), 7.21-7.12 (m, 1H), 6.92-6.85 (m, 1H), 6.81 (d, J=8.7 Hz, 1H), 4.97-4.87 (m, 1H), 4.01-3.87 (m, 2H), 2.22-2.09 (m, 2H), 1.42-1.30 (m, 4H), 1.24 (d, J=9.8 Hz, 1H), 1.19-1.10 (m, 1H).

Example 19B (2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

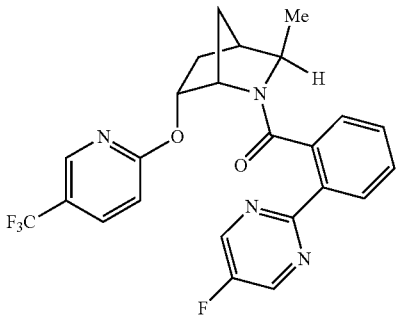

Enantiomeric purity (SFC/Chiralpak AD-H): 100%. R$_t$: 5.19 min. MS (ESI): mass calcd. for C$_{24}$H$_{20}$F$_4$N$_4$O$_2$, 472.2. m/z found, 473.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.37 min at 280 nm. $^1$H NMR is in agreement with Example 19A.

Example 20

(R/S)-(3-fluoro-2-(5-fluoropyrimidin-2-yl)phenyl)(3-methyl-6-((5-(trifluoromethyl)pyridin-2-yl)oxy)-2-azabicyclo[2.2.1]heptan-2-yl)methanone

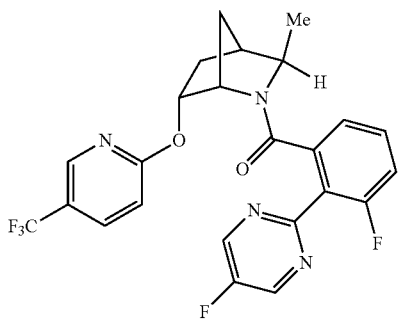 [SMILES: CC1C2CC(Oc3ccc(C(F)(F)F)cn3)C(C2)N1C(=O)c1cccc(F)c1-c1ncc(F)cn1]

The title compound was prepared analogous to Example 18 substituting intermediate A-6 with intermediate A-9 and intermediate C-1 with intermediate C-2. MS (ESI): mass calcd. for $C_{24}H_{19}F_5N_4O_2$, 490.1. m/z found, 491.2 [M+H]$^+$. MP=162° C. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.25 min at 280 nm.

Example 20 was subjected to Chiral SFC purification [Stationary phase: Chiralpak AD-H (5 μm 250×20 mm), Mobile phase of 25% MeOH: 75% CO$_2$] to provide the corresponding single enantiomers (Example 20A and Example 20B) were the absolute stereochemistry was not determined. The enantiomeric purity was confirmed by analytical SFC using a Chiralpak AD-H column (5 μm 150×4.6 mm), mobile phase of 25% MeOH (0.3% iPrNH$_2$): 75% CO$_2$, and a flow rate of 3 mL/min over 7 minutes (Temperature=35° C.).

Example 20A (3-fluoro-2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone

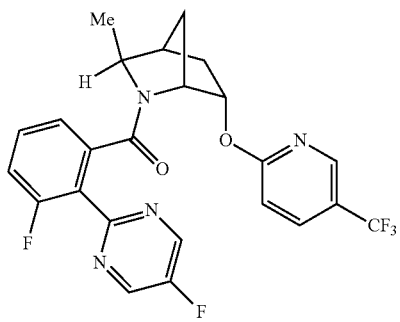 [SMILES: CC1C2CC(Oc3ccc(C(F)(F)F)cn3)C(C2)N1C(=O)c1cccc(F)c1-c1ncc(F)cn1]

Enantiomeric purity (SFC/Chiralpak AD-H): 100%. R$_t$: 1.01 min. MS (ESI): mass calcd. for $C_{24}H_{19}F_5N_4O_2$, 490.1. m/z found, 491.1 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.30 min at 280 nm. $^1$H NMR (500 MHz, Chloroform-d) δ 8.74 (s, 2H), 8.12-8.04 (m, 1H), 7.76 (dd, J=8.8, 2.6 Hz, 1H), 7.08-7.00 (m, 1H), 6.98 (dd, J=7.7, 1.4 Hz, 1H), 6.96-6.87 (m, 1H), 6.82 (d, J=8.7 Hz, 1H), 5.01-4.93 (m, 1H), 4.13-4.06 (m, 1H), 3.87-3.80 (m, 1H), 2.21-2.12 (m, 1H), 2.11-2.06 (m, 1H), 1.34-1.26 (m, 2H), 1.01 (d, J=6.4 Hz, 3H), 0.96-0.89 (m, 1H).

Example 20B (3-fluoro-2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

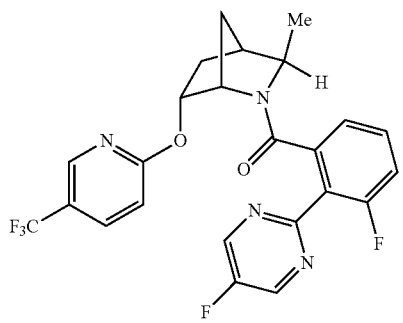 [SMILES: CC1C2CC(Oc3ccc(C(F)(F)F)cn3)C(C2)N1C(=O)c1cccc(F)c1-c1ncc(F)cn1]

Enantiomeric purity (SFC/Chiralpak AD-H): 100%. R$_t$: 4.02 min. MS (ESI): mass calcd. for $C_{24}H_{19}F_5N_4O_2$, 490.1. m/z found, 491.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=7.28 min at 280 nm. $^1$H NMR is in agreement with Example 20A.

Example 21

(R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone

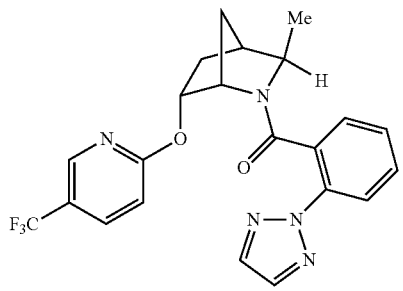 [SMILES: CC1C2CC(Oc3ccc(C(F)(F)F)cn3)C(C2)N1C(=O)c1ccccc1-n1nccn1]

The title compound was prepared analogous to Example 12 substituting intermediate A-30 with intermediate A-1.

MS (ESI): mass calcd. for $C_{22}H_{20}F_3N_5O_2$, 443.2. m/z found, 444.2 [M+H]+. ¹H NMR (500 MHz, Chloroform-d) δ 8.03-7.95 (m, 1H), 7.84 (s, 2H), 7.75 (dd, J=8.7, 2.5 Hz, 1H), 7.66 (d, J=8.2, 1.2 Hz, 1H), 7.30 (td, J=7.8, 1.6 Hz, 1H), 7.18 (dd, J=7.7, 1.5 Hz, 1H), 6.84 (t, J=7.6 Hz, 1H), 6.79 (d, J=8.6 Hz, 1H), 4.96-4.86 (m, 1H), 3.93-3.79 (m, 2H), 2.23-2.08 (m, 2H), 1.37-1.32 (buried m, 1H), 1.31 (d, J=6.3 Hz, 3H), 1.23 (br. s, 2H).

Example 21 was subjected to Chiral SFC purification [Stationary phase: Chiralpak AD-H (5 µm 250×20 mm), Mobile phase of 30% MeOH (0.3% iPrNH₂): 70% CO₂] to provide the corresponding single enantiomers (Example 21A and Example 21B) were the absolute stereochemistry was not determined. The enantiomeric purity was confirmed by analytical SFC using a Chiralpak AD-H column (5 µm 150×4.6 mm), mobile phase of 30% MeOH (0.3% iPrNH₂): 70% CO₂, and a flow rate of 3 mL/min over 7 minutes (Temperature=35° C.).

Example 21A (2-(2H-1,2,3-triazol-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone

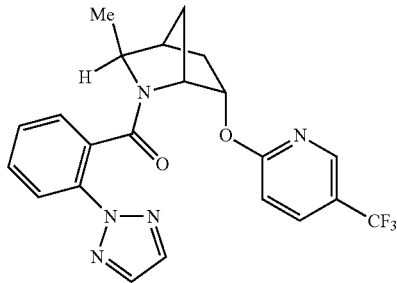 [SMILES: CC1C2CC(Oc3ccc(C(F)(F)F)cn3)C(C2)N1C(=O)c1ccccc1-n1nccn1]

Enantiomeric purity (SFC/Chiralpak AD-H): >97%. $R_t$: 1.07 min. MS (ESI): mass calcd. for $C_{22}H_{20}F_3N_5O_2$, 443.2. m/z found, 444.2 [M+H]+. ¹H NMR (500 MHz, Chloroform-d) δ 8.03-7.98 (m, 1H), 7.84 (s, 2H), 7.75 (dd, J=8.7, 2.5 Hz, 1H), 7.66 (dd, J=8.1, 1.1 Hz, 1H), 7.34-7.27 (m, 1H), 7.18 (dd, J=7.7, 1.5 Hz, 1H), 6.84 (td, J=7.6, 1.2 Hz, 1H), 6.79 (d, J=8.7 Hz, 1H), 4.96-4.83 (m, 1H), 3.91-3.82 (m, 2H), 2.24-2.08 (m, 2H), 1.37-1.33 (m, 1H), 1.31 (d, J=6.3 Hz, 3H), 1.25-1.21 (m, 2H).

Example 21B (2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

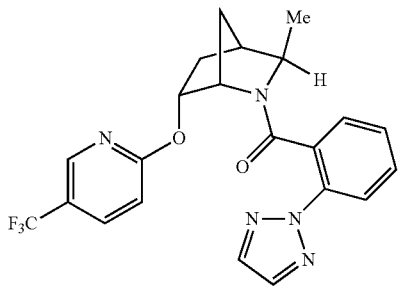

Enantiomeric purity (SFC/Chiralpak AD-H): >98%. $R_t$: 2.15 min. MS (ESI): mass calcd. for $C_{22}H_{20}F_3N_5O_2$, 443.2. m/z found, 444.2 [M+H]+. ¹H NMR (500 MHz, Chloroform-d) δ 8.02-7.97 (m, 1H), 7.84 (s, 2H), 7.75 (dd, J=8.7, 2.6 Hz, 1H), 7.66 (dd, J=8.1, 1.1 Hz, 1H), 7.33-7.27 (m, 1H), 7.18 (dd, J=7.7, 1.5 Hz, 1H), 6.84 (td, J=7.6, 1.2 Hz, 1H), 6.79 (d, J=8.7 Hz, 1H), 4.99-4.84 (m, 1H), 3.97-3.82 (m, 2H), 2.22-2.10 (m, 2H), 1.37-1.32 (m, 1H), 1.31 (d, J=6.3 Hz, 3H), 1.25-1.21 (m, 2H).

Example 22

(R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone

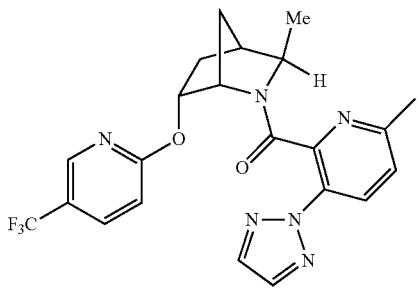 [SMILES: Cc1ccc(-n2nccn2)c(C(=O)N2C(C)C3CC(Oc4ccc(C(F)(F)F)cn4)C2C3)n1]

The title compound was prepared analogous to Example 12 substituting intermediate A-30 with intermediate A-26. MS (ESI): mass calcd. for $C_{22}H_{21}F_3N_6O_2$, 458.2. m/z found, 459.2 [M+H]+. ¹H NMR (500 MHz, Chloroform-d) δ 8.08-8.01 (m, 1H), 7.89-7.83 (m, 3H), 7.68 (dd, J=8.8, 2.5 Hz, 1H), 7.08 (d, J=8.3 Hz, 1H), 6.95-6.88 (m, 1H), 4.96-4.87 (m, 1H), 4.13-4.08 (m, 1H), 4.01-3.91 (m, 1H), 2.31 (s, 3H), 2.24-2.13 (m, 2H), 1.53-1.43 (m, 1H), 1.41-1.36 (m, 1H), 1.35 (d, J=6.4 Hz, 3H), 1.34-1.31 (m, 1H).

Example 22 was subjected to Chiral SFC purification [Stationary phase: Chiralpak AD-H (5 µm 250×20 mm), Mobile phase of 20% EtOH (0.3% iPrNH₂): 80% CO₂] to provide the corresponding single enantiomers (Example 22A and Example 22B) were the absolute stereochemistry was not determined. The enantiomeric purity was confirmed by analytical SFC using a Chiralpak AD-H column (5 µm 150×4.6 mm), mobile phase of 15% EtOH (0.3% iPrNH₂): 85% CO₂, and a flow rate of 3 mL/min over 7 minutes (Temperature=35° C.).

Example 22A (6-methyl-3-(2H-1,2,3-triazol-2-yl)pyridin-2-yl)((1R*,3S*,4S*,6S*)-3-methyl-6-((5-(trifluoromethyl)pyridin-2-yl)oxy)-2-azabicyclo[2.2.1]heptan-2-yl)methanone

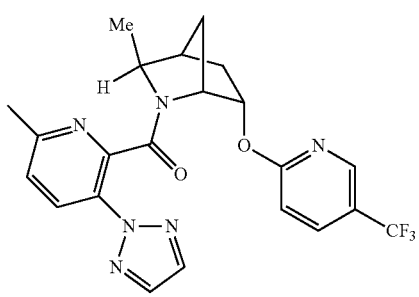 [SMILES: Cc1ccc(-n2nccn2)c(C(=O)N2C(C)C3CC(Oc4ccc(C(F)(F)F)cn4)C2C3)n1]

Enantiomeric purity (SFC/Chiralpak AD-H): 100%. R$_t$: 2.04 min. MS (ESI): mass calcd. for C$_{22}$H$_{21}$F$_3$N$_6$O$_2$, 458.2. m/z found, 459.2 [M+H]$^+$. $^1$H NMR (500 MHz, Chloroform-d) δ 8.08-8.00 (m, 1H), 7.88-7.84 (m, 3H), 7.69 (dd, J=8.7, 2.5 Hz, 1H), 7.08 (d, J=8.3 Hz, 1H), 6.96-6.89 (m, 1H), 4.98-4.88 (m, 1H), 4.14-4.08 (m, 1H), 4.00-3.89 (m, 1H), 2.31 (s, 3H), 2.25-2.14 (m, 2H), 1.52-1.43 (m, 1H), 1.41-1.30 (m, 5H).

Example 22B (6-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone

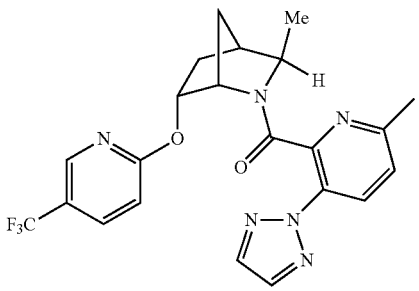 [SMILES: Cc1ccc(-n2nccn2)c(C(=O)N2C(C)C3CC(Oc4ccc(C(F)(F)F)cn4)C2C3)n1]

Enantiomeric purity (SFC/Chiralpak AD-H): 98.79%. R$_t$: 4.19 min. MS (ESI): mass calcd. for C$_{22}$H$_{21}$F$_3$N$_6$O$_2$, 458.2. m/z found, 459.2 [M+H]$^+$. $^1$H NMR (500 MHz, Chloroform-d) δ 8.06-8.02 (m, 1H), 7.89-7.83 (m, 3H), 7.69 (dd, J=8.7, 2.5 Hz, 1H), 7.08 (d, J=8.3 Hz, 1H), 6.95-6.89 (m, 1H), 5.02-4.86 (m, 1H), 4.16-4.08 (m, 1H), 4.01-3.90 (m, 1H), 2.31 (s, 3H), 2.25-2.13 (m, 2H), 1.51-1.44 (m, 1H), 1.44-1.29 (m, 5H).

Example 23

(3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone

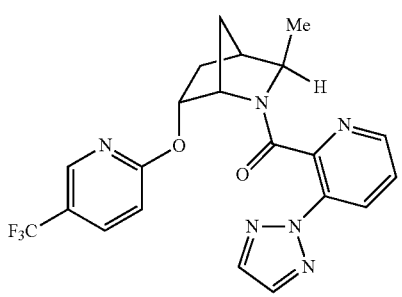

The title compound was prepared analogous to Example 28 substituting intermediate A-12 with intermediate A-15. MS (ESI): mass calcd. for C$_{21}$H$_{19}$F$_3$N$_6$O$_2$, 444.2. m/z found, 445.2 [M+H]$^+$. $^1$H NMR (400 MHz, Chloroform-d) δ 8.02 (dd, J=8.2, 1.5 Hz, 1H), 8.00-7.94 (m, 2H), 7.87 (s, 2H), 7.70 (dd, J=8.7, 2.6 Hz, 1H), 7.20 (dd, J=8.2, 4.7 Hz, 1H), 6.96-6.88 (m, 1H), 5.04-4.92 (m, 1H), 4.15-4.07 (m, 1H), 4.05-3.94 (m, 1H), 2.27-2.14 (m, 2H), 1.56-1.53 (m, 1H), 1.51-1.42 (m, 1H), 1.43-1.34 (m, 4H).

Example 24

(5-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone

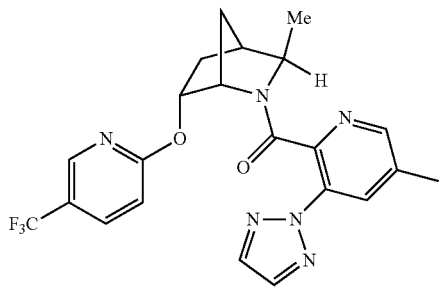

The title compound was prepared analogous to Example 28 substituting intermediate A-12 with intermediate A-19. MS (ESI): mass calcd. for C$_{22}$H$_{21}$F$_3$N$_6$O$_2$, 458.2. m/z found, 459.2 [M+H]+. $^1$H NMR (400 MHz, Chloroform-d) δ 7.99-7.93 (m, 1H), 7.85 (s, 2H), 7.84-7.79 (m, 1H), 7.79-7.74 (m, 1H), 7.70 (dd, J=8.8, 2.6 Hz, 1H), 6.96-6.88 (m, 1H), 5.03-4.87 (m, 1H), 4.17-4.06 (m, 1H), 4.04-3.90 (m, 1H), 2.28 (s, 3H), 2.26-2.12 (m, 2H), 1.56-1.50 (m, 1H), 1.49-1.42 (m, 1H), 1.41-1.33 (m, 4H).

Example 25

(6-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone

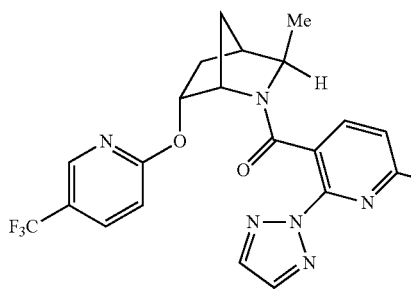

The title compound was prepared analogous to Example 28 substituting intermediate A-12 with intermediate A-3. MS (ESI): mass calcd. for C$_{22}$H$_{21}$F$_3$N$_6$O$_2$, 458.2. m/z found, 459.2 [M+H]$^+$. $^1$H NMR (400 MHz, Chloroform-d) δ 8.09-7.99 (m, 1H), 7.90 (s, 2H), 7.76 (dd, J=8.7, 2.5 Hz, 1H), 7.43 (d, J=7.7 Hz, 1H), 6.84-6.74 (m, 1H), 6.62 (d, J=7.8 Hz, 1H), 4.95-4.82 (m, 1H), 3.94-3.87 (m, 1H), 3.87-3.84 (m, 1H), 2.54 (s, 3H), 2.21-2.10 (m, 2H), 1.39-1.30 (m, 4H), 1.30-1.22 (m, 2H).

Example 26

(5-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone

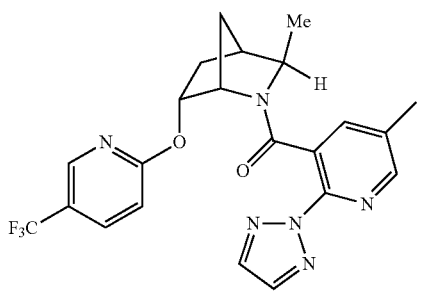 [SMILES: Cc1cnc(-n2nccn2)c(C(=O)N2C(C)C3CC(Oc4ccc(C(F)(F)F)cn4)C2C3)c1]

The title compound was prepared analogous to Example 28 substituting intermediate A-12 with intermediate A-25. MS (ESI): mass calcd. for $C_{22}H_{21}F_3N_6O_2$, 458.2. m/z found, 459.2 [M+H]$^+$. $^1$H NMR (400 MHz, Chloroform-d) δ 8.27-8.19 (m, 1H), 8.14-8.07 (m, 1H), 7.90 (s, 2H), 7.77 (dd, J=8.7, 2.7 Hz, 1H), 7.52-7.45 (m, 1H), 6.81-6.71 (m, 1H), 4.99-4.85 (m, 1H), 3.97-3.89 (m, 1H), 3.89-3.84 (m, 1H), 2.24-2.11 (m, 2H), 2.05 (s, 3H), 1.43-1.34 (m, 5H), 1.36-1.24 (m, 1H).

Example 27

(3-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

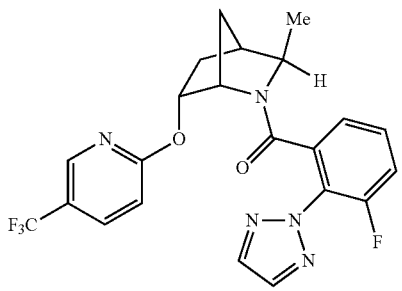

The title compound was prepared analogous to Example 28 substituting intermediate A-12 with intermediate A-16. MS (ESI): mass calcd. for $C_{22}H_{19}F_4N_5O_2$, 461.1. m/z found, 462.2 [M+H]$^+$. $^1$H NMR (400 MHz, Chloroform-d) δ 8.13-8.06 (m, 1H), 7.90 (s, 2H), 7.77 (dd, J=8.7, 2.6 Hz, 1H), 7.17-7.09 (m, 1H), 7.04-6.93 (m, 2H), 6.86-6.78 (m, 1H), 4.98 (dt, J=10.1, 3.3 Hz, 1H), 4.10-4.02 (m, 1H), 3.86-3.76 (m, 1H), 2.23-2.13 (m, 1H), 2.13-2.09 (m, 1H), 1.36-1.25 (m, 2H), 1.26-1.16 (m, 1H), 1.05 (d, J=6.3 Hz, 3H).

Example 28

(4-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

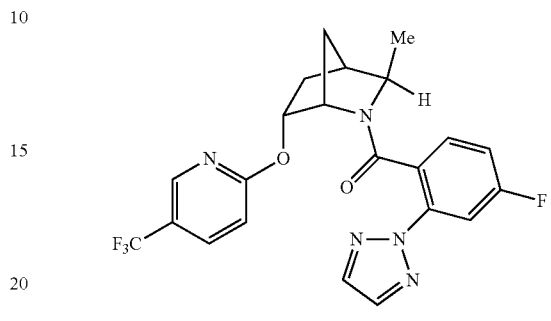

Step A: (1S*,3R*,4R*,6R*)-tert-butyl 3-methyl-6-((5-(trifluoromethyl)pyridin-2-yl)oxy)-2-azabicyclo[2.2.1]heptane-2-carboxylate. To Intermediate B-14A (421 mg, 1.85 mmol) and 2-chloro-5-(trifluoromethyl)pyridine (538 mg, 2.96 mmol) dissolved in DMF (5 mL) was added NaH (119 mg, 2.96 mmol, 60% dispersion in mineral oil). After addition of NaH the sides of the flask were rinsed with additional DMF (3.0 mL) and the reaction left to stir at room temperature. After stirring for 2.75 h, the mixture was carefully quenched with H$_2$O, and the aqueous layer extracted with EtOAc (3×). The combined organics were washed with 5% LiCl solution, brine, dried with MgSO$_4$, filtered and concentrated. Purification via silica gel chromatography (0-20% EtOAc in hexanes) gave the title compound (473 mg). MS (ESI) mass calcd. for $C_{18}H_{23}F_3N_2O_3$, 372.2; m/z found 373.2 [M+H]$^+$.

Step B: (1S*,3R*,4R*,6R*)-3-methyl-6-((5-(trifluoromethyl)pyridin-2-yl)oxy)-2-azabicyclo[2.2.1]heptane.xHCl. To the title compound of step A (473 mg) in EtOAc (1 mL) was added 4M HCl in dioxane (5 mL). After 1 h the reaction was concentrated to give the title compound of step B (416 mg) which was used without further purification. MS (ESI) mass calcd. for $C_{13}H_{15}F_3N_2O$, 272.1. m/z found 273.2 [M+H]$^+$.

Step C: (4-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone. To the title compound of step B (30 mg) and intermediate A-12 (22 mg, 0.11 mmol) in DMF (0.4 mL) was added DIPEA (0.1 mL, 0.6 mmol) and HATU (41 mg, 0.11 mmol). Upon completion, the reaction was diluted with H$_2$O and the aqueous extracted with EtOAc (3×). The combined organics were concentrated, dissolved in MeOH, filtered, and purified using Agilent Prep Method X to give the title compound (30 mg). MS (ESI) mass calcd. for $C_{22}H_{19}F_4N_5O_2$, 461.1. m/z found, 462.2 [M+H]$^+$. $^1$H NMR (400 MHz, Chloroform-d) δ 8.12-8.03 (m, 1H), 7.85 (s, 2H), 7.77 (dd, J=8.8, 2.5 Hz, 1H), 7.45 (dd, J=9.2, 2.5 Hz, 1H), 7.18 (dd, J=8.6, 5.9 Hz, 1H), 6.79 (d, J=8.7 Hz, 1H), 6.61-6.49 (m, 1H), 4.99-4.88 (m, 1H), 3.95-3.86 (m, 1H), 3.83 (s, 1H), 2.28-2.09 (m, 2H), 1.39-1.28 (m, 4H), 1.29-1.20 (m, 2H).

Example 29

(5-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

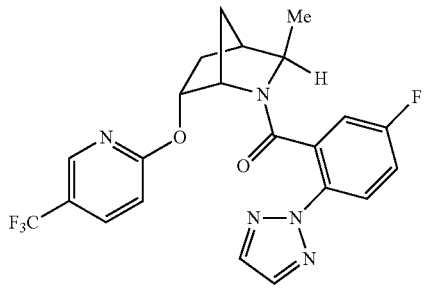 [SMILES: CC1C2CC(Oc3ccc(C(F)(F)F)cn3)C(C2)N1C(=O)c1cc(F)ccc1-n1nccn1]

The title compound was prepared analogous to Example 28 substituting intermediate A-12 with intermediate A-10. MS (ESI): mass calcd. for $C_{22}H_{19}F_4N_5O_2$, 461.1. m/z found, 462.2 [M+H]+. 1H NMR (400 MHz, Chloroform-d) δ 8.11-7.99 (m, 1H), 7.83 (s, 2H), 7.80 (dd, J=8.8, 2.5 Hz, 1H), 7.64 (dd, J=8.9, 4.8 Hz, 1H), 7.02-6.93 (m, 1H), 6.90 (dd, J=8.2, 2.9 Hz, 1H), 6.79 (d, J=8.7 Hz, 1H), 5.00-4.88 (m, 1H), 3.96-3.81 (m, 2H), 2.25-2.08 (m, 2H), 1.44-1.20 (m, 6H).

Example 30

(2-fluoro-6-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

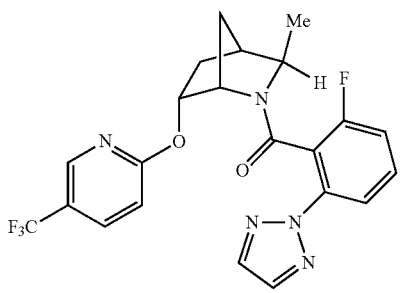

The title compound was prepared analogous to Example 28 substituting intermediate A-12 with intermediate A-11. MS (ESI): mass calcd. for $C_{22}H_{19}F_4N_5O_2$, 461.1. m/z found, 462.2 [M+H]+. 1H NMR (400 MHz, Chloroform-d) δ 8.12-8.05 (m, 1H), 7.86 (s, 2H), 7.80-7.73 (m, 1H), 7.58 (dt, J=8.3, 1.0 Hz, 1H), 7.34-7.27 (m, 1H), 6.93 (d, J=8.5 Hz, 1H), 6.71 (td, J=8.6, 1.1 Hz, 1H), 5.01-4.88 (m, 1H), 3.98-3.88 (m, 1H), 3.83-3.75 (m, 1H), 2.26-2.13 (m, 2H), 1.36 (d, J=6.3 Hz, 3H), 1.34-1.28 (m, 1H), 1.27-1.23 (m, 2H).

Example 31

(4-methoxy-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone

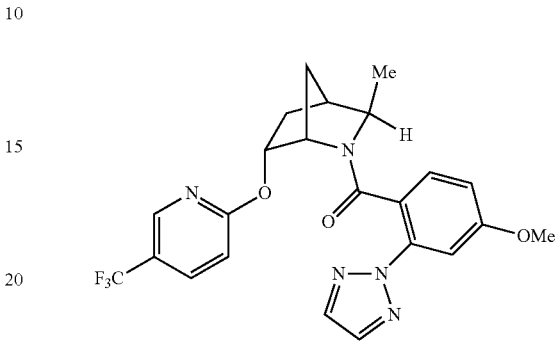

The title compound was prepared analogous to Example 28 substituting intermediate A-12 with intermediate A-5. MS (ESI): mass calcd. for $C_{23}H_{22}F_3N_5O_3$, 473.2. m/z found, 474.2 [M+H]+. 1H NMR (400 MHz, Chloroform-d) δ 8.11-8.03 (m, 1H), 7.83 (s, 2H), 7.75 (dd, J=8.7, 2.6 Hz, 1H), 7.18 (d, J=2.5 Hz, 1H), 7.12 (d, J=8.5 Hz, 1H), 6.84-6.74 (m, 1H), 6.40 (dd, J=8.6, 2.5 Hz, 1H), 4.96-4.87 (m, 1H), 3.93-3.82 (m, 2H), 3.78 (s, 3H), 2.24-2.08 (m, 2H), 1.36-1.26 (m, 4H), 1.24-1.16 (m, 2H).

Example 32

((1S*,3R*,4R*,6R*)-3-methyl-6-((5-(trifluoromethyl)pyridin-2-yl)oxy)-2-azabicyclo[2.2.1]heptan-2-yl)(3-(pyrimidin-2-yl)pyridin-2-yl)methanone

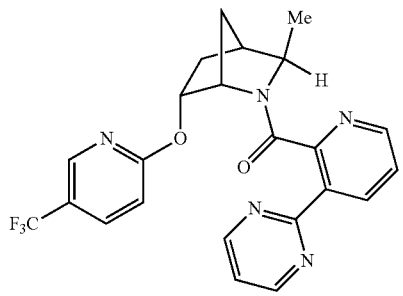

The title compound was prepared analogous to Example 28 substituting intermediate A-12 with intermediate A-28 and using the alternative coupling conditions for Step C reported below.

Step C: ((1S*,3R*,4R*,6R*)-3-methyl-6-((5-(trifluoromethyl)pyridin-2-yl)oxy)-2-azabicyclo[2.2.1]heptan-2-yl)(3-

(pyrimidin-2-yl)pyridin-2-yl)methanone. To the free base of the title compound of step B (30 mg) dissolved in DCM (1.1 mL) was added DIPEA (0.1 mL, 0.6 mmol), and intermediate A-28 (27 mg, 0.13 mmol). T$_3$P (50% solution in DMF, 0.2 mL, 0.3 mmol) was then added dropwise and the reaction heated to 45° C. Upon completion, the reaction concentrated, dissolved in MeOH, filtered, and purified using Agilent Prep Method X to give the title compound (11 mg).

MS (ESI): mass calcd. for C$_{23}$H$_{20}$F$_3$N$_5$O$_2$, 455.2. m/z found, 456.2 [M+H]$^+$. $^1$H NMR (400 MHz, Chloroform-d) δ 8.82 (d, J=4.9 Hz, 2H), 8.27 (dd, J=7.9, 1.7 Hz, 1H), 7.99-7.89 (m, 2H), 7.71 (dd, J=8.8, 2.6 Hz, 1H), 7.30-7.27 (m, 1H), 7.14 (dd, J=8.0, 4.7 Hz, 1H), 6.98 (d, J=8.7 Hz, 1H), 5.05-4.90 (m, 1H), 4.19-4.12 (m, 1H), 4.08-3.95 (m, 1H), 2.27-2.11 (m, 2H), 1.52-1.42 (m, 1H), 1.40 (d, J=6.2 Hz, 4H), 1.37-1.27 (m, 1H).

Example 33

((1S*,3R*,4R*,6R*)-3-methyl-6-((5-(trifluoromethyl)pyridin-2-yl)oxy)-2-azabicyclo[2.2.1]heptan-2-yl)(2-(pyrimidin-2-yl)phenyl)methanone

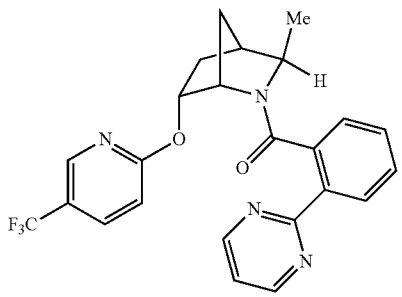

The title compound was prepared analogous to Example 28 substituting intermediate A-12 with intermediate A-4 and carrying out an additional cross coupling step (Step D).

Step D: A microwave vial containing (2-iodophenyl)((1S*,3R*,4R*,6R*)-3-methyl-6-((5-(trifluoromethyl)pyridin-2-yl)oxy)-2-azabicyclo[2.2.1]heptan-2-yl)methanone (100 mg, 0.199 mmol), CuI (5.7 mg, 0.03 mmol), intermediate C-1 (0.1 mL, 0.3 mmol), and Pd(PPh$_3$)$_4$ (35 mg, 0.03 mmol) in toluene (5 mL) was capped and heated in the microwave to 150° C. for 90 min. The crude reaction mixture was directly purified via silica gel chromatography (0-100% EtOAc in hexane) to give the title compound (47 mg). MS (ESI): mass calcd. for C$_{24}$H$_{21}$F$_3$N$_4$O$_2$, 454.2. m/z found, 455.2 [M+H]$^+$. $^1$H NMR (400 MHz, Chloroform-d) δ 8.83 (d, J=4.8 Hz, 2H), 8.04-7.97 (m, 1H), 7.92 (dd, J=7.7, 1.2 Hz, 1H), 7.75 (dd, J=8.8, 2.5 Hz, 1H), 7.28 (dd, J=7.6, 1.4 Hz, 1H), 7.24 (t, J=4.4 Hz, 1H), 7.17 (dd, J=7.6, 1.4 Hz, 1H), 6.88 (td, J=7.6, 1.3 Hz, 1H), 6.84-6.77 (m, 1H), 5.01-4.83 (m, 1H), 3.99-3.95 (m, 1H), 3.96-3.89 (m, 1H), 2.21-2.09 (m, 2H), 1.40-1.29 (m, 4H), 1.22-1.15 (m, 1H), 1.11-1.01 (m, 1H).

Example 34

(3-fluoro-5'-methyl-[2,3'-bipyridin]-2'-yl)((1S*,3R*, 4R*,6R*)-3-methyl-6-((5-(trifluoromethyl)pyridin-2-yl)oxy)-2-azabicyclo[2.2.1]heptan-2-yl)methanone

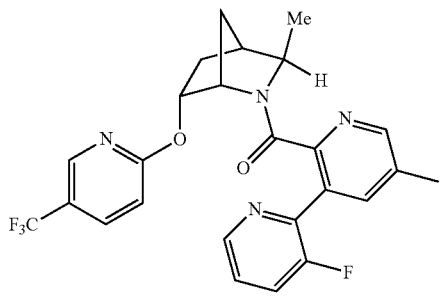 [SMILES: Cc1cnc(C(=O)N2C(C)C3CC(Oc4ccc(C(F)(F)F)cn4)C2C3)c(-c2ncccc2F)c1]

The title compound was prepared analogous to Example 32 substituting intermediate A-28 with intermediate A-23. MS (ESI): mass calcd. for C$_{25}$H$_{22}$F$_4$N$_4$O$_2$, 486.2. m/z found, 487.2 [M+H]$^+$. Analytical HPLC was obtained on a Agilent 1100 Series using a XBridge C18 column (5 nm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.28 min (major rotamer) at 254 nm.

Example 35

(5-methyl-3-(pyrimidin-2-yl)pyridin-2-yl)((1S*,3R*, 4R*,6R*)-3-methyl-6-((5-(trifluoromethyl)pyridin-2-yl)oxy)-2-azabicyclo[2.2.1]heptan-2-yl)methanone

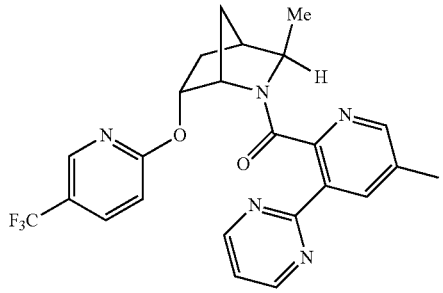 [SMILES: Cc1cnc(C(=O)N2C(C)C3CC(Oc4ccc(C(F)(F)F)cn4)C2C3)c(-c2ncccn2)c1]

The title compound was prepared analogous to Example 28 substituting intermediate A-12 with intermediate A-29. MS (ESI): mass calcd. for C$_{24}$H$_{22}$F$_3$N$_5$O$_2$, 469.2. m/z found, 470.2 [M+H]$^+$. $^1$H NMR (500 MHz, Chloroform-d) δ 8.82 (d, J=4.9 Hz, 2H), 8.06-8.04 (m, 1H), 7.98-7.95 (m, 1H), 7.75-7.73 (m, 1H), 7.71 (dd, J=8.8, 2.6 Hz, 1H), 7.28-7.25 (m, 1H), 7.00-6.97 (m, 1H), 4.98-4.93 (m, 1H), 4.19-4.16 (m, 1H), 4.00 (q, J=6.3 Hz, 1H), 2.25 (s, 3H), 2.22-2.14 (m, 2H), 1.49-1.43 (m, 1H), 1.42-1.36 (m, 4H), 1.35-1.30 (m, 1H).

Example 36

(4'-fluoro-[1,1'-biphenyl]-3-yl)((1S,3R,4R,6R)-3-methyl-6-((5-(trifluoromethyl)pyridin-2-yl)oxy)-2-azabicyclo[2.2.1]heptan-2-yl)methanone

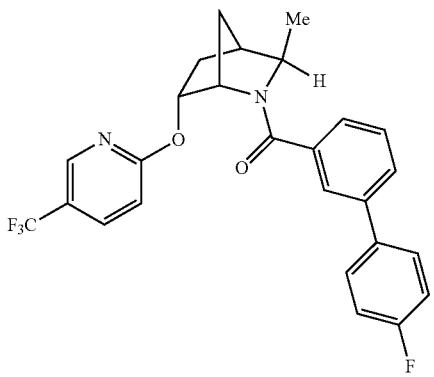 [SMILES: CC1C2CC(Oc3ccc(C(F)(F)F)cn3)C(C2)N1C(=O)c1cccc(-c2ccc(F)cc2)c1]

The title compound was prepared analogous to Example 28 substituting intermediate A-12 with intermediate A-18. MS (ESI): mass calcd. for $C_{26}H_{22}F_4N_2O_2$, 470.2. m/z found, 471.2 [M+H]⁺. ¹H NMR (400 MHz, Chloroform-d) δ 7.97-7.93 (m, 1H), 7.53-7.40 (m, 4H), 7.38-7.34 (m, 1H), 7.24-7.19 (m, 1H), 7.17-7.08 (m, 3H), 6.68-6.62 (m, 1H), 5.08 (dt, J=10.1, 3.2 Hz, 1H), 4.79-4.75 (m, 1H), 4.07 (q, J=6.3 Hz, 1H), 2.39-2.31 (m, 1H), 2.30-2.22 (m, 1H), 2.21-2.15 (m, 1H), 1.68-1.60 (m, 1H), 1.47-1.37 (m, 4H).

Example 37

(3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone

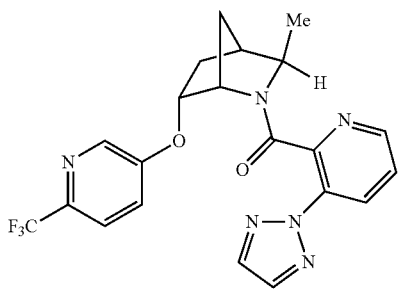 [SMILES: CC1C2CC(Oc3ccc(C(F)(F)F)nc3)C(C2)N1C(=O)c1ncccc1-n1nccn1]

Step A: (1S*,3R*,4R*,6R*)-tert-butyl 3-methyl-6-((6-(trifluoromethyl)pyridin-3-yl)oxy)-2-azabicyclo[2.2.1]heptane-2-carboxylate. The title compound was prepared analogous to Example 26 substituting 2-chloro-5-(trifluoromethyl)pyridine with 5-fluoro-2-(trifluoromethyl)pyridine. MS (ESI): mass calcd. for $C_{18}H_{23}F_3N_2O_3$, 372.2. m/z found, 373.2 [M+H]⁺.

Step B: (1S*,3R*,4R*,6R*)-3-methyl-6-((6-(trifluoromethyl)pyridin-3-yl)oxy)-2-azabicyclo[2.2.1]heptane. To the title compound of step A (274 mg) in DCM (4.9 mL) was added 4M HCl in dioxane (0.9 mL). Upon completion, the reaction was concentrated, the residue dissolved in DCM, neutralized with aqueous 5% Na₂CO₃, and the aqueous layer extracted with DCM (2×). The combined organics were dried with Na₂SO₄, filtered, and concentrated to give the title compound of step B (193 mg) which was used without further purification. MS (ESI): mass calcd. for $C_{13}H_{15}F_3N_2O$, 272.1. m/z found, 273.1 [M+H]⁺.

Step C: (3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone. The title compound was prepared analogous to Example 28 substituting intermediate A-12 with intermediate A-15. MS (ESI): mass calcd. for $C_{21}H_{19}F_3N_6O_2$, 444.2. m/z found, 445.2 [M+H]⁺. Analytical HPLC was obtained on a Agilent 1100 Series using a XBridge C18 column (5 μm, 100×4 6 mm), mobile phase of 10-100% ACN in 20 mM NH₄OH over 8 min and then hold at 100% ACN for 3 min, at a flow rate of 1 mL/min (Temperature=45° C.). $R_t$=5.66 min (major rotamer) at 254 nm.

Example 38

(3-fluoro-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone

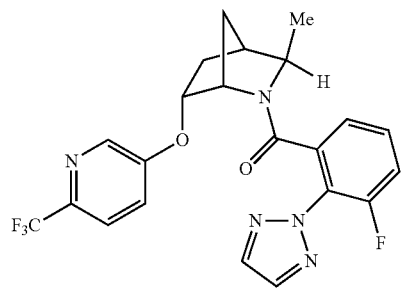 [SMILES: CC1C2CC(Oc3ccc(C(F)(F)F)nc3)C(C2)N1C(=O)c1cccc(F)c1-n1nccn1]

The title compound was prepared analogous to Example 37 substituting intermediate A-15 with intermediate A-16. MS (ESI): mass calcd. for $C_{22}H_{19}F_4N_5O_2$, 461.1. m/z found, 462.2 [M+H]⁺. ¹H NMR (500 MHz, Chloroform-d) δ 8.22 (d, J=2.8 Hz, 1H), 7.92 (s, 2H), 7.50 (d, J=8.7 Hz, 1H), 7.25-7.17 (m, 3H), 7.01 (dd, J=8.7, 2.9 Hz, 1H), 4.48-4.42 (m, 1H), 4.00-3.94 (m, 1H), 3.84-3.78 (m, 1H), 2.23-2.14 (m, 2H), 1.36-1.27 (m, 3H), 1.06 (d, J=6.3 Hz, 3H).

Example 39

(3-methyl-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone

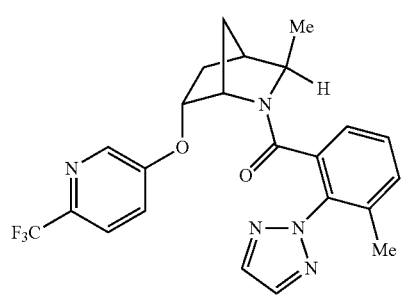 [SMILES: Cc1cccc(C(=O)N2C(C)C3CC(Oc4ccc(C(F)(F)F)nc4)C2C3)c1-n1nccn1]

The title compound was prepared analogous to Example 37 substituting intermediate A-15 with intermediate A-17. MS (ESI): mass calcd. for $C_{23}H_{22}F_3N_5O_2$, 457.2. m/z found, 458.2 [M+H]$^+$. $^1$H NMR (500 MHz, Chloroform-d) δ 8.22 (d, J=2.8 Hz, 1H), 7.87 (d, J=1.3 Hz, 2H), 7.50 (d, J=8.8 Hz, 1H), 7.28-7.24 (m, 2H), 7.15-7.09 (m, 1H), 7.07-7.01 (m, 1H), 4.47-4.41 (m, 1H), 4.10-4.03 (m, 1H), 3.82-3.73 (m, 1H), 2.22-2.13 (m, 2H), 2.10 (s, 3H), 1.43-1.26 (m, 3H), 0.97 (d, J=6.3 Hz, 3H).

Example 40

(6-methyl-3-(2H-1,2,3-triazol-2-yl)pyridin-2-yl) ((1S*,3R*,4R*,6R*)-3-methyl-6-((6-(trifluoromethyl)pyridin-3-yl)oxy)-2-azabicyclo[2.2.1]heptan-2-yl)methanone

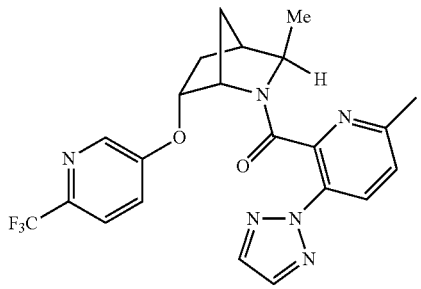 [SMILES: Cc1ccc(-n2nccn2)c(C(=O)N2C(C)C3CC(Oc4ccc(C(F)(F)F)nc4)C2C3)n1]

The title compound was prepared analogous to Example 37 substituting intermediate A-15 with intermediate A-26. MS (ESI): mass calcd. for $C_{22}H_{21}F_3N_6O_2$, 458.2. m/z found, 459.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=5.89 min (major rotamer) at 254 nm.

Example 41

(2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone

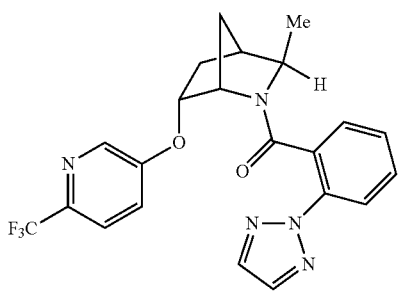 [SMILES: CC1C2CC(Oc3ccc(C(F)(F)F)nc3)C(C2)N1C(=O)c1ccccc1-n1nccn1]

The title compound was prepared analogous to Example 37 substituting intermediate A-15 with intermediate A-1. MS (ESI): mass calcd. for $C_{22}H_{20}F_3N_5O_2$, 443.2. m/z found, 444.2 [M+H]$^+$. $^1$H NMR (500 MHz, Chloroform-d) δ 8.25-8.11 (m, 1H), 7.92-7.82 (m, 2H), 7.72-7.67 (m, 1H), 7.49-7.34 (m, 3H), 7.12-7.04 (m, 1H), 6.96-6.90 (m, 1H), 4.42-4.35 (m, 1H), 3.94-3.87 (m, 1H), 3.78-3.72 (m, 1H), 2.27-2.14 (m, 2H), 1.40-1.19 (m, 6H).

Example 42

(R/S)-(6-methyl-3-(2H-1,2,3-triazol-2-yl)pyridin-2-yl)(3-methyl-6-((5-(trifluoromethyl)pyrazin-2-yl)oxy)-2-azabicyclo[2.2.1]heptan-2-yl)methanone

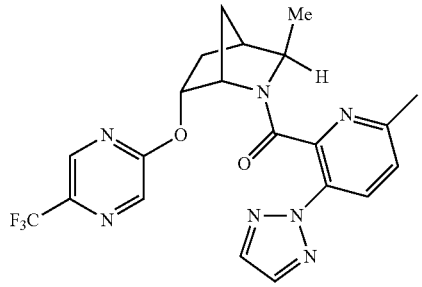 [SMILES: Cc1ccc(-n2nccn2)c(C(=O)N2C(C)C3CC(Oc4cnc(C(F)(F)F)cn4)C2C3)n1]

The title compound was prepared analogous to Example 46 substituting intermediate B-14A with intermediate B-14. MS (ESI): mass calcd. for $C_{21}H_{20}F_3N_7O_2$, 459.2. m/z found, 460 [M+H]$^+$. MP=245.6° C.

Example 43

(R/S)-(2-(2H-1,2,3-triazol-2-yl)phenyl)(3-methyl-6-((5-(trifluoromethyl)pyrazin-2-yl)oxy)-2-azabicyclo[2.2.1]heptan-2-yl)methanone

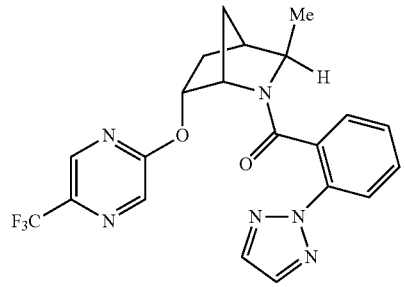 [SMILES: CC1C2CC(Oc3cnc(C(F)(F)F)cn3)C(C2)N1C(=O)c1ccccc1-n1nccn1]

The title compound was prepared analogous to Example 46 substituting intermediate B-14A with intermediate B-14 and intermediate A-26 with intermediate A-1. MS (ESI): mass calcd. for $C_{21}H_{19}F_3N_6O_2$, 444.2. m/z found, 445 [M+H]$^+$. MP=188.2° C.

Example 44

(R/S)-(6-methyl-3-(pyrimidin-2-yl)pyridin-2-yl)(3-methyl-6-((5-(trifluoromethyl)pyrazin-2-yl)oxy)-2-azabicyclo[2.2.1]heptan-2-yl)methanone

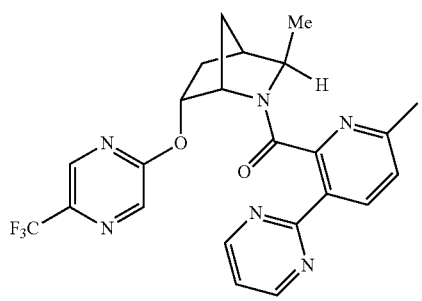

The title compound was prepared analogous to Example 46 substituting intermediate B-14A with intermediate B-14 and intermediate A-26 with intermediate A-27. MS (ESI): mass calcd. for $C_{23}H_{21}F_3N_6O_2$, 470.2. m/z found, 471 [M+H]$^+$.

Example 45

(R/S)-3-methyl-6-((5-(trifluoromethyl)pyrazin-2-yl)oxy)-2-azabicyclo[2.2.1]heptan-2-yl)(2-(pyrimidin-2-yl)phenyl)methanone

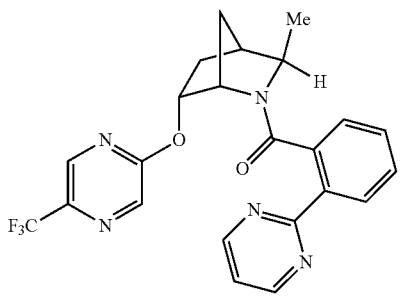 [SMILES: CC1C2CC(Oc3cnc(C(F)(F)F)cn3)C(C2)N1C(=O)c1ccccc1-c1ncccn1]

The title compound was prepared analogous to Example 46 substituting intermediate B-14A with intermediate B-14 and intermediate A-26 with intermediate A-4 and carrying out an additional cross coupling step (Step D).

Step D: To a sealable tube containing (R/S)-(2-iodophenyl)(3-methyl-6-((5-(trifluoromethyl)pyrazin-2-yl)oxy)-2-azabicyclo[2.2.1]heptan-2-yl)methanone (114 mg, 0.215 mmol) and CuI (3 mg, 0.02 mmol) in DME (2 mL) was bubbled N$_2$ gas for 5 minutes. Intermediate C-1 (119 mg, 0.323 mmol), and Pd(PPh$_3$)$_4$ (18.5 mg, 0.016 mmol) were then added, the vessel sealed, and heated to 120° C. After 3 hours the reaction was concentrated and the residual purified via silica gel chromatography (0-90% EtOAc in heptane) to give the title compound (18 mg). MS (ESI): mass calcd. for $C_{23}H_{20}F_3N_5O_2$, 455.2. m/z found, 456 [M+H]$^+$.

Example 46

(6-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone

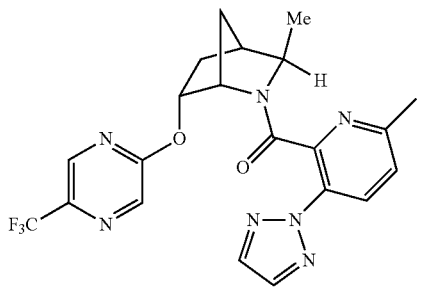 [SMILES: Cc1ccc(-n2nccn2)c(C(=O)N2C(C)C3CC(Oc4cnc(C(F)(F)F)cn4)C2C3)n1]

Step A: (1S*,3R*,4R*,6R*)-tert-butyl 3-methyl-6-((5-(trifluoromethyl)pyrazin-2-yl)oxy)-2-azabicyclo[2.2.1]heptane-2-carboxylate. To intermediate B-14A (500 mg, 2.200 mmol) and 2-chloro-5-(trifluoromethyl)pyrazine (401 mg, 2.197 mmol) dissolved in DMF (5 mL) was added NaH (141 mg, 3.53 mmol, 60% dispersion in mineral oil). After addition of NaH the sides of the flask were rinsed with additional DMF (3.0 mL) and the reaction left to stir at room temperature. After stirring for 2 h, the mixture was carefully quenched with H$_2$O, and the aqueous layer extracted with EtOAc (3×). The combined organics were washed with 5% LiCl solution, brine, dried with MgSO$_4$, filtered and concentrated. Purification via silica gel chromatography (0-20% EtOAc in hexanes) gave the title compound (834 mg). MS (ESI) mass calcd. for $C_{12}H_{22}F_3N_3O_3$, 373.2; m/z found 318.1 [M+2H-tBu]$^+$.

Step B: (1S*,3R*,4R*,6R*)-3-methyl-6-((5-(trifluoromethyl)pyrazin-2-yl)oxy)-2-azabicyclo[2.2.1]heptane.xHCl.

To the title compound of step A (834 mg, 2.234 mmol) in EtOAc (4 mL) was added 4M HCl in dioxane (15 mL). After 30 minutes the reaction was incomplete so additional 4M HCl in dioxane (5 mL) was added and the reaction gently warmed with a heat gun. After an additional 35 min, the reaction was concentrated to give the title compound of step B (795 mg) which was used without further purification. MS (ESI) mass calcd. for $C_{12}H_{14}F_3N_3O$, 273.1. m/z found 274.2 [M+H]$^+$.

Step C: (6-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone. To the title compound of step B (30 mg) and intermediate A-26 (22 mg, 0.11 mmol) in DMF (0.4 mL) was added DIPEA (0.1 mL, 0.6 mmol) and HATU (41 mg, 0.11 mmol). Upon completion, the reaction was diluted with MeOH, filtered, and purified using Agilent Prep Method X to give the title compound (20 mg). MS (ESI): mass calcd. for $C_{21}H_{20}F_3N_7O_2$, 459.2. m/z found, 460.2 [M+H]$^+$. $^1$H NMR (400 MHz, Chloroform-d) δ 8.35 (d, J=1.3 Hz, 1H), 8.09-8.03 (m, 1H), 7.91-7.83 (m, 3H), 7.08 (d, J=8.3 Hz, 1H), 5.03-4.90 (m, 1H), 4.21-4.12 (m, 1H), 4.05-3.94 (m, 1H), 2.32 (s, 3H), 2.27-2.18 (m, 2H), 1.63-1.56 (m, 1H), 1.51-1.41 (m, 1H), 1.40-1.34 (m, 4H).

Example 47

(3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone

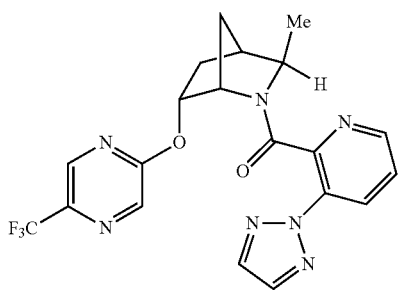

The title compound was prepared analogous to Example 46 substituting intermediate A-26 with intermediate A-15. MS (ESI): mass calcd. for $C_{20}H_{18}F_3N_7O_2$, 445.1. m/z found, 446.2 [M+H]$^+$. $^1$H NMR (400 MHz, Chloroform-d) δ 8.37 (d, J=1.3 Hz, 1H), 8.04 (dd, J=8.2, 1.5 Hz, 1H), 8.00-7.98 (m, 1H), 7.92 (dd, J=4.7, 1.5 Hz, 1H), 7.87 (s, 2H), 7.22 (dd, J=8.3, 4.7 Hz, 1H), 5.10-5.00 (m, 1H), 4.17-4.09 (m, 1H), 4.09-3.97 (m, 1H), 2.31-2.21 (m, 2H), 1.74-1.66 (m, 1H), 1.57-1.50 (m, 1H), 1.45-1.38 (m, 4H).

Example 48

(5-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone

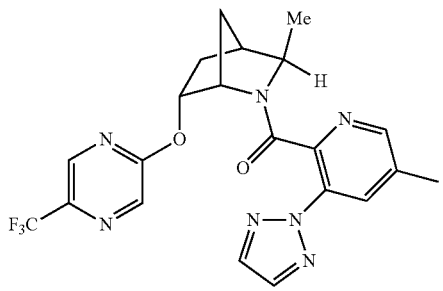 [SMILES: Cc1cnc(C(=O)N2C(C)C3CC(Oc4cnc(C(F)(F)F)cn4)C2C3)c(-n2nccn2)c1]

The title compound was prepared analogous to Example 46 substituting intermediate A-26 with intermediate A-19. MS (ESI): mass calcd. for $C_{21}H_{20}F_3N_7O_2$, 459.2. m/z found, 460.2 [M+H]$^+$. $^1$H NMR (400 MHz, Chloroform-d) δ 8.37 (d, J=1.3 Hz, 1H), 8.01-7.96 (m, 1H), 7.85 (s, 2H), 7.83-7.81 (m, 1H), 7.75-7.70 (m, 1H), 5.08-4.91 (m, 1H), 4.17-4.11 (m, 1H), 4.08-3.91 (m, 1H), 2.29 (s, 3H), 2.28-2.25 (m, 1H), 2.25-2.18 (m, 1H), 1.72-1.63 (m, 1H), 1.53 (dt, J=13.3, 3.6 Hz, 1H), 1.44-1.35 (m, 4H).

Example 49

(6-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone

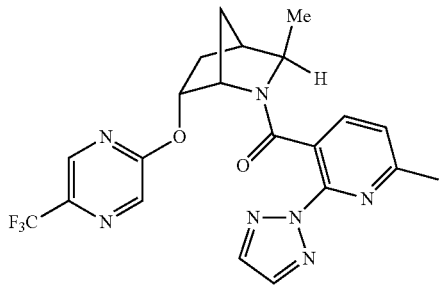

The title compound was prepared analogous to Example 46 substituting intermediate A-26 with intermediate A-3. MS (ESI): mass calcd. for $C_{21}H_{20}F_3N_7O_2$, 459.2. m/z found, 460.2 [M+H]$^+$. $^1$H NMR (400 MHz, Chloroform-d) δ 8.29-8.21 (m, 1H), 8.11-8.02 (m, 1H), 7.90 (s, 2H), 7.47 (d, J=7.8 Hz, 1H), 6.65 (d, J=7.8 Hz, 1H), 5.00-4.84 (m, 1H), 4.02-3.90 (m, 1H), 3.86-3.79 (m, 1H), 2.55 (s, 3H), 2.26-2.11 (m, 2H), 1.49-1.30 (m, 5H), 1.30-1.22 (m, 1H).

Example 50

(5-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone

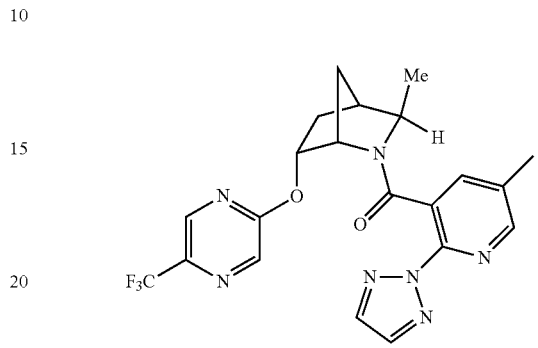

The title compound was prepared analogous to Example 46 substituting intermediate A-26 with intermediate A-25. MS (ESI): mass calcd. for $C_{21}H_{20}F_3N_7O_2$, 459.2. m/z found, 460.2 [M+H]$^+$. $^1$H NMR (400 MHz, Chloroform-d) δ 8.22-8.20 (m, 1H), 8.19 (d, J=1.3 Hz, 1H), 8.15-8.12 (m, 1H), 7.90 (s, 2H), 7.52 (dd, J=2.2, 0.8 Hz, 1H), 4.95-4.85 (m, 1H), 4.01-3.91 (m, 1H), 3.81 (s, 1H), 2.27-2.15 (m, 2H), 2.09 (s, 3H), 1.46-1.34 (m, 5H), 1.32-1.24 (m, 1H).

Example 51

(2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone

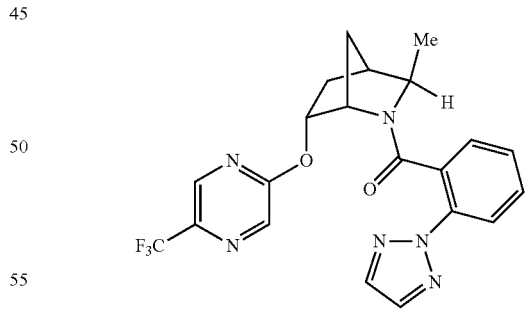

The title compound was prepared analogous to Example 46 substituting intermediate A-26 with intermediate A-1. MS (ESI): mass calcd. for $C_{21}H_{19}F_3N_6O_2$, 444.2. m/z found, 445.2 [M+H]$^+$. $^1$H NMR (400 MHz, Chloroform-d) δ 8.24 (s, 1H), 8.02-7.96 (m, 1H), 7.85 (s, 2H), 7.66 (dd, J=8.1, 1.2 Hz, 1H), 7.35-7.27 (m, 1H), 7.18 (dd, J=7.8, 1.5 Hz, 1H), 6.82 (t, J=7.6 Hz, 1H), 4.96-4.83 (m, 1H), 4.01-3.89 (m, 1H), 3.83 (s, 1H), 2.24-2.11 (m, 2H), 1.47-1.38 (m, 1H), 1.33 (d, J=6.3 Hz, 3H), 1.31-1.19 (m, 2H).

Example 52

(3-fluoro-2-(2H-1,2,3-triazol-2-yl)phenyl)((1S*,3R*, 4R*,6R*)-3-methyl-6-((5-(trifluoromethyl)pyrazin-2-yl)oxy)-2-azabicyclo[2.2.1]heptan-2-yl)methanone

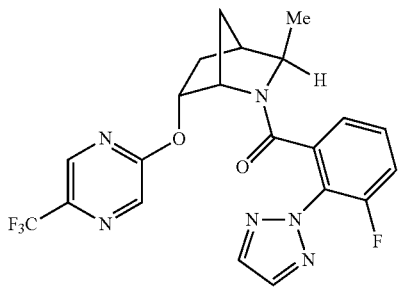 [SMILES: CC1C2CC(Oc3cnc(C(F)(F)F)cn3)C(C2)N1C(=O)c1cccc(F)c1-n1nccn1]

The title compound was prepared analogous to Example 46 substituting intermediate A-26 with intermediate A-16. MS (ESI): mass calcd. for $C_{21}H_{18}F_4N_6O_2$, 462.1. m/z found, 463.2 [M+H]$^+$. $^1$H NMR (400 MHz, Chloroform-d) δ 8.27 (d, J=1.3 Hz, 1H), 8.13-8.07 (m, 1H), 7.91 (s, 2H), 7.18-7.10 (m, 1H), 7.04-6.92 (m, 2H), 5.02-4.94 (m, 1H), 4.10-3.99 (m, 1H), 3.89-3.79 (m, 1H), 2.25-2.17 (m, 1H), 2.17-2.13 (m, 1H), 1.40-1.34 (m, 1H), 1.34-1.28 (m, 1H), 1.26-1.17 (m, 1H), 1.08 (d, J=6.3 Hz, 3H).

Example 53

(4-fluoro-2-(2H-1,2,3-triazol-2-yl)phenyl)((1S*,3R*, 4R*,6R*)-3-methyl-6-((5-(trifluoromethyl)pyrazin-2-yl)oxy)-2-azabicyclo[2.2.1]heptan-2-yl)methanone

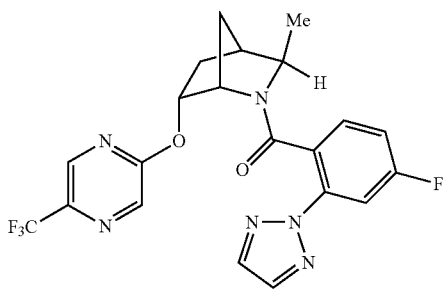 [SMILES: CC1C2CC(Oc3cnc(C(F)(F)F)cn3)C(C2)N1C(=O)c1ccc(F)cc1-n1nccn1]

The title compound was prepared analogous to Example 46 substituting intermediate A-26 with intermediate A-12. MS (ESI): mass calcd. for $C_{21}H_{18}F_4N_6O_2$, 462.1. m/z found, 463.2 [M+H]$^+$. $^1$H NMR (400 MHz, Chloroform-d) δ 8.24 (s, 1H), 8.12-8.06 (m, 1H), 7.86 (s, 2H), 7.45 (dd, J=9.2, 2.5 Hz, 1H), 7.18 (dd, J=8.6, 5.9 Hz, 1H), 6.61-6.48 (m, 1H), 4.96-4.86 (m, 1H), 4.00-3.89 (m, 1H), 3.80 (s, 1H), 2.26-2.11 (m, 2H), 1.46-1.38 (m, 1H), 1.35 (d, J=6.3 Hz, 3H), 1.32-1.20 (m, 2H).

Example 54

(5-fluoro-2-(2H-1,2,3-triazol-2-yl)phenyl)((1S*,3R*, 4R*,6R*)-3-methyl-6-((5-(trifluoromethyl)pyrazin-2-yl)oxy)-2-azabicyclo[2.2.1]heptan-2-yl)methanone

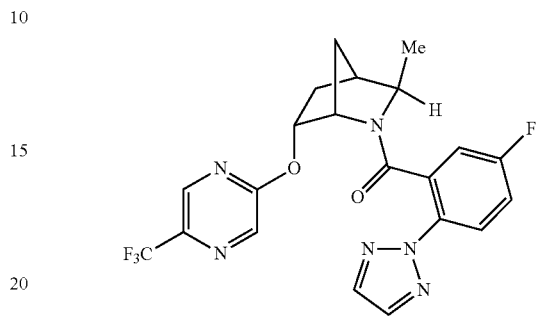

The title compound was prepared analogous to Example 46 substituting intermediate A-26 with intermediate A-10. MS (ESI): mass calcd. for $C_{21}H_{18}F_4N_6O_2$, 462.1. m/z found, 463.2 [M+H]$^+$. $^1$H NMR (400 MHz, Chloroform-d) δ 8.27 (s, 1H), 8.16-8.08 (m, 1H), 7.84 (s, 2H), 7.67 (dd, J=8.9, 4.7 Hz, 1H), 7.07-7.00 (m, 1H), 6.96 (dd, J=8.1, 2.9 Hz, 1H), 4.96-4.86 (m, 1H), 3.97-3.88 (m, 1H), 3.84 (s, 1H), 2.27-2.14 (m, 2H), 1.42-1.29 (m, 4H), 1.29-1.24 (m, 1H). 1H buried under solvent.

Example 55

(2-fluoro-6-(2H-1,2,3-triazol-2-yl)phenyl)((1S*,3R*, 4R*,6R*)-3-methyl-6-((5-(trifluoromethyl)pyrazin-2-yl)oxy)-2-azabicyclo[2.2.1]heptan-2-yl)methanone

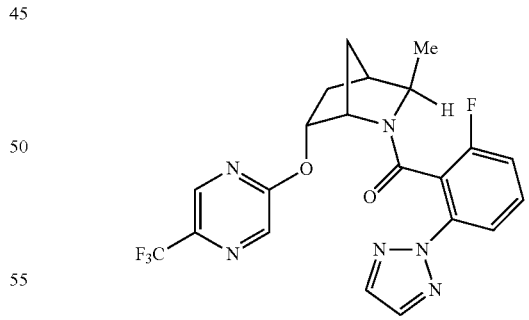

The title compound was prepared analogous to Example 46 substituting intermediate A-26 with intermediate A-11. MS (ESI): mass calcd. for $C_{21}H_{18}F_4N_6O_2$, 462.1. m/z found, 463.2 [M+H]$^+$. $^1$H NMR (400 MHz, Chloroform-d) δ 8.41-8.36 (m, 1H), 8.10 (s, 1H), 7.86 (s, 2H), 7.67-7.56 (m, 1H), 7.36-7.27 (m, 1H), 6.76-6.65 (m, 1H), 5.05-4.86 (m, 1H), 4.06-3.90 (m, 1H), 3.86-3.77 (m, 1H), 2.32-2.16 (m, 2H), 1.46-1.24 (m, 6H).

Example 56

(3-ethoxy-6-methylpyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone

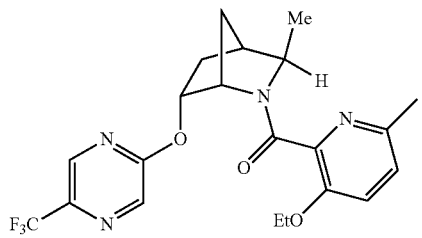 [SMILES: CCOc1ccc(C)nc1C(=O)N1C(C)C2CC(Oc3cnc(C(F)(F)F)cn3)C1C2]

The title compound was prepared analogous to Example 46 substituting intermediate A-26 with intermediate A-8. MS (ESI): mass calcd. for $C_{21}H_{23}F_3N_4O_3$, 436.2. m/z found, 437.2 [M+H]$^+$. $^1$H NMR (400 MHz, Chloroform-d) δ 8.28 (d, J=1.3 Hz, 1H), 7.96-7.91 (m, 1H), 6.89-6.80 (m, 2H), 5.06-4.93 (m, 1H), 4.68-4.60 (m, 1H), 4.10-4.02 (m, 1H), 4.01-3.87 (m, 2H), 2.37-2.32 (m, 1H), 2.33-2.26 (m, 1H), 2.24 (s, 3H), 2.21-2.15 (m, 1H), 1.64-1.58 (m, 1H), 1.56-1.48 (m, 1H), 1.44 (d, J=6.3 Hz, 3H), 1.41 (t, J=7.0 Hz, 3H).

Example 57

(4-methoxy-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone

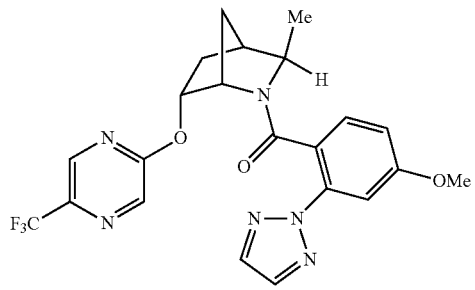 [SMILES: COc1ccc(C(=O)N2C(C)C3CC(Oc4cnc(C(F)(F)F)cn4)C2C3)c(-n2nccn2)c1]

The title compound was prepared analogous to Example 46 substituting intermediate A-26 with intermediate A-5. MS (ESI): mass calcd. for $C_{22}H_{21}F_3N_6O_3$, 474.2. m/z found, 475.2 [M+H]$^+$. $^1$H NMR (400 MHz, Chloroform-d) δ 8.23 (d, J=1.3 Hz, 1H), 8.09-8.02 (m, 1H), 7.84 (s, 2H), 7.16 (d, J=2.5 Hz, 1H), 7.11 (d, J=8.6 Hz, 1H), 6.38 (dd, J=8.6, 2.6 Hz, 1H), 4.95-4.84 (m, 1H), 3.94-3.88 (m, 1H), 3.87-3.81 (m, 1H), 3.79 (s, 3H), 2.22-2.11 (m, 2H), 1.45-1.35 (m, 1H), 1.31 (d, J=6.3 Hz, 3H), 1.27-1.21 (m, 2H).

Example 58

(R/S)-(6-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone

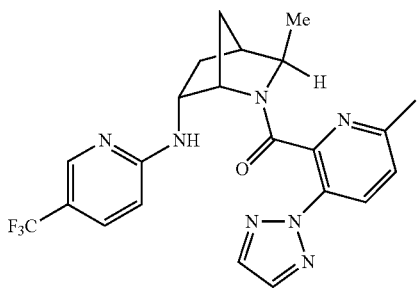

The title compound was prepared analogous to Example 61 substituting intermediate A-19 with intermediate A-26. MS (ESI): mass calcd. for $C_{22}H_{22}F_3N_7O$, 457.2. m/z found, 458 [M+H]$^+$.

Example 59

(R/S)-(5-methyl-3-(pyrimidin-2-yl)pyridin-2-yl)(3-methyl-6-((5-(trifluoromethyl)pyridin-2-yl)amino)-2-azabicyclo[2.2.1]heptan-2-yl)methanone

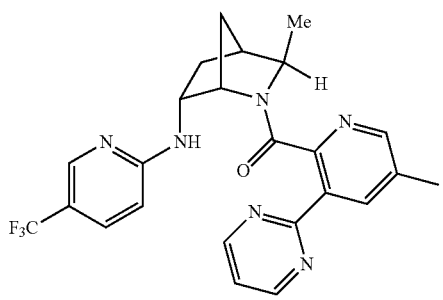 [SMILES: Cc1cnc(C(=O)N2C(C)C3CC(Nc4ccc(C(F)(F)F)cn4)C2C3)c(-c2ncccn2)c1]

The title compound was prepared analogous to Example 61 substituting intermediate A-19 with intermediate A-29. MS (ESI): mass calcd. for $C_{24}H_{23}F_3N_6O$, 468.2. m/z found, 469 [M+H]$^+$.

Example 60

(6-methyl-3-(pyrimidin-2-yl)pyridin-2-yl)((1S,3R,4S,6R)-3-methyl-6-((5-(trifluoromethyl)pyridin-2-yl)amino)-2-azabicyclo[2.2.1]heptan-2-yl)methanone

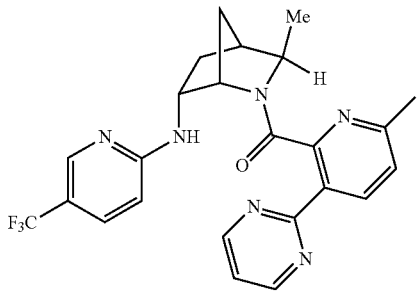 [SMILES: Cc1ccc(-c2ncccn2)c(C(=O)N2C(C)C3CC(Nc4ccc(C(F)(F)F)cn4)C2C3)n1]

The title compound was prepared analogous to Example 61 substituting intermediate A-19 with intermediate A-27. MS (ESI): mass calcd. for $C_{24}H_{23}F_3N_6O$, 468.2. m/z found, 469 [M+H]$^+$.

Example 61

(R/S)-(5-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone

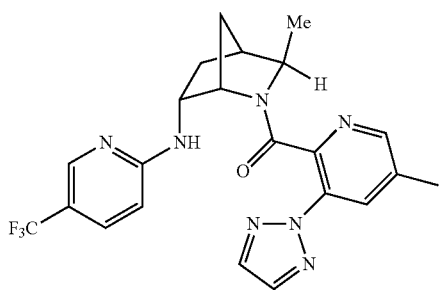 [SMILES: Cc1cnc(C(=O)N2C(C)C3CC(Nc4ccc(C(F)(F)F)cn4)C2C3)c(-n2nccn2)c1]

Step A: (R/S)-tert-butyl 3-methyl-6-((5-(trifluoromethyl)pyridin-2-yl)amino)-2-azabicyclo[2.2.1]heptane-2-carboxylate. To intermediate B-16 (625 mg, 2.762 mmol) dissolved in DMSO (25 mL) was added 2-fluoro-5-(trifluoromethyl)pyridine (912 mg, 5.524 mmol) and DIPEA (0.95 mL, 5.542 mmol) and the reaction mixture heated to 100° C. for 4 h. Saturated NaHCO$_3$ solution was then added and the aqueous layer extracted with DCM (×3). The combined organics were washed with brine, dried with MgSO$_4$, filtered, and concentrated. Purification via silica gel chromatography (0-10% EtOAc in heptanes) yielded the title compound (780 mg). MS (ESI) mass calcd. for $C_{18}H_{24}F_3N_3O_2$, 371.2. m/z found 372 [M+H]$^+$.

Step B: (R/S)-3-methyl-N-(5-(trifluoromethyl)pyridin-2-yl)-2-azabicyclo[2.2.1]heptan-6-amine.xHCl. To the title compound of step A (780 mg) in dioxane (6 mL) was added 6M HCl in 2-propanol (2.1 mL) and the reaction was heated to 60° C. overnight. Upon completion, the reaction was concentrated to give the title compound of step B which was used without further purification. MS (ESI) mass calcd. for $C_{13}H_{16}F_3N_3$, 271.1. m/z found 272 [M+H]$^+$.

Step C: (R/S)-(6-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone. To intermediate A-19 (77 mg, 0.38 mmol) in DMF (2 mL) was added DIPEA (0.25 mL, 1.5 mmol) and HATU (166 mg, 0.436 mmol). After 10 minutes the title compound of step B (100 mg) was added and the reaction was left to stir overnight. Upon completion, the reaction was diluted with a saturated aqueous NaHCO$_3$ solution and the aqueous layer extracted with EtOAc (×3). The combined organics were dried with MgSO$_4$, filtered and concentrated. Purification via silica gel chromatography (0-60% EtOAc in heptanes) and trituration with DIPE gave the title compound (24 mg). MS (ESI): mass calcd. for $C_{22}H_{22}F_3N_7O$, 457.2. m/z found, 458 [M+H]$^+$. MP=143° C.

Example 62

((1S*,3R*,4S*,6R*)-3-methyl-6-((5-(trifluoromethyl)pyridin-2-yl)amino)-2-azabicyclo[2.2.1]heptan-2-yl)(3-(pyrimidin-2-yl)pyridin-2-yl)methanone

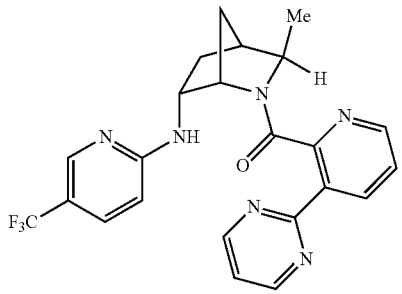 [SMILES: CC1C2CC(Nc3ccc(C(F)(F)F)cn3)C(C2)N1C(=O)c1ncccc1-c1ncccn1]

Step A: (1S*,3R*,4S*,6R*)-tert-butyl 3-methyl-6-((5-(trifluoromethyl)pyridin-2-yl)amino)-2-azabicyclo[2.2.1]heptane-2-carboxylate. To a microwave vial containing degassed toluene (13 mL) was added Pd(OAc)$_2$ (35 mg, 0.053 mmol) and racemic BINAP (33 mg, 0.053 mmol) at room temperature and the reaction mixture was purged with N$_2$ for 5 min. Then, 2-chloro-5-(trifluoromethyl)pyridine (478 mg, 2.63 mmol), intermediate B-16A (656 mg, 2.89 mmol), and sodium tert-butoxide (182 mg, 1.84 mmol) were added and the reaction mixture heated to 70° C. overnight. Upon completion of the reaction, the mixture was cooled to room temperature, filtered through Celite and washed with EtOAc. The filtrate was concentrated in vacuo and the crude residue subjected directly to silica gel chromatography (0-60% EtOAc in hexanes) to give the title compound (409 mg, 1.101 mmol, 42%). MS (ESI) mass calcd. for $C_{18}H_{24}F_3N_3O_2$, 371.2; m/z found 372.20 [M+H]$^+$.

Step B: (1S*,3R*,4R*,6R*)-3-methyl-N-(5-(trifluoromethyl)pyridin-2-yl)-2-azabicyclo[2.2.1]heptan-6-amine. To the title compound of step A (409 mg, 1.101 mmol) in DCM (13.8 mL) was added 4M HCl in dioxane (1.4 mL). Upon completion, the reaction was neutralized with aqueous 5% Na$_2$CO$_3$, and the aqueous layer extracted with DCM (3×). The combined organics were dried with MgSO$_4$, filtered, and concentrated to give the title compound of step B which was used without further purification. MS (ESI) mass calcd. for $C_{13}H_{16}F_3N_3$, 271.1. m/z found 272.2 [M+H]$^+$.

Step C: ((1S*,3R*,4S*,6R*)-3-methyl-6-((5-(trifluoromethyl)pyridin-2-yl)amino)-2-azabicyclo[2.2.1]heptan-2-yl)(3-(pyrimidin-2-yl)pyridin-2-yl)methanone. To the title compound of step B (40 mg) and DIPEA (0.03 mL, 0.16 mmol) in DMF (1.5 mL) was added and intermediate A-28 (49 mg, 0.18 mmol) and HATU (62 mg, 0.16 mmol). Upon completion, the reaction was diluted with MeOH, filtered, and purified using Agilent Prep Method X to give the title compound (13 mg). MS (ESI): mass calcd. for $C_{23}H_{21}F_3N_6O$, 454.2. m/z found, 455.2 [M+H]$^+$. $^1$H NMR (500 MHz, CDCl$_3$) δ 8.84 (d, J=4.8 Hz, 2H), 8.52 (dd, J=4.8, 1.7 Hz, 1H), 8.45 (dd, J=7.9, 1.7 Hz, 1H), 8.22-8.16 (m, 1H), 7.80-7.70 (m, 1H), 7.40-7.35 (m, 2H), 7.31 (t, J=4.9 Hz, 1H), 6.31 (d, J=8.7 Hz, 1H), 4.43-4.37 (m, 1H), 4.24-4.15 (m, 1H), 3.90 (q, J=6.3 Hz, 1H), 2.50-2.41 (m, 1H), 2.40-2.35 (m, 1H), 2.13-2.05 (m, 1H), 1.61 (d, J=10.4 Hz, 1H), 1.51-1.46 (m, 3H), 1.19 (ddd, J=12.9, 4.7, 2.9 Hz, 1H).

Example 63

(6-methyl-3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone

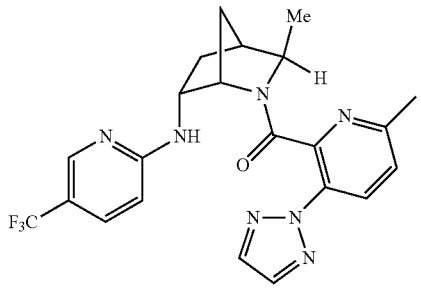 [SMILES: Cc1ccc(-n2nccn2)c(C(=O)N2C(C)C3CC(Nc4ccc(C(F)(F)F)cn4)C2C3)n1]

The title compound was prepared analogous to Example 62 substituting intermediate A-28 with intermediate A-26. MS (ESI): mass calcd. for $C_{22}H_{22}F_3N_7O$, 457.2. m/z found, 458.2 [M+H]$^+$. $^1$H NMR (500 MHz, CDCl$_3$) δ 8.22-8.17 (m, 1H), 8.01 (d, J=8.4 Hz, 1H), 7.87 (s, 2H), 7.38 (dd, J=8.8, 2.5 Hz, 1H), 7.26-7.22 (m, 1H), 7.20 (d, J=8.4 Hz, 1H), 4.38 (s, 1H), 4.13 (s, 1H), 3.86 (q, J=6.3 Hz, 1H), 2.56 (s, 3H), 2.43 (ddd, J=13.0, 10.2, 4.8 Hz, 1H), 2.38-2.31 (m, 1H), 2.08 (ddd, J=10.8, 3.4, 2.0 Hz, 1H), 1.76 (s, 1H), 1.62-1.55 (m, 1H), 1.45 (d, J=6.3 Hz, 3H), 1.17 (ddd, J=13.1, 4.7, 3.0 Hz, 1H).

Example 64

(3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone

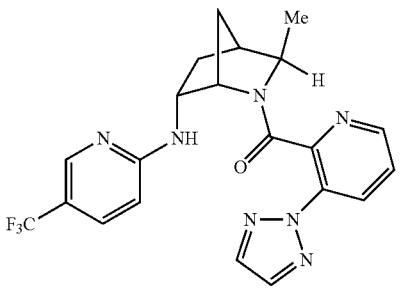 [SMILES: CC1C2CC(Nc3ccc(C(F)(F)F)cn3)C(C2)N1C(=O)c1ncccc1-n1nccn1]

The title compound was prepared analogous to Example 62 substituting intermediate A-28 with intermediate A-15. MS (ESI): mass calcd. for $C_{21}H_{20}F_3N_7O$, 443.2. m/z found, 444.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.27 min (major rotamer) at 254 nm.

Example 65

(3-fluoro-2-(2H-1,2,3-triazol-2-yl)phenyl)((1S*,3R*,4S*,6R*)-3-methyl-6-((5-(trifluoromethyl)pyridin-2-yl)amino)-2-azabicyclo[2.2.1]heptan-2-yl)methanone

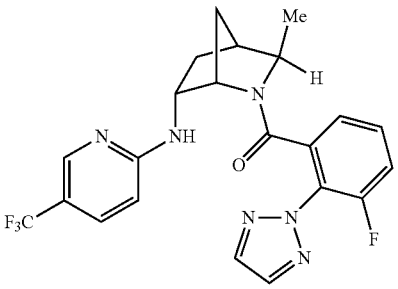 [SMILES: CC1C2CC(Nc3ccc(C(F)(F)F)cn3)C(C2)N1C(=O)c1cccc(F)c1-n1nccn1]

The title compound was prepared analogous to Example 62 substituting intermediate A-28 with intermediate A-16. MS (ESI): mass calcd. for $C_{22}H_{20}F_4N_6O$, 460.2. m/z found, 461.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.72 min (major rotamer) at 254 nm.

Example 66

(5-methyl-3-(2H-1,2,3-triazol-2-yl)pyridin-2-yl)((1S*,3R*,4S*,6R*)-3-methyl-6-((5-(trifluoromethyl)pyridin-2-yl)amino)-2-azabicyclo[2.2.1]heptan-2-yl)methanone

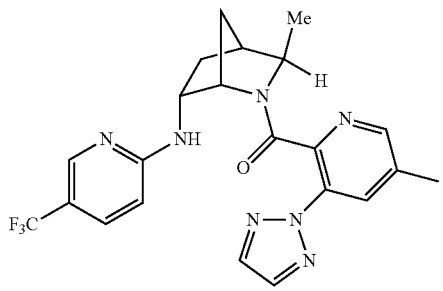 [SMILES: Cc1cnc(C(=O)N2C(C)C3CC(Nc4ccc(C(F)(F)F)cn4)C2C3)c(-n2nccn2)c1]

The title compound was prepared analogous to Example 62 substituting intermediate A-28 with intermediate A-19. MS (ESI): mass calcd. for $C_{22}H_{22}F_3N_7O$, 457.2. m/z found, 458.2 [M+H]$^+$. $^1$H NMR (500 MHz, CDCl$_3$) δ 8.25-8.20 (m, 1H), 8.16-8.10 (m, 1H), 7.94-7.87 (m, 3H), 7.36 (dd, J=8.8, 2.5 Hz, 1H), 6.24 (d, J=8.8 Hz, 1H), 4.43-4.36 (m, 1H), 4.24-4.13 (m, 1H), 3.89 (q, J=6.3 Hz, 1H), 2.45-2.37 (m, 1H), 2.36-2.29 (m, 4H), 2.09-2.02 (m, 1H), 1.79 (s, 1H), 1.62-1.55 (m, 1H), 1.44 (d, J=6.3 Hz, 3H), 1.15 (ddd, J=13.1, 4.9, 2.9 Hz, 1H).

Example 67

(R/S)-(3-fluoro-2-(pyrimidin-2-yl)phenyl)(3-methyl-6-((5-(trifluoromethyl)pyrazin-2-yl)amino)-2-azabicyclo[2.2.1]heptan-2-yl)methanone

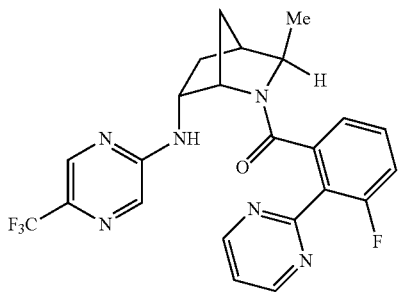 [SMILES: CC1C2CC(Nc3cnc(C(F)(F)F)cn3)C(C2)N1C(=O)c1cccc(F)c1-c1ncccn1]

The title compound was prepared analogous to Example 4 substituting intermediate B-8 with intermediate B-16. MS (ESI): mass calcd. for $C_{23}H_{20}F_4N_6O$, 472.2. m/z found, 473 [M+H]$^+$.

Example 68

(R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone

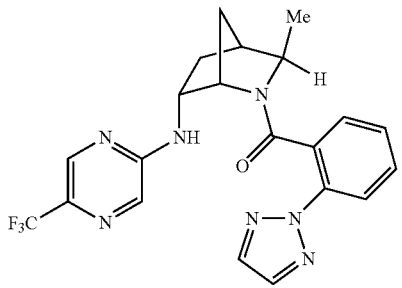 [SMILES: CC1C2CC(Nc3cnc(C(F)(F)F)cn3)C(C2)N1C(=O)c1ccccc1-n1nccn1]

The title compound was prepared analogous to Example 5 substituting intermediate B-8 with intermediate B-16. MS (ESI): mass calcd. for $C_{21}H_{20}F_3N_7O$, 443.2. m/z found, 444.2 [M+H]$^+$. MP=186.4° C. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.63 min at 254 nm.

Example 68 was subjected to Chiral SFC purification [Stationary phase: Chiralpak AD-H (5 μm 250×20 mm), Mobile phase of 15% EtOH (0.3% iPrNH$_2$): 85% CO$_2$] to provide the corresponding single enantiomers (Example 68A and Example 68B) were the absolute stereochemistry was not determined. The enantiomeric purity was confirmed by analytical SFC using a Chiralpak AD-H column (5 μm 150×4.6 mm), mobile phase of 15% EtOH (0.3% iPrNH$_2$): 85% CO$_2$, and a flow rate of 3 mL/min over 7 minutes (Temperature=35° C.).

Example 68A (2-(2H-1,2,3-triazol-2-yl)phenyl)((1R*,3S*,4R*,6S*)-3-methyl-6-((5-(trifluoromethyl)pyrazin-2-yl)amino)-2-azabicyclo[2.2.1]heptan-2-yl)methanone

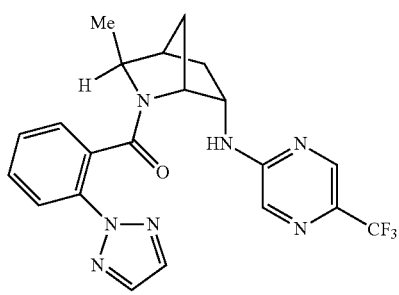 [SMILES: CC1C2CC(Nc3cnc(C(F)(F)F)cn3)C(C2)N1C(=O)c1ccccc1-n1nccn1]

Enantiomeric purity (SFC/Chiralpak AD-H): >99%. R$_t$: 2.58 min. MS (ESI): mass calcd. for $C_{21}H_{20}F_3N_7O$, 443.2. m/z found, 444.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.41 min at 254 nm.

Example 68B (2-(2H-1,2,3-triazol-2-yl)phenyl)((1S*,3R*,4S*,6R*)-3-methyl-6-((5-(trifluoromethyl)pyrazin-2-yl)amino)-2-azabicyclo[2.2.1]heptan-2-yl)methanone

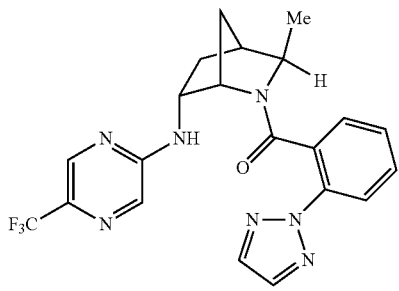 [SMILES: CC1C2CC(Nc3cnc(C(F)(F)F)cn3)C(C2)N1C(=O)c1ccccc1-n1nccn1]

Enantiomeric purity (SFC/Chiralpak AD-H): >98%. R$_t$: 3.36 mM MS (ESI): mass calcd. for $C_{21}H_{20}F_3N_7O$, 443.2. m/z found, 444.2 [M+H]$^+$. Analytical HPLC was obtained on a Agilent 1100 Series using a XBridge C18 column (5 μm, 100×4 6 mm), mobile phase of 10-100% ACN in 20 mM NH$_4$OH over 8 min and then hold at 100% ACN for 3 min, at a flow rate of 1 mL/min (Temperature=45° C.). R$_t$=6.35 min at 254 nm.

Example 69

(R/S)-(6-methyl-3-(2H-1,2,3-triazol-2-yl)pyridin-2-yl)(3-methyl-6-((5-(trifluoromethyl)pyrazin-2-yl)amino)-2-azabicyclo[2.2.1]heptan-2-yl)methanone

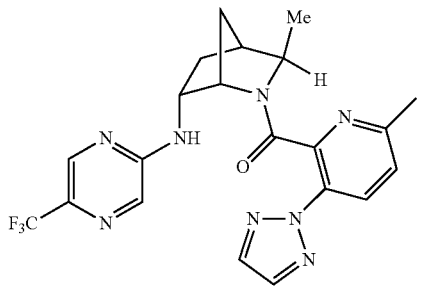 [SMILES: Cc1ccc(-n2nccn2)c(C(=O)N2C(C)C3CC(Nc4cnc(C(F)(F)F)cn4)C2C3)n1]

The title compound was prepared analogous to Example 6 substituting intermediate B-8 with intermediate B-16. MS (ESI): mass calcd. for $C_{21}H_{21}F_3N_8O$, 458.2. m/z found, 459.2 [M+H]$^+$. MP=252° C. $^1$H NMR (500 MHz, Chloroform-d) δ 8.17 (s, 1H), 8.04 (d, J=8.4 Hz, 1H), 7.87 (s, 2H), 7.84 (s, 1H), 7.23 (d, J=8.4 Hz, 1H), 4.41 (br. s, 1H), 4.11 (br. s, 1H), 3.94-3.83 (m, 1H), 2.57 (s, 3H), 2.49-2.40 (m, 1H), 2.40-2.35 (m, 1H), 2.19-2.07 (m, 1H), 1.60 (d, J=10.8 Hz, 1H), 1.45 (d, J=6.2 Hz, 3H), 1.20 (dt, J=13.3, 3.6 Hz, 1H).

Example 69 was subjected to Chiral SFC purification [Stationary phase: Chiralpak AD-H (5 μm 250×20 mm), Mobile phase of 25% EtOH (0.3% iPrNH$_2$): 75% CO$_2$] to provide the corresponding single enantiomers (Example 69A and Example 69B) were the absolute stereochemistry was not determined. The enantiomeric purity was confirmed by analytical SFC using a Chiralpak AD-H column (5 μm 150×4.6 mm), mobile phase of 20% EtOH (0.3% iPrNH$_2$): 80% CO$_2$, and a flow rate of 3 mL/min over 7 minutes (Temperature=35° C.).

Example 69A (6-methyl-3-(2H-1,2,3-triazol-2-yl)pyridin-2-yl)((1R*,3S*,4R*,6S*)-3-methyl-6-((5-(trifluoromethyl)pyrazin-2-yl)amino)-2-azabicyclo[2.2.1]heptan-2-yl)methanone

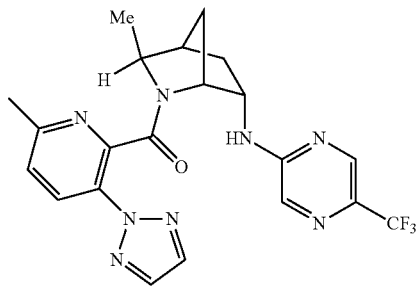 [SMILES: Cc1ccc(-n2nccn2)c(C(=O)N2C(C)C3CC(Nc4cnc(C(F)(F)F)cn4)C2C3)n1]

Enantiomeric purity (SFC/Chiralpak AD-H): 100%. R$_t$: 1.69 min. MS (ESI): mass calcd. for $C_{21}H_{21}F_3N_8O$, 458.2. m/z found, 459.2 [M+H]$^+$. $^1$H NMR (500 MHz, Chloroform-d) δ 8.18 (s, 1H), 8.04 (d, J=8.3 Hz, 1H), 7.87 (s, 2H), 7.83 (s, 1H), 7.23 (d, J=8.4 Hz, 1H), 4.43 (s, 1H), 4.17-4.06 (m, 1H), 3.94-3.81 (m, 1H), 2.57 (s, 3H), 2.50-2.41 (m, 1H), 2.40-2.35 (m, 1H), 2.18-2.09 (m, 1H), 1.60-1.57 (m, 1H), 1.45 (d, J=6.3 Hz, 3H), 1.23-1.15 (m, 1H).

Example 69B (6-methyl-3-(2H-1,2,3-triazol-2-yl)pyridin-2-yl)((1S*,3R*,4S*,6R*)-3-methyl-6-((5-(trifluoromethyl)pyrazin-2-yl)amino)-2-azabicyclo[2.2.1]heptan-2-yl)methanone

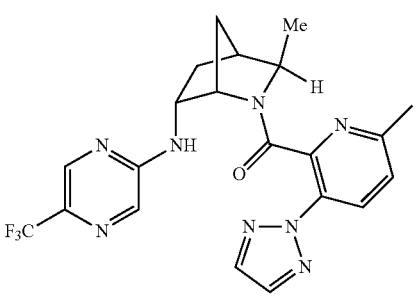

Enantiomeric purity (SFC/Chiralpak AD-H): >99%. R$_t$: 3.89 min. MS (ESI): mass calcd. for $C_{21}H_{21}F_3N_8O$, 458.2. m/z found, 459.2 [M+H]$^+$. $^1$H NMR (500 MHz, Chloroform-d) δ 8.18 (s, 1H), 8.05 (d, J=8.3 Hz, 1H), 7.87 (s, 2H), 7.83 (s, 1H), 7.24 (d, J=8.4 Hz, 1H), 4.43 (s, 1H), 4.17-4.08 (m, 1H), 3.92-3.82 (m, 1H), 2.57 (s, 3H), 2.49-2.41 (m, 1H), 2.41-2.36 (m, 1H), 2.19-2.09 (m, 1H), 1.62-1.59 (m, 1H), 1.46 (d, J=6.3 Hz, 3H), 1.22-1.15 (m, 1H).

Example 70

(R/S)-3-(fluoromethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone

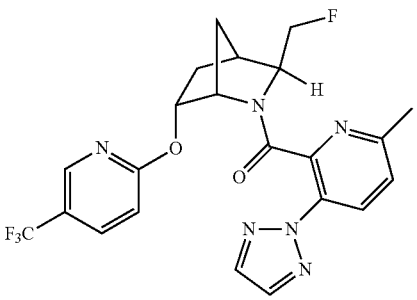 [SMILES: Cc1ccc(-n2nccn2)c(C(=O)N2C(CF)C3CC(Oc4ccc(C(F)(F)F)cn4)C2C3)n1]

Step A: (R/S)-tert-butyl 3-(fluoromethyl)-6-((5-(trifluoromethyl)pyridin-2-yl)oxy)-2-azabicyclo[2.2.1]heptane-2-carboxylate. To Intermediate B-22 (170 mg, 0.693 mmol) and 2-chloro-5-(trifluoromethyl)pyridine (164 mg, 0.903 mmol) dissolved in DMF (4 mL) was added NaH (45 mg, 1.1 mmol, 60% dispersion in mineral oil). After 1.25 h additional NaH (20 mg, 0.50 mmol, 60% dispersion in mineral oil) was added. After stirring for another 45 min, the mixture was carefully quenched with H$_2$O, and the aqueous layer extracted with EtOAc (3×). The combined organics were washed with 5% LiCl solution, brine, dried with MgSO₄, filtered and concentrated. Purification via silica gel chromatography (0-20% EtOAc in hexanes) gave the title compound (170 mg, 0.435 mmol, 63%). MS (ESI) mass calcd. for $C_{18}H_{22}F_4N_2O_3$, 390.2. m/z found 335.1 [M+2H-tBu]⁺.

Step B: (R/S)-3-(fluoromethyl)-6-((5-(trifluoromethyl)pyridin-2-yl)oxy)-2-azabicyclo[2.2.1]heptane.xHCl. To the title compound of step A (170 mg, 0.435 mmol) in EtOAc (1.5 mL) was added 4M HCl in dioxane (4 mL). After 30 min the reaction was concentrated to give the title compound of step B (144 mg) which was used without further purification. MS (ESI) mass calcd. for $C_{13}H_{14}F_4N_2O$, 290.1. m/z found 291.1 [M+H]⁺.

Step C: (R/S)-3-(fluoromethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone.
To the title compound of step B (29 mg) and intermediate A-26 (20 mg, 0.11 mmol) in DMF (0.4 mL) was added DIPEA (0.1 mL, 0.6 mmol) and HATU (41 mg, 0.098 mmol). Upon completion, the reaction was diluted with MeOH, filtered, and purified using Agilent Prep Method X to give the title compound (17 mg). MS (ESI): mass calcd. for $C_{22}H_{20}F_4N_6O_2$, 476.2. m/z found, 477.2 [M+H]⁺. ¹H NMR (500 MHz, Chloroform-d) δ 8.07-8.02 (m, 1H), 7.90 (d, J=8.3 Hz, 1H), 7.85 (s, 2H), 7.71 (dd, J=9.0, 2.8 Hz, 1H), 7.11 (d, J=8.4 Hz, 1H), 6.98-6.91 (m, 1H), 5.02-4.87 (m, 2H), 4.64-4.41 (m, 1H), 4.13-4.01 (m, 2H), 2.69-2.60 (m, 1H), 2.31 (s, 3H), 2.29-2.20 (m, 1H), 1.54-1.47 (m, 1H), 1.41 (dt, J=13.6, 3.6 Hz, 1H), 1.38-1.32 (m, 1H).

Example 71

(R/S)-(2-fluoro-6-(oxazol-2-yl)phenyl)-3-(fluoromethyl)-6-((5-(trifluoromethyl)pyridin-2-yl)oxy)-2-azabicyclo[2.2.1]heptan-2-yl)methanone

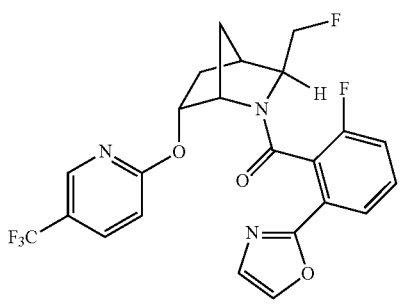 [SMILES: O=C(c1c(F)cccc1-c1ncco1)N1C(CF)C2CC(Oc3ccc(C(F)(F)F)cn3)C1C2]

The title compound was prepared analogous to Example 70 substituting intermediate A-26 with intermediate A-31. MS (ESI): mass calcd. for $C_{23}H_{18}F_5N_3O_3$, 479.1. m/z found, 480.2 [M+H]⁺. ¹H NMR (500 MHz, Chloroform-d) δ 8.10-8.05 (m, 1H), 7.79-7.76 (m, 1H), 7.76-7.73 (m, 2H), 7.34-7.25 (m, 2H), 6.95 (d, J=8.3 Hz, 1H), 6.79-6.69 (m, 1H), 5.17-4.96 (m, 2H), 4.82 (ddd, J=47.9, 9.6, 6.3 Hz, 1H), 4.14-4.04 (m, 1H), 3.99-3.94 (m, 1H), 2.75-2.70 (m, 1H), 2.37-2.27 (m, 1H), 1.73-1.64 (m, 1H), 1.43-1.35 (m, 2H).

Example 72

(R/S)-3-(fluoromethyl)-6-((5-(trifluoromethyl)pyridin-2-yl)oxy)-2-azabicyclo[2.2.1]heptan-2-yl)(5-methyl-2-(2H-1,2,3-triazol-2-yl)pyridin-3-yl)methanone

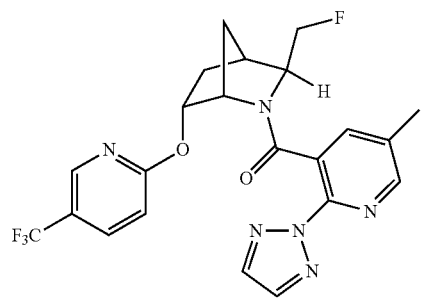 [SMILES: Cc1cnc(-n2nccn2)c(C(=O)N2C(CF)C3CC(Oc4ccc(C(F)(F)F)cn4)C2C3)c1]

The title compound was prepared analogous to Example 70 substituting intermediate A-26 with intermediate A-25. MS (ESI): mass calcd. for $C_{22}H_{20}F_4N_6O_2$, 476.2. m/z found, 477.2 [M+H]⁺. ¹H NMR (500 MHz, Chloroform-d) δ 8.27-8.22 (m, 1H), 8.14-8.10 (m, 1H), 7.89 (s, 2H), 7.79 (dd, J=8.6, 2.4 Hz, 1H), 7.49-7.45 (m, 1H), 6.78 (d, J=8.6 Hz, 1H), 5.07-4.83 (m, 2H), 4.53 (ddd, J=47.9, 9.5, 6.6 Hz, 1H), 4.09-3.95 (m, 1H), 3.93-3.81 (m, 1H), 2.71-2.61 (m, 1H), 2.32-2.18 (m, 1H), 2.05 (s, 3H), 1.43-1.35 (m, 2H), 1.34-1.28 (m, 1H).

Example 73

(R/S)-(2-(2H-1,2,3-triazol-2-yl)phenyl)(3-(fluoromethyl)-6-((5-(trifluoromethyl)pyridin-2-yl)oxy)-2-azabicyclo[2.2.1]heptan-2-yl)methanone

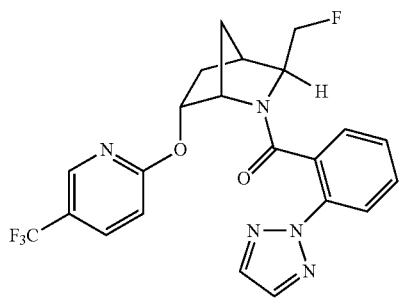 [SMILES: O=C(c1ccccc1-n1nccn1)N1C(CF)C2CC(Oc3ccc(C(F)(F)F)cn3)C1C2]

The title compound was prepared analogous to Example 70 substituting intermediate A-26 with intermediate A-1. MS (ESI): mass calcd. for $C_{22}H_{19}F_4N_5O_2$, 461.1. m/z found, 462.2 [M+H]⁺. ¹H NMR (500 MHz, Chloroform-d) δ 8.03-7.98 (m, 1H), 7.83 (s, 2H), 7.77 (dd, J=8.6, 2.4 Hz, 1H), 7.70 (dd, J=8.2, 1.1 Hz, 1H), 7.37-7.31 (m, 1H), 7.17 (dd, J=7.7, 1.5 Hz, 1H), 6.85 (td, J=7.6, 1.1 Hz, 1H), 6.81 (d, J=8.7 Hz, 1H), 5.06-4.83 (m, 2H), 4.44 (ddd, J=47.9, 9.5, 6.8 Hz, 1H), 4.09-3.95 (m, 1H), 3.87 (s, 1H), 2.66-2.53 (m, 1H), 2.29-2.14 (m, 1H), 1.46-1.32 (m, 1H), 1.30-1.22 (m, 2H).

Example 74

(((1S,3S,4R,6R)-3-(fluoromethyl)-6-((5-(trifluoromethyl)pyridin-2-yl)oxy)-2-azabicyclo[2.2.2]octan-2-yl)(6-methyl-3-(pyrimidin-2-yl)pyridin-2-yl)methanone

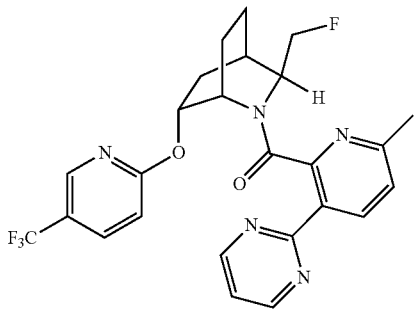 [SMILES: Cc1ccc(-c2ncccn2)c(C(=O)N2C(CF)C3CCC2C(Oc2ccc(C(F)(F)F)cn2)C3)n1]

Step A: (1S*,3R*,4R*,6R*)-tert-butyl 3-methyl-6-((5-(trifluoromethyl)pyrazin-2-yl)oxy)-2-azabicyclo[2.2.1]heptane-2-carboxylate. To B-29 (700 mg) dissolved in DMF (20 mL) was added NaH (140 mg, 3.51 mmol, 60% dispersion in mineral oil). After 5 minutes 2-chloro-5-(trifluoromethyl)pyridine (735 mg, 4.05 mmol) was added and the reaction left to stir at room temperature. After stirring for 5 h, the mixture was carefully quenched with H$_2$O, and the aqueous layer extracted with EtOAc (3×). The combined organics were washed with, brine, dried with MgSO$_4$, filtered and concentrated. Purification via silica gel chromatography (0-20% EtOAc in hexanes) gave the title compound (310 mg). MS (ESI) mass calcd. for C$_{19}$H$_{24}$F$_4$N$_2$O$_3$, 404.2; m/z found 349.1 [M+2H-tBu]$^+$.

Step B: (1S,3S,4R,6R)-3-(fluoromethyl)-6-((5-(trifluoromethyl)pyridin-2-yl)oxy)-2-azabicyclo[2.2.2]octane.x-HCl. To the title compound of step A (310 mg, 0.767 mmol) in DCM (3 mL) was added 4M HCl in dioxane (12 mL) and the reaction mixture was stirred for 3 h at room temperature after which the reaction was concentrated to give the title compound of step B (250 mg), which was used without further purification. MS (ESI) mass calcd. for C$_{12}$H$_{14}$F$_3$N$_3$O, 304.1; m/z found 304.9 [M+H]$^+$.

Step C: ((1S,3S,4R,6R)-3-(fluoromethyl)-6-((5-(trifluoromethyl)pyridin-2-yl)oxy)-2-azabicyclo[2.2.2]octan-2-yl)(6-methyl-3-(pyrimidin-2-yl)pyridin-2-yl)methanone. To the title compound of step B (46 mg) and intermediate A-27 (39 mg, 0.18 mmol) in DCM (0.94 mL) was added DIPEA (0.52 mL, 0.30 mmol), EDCI (35 mg, 0.18 mmol), and HOBt (25 mg, 0.18 mmol). Upon completion, the reaction was diluted with DCM, washed with H$_2$O, concentrated, and purified via silica gel chromatography (0-100% EtOAc in hexanes) to give the title compound (44 mg). MS (ESI): mass calcd. for C$_{25}$H$_{23}$F$_4$N$_5$O$_2$, 501.2. m/z found, 502.0 [M+H]$^+$. Analytical HPLC was obtained on a Agilent 1100 Series using a Zorbax SB-C18 column (3.5 µm, 150×4.6 mm), mobile phase of 5-99% ACN in 0.05% TFA over 7 min and then hold at 99% ACN for 3 min, at a flow rate of 2 mL/min (Temperature=30° C.). R$_t$=6.25 min at 280 nm.

Example 75

((1S,3S,4R,6R)-3-(fluoromethyl)-6-((5-(trifluoromethyl)pyridin-2-yl)oxy)-2-azabicyclo[2.2.2]octan-2-yl)(2-(pyrimidin-2-yl)phenyl)methanone

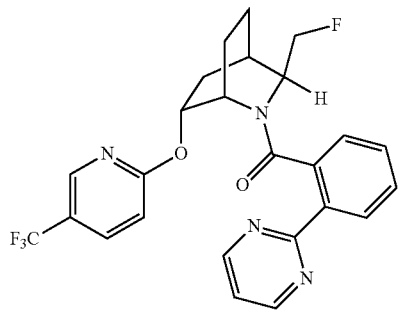 [SMILES: O=C(c1ccccc1-c1ncccn1)N1C(CF)C2CCC1C(Oc1ccc(C(F)(F)F)cn1)C2]

The title compound was prepared analogous to Example 74 substituting intermediate A-27 with intermediate A-24. Analytical HPLC was obtained on a Agilent 1100 Series using a Zorbax SB-C18 column (3.5 µm, 150×4.6 mm), mobile phase of 5-99% ACN in 0.05% TFA over 7 min and then hold at 99% ACN for 3 min, at a flow rate of 2 mL/min (Temperature=30° C.). R$_t$=6.53 min at 280 nm.

Example 76

(5-fluoro-2-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone

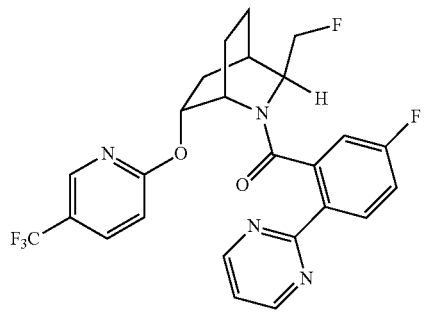 [SMILES: O=C(c1cc(F)ccc1-c1ncccn1)N1C(CF)C2CCC1C(Oc1ccc(C(F)(F)F)cn1)C2]

The title compound was prepared analogous to Example 74 substituting intermediate A-27 with intermediate A-7. MS (ESI): mass calcd. for C$_{25}$H$_{21}$F$_5$N$_4$O$_2$, 504.2. m/z found, 504.9 [M+H]$^+$. Analytical HPLC was obtained on a Agilent 1100 Series using a Zorbax SB-C18 column (3.5 µm, 150×4.6 mm), mobile phase of 5-99% ACN in 0.05% TFA over 7 min and then hold at 99% ACN for 3 min, at a flow rate of 2 mL/min (Temperature=30° C.). R$_t$=6.68 min at 280 nm.

Example 77

((1S,3S,4R,6R)-3-(fluoromethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone

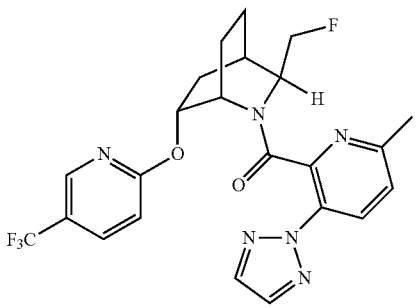 [SMILES: Cc1ccc(-n2nccn2)c(C(=O)N2C(CF)C3CCC2C(Oc2ccc(C(F)(F)F)cn2)C3)n1]

The title compound was prepared analogous to Example 74 substituting intermediate A-27 with intermediate A-26. MS (ESI): mass calcd. for $C_{23}H_{22}F_4N_6O_2$, 490.2. m/z found, 490.9 [M+H]$^+$. Analytical HPLC was obtained on a Agilent 1100 Series using a Zorbax SB-C18 column (3.5 μm, 150×4.6 mm), mobile phase of 5-99% ACN in 0.05% TFA over 7 min and then hold at 99% ACN for 3 min, at a flow rate of 2 mL/min (Temperature=30° C.). $R_t$=6.31 min at 280 nm. MS (ESI): mass calcd. for $C_{23}H_{22}F_4N_6O_2$, 490.2. m/z found, 491.0 [M+H]$^+$. $^1$H NMR (400 MHz, CDCl$_3$) δ 8.50-8.39 (m, 1H), 8.23-8.17 (d, J=8.4 Hz, 1H), 7.87-7.80 (s, 2H), 7.79-7.72 (m, 1H), 7.41-7.28 (dd, J=8.4, 0.6 Hz, 1H), 6.88-6.63 (m, 1H), 5.50-5.31 (m, 1H), 5.31-5.17 (dd, J=8.9, 4.4 Hz, 1H), 5.17-5.06 (dd, J=8.6, 4.1 Hz, 1H), 4.70-4.63 (m, 1H), 4.58-4.51 (d, J=8.8 Hz, 1H), 3.54-3.44 (s, 1H), 2.73-2.55 (m, 5H), 1.94-1.76 (dt, J=35.2, 17.6 Hz, 1H), 1.68-1.55 (s, 2H), 1.45-1.34 (m, 1H).

Example 78

(5-fluoro-2-(2H-1,2,3-triazol-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone

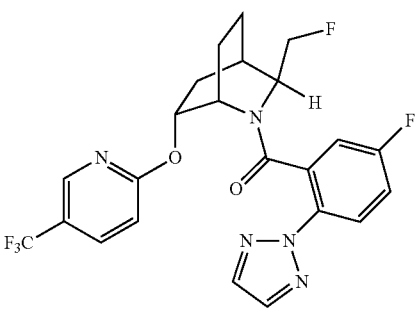 [SMILES: O=C(c1cc(F)ccc1-n1nccn1)N1C(CF)C2CCC1C(Oc1ccc(C(F)(F)F)cn1)C2]

The title compound was prepared analogous to Example 74 substituting intermediate A-27 with intermediate A-10. MS (ESI): mass calcd. for $C_{25}H_{20}F_5N_5O_2$, 493.2. m/z found, 493.9 [M+H]$^+$. Analytical HPLC was obtained on a Agilent 1100 Series using a Zorbax SB-C18 column (3.5 μm, 150×4.6 mm), mobile phase of 5-99% ACN in 0.05% TFA over 7 min and then hold at 99% ACN for 3 min, at a flow rate of 2 mL/min (Temperature=30° C.). $R_t$=6.57 min at 280 nm.

Example 79

(3-fluoro-2-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone

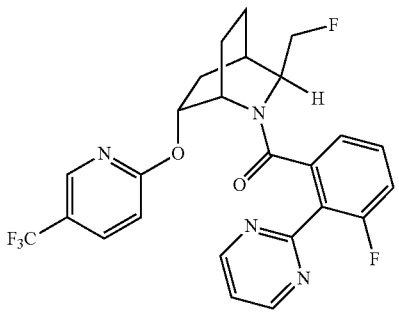 [SMILES: O=C(c1cccc(F)c1-c1ncccn1)N1C(CF)C2CCC1C(Oc1ccc(C(F)(F)F)cn1)C2]

The title compound was prepared analogous to Example 74 substituting intermediate A-27 with intermediate A-2. Analytical HPLC was obtained on a Agilent 1100 Series using a Zorbax SB-C18 column (3.5 μm, 150×4.6 mm), mobile phase of 5-99% ACN in 0.05% TFA over 7 min and then hold at 99% ACN for 3 min, at a flow rate of 2 mL/min (Temperature=30° C.). $R_t$=5.98 min at 280 nm.

Example 80

(5-fluoro-2-(5-fluoropyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone

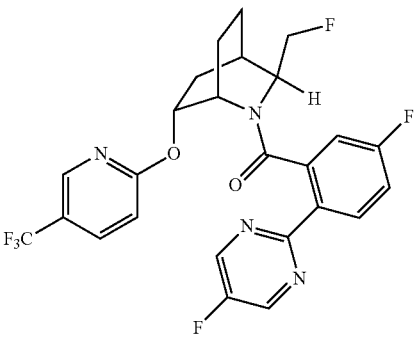 [SMILES: O=C(c1cc(F)ccc1-c1ncc(F)cn1)N1C(CF)C2CCC1C(Oc1ccc(C(F)(F)F)cn1)C2]

The title compound was prepared analogous to Example 74 substituting intermediate A-27 with intermediate A-22. MS (ESI): mass calcd. for $C_{25}H_{20}F_6N_4O_2$, 522.1. m/z found, 523.0 [M+H]$^+$. Analytical HPLC was obtained on a Agilent 1100 Series using a Zorbax SB-C18 column (3.5 μm, 150×4.6 mm), mobile phase of 5-99% ACN in 0.05% TFA over 7 min and then hold at 99% ACN for 3 min, at a flowrate of 2 mL/min (Temperature=30° C.). $R_t$=6.87 min at 280 nm.

Examples 81-109, shown below in Table 1, are also contemplated within the scope of embodiments presented herein and may be prepared using the procedures described above.

TABLE 1

| Ex. No. | Compound | Chemical Name |
|---|---|---|
| 81 | | ((1S,3R,4R,6R)-3-ethyl-6-((5-(trifluoromethyl)pyridin-2-yl)oxy)-2-azabicyclo[2.2.1]heptan-2-yl)(2-(pyrimidin-2-yl)phenyl)methanone |
| 82 | | ((1S,3R,4R,6R)-3-ethyl-6-((5-(trifluoromethyl)pyridin-2-yl)oxy)-2-azabicyclo[2.2.1]heptan-2-yl)(3-fluoro-2-(pyrimidin-2-yl)phenyl)methanone |
| 83 | | ((1S,3R,4R,6R)-3-ethyl-6-((5-(trifluoromethyl)pyridin-2-yl)oxy)-2-azabicyclo[2.2.1]heptan-2-yl)(2-(5-fluoropyrimidin-2-yl)phenyl)methanone |
| 84 | | ((1S,3R,4S,6R)-3-ethyl-6-((5-(trifluoromethyl)pyridin-2-yl)amino)-2-azabicyclo[2.2.1]heptan-2-yl)(2-(pyrimidin-2-yl)phenyl)methanone |

TABLE 1-continued

| Ex. No. | Compound | Chemical Name |
|---|---|---|
| 85 | | (2-(2H-1,2,3-triazol-2-yl)phenyl)((1S,3R,4S,6R)-3-ethyl-6-((5-(trifluoromethyl)pyridin-2-yl)amino)-2-azabicyclo[2.2.1]heptan-2-yl)methanone |
| 86 | | ((1S,3R,4S,6R)-3-ethyl-6-((5-(trifluoromethyl)pyridin-2-yl)amino)-2-azabicyclo[2.2.1]heptan-2-yl)(6-methyl-3-(2H-1,2,3-triazol-2-yl)pyridin-2-yl)methanone |
| 87 | | ((1S,3R,4S,6R)-3-ethyl-6-((5-(trifluoromethyl)pyridin-2-yl)amino)-2-azabicyclo[2.2.1]heptan-2-yl)(6-methyl-3-(2H-1,2,3-triazol-2-yl)pyridin-2-yl)methanone |
| 88 | | (2-(2H-1,2,3-triazol-2-yl)phenyl)((1S,3R,4R,6R)-3-ethyl-6-((5-(trifluoromethyl)pyridin-2-yl)oxy)-2-azabicyclo[2.2.1]heptan-2-yl)methanone |
| 89 | | ((1S,3R,4R,6R)-3-ethyl-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |

TABLE 1-continued

| Ex. No. | Compound | Chemical Name |
|---|---|---|
| 90 | | ((1S,3R,4R,6R)-3-ethyl-6-((5-(trifluoromethyl)pyridin-2-yl)oxy)-2-azabicyclo[2.2.1]heptan-2-yl)(5-methyl-3-(2H-1,2,3-triazol-2-yl)pyridin-2-yl)methanone |
| 91 | | ((1S,3R,4S,6R)-3-ethyl-6-((5-(trifluoromethyl)pyrazin-2-yl)amino)-2-azabicyclo[2.2.1]heptan-2-yl)(2-(pyrimidin-2-yl)phenyl)methanone |
| 92 | | (2-(2H-1,2,3-triazol-2-yl)phenyl)((1S,3R,4S,6R)-3-ethyl-6-((5-(trifluoromethyl)pyrazin-2-yl)amino)-2-azabicyclo[2.2.1]heptan-2-yl)methanone |
| 93 | | ((1S,3R,4S,6R)-3-ethyl-6-((5-(trifluoromethyl)pyrazin-2-yl)amino)-2-azabicyclo[2.2.1]heptan-2-yl)(6-methyl-3-(2H-1,2,3-triazol-2-yl)pyridin-2-yl)methanone |
| 94 | | ((1S,3R,4R,6R)-3-isobutyl-6-((5-(trifluoromethyl)pyridin-2-yl)oxy)-2-azabicyclo[2.2.1]heptan-2-yl)(2-(pyrimidin-2-yl)phenyl)methanone |

TABLE 1-continued

| Ex. No. | Compound | Chemical Name |
|---|---|---|
| 95 | 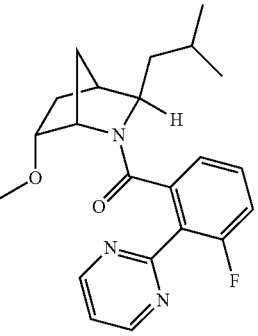 | (3-fluoro-2-(pyrimidin-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone |
| 96 | 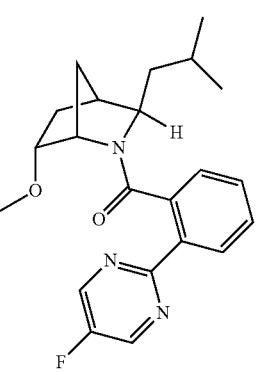 | (2-(5-fluoropyrimidin-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone |
| 97 | 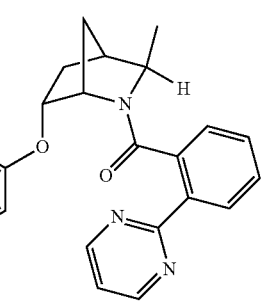 | ((1S,3R,4R,6R)-6-((5-(fluoromethyl)pyridin-2-yl)oxy)-3-methyl-2-azabicyclo[2.2.1]heptan-2-yl)(2-(pyrimidin-2-yl)phenyl)methanone |
| 98 | 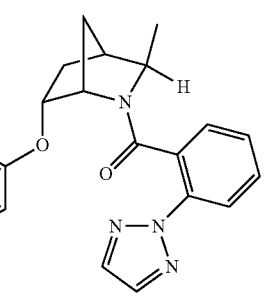 | (2-(2H-1,2,3-triazol-2-yl)phenyl)((1S,3R,4R,6R)-6-((5-(fluoromethyl)pyridin-2-yl)oxy)-3-methyl-2-azabicyclo[2.2.1]heptan-2-yl)methanone |
| 99 | 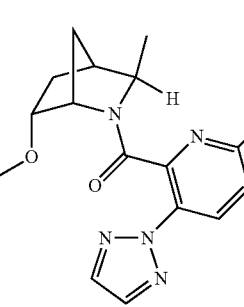 | ((1S,3R,4R,6R)-6-((5-(fluoromethyl)pyridin-2-yl)oxy)-3-methyl-2-azabicyclo[2.2.1]heptan-2-yl)(6-methyl-3-(2H-1,2,3-triazol-2-yl)pyridin-2-yl)methanone |

TABLE 1-continued

| Ex. No. | Compound | Chemical Name |
|---|---|---|
| 100 | | (2-(2H-1,2,3-triazol-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone |
| 101 | | ((1S,3R,4R,6R)-3-isobutyl-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |
| 102 | | ((1S,3R,4R,6R)-3-isobutyl-6-((5-(trifluoromethyl)pyridin-2-yl)oxy)-2-azabicyclo[2.2.1]heptan-2-yl)(5-methyl-3-(2H-1,2,3-triazol-2-yl)pyridin-2-yl)methanone |
| 103 | | ((1S,3S,4R,6R)-3-(methoxymethyl)-6-((5-(trifluoromethyl)pyridin-2-yl)oxy)-2-azabicyclo[2.2.1]heptan-2-yl)(2-(pyrimidin-2-yl)phenyl)methanone |

TABLE 1-continued

| Ex. No. | Compound | Chemical Name |
|---|---|---|
| 104 | | (2-(2H-1,2,3-triazol-2-yl)phenyl)((1S,3S,4R,6R)-3-(methoxymethyl)-6-((5-(trifluoromethyl)pyridin-2-yl)oxy)-2-azabicyclo[2.2.1]heptan-2-yl)methanone |
| 105 | | ((1S,3S,4R,6R)-3-(methoxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |
| 106 | | ((1S,3R,4R,6R)-3-methyl-6-((5-(trifluoromethyl)pyridin-2-yl)oxy)-2-azabicyclo[2.2.1]heptan-2-yl)(2-(pyridazin-3-yl)phenyl)methanone |
| 107 | | (5-(4-fluorophenyl)-2-methylthiazol-4-yl)((1S,3R,4R,6R)-3-methyl-6-((5-(trifluoromethyl)pyridin-2-yl)oxy)-2-azabicyclo[2.2.1]heptan-2-yl)methanone |

TABLE 1-continued

| Ex. No. | Compound | Chemical Name |
|---|---|---|
| 108 | | ((1S,3R,4R,6R)-6-((5-(difluoromethyl)pyridin-2-yl)oxy)-3-methyl-2-azabicyclo[2.2.1]heptan-2-yl)(2-(pyrimidin-2-yl)phenyl)methanone |
| 109 | | (2-(2H-1,2,3-triazol-2-yl)phenyl)((1S,3R,4R,6R)-6-((5-(difluoromethyl)pyridin-2-yl)oxy)-3-methyl-2-azabicyclo[2.2.1]heptan-2-yl)methanone |

Example 110

[(1R,2R,4S,5R)-5-[[5-(difluoromethyl)-2-pyridyl]oxy]-2-methyl-3-azabicyclo[2.2.1]heptan-3-yl]-[6-methyl-3-(triazol-2-yl)-2-pyridyl]methanone

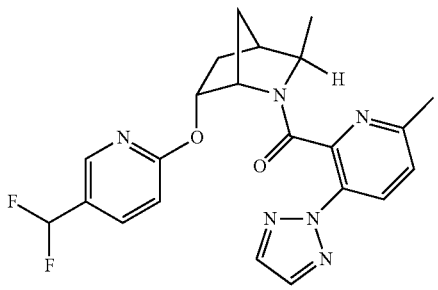 [SMILES: Cc1ccc(-n2nccn2)c(C(=O)N2C(C)C3CC(Oc4ccc(C(F)F)cn4)C2C3)n1]

The title compound was prepared analogous to Example 28 substituting intermediate A-12 with intermediate A-26 and 2-chloro-5-(trifluoromethyl)pyridine with 2-chloro-5-(difluoromethyl)pyridine. MS (ESI): mass calcd. for $C_{22}H_{22}F_2N_6O_2$, 440.2. m/z found, 441.1 [M+H]$^+$. $^1$H NMR (500 MHz, CDCl$_3$) δ 7.89 (q, J=2.0 Hz, 1H), 7.87-7.83 (m, 3H), 7.64 (dt, J=8.6, 1.6 Hz, 1H), 7.07 (d, J=8.3 Hz, 1H), 6.91 (d, J=8.6 Hz, 1H), 6.57 (t, J=56.0 Hz, 1H), 4.95-4.84 (m, 1H), 4.09 (t, J=2.4 Hz, 1H), 3.95 (q, J=6.3 Hz, 1H), 2.32 (s, 3H), 2.22-2.14 (m, 2H), 1.51-1.42 (m, 1H), 1.40-1.29 (m, 5H).

Examples 111-120, shown below in Table 2, are also contemplated within the scope of embodiments presented herein and may be prepared using the procedures described above.

TABLE 2

| Ex. No. | Compound | Chemical Name |
|---|---|---|
| 111 | | ((1S,3S,4R,6R)-3-(1-methoxyethyl)-6-((5-(trifluoromethyl)pyridin-2-yl)oxy)-2-azabicyclo[2.2.1]heptan-2-yl)(2-(pyrimidin-2-yl)phenyl)methanone |

TABLE 2-continued

| Ex. No. | Compound | Chemical Name |
|---|---|---|
| 112 | | (2-(2H-1,2,3-triazol-2-yl)phenyl)((1S,3S,4R,6R)-3-(1-methoxyethyl)-6-((5-(trifluoromethyl)pyridin-2-yl)oxy)-2-azabicyclo[2.2.1]heptan-2-yl)methanone |
| 113 | | ((1S,3S,4R,6R)-3-(1-methoxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |
| 114 | | ((1S,3R,4R,6R)-3-methyl-6-((5-methylpyridin-2-yl)oxy)-2-azabicyclo[2.2.1]heptan-2-yl)(2-(pyrimidin-2-yl)phenyl)methanone |
| 115 | | (2-(2H-1,2,3-triazol-2-yl)phenyl)((1S,3R,4R,6R)-3-methyl-6-((5-methylpyridin-2-yl)oxy)-2-azabicyclo[2.2.1]heptan-2-yl)methanone |
| 116 | | (6-methyl-3-(2H-1,2,3-triazol-2-yl)pyridin-2-yl)((1S,3R,4R,6R)-3-methyl-6-((5-methylpyridin-2-yl)oxy)-2-azabicyclo[2.2.1]heptan-2-yl)methanone |

TABLE 2-continued

| Ex. No. | Compound | Chemical Name |
|---|---|---|
| 117 | | ((1S,3S,4R,6R)-3-(hydroxymethyl)-6-((5-(trifluoromethyl)pyridin-2-yl)oxy)-2-azabicyclo[2.2.1]heptan-2-yl)(2-(pyrimidin-2-yl)phenyl)methanone |
| 118 | | (2-(2H-1,2,3-triazol-2-yl)phenyl)((1S,3S,4R,6R)-3-(hydroxymethyl)-6-((5-(trifluoromethyl)pyridin-2-yl)oxy)-2-azabicyclo[2.2.1]heptan-2-yl)methanone |
| 119 | | ((1S,3S,4R,6R)-3-(hydroxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |
| 120 | | ((1S,3R,4R,6R)-6-((5-chloropyridin-2-yl)oxy)-3-methyl-2-azabicyclo[2.2.1]heptan-2-yl)(2-(pyrimidin-2-yl)phenyl)methanone |

Example 121

[(1R,2R,4S,5R)-5-[(5-chloro-2-pyridyl)oxy]-2-methyl-3-azabicyclo[2.2.1]heptan-3-yl]-[2-(triazol-2-yl)phenyl]methanone

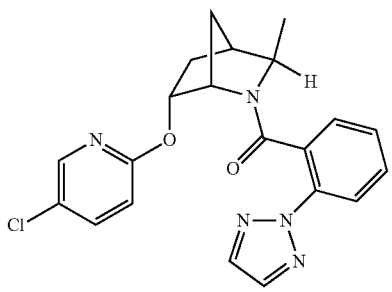 [SMILES: CC1C2CC(Oc3ccc(Cl)cn3)C(C2)N1C(=O)c1ccccc1-n1nccn1]

Step A: (1S,3R,4R,6R)-tert-butyl 6-((5-chloropyridin-2-yl)oxy)-3-methyl-2-azabicyclo[2.2.1]heptane-2-carboxylate. To Intermediate B-14A (100 mg, 0.44 mmol) and 5-chloro-2-fluoropyridine (87 mg, 0.66 mmol) dissolved in DMF (4 mL) was added NaH (26 mg, 0.65 mmol, 60% dispersion in mineral oil). After addition of NaH the sides of the flask were rinsed with additional DMF (2 mL) and the reaction left to stir at room temperature. After stirring for 3 h, the mixture was carefully quenched with $H_2O$, and the aqueous layer extracted with EtOAc (3×). The combined organics were washed with 5% LiCl solution, brine, dried with $MgSO_4$, filtered and concentrated. Purification via silica gel chromatography (0-20% EtOAc in hexanes) gave the title compound (142 mg, 0.42 mmol, 95%). MS (ESI) mass calcd. for $C_{12}H_{23}ClN_2O_3$, 338.1; m/z found 339.2 [M+H]$^+$.

Step B: (1S,3R,4R,6R)-6-(5-chloropyridin-2-yl)oxy)-3-methyl-2-azabicyclo[2.2.1]heptane.xHCl. To the title compound of step A (142 mg) in EtOAc (4 mL) was added 4M HCl in dioxane (8 mL). After 7.75 h the reaction was concentrated to give the title compound of step B (121 mg) which was used without further purification. MS (ESI) mass calcd. for $C_{12}H_{15}ClN_2O$, 238.1; m/z found 239.0 [M+H]$^+$.

Step C: [(1R,2R,4S,5R)-5-[(5-chloro-2-pyridyl)oxy]-2-methyl-3-azabicyclo[2.2.1]heptan-3-yl]-[2-(triazol-2-yl)phenyl]methanone. To the compound of step B (30 mg) and intermediate A-1 (22 mg, 0.12 mmol) in DMF (0.7 mL) was added DIPEA (0.05 mL, 0.3 mmol) and HATU (44 mg, 0.12 mmol). Upon completion, the reaction was diluted with MeOH, filtered, and purified using Agilent Prep Method X to give the title compound (24 mg). MS (ESI): mass calcd. for $C_{21}H_{20}ClN_5O_2$, 409.1. m/z found, 410.0 [M+H]$^+$. $^1$H NMR (500 MHz, Chloroform-d) δ 7.83 (s, 2H), 7.69-7.65 (m, 2H), 7.50 (dd, J=8.8, 2.7 Hz, 1H), 7.36 (ddd, J=8.1, 7.4, 1.5 Hz, 1H), 7.24 (dd, J=7.7, 1.5 Hz, 1H), 6.95 (td, J=7.6, 1.2 Hz, 1H), 6.67 (d, J=8.8 Hz, 1H), 4.85-4.79 (m, 1H), 3.87 (q, J=6.3 Hz, 1H), 3.82 (br. s, 1H), 2.17-2.09 (m, 2H), 1.32-1.17 (m, 3H), 1.30 (d, J=6.3 Hz, 3H).

Example 122

[(1R,2R,4S,5R)-5-[(5-chloro-2-pyridyl)oxy]-2-methyl-3-azabicyclo[2.2.1]heptan-3-yl]-[6-methyl-3-(triazol-2-yl)-2-pyridyl]methanone

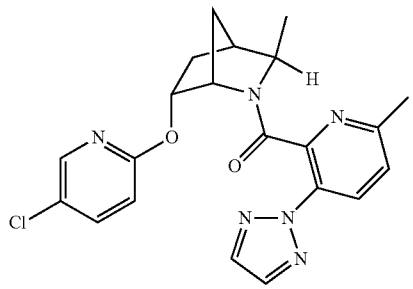

The title compound was prepared analogous to Example 121 substituting intermediate A-1 with intermediate A-26. MS (ESI): mass calcd. for $C_{21}H_{21}ClN_6O_2$, 424.1. m/z found 425.0, [M+H]$^+$. $^1$H NMR (500 MHz, Chloroform-d) δ 7.87 (d, J=8.3 Hz, 1H), 7.85 (s, 2H), 7.68-7.66 (dd, J=2.7, 0.7 Hz, 1H), 7.44 (dd, J=8.8, 2.7 Hz, 1H), 7.13 (d, J=8.3 Hz, 1H), 6.80 (dd, J=8.8, 0.7 Hz, 1H), 4.83-4.77 (m, 1H), 4.08-4.05 (m, 1H), 3.93 (q, J=6.3 Hz, 1H), 2.36 (s, 3H), 2.19-2.11 (m, 2H), 1.44-1.39 (m, 1H), 1.37-1.31 (m, 4H), 1.31-1.27 (m, 1H).

Examples 123-147, shown below in Table 3, are also contemplated within the scope of embodiments presented herein and may be prepared using the procedures described above.

TABLE 3

| Ex. No. | Compound | Chemical Name |
|---|---|---|
| 123 | ![structure] | ((1S,3S,4R,6R)-3-(1-hydroxyethyl)-6-((5-(trifluoromethyl)pyridin-2-yl)oxy)-2-azabicyclo[2.2.1]heptan-2-yl)(2-(pyrimidin-2-yl)phenyl)methanone |

TABLE 3-continued

| Ex. No. | Compound | Chemical Name |
|---|---|---|
| 124 | | (2-(2H-1,2,3-triazol-2-yl)phenyl)((1S,3S,4R,6R)-3-(1-hydroxyethyl)-6-((5-(trifluoromethyl)pyridin-2-yl)oxy)-2-azabicyclo[2.2.1]heptan-2-yl)methanone |
| 125 | | ((1S,3S,4R,6R)-3-(1-hydroxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone |
| 126 | | ((1S,3R,4S,6R)-6-((3-fluoro-5-(trifluoromethyl)pyridin-2-yl)amino)-3-methyl-2-azabicyclo[2.2.1]heptan-2-yl)(2-(pyrimidin-2-yl)phenyl)methanone |
| 127 | | (2-(2H-1,2,3-triazol-2-yl)phenyl)((1S,3R,4S,6R)-6-((3-fluoro-5-(trifluoromethyl)pyridin-2-yl)amino)-3-methyl-2-azabicyclo[2.2.1]heptan-2-yl)methanone |
| 128 | | ((1S,3R,4S,6R)-6-((3-fluoro-5-(trifluoromethyl)pyridin-2-yl)amino)-3-methyl-2-azabicyclo[2.2.1]heptan-2-yl)(6-methyl-3-(2H-1,2,3-triazol-2-yl)pyridin-2-yl)methanone |

TABLE 3-continued

| Ex. No. | Compound | Chemical Name |
|---|---|---|
| 129 | | ((1S,3R,4S,6R)-6-(benzo[d]oxazol-2-ylamino)-3-methyl-2-azabicyclo[2.2.1]heptan-2-yl)(2-(pyrimidin-2-yl)phenyl)methanone |
| 130 | | (2-(2H-1,2,3-triazol-2-yl)phenyl)((1S,3R,4S,6R)-6-(benzo[d]oxazol-2-ylamino)-3-methyl-2-azabicyclo[2.2.1]heptan-2-yl)methanone |
| 131 | | ((1S,3R,4S,6R)-6-(benzo[d]oxazol-2-ylamino)-3-methyl-2-azabicyclo[2.2.1]heptan-2-yl)(6-methyl-3-(2H-1,2,3-triazol-2-yl)pyridin-2-yl)methanone |
| 132 | | ((1S,3R,4S,6R)-3-methyl-6-((5-(trifluoromethyl)pyrimidin-2-yl)amino)-2-azabicyclo[2.2.1]heptan-2-yl)(2-(pyrimidin-2-yl)phenyl)methanone |
| 133 | | (2-(2H-1,2,3-triazol-2-yl)phenyl)((1S,3R,4S,6R)-3-methyl-6-((5-(trifluoromethyl)pyrimidin-2-yl)amino)-2-azabicyclo[2.2.1]heptan-2-yl)methanone |

TABLE 3-continued

| Ex. No. | Compound | Chemical Name |
|---|---|---|
| 134 | | (6-methyl-3-(2H-1,2,3-triazol-2-yl)pyridin-2-yl)((1S,3R,4S,6R)-3-methyl-6-((5-(trifluoromethyl)pyrimidin-2-yl)amino)-2-azabicyclo[2.2.1]heptan-2-yl)methanone |
| 135 | | ((1S,3R,4R,6R)-6-((5-bromopyridin-2-yl)oxy)-3-methyl-2-azabicyclo[2.2.1]heptan-2-yl)(2-(pyrimidin-2-yl)phenyl)methanone |
| 136 | | (2-(2H-1,2,3-triazol-2-yl)phenyl)((1S,3R,4R,6R)-6-((5-bromopyridin-2-yl)oxy)-3-methyl-2-azabicyclo[2.2.1]heptan-2-yl)methanone |
| 137 | | ((1S,3R,4R,6R)-6-((5-bromopyridin-2-yl)oxy)-3-methyl-2-azabicyclo[2.2.1]heptan-2-yl)(6-methyl-3-(2H-1,2,3-triazol-2-yl)pyridin-2-yl)methanone |
| 138 | | ((1S,3 S,4R,6R)-3-(fluoromethyl)-6-((5-(trifluoromethyl)pyridin-2-yl)oxy)-2-azabicyclo[2.2.2]octan-2-yl)(2-methoxy-6-(pyrimidin-2-yl)phenyl)methanone |

TABLE 3-continued

| Ex. No. | Compound | Chemical Name |
|---|---|---|
| 139 | | ((1S,3S,4R,6R)-3-(fluoromethyl)-6-((5-(trifluoromethyl)pyridin-2-yl)oxy)-2-azabicyclo[2.2.2]octan-2-yl)(4-methyl-2-(2H-1,2,3-triazol-2-yl)phenyl)methanone |
| 140 | | ((1S,3S,4R,6R)-3-(fluoromethyl)-6-((5-(trifluoromethyl)pyridin-2-yl)oxy)-2-azabicyclo[2.2.2]octan-2-yl)(2-methyl-6-(2H-1,2,3-triazol-2-yl)phenyl)methanone |
| 141 | | (2-fluoro-6-(pyrimidin-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone |
| 142 | | (2-(2H-1,2,3-triazol-2-yl)phenyl)((1S,3S,4R,6R)-3-(fluoromethyl)-6-((5-(trifluoromethyl)pyridin-2-yl)oxy)-2-azabicyclo[2.2.2]octan-2-yl)methanone |
| 143 | | ((1S,3S,4R,6R)-3-(fluoromethyl)-6-((5-(trifluoromethyl)pyridin-2-yl)oxy)-2-azabicyclo[2.2.2]octan-2-yl)(3-methyl-2-(oxazol-2-yl)phenyl)methanone |

TABLE 3-continued

| Ex. No. | Compound | Chemical Name |
|---|---|---|
| 144 | | ((1S,3S,4R,6R)-3-(fluoromethyl)-6-((5-(trifluoromethyl)pyridin-2-yl)oxy)-2-azabicyclo[2.2.2]octan-2-yl)(3-methyl-2-(pyridin-2-yl)phenyl)methanone |
| 145 | | ((1S,3S,4R,6R)-3-(fluoromethyl)-6-((5-(trifluoromethyl)pyridin-2-yl)oxy)-2-azabicyclo[2.2.2]octan-2-yl)(2-(5-fluoropyrimidin-2-yl)phenyl)methanone |
| 146 | | ((1S,3S,4R,6R)-3-(fluoromethyl)-6-((5-(trifluoromethyl)pyridin-2-yl)oxy)-2-azabicyclo[2.2.2]octan-2-yl)(5-methyl-3-(2H-1,2,3-triazol-2-yl)pyridin-2-yl)methanone |
| 147 | | (2-bromo-3-fluorophenyl)((1S,3S,4R,6R)-3-(fluoromethyl)-6-((5-(trifluoromethyl)pyridin-2-yl)oxy)-2-azabicyclo[2.2.2]octan-2-yl)methanone |

Example 148

(3-fluoro-2-pyrimidin-2-yl-phenyl)-[(1R,2R,4S,5R)-2-methyl-5-[[5-(trifluoromethyl)-2-pyridyl]oxy]-3-azabicyclo[2.2.2]octan-3-yl]methanone

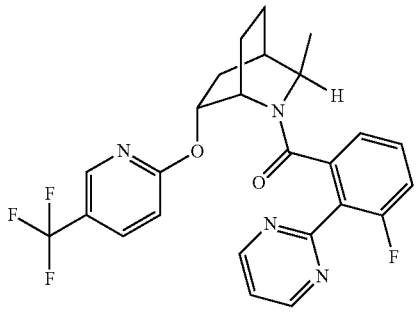 [SMILES: CC1C2CCC(C(Oc3ccc(C(F)(F)F)cn3)C2)N1C(=O)c1cccc(F)c1-c1ncccn1]

Step A: (1S,3R,4R,6S)-3-methyl-2-((R)-1-phenylethyl)-2-azabicyclo[2.2.2]octan-6-ol. (1S,3R,4R,6S)-3-methyl-2-((R)-1-phenylethyl)-2-azabicyclo[2.2.2]octan-6-ol was prepared analogous to intermediate B-26, substituting intermediate B-25 with intermediate B-30. The title compound, along with some of the undesired regioisomer, was obtained as a mixture and purified by silica gel chromatography (5-20% MeOH (with 10% 2 N NH$_3$) in DCM), to give the title compound (177 mg, 0.721 mmol, 33%) and the undesired regioisomer, (1S,3R,4S,5R)-3-methyl-2-((R)-1-phenylethyl)-2-azabicyclo[2.2.2]octan-5-ol (168 mg). MS (ESI) mass calcd. for: C$_{16}$H$_{23}$NO, 245.2. m/z found 246.1 [M+H]$^+$.

Step B: tert-butyl (1S,3R,4R,6S)-6-hydroxy-3-methyl-2-azabicyclo[2.2.2]octane-2-carboxylate. Tert-butyl (1S,3R,4R,6S)-6-hydroxy-3-methyl-2-azabicyclo[2.2.2]octane-2-carboxylate was prepared analogous to intermediate B-27, substituting intermediate B-26 with (1S,3R,4R,6S)-3-methyl-2-((R)-1-phenylethyl)-2-azabicyclo[2.2.2]octan-6-ol from step A. MS (ESI) mass calcd. for: C$_{13}$H$_{23}$NO$_3$, 241.2. m/z found 186.1 [M+H-tBu]$^+$.

Step C: tert-butyl (1S,3R,4R)-3-methyl-6-oxo-2-azabicyclo[2.2.2]octane-2-carboxylate. Tert-butyl (1S,3R,4R)-3-methyl-6-oxo-2-azabicyclo[2.2.2]octane-2-carboxylate was prepared analogous to intermediate B-28, substituting intermediate B-27 with tert-butyl (1S,3R,4R,6S)-6-hydroxy-3-methyl-2-azabicyclo[2.2.2]octane-2-carboxylate from step B. MS (ESI) mass calcd. for: C$_{13}$H$_{21}$NO$_3$, 239.2. m/z found 184.1 [M+H-tBu]$^+$.

Step D: (1S,3R,4R)-2-(3-fluoro-2-(pyrimidin-2-yl)benzoyl)-3-methyl-2-azabicyclo[2.2.2]octan-6-one. To the title compound of step C (110 mg, 0.46 mmol) in dioxane (2 mL) was added 4M HCl in dioxane (0.58 mL) and the reaction was stirred at room temperature overnight after which the reaction was concentrated to give (1S,3R,4R)-3-methyl-2-azabicyclo[2.2.2]octan-6-one.xHCl, which was used without further purification.

To (1S,3R,4R)-3-methyl-2-azabicyclo[2.2.2]octan-6-one.xHCl (25 mg, 0.14 mmol) and intermediate A-2 in DMF (1.4 mL) was added DIPEA (0.15 mL, 0.85 mmol) and HATU (60 mg, 0.16 mmol), and the reaction mixture was stirred at room temperature for 1.5 h. Upon completion, the reaction was diluted with H$_2$O and the aqueous layer extracted with EtOAc (3×). The combined organics were dried with Na$_2$SO$_4$, filtered and concentrated. Purification via silica gel chromatography (0-10% MeOH (with 10% 2 N NH$_3$) in DCM), gave the title compound. MS (ESI): mass calcd. for C$_{19}$H$_{18}$FN$_3$O$_2$, 339.1. m/z found, 340.1 [M+H]$^+$.

Step E: (3-fluoro-2-pyrimidin-2-yl-phenyl)-[(1R,2R,4S,5R)-2-methyl-5-[[5-(trifluoromethyl)-2-pyridyl]oxy]-3-azabicyclo[2.2.2]octan-3-yl]methanone. To the title compound of step D (46 mg, 0.14 mmol) in DCM (0.6 mL)/MeOH (0.06 mL) at 0° C. was added NaBH$_4$ (7.7 mg, 0.203 mmol) in a single portion, and the resulting reaction mixture was stirred for 1 h at 0° C. The completed reaction was quenched with H$_2$O and extract with DCM (3×), dried with Na$_2$SO$_4$, filtered, and concentrated under reduced pressure to provide (3-fluoro-2-(pyrimidin-2-yl)phenyl)((1S,3R,4R,6R)-6-hydroxy-3-methyl-2-azabicyclo[2.2.2]octan-2-yl) methanone along with some of the undesired regioisomer. This material was carried on to the next step without further purification.

To a mixture of (3-fluoro-2-(pyrimidin-2-yl)phenyl)((1S,3R,4R,6R)-6-hydroxy-3-methyl-2-azabicyclo[2.2.2]octan-2-yl)methanone and the undesired regioisomer (46 mg, 0.14 mmol) and 2-chloro-5-(trifluoromethyl)pyridine (34 mg, 0.19 mmol) in DMF (1.3 mL) was added NaH (8 mg, 0.2 mmol, 60% dispersion in mineral oil), and the reaction mixture was stirred at room temperature for 1 h. The mixture was carefully quenched with H$_2$O, and the aqueous layer extracted with EtOAc (3×). The combined organics were dried with Na$_2$SO$_4$, filtered and concentrated. The concentrate was re-dissolved in MeOH and purified directly using Gilson Prep Method X to give the title compound and Example 162. MS (ESI): mass calcd. for C$_{25}$H$_{22}$F$_4$N$_4$O$_2$, 486.2. m/z found, 487.0 [M+H]$^+$. $^1$H NMR (500 MHz, Methanol-d4) δ 8.92 (d, J=5.0 Hz, 2H), 8.22-8.12 (m, 1H), 7.96-7.89 (m, 1H), 7.59-7.48 (m, 1H), 7.07-6.99 (m, 3H), 6.96-6.90 (m, 1H), 4.99-4.90 (m, 1H), 4.16-4.05 (m, 1H), 3.85-3.66 (m, 1H), 2.35-2.22 (m, 1H), 1.85-1.78 (m, 1H), 1.70-1.57 (m, 2H), 1.53-1.42 (m, 1H), 1.37-1.22 (m, 1H), 1.11 (d, J=6.4 Hz, 3H), 0.74-0.53 (m, 1H).

Examples 149-155, shown below in Table 4, are also contemplated within the scope of embodiments presented herein and may be prepared using the procedures described above.

TABLE 4

| Ex. No. | Compound | Chemical Name |
|---|---|---|
| 149 | (structure) | (3-fluoro-2-(pyrimidin-2-yl)phenyl)((1S,3S,4R,6R)-3-(hydroxymethyl)-6-((5-(trifluoromethyl)pyridin-2-yl)oxy)-2-azabicyclo[2.2.2]octan-2-yl)methanone |

TABLE 4-continued

| Ex. No. | Compound | Chemical Name |
|---|---|---|
| 150 | | (3-fluoro-2-(pyrimidin-2-yl)phenyl)((1S,3S,4R,6R)-3-(methoxymethyl)-6-((5-(trifluoromethyl)pyridin-2-yl)oxy)-2-azabicyclo[2.2.2]octan-2-yl)methanone |
| 151 | | (3-fluoro-2-(2H-1,2,3-triazol-2-yl)phenyl)((1S,3R,4R,6R)-3-methyl-6-((5-(trifluoromethyl)pyridin-2-yl)oxy)-2-azabicyclo[2.2.2]octan-2-yl)methanone |
| 152 | | (3-fluoro-2-(2H-1,2,3-triazol-2-yl)phenyl)((1S,3S,4R,6R)-3-(hydroxymethyl)-6-((5-(trifluoromethyl)pyridin-2-yl)oxy)-2-azabicyclo[2.2.2]octan-2-yl)methanone |
| 153 | | (3-fluoro-2-(2H-1,2,3-triazol-2-yl)phenyl)((1S,3S,4R,6R)-3-(methoxymethyl)-6-((5-(trifluoromethyl)pyridin-2-yl)oxy)-2-azabicyclo[2.2.2]octan-2-yl)methanone |

TABLE 4-continued

| Ex. No. | Compound | Chemical Name |
|---|---|---|
| 154 | | (3-fluoro-2-(pyrimidin-2-yl)phenyl)((1S,3S,4R,6R)-3-((methoxymethoxy)methyl)-6-((5-(trifluoromethyl)pyridin-2-yl)oxy)-2-azabicyclo[2.2.2]octan-2-yl)methanone |
| 155 | | (3-fluoro-2-(2H-1,2,3-triazol-2-yl)phenyl)((1S,3S,4R,6R)-3-((methoxymethoxy)methyl)-6-((5-(trifluoromethyl)pyridin-2-yl)oxy)-2-azabicyclo[2.2.2]octan-2-yl)methanone |

Example 156

[6-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone

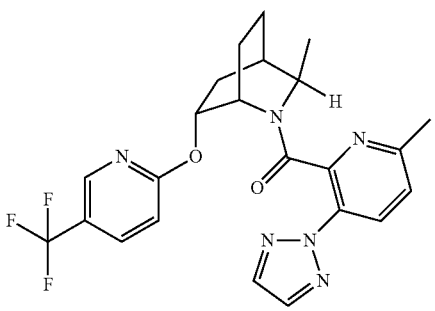 [SMILES: Cc1ccc(-n2nccn2)c(C(=O)N2C(C)C3CCC2C(Oc2ccc(C(F)(F)F)cn2)C3)n1]

The title compound was prepared analogous to Example 74 substituting intermediate B-29 in step A with intermediate B-31, and intermediate A-27 in step C with intermediate A-26. MS (ESI): mass calcd. for $C_{23}H_{23}F_3N_6O_2$, 472.2. m/z found, 473.1 [M+H]$^+$. $^1$H NMR (500 MHz, Methanol-d4) δ 8.13-8.10 (m, 1H), 8.04-7.98 (m, 3H), 7.90 (dd, J=8.8, 2.6 Hz, 1H), 7.19 (d, J=8.4 Hz, 1H), 6.85 (d, J=8.7 Hz, 1H), 4.22-4.13 (m, 1H), 3.79-3.70 (m, 1H), 2.35-2.26 (m, 1H), 2.26 (s, 3H), 1.92-1.85 (m, 1H), 1.85-1.76 (m, 1H), 1.76-1.68 (m, 1H), 1.50-1.43 (m, 1H), 1.42 (d, J=6.4 Hz, 3H), 1.40-1.33 (m, 1H), 1.03-0.93 (m, 1H). 1H buried under MeOH-d4.

Example 157

[(1R,2R,4S,5R)-2-methyl-5-[[5-(trifluoromethyl)-2-pyridyl]oxy]-3-azabicyclo[2.2.2]octan-3-yl]-[2-(triazol-2-yl)phenyl]methanone

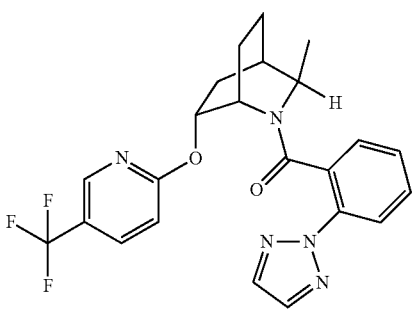 [SMILES: CC1C2CCC(C(Oc3ccc(C(F)(F)F)cn3)C2)N1C(=O)c1ccccc1-n1nccn1]

The title compound was prepared analogous to Example 74 substituting intermediate B-29 in step A with intermediate B-31, and intermediate A-27 in step C with intermediate A-1. MS (ESI): mass calcd. for $C_{23}H_{22}F_3N_5O_2$, 457.2. m/z found, 458.1 [M+H]$^+$. $^1$H NMR (500 MHz, Methanol-d4) δ

8.11-8.06 (m, 1H), 7.97 (s, 2H), 7.92 (dd, J=8.6, 2.5 Hz, 1H), 7.68 (dd, J=8.2, 1.1 Hz, 1H), 7.34-7.27 (m, 1H), 7.18 (dd, J=7.7, 1.5 Hz, 1H), 6.97-6.93 (m, 1H), 6.90 (td, J=7.6, 1.2 Hz, 1H), 4.92-4.86 (m, 1H), 4.18-4.11 (m, 1H), 3.63-3.57 (m, 1H), 2.35-2.25 (m, 1H), 1.87-1.82 (m, 1H), 1.77-1.69 (m, 1H), 1.69-1.63 (m, 1H), 1.44-1.38 (m, 1H), 1.37 (d, J=6.5 Hz, 3H), 1.34-1.27 (m, 1H), 0.87-0.76 (m, 1H).

Example 158

(6-methyl-3-pyrimidin-2-yl-2-pyridyl)-[(1R,2R,4S,5R)-2-methyl-5-[[5-(trifluoromethyl)-2-pyridyl]oxy]-3-azabicyclo[2.2.2]octan-3-yl]methanone

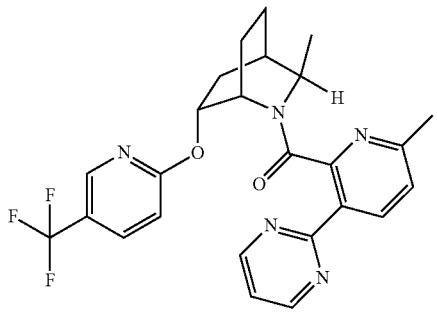 [SMILES: Cc1ccc(-c2ncccn2)c(C(=O)N2C(C)C3CCC2C(Oc2ccc(C(F)(F)F)cn2)C3)n1]

The title compound was prepared analogous to Example 74 substituting intermediate B-29 in step A with intermediate B-31. MS (ESI): mass calcd. for C$_{25}$H$_{24}$F$_3$N$_5$O$_2$, 483.2. m/z found, 484.0 [M+H]$^+$. $^1$H NMR (500 MHz, Methanol-d4) δ 8.89 (d, J=4.9 Hz, 2H), 8.27 (d, J=8.1 Hz, 1H), 8.12-8.04 (m, 1H), 7.88 (dd, J=8.7, 2.6 Hz, 1H), 7.50-7.44 (m, 1H), 7.12 (d, J=8.1 Hz, 1H), 6.83 (d, J=8.7 Hz, 1H), 4.29-4.13 (m, 1H), 3.85-3.78 (m, 1H), 2.34-2.27 (m, 1H), 2.26 (s, 3H), 1.90-1.84 (m, 1H), 1.82-1.70 (m, 2H), 1.46 (d, J=6.4 Hz, 3H), 1.45-1.40 (m, 1H), 1.39-1.31 (m, 1H), 0.91-0.82 (m, 1H).

Example 159

[(1R,2R,4S,5R)-2-methyl-5-[[5-(trifluoromethyl)-2-pyridyl]oxy]-3-azabicyclo[2.2.2]octan-3-yl]-[3-(triazol-2-yl)-2-pyridyl]methanone

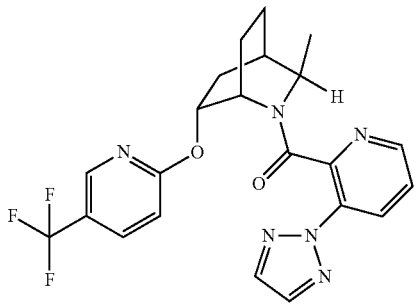 [SMILES: CC1C2CCC(C(Oc3ccc(C(F)(F)F)cn3)C2)N1C(=O)c1ncccc1-n1nccn1]

The title compound was prepared analogous to Example 74 substituting intermediate B-29 in step A with intermediate B-31, and intermediate A-27 in step C with intermediate A-15. MS (ESI): mass calcd. for C$_{22}$H$_{21}$F$_3$N$_6$O$_2$, 458.2. m/z found, 459.1 [M+H]$^+$. $^1$H NMR (400 MHz, Methanol-d4) δ

8.18 (dd, J=8.3, 1.4 Hz, 1H), 8.09-8.05 (m, 1H), 8.04 (s, 2H), 7.96 (dd, J=4.7, 1.4 Hz, 1H), 7.90 (dd, J=8.8, 2.6 Hz, 1H), 7.31 (dd, J=8.3, 4.7 Hz, 1H), 6.87 (d, J=8.8 Hz, 1H), 4.95-4.85 (m, 1H), 4.25-4.12 (m, 1H), 3.71-3.61 (m, 1H), 2.41-2.24 (m, 1H), 1.95-1.90 (m, 1H), 1.90-1.80 (m, 1H), 1.80-1.72 (m, 1H), 1.57-1.48 (m, 1H), 1.45 (d, J=6.5 Hz, 3H), 1.43-1.35 (m, 1H), 1.27-1.15 (m, 1H).

Example 160

[5-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone

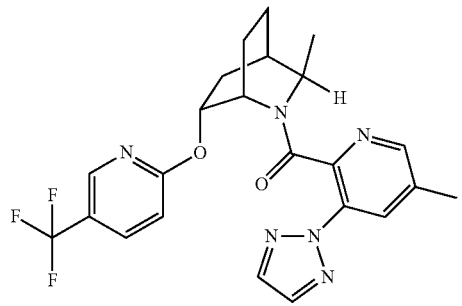 [SMILES: Cc1cnc(C(=O)N2C(C)C3CCC2C(Oc2ccc(C(F)(F)F)cn2)C3)c(-n2nccn2)c1]

The title compound was prepared analogous to Example 74 substituting intermediate B-29 in step A with intermediate B-31, and intermediate A-27 in step C with intermediate A-19. MS (ESI): mass calcd. for C$_{23}$H$_{23}$F$_3$N$_6$O$_2$, 472.2. m/z found, 473.1 [M+H]$^+$. $^1$H NMR (500 MHz, Methanol-d4) δ 8.10-8.06 (m, 1H), 8.02 (s, 2H), 8.01-7.98 (m, 1H), 7.95-7.89 (m, 1H), 7.78-7.70 (m, 1H), 6.88 (d, J=8.8 Hz, 1H), 4.23-4.13 (m, 1H), 3.73-3.63 (m, 1H), 2.35-2.27 (m, 1H), 4.91-4.84 (m, 1H), 2.25 (s, 3H), 1.94-1.87 (m, 1H), 1.87-1.80 (m, 1H), 1.79-1.73 (m, 1H), 1.53-1.46 (m, 1H), 1.43 (d, J=6.4 Hz, 3H), 1.41-1.34 (m, 1H), 1.18-1.07 (m, 1H).

Example 161

(5-methyl-3-pyrimidin-2-yl-2-pyridyl)-[(1R,2R,4S,5R)-2-methyl-5-[[5-(trifluoromethyl)-2-pyridyl]oxy]-3-azabicyclo[2.2.2]octan-3-yl]methanone

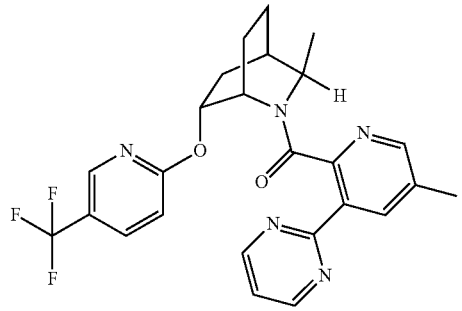 [SMILES: Cc1cnc(C(=O)N2C(C)C3CCC2C(Oc2ccc(C(F)(F)F)cn2)C3)c(-c2ncccn2)c1]

The title compound was prepared analogous to Example 74 substituting intermediate B-29 in step A with intermediate B-31, and intermediate A-27 in step C with intermediate A-29. MS (ESI): mass calcd. for C$_{25}$H$_{24}$F$_3$N$_5$O$_2$, 483.2. m/z found, 484.2 [M+H]$^+$. $^1$H NMR (500 MHz, Methanol-d4) δ

8.89 (d, J=4.9 Hz, 2H), 8.27-8.21 (m, 1H), 8.08-8.03 (m, 1H), 7.92 (dd, J=8.4, 2.2 Hz, 1H), 7.79-7.73 (m, 1H), 7.48 (t, J=4.9 Hz, 1H), 6.96-6.84 (m, 1H), 4.85-4.83 (m, 1H), 4.27-4.15 (m, 1H), 3.77-3.66 (m, 1H), 2.36-2.26 (m, 1H), 2.22 (s, 3H), 1.97-1.89 (m, 1H), 1.86-1.73 (m, 2H), 1.52-1.44 (m, 4H), 1.42-1.33 (m, 1H), 1.12-0.99 (m, 1H).

Example 162

(3-fluoro-2-pyrimidin-2-yl-phenyl)-[(1R,2R,4S,5S)-2-methyl-5-[[5-(trifluoromethyl)-2-pyridyl]oxy]-3-azabicyclo[2.2.2]octan-3-yl]methanone

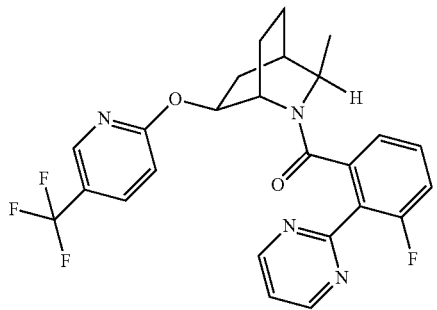 [SMILES: CC1C2CCC(C(Oc3ccc(C(F)(F)F)cn3)C2)N1C(=O)c1cccc(F)c1-c1ncccn1]

The title compound was prepared analogous to Example 148. (ESI): mass calcd. for C$_{25}$H$_{22}$F$_4$N$_4$O$_2$, 486.2. m/z found, 487.1[M+H]$^+$. Analytical HPLC using a XBridge C18 column (5 μm, 100×4 6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.19 min at 280 nm.

Example 163

[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[2-(triazol-2-yl)phenyl]methanone

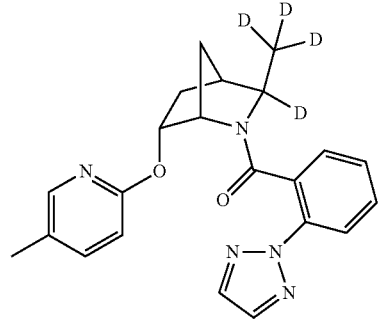 [SMILES: [2H]C([2H])([2H])C1([2H])C2CC(Oc3ccc(C)cn3)C(C2)N1C(=O)c1ccccc1-n1nccn1]

The title compound was prepared analogous to Example 12 substituting intermediate B-14 in step A with tert-butyl (1S,3R,4R,6R)-6-hydroxy-3-(methyl-d$_3$)-2-azabicyclo[2.2.1]heptane-2-carboxylate-3-d, and intermediate A-30 in step C with intermediate A-1. Tert-butyl (1S,3R,4R,6R)-6-hydroxy-3-(methyl-d$_3$)-2-azabicyclo[2.2.1]heptane-2-carboxylate-3-d was prepared according to the procedure of S. D. Larsen and P. A. Grieco [*J. Am. Chem. Soc.* 1985, 107, 1768-1769], substituting formaldehyde for acetaldehyde-d$_4$. MS (ESI): mass calcd. for C$_{22}$H$_{16}$D$_4$F$_3$N$_5$O$_2$, 447.2. m/z found, 448.1 [M+H]$^+$. $^1$H NMR (500 MHz, Methanol-d4) δ 8.07-8.02 (m, 1H), 7.99 (s, 2H), 7.92 (dd, J=8.8, 2.6 Hz, 1H), 7.72-7.65 (m, 1H), 7.43-7.29 (m, 1H), 7.14 (dd, J=7.7, 1.5 Hz, 1H), 6.95 (d, J=8.7 Hz, 1H), 6.92-6.83 (m, 1H), 5.04-4.91 (m, 1H), 3.92-3.84 (m, 1H), 2.27-2.17 (m, 2H), 1.41-1.30 (m, 2H), 1.31-1.21 (m, 1H).

Example 164

[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[3-fluoro-2-(triazol-2-yl)phenyl]methanone

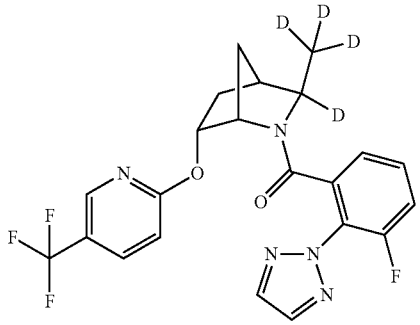 [SMILES: [2H]C([2H])([2H])C1([2H])C2CC(Oc3ccc(C(F)(F)F)cn3)C(C2)N1C(=O)c1cccc(F)c1-n1nccn1]

The title compound was prepared analogous to Example 164 substituting intermediate A-1 with intermediate A-16. MS (ESI): mass calcd. for C$_{22}$H$_{15}$D$_4$F$_4$N$_5$O$_2$, 465.2. m/z found, 466.0 [M+H]$^+$. $^1$H NMR (500 MHz, Methanol-d4) δ 8.19-8.12 (m, 1H), 8.04 (s, 2H), 7.99-7.93 (m, 1H), 7.31-7.23 (m, 1H), 7.12-7.05 (m, 1H), 7.02-7.00 (m, 1H), 7.00-6.98 (m, 1H), 5.10-5.02 (m, 1H), 4.11-4.07 (m, 1H), 2.30-2.19 (m, 1H), 2.19-2.14 (m, 1H), 1.49-1.40 (m, 1H), 1.34-1.29 (m, 1H), 1.28-1.23 (m, 1H).

Example 165

[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[6-methyl-3-(triazol-2-yl)-2-pyridyl]methanone

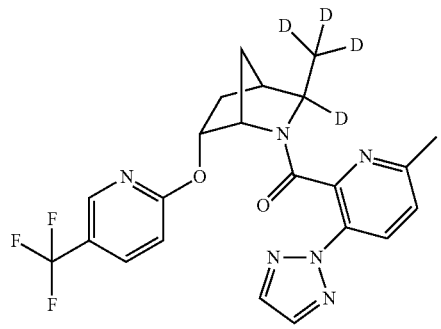 [SMILES: [2H]C([2H])([2H])C1([2H])C2CC(Oc3ccc(C(F)(F)F)cn3)C(C2)N1C(=O)c1nc(C)ccc1-n1nccn1]

The title compound was prepared analogous to Example 164 substituting intermediate A-1 with intermediate A-26. MS (ESI): mass calcd. for C$_{22}$H$_{17}$D$_4$F$_3$N$_6$O$_2$, 462.2. m/z found, 463.2 [M+H]⁺. ¹H NMR (500 MHz, Methanol-d4) δ 8.06-8.04 (m, 1H), 8.04-8.00 (m, 3H), 7.89 (dd, J=8.8, 2.6 Hz, 1H), 7.25 (d, J=8.4 Hz, 1H), 6.95-6.89 (m, 1H), 4.99-4.89 (m, 1H), 4.07-4.01 (m, 1H), 2.32-2.16 (m, 5H), 1.44-1.35 (m, 3H).

Example 166

[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[5-methyl-3-(triazol-2-yl)-2-pyridyl]methanone

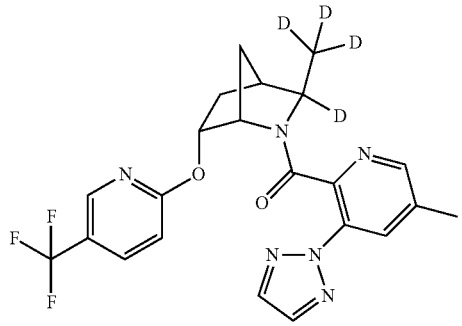 [SMILES: [2H]C([2H])([2H])C1([2H])C2CC(Oc3ccc(C(F)(F)F)cn3)C(C2)N1C(=O)c1ncc(C)cc1-n1nccn1]

The title compound was prepared analogous to Example 164 substituting intermediate A-1 with intermediate A-19. MS (ESI): mass calcd. for C₂₂H₁₇D₄F₃N₆O₂, 462.2. m/z found, 463.1 [M+H]⁺. ¹H NMR (500 MHz, Methanol-d4) δ 8.03 (s, 2H), 8.02-7.98 (m, 2H), 7.92-7.84 (m, 1H), 7.72-7.67 (m, 1H), 6.97-6.86 (m, 1H), 5.03-4.91 (m, 1H), 4.03-3.96 (m, 1H), 2.31 (s, 3H), 2.28-2.22 (m, 2H), 1.53-1.36 (m, 3H).

Example 167

[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-(5-fluoro-2-pyrimidin-2-yl-phenyl)methanone

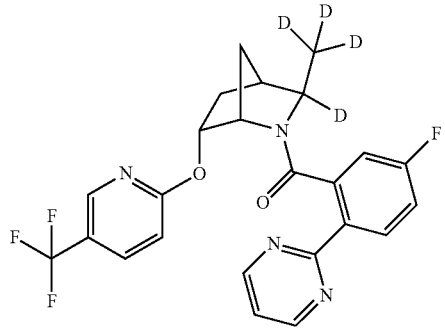 [SMILES: [2H]C([2H])([2H])C1([2H])C2CC(Oc3ccc(C(F)(F)F)cn3)C(C2)N1C(=O)c1cc(F)ccc1-c1ncccn1]

The title compound was prepared analogous to Example 18 substituting intermediate B-14 in step A with tert-butyl (1S,3R,4R,6R)-6-hydroxy-3-(methyl-d₃)-2-azabicyclo[2.2.1]heptane-2-carboxylate-3-d. Tert-butyl (1S,3R,4R,6R)-6-hydroxy-3-(methyl-d₃)-2-azabicyclo[2.2.1]heptane-2-carboxylate-3-d was prepared according to the procedure of S. D. Larsen and P. A. Grieco [J. Am. Chem. Soc. 1985, 107, 1768-1769], substituting formaldehyde for acetaldehyde-d₄. MS (ESI): mass calcd. for C₂₄H₁₆D₄F₄N₄O₂, 476.2; m/z found, 477.1 [M+H]⁺. ¹H NMR (500 MHz, Methanol-d4) δ 8.87 (d, J=4.9 Hz, 2H), 8.08-8.05 (m, 1H), 7.98 (dd, J=8.7, 5.5 Hz, 1H), 7.93 (dd, J=8.8, 2.5 Hz, 1H), 7.49-7.42 (m, 1H), 7.02 (td, J=8.4, 2.7 Hz, 1H), 6.94 (d, J=8.7 Hz, 1H), 6.78 (dd, J=8.7, 2.7 Hz, 1H), 5.03-4.94 (m, 1H), 4.03-3.97 (m, 1H), 2.27-2.15 (m, 2H), 1.42-1.35 (m, 1H), 1.34-1.30 (m, 1H), 1.17-1.04 (m, 1H).

Example 168

[2-[4-(3-fluoropropyl)triazol-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone

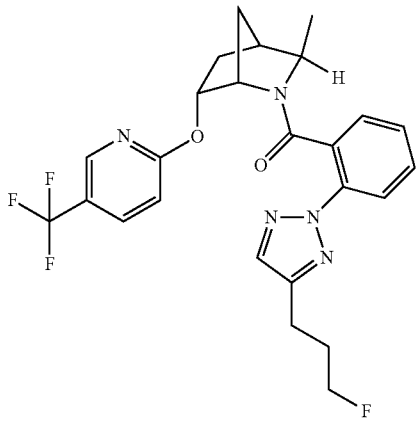 [SMILES: CC1C2CC(Oc3ccc(C(F)(F)F)cn3)C(C2)N1C(=O)c1ccccc1-n1ncc(CCCF)n1]

Step A: pent-4-yn-1-yl 4-methylbenzenesulfonate. To a solution of pent-4-yn-1-ol (15 g, 0.18 mol) and trimethylamine (37 ml, 0.27 mol) in DCM (64 mL) cooled at 0° C., was slowly added TsCl (37.8 g, 0.21 mol) in DCM (50 mL). The reaction mixture was allowed to warm to room temperature and stirred for 16 hours. The white precipitates were filtered off; the filtrates were concentrated under vacuum, diluted with diethyl ether (250 mL). Solid precipitate was filtered again. The filtrates were dried, concentrated, and purified on a silica gel chromatography to afford a colorless liquid (35.9 g, Yield 84%). MS (ESI): mass calcd. for C₁₂H₁₄O₃S, 238.07. m/z found, 239.1 [M+H]⁺.

Step B: 5-fluoropent-1-yne. To a pressure-resisted reaction vessel, were added title compound in Step A (20 g, 84 mmol) and TBAF (75% wt in water, 30 ml, 84 mmol). The sealed vessel was heated at 45° C. for 1 hour. The mixture was transferred to a distillation apparatus. The oil bath was increased to 140-155° C. The cold water is used for condensing. The collected fraction was cold at −78° C. The volatiles below 90° C. were collected to afford the desired product as a colorless liquid (3.9 g, Yield 65%) ¹H NMR (500 MHz, Chloroform-d) δ 4.64-4.48 (td, J=47.1, 5.8 Hz, 2H), 2.41-2.32 (td, J=7.0, 2.7 Hz, 2H), 1.99-1.85 (m, 3H).

Step C: 5-(3-fluoropropyl)-1H-1,2,3-triazole. Title compound in Step B (500 mg, 5.8 mmol) and trimethylsilyl azide (0.92 ml, 7.0 mmol) were mixed in a sealed vial, to the mixture were added CuI (220 mg, 1.6 mmol), MeOH (2 mL) and DMF (8 mL). Reaction mixture was heated in a sealed reaction vessel overnight at 100° C. The reaction turns into dark brown color. The mixture was filtered via vacuum filtration. The filtrated was concentrated and purified on a silica gel column to afford a colorless liquid (420 mg, Yield 56%). MS (ESI): mass calcd. for C₅H₈FN₃, 129.1. m/z found, 130.1 [M+H]⁺. ¹H NMR (500 MHz, Chloroform-d) δ ¹H NMR (500 MHz, CDCl₃) δ 12.38-12.34 (br, 1H), 7.57 (s, 1H), 4.62-4.54 (t, J=5.8 Hz, 1H), 4.53-4.45 (t, J=5.8 Hz, 1H), 2.96-2.89 (t, J=7.6 Hz, 2H), 2.22-2.05 (m, 2H).

Step D: 2-(4-(3-fluoropropyl)-2H-1,2,3-triazol-2-yl)benzonitrile. 2-iodobenzonitrile (864 mg, 3.7 mmol) and title compound in Step C (405 mg, 3.1 mmol) were placed in an oven-dried vial charged with Pd₂(dba)₃ (120 mg, 0.131 mmol), Me₄ᵗBuXphos (151 mg, 0.3 mmol). K₃PO₄ (1.3 g, 6.2 mmol) and Toluene (20 mL) were added after purged with nitrogen. The vial was sealed and heated at 120° C. for 2 hours. The resulted solution was concentrated and directly purified on a silica gel chromatography to afford the desired product (150 mg, Yield 21%). ¹H NMR (500 MHz, Chloroform-d) δ 8.02-7.96 (m, 1H), 7.78-7.72 (dd, J=7.8, 1.5, 1H), 7.68-7.60 (m, 2H), 7.41-7.34 (td, J=7.6, 1.2 Hz, 1H), 4.59-4.52 (t, J=5.8 Hz, 1H), 4.49-4.43 (t, J=5.8 Hz, 1H), 2.93-2.86 (t, J=7.5 Hz, 2H), 2.18-2.12 (d, J=7.8 Hz, 2H).

Step E: 2-(4-(3-fluoropropyl)-2H-1,2,3-triazol-2-yl)benzoic acid. Title compound in step D in MeOH/NaOH (1 mL, 4M, aq) was heated to 90° C. in a sealed tube. The resulting yellow solution was acidified with HCl (1M, 5 mL) and purified on HPLC to afford the desired product (5 mg, Yield 5%) MS (ESI): mass calcd. for C₁₂H₁₂FN₃O₂, 249.09. m/z found, 250.1 [M+H]⁺.

Step F: [2-[4-(3-fluoropropyl)triazol-2-yl]phenyl]-[(1R, 2R,4S,5R)-2-methyl-5-[[5-(trifluoromethyl)-2-pyridyl]oxy]-3-azabicyclo[2.2.1]heptan-3-yl]methanone. The title compound was prepared analogous to Example 12 using title compound in step E, intermediate B-14A, and 2-fluoro-3-trifluoromethylpyridine. MS (ESI): mass calcd. for C₂₅H₂₅F₄N₅O₂, 503.2. m/z found, 504.3 [M+H]⁺. ¹H NMR (400 MHz, CD₃CN) δ 7.84-7.79 (s, 1H), 7.68-7.61 (d, J=8.8 Hz, 1H), 7.57-7.52 (s, 1H), 7.38-7.31 (d, J=8.2 Hz, 1H), 7.15-7.05 (t, J=8.0 Hz, 1H), 6.91-6.84 (d, J=7.7 Hz, 1H), 6.70-6.59 (t, J=8.3 Hz, 2H), 4.73-4.66 (d, J=9.4 Hz, 1H), 4.42-4.34 (t, J=6.1 Hz, 1H), 4.31-4.23 (t, J=6.0 Hz, 1H), 3.58-3.47 (m, 2H), 2.71-2.62 (t, J=7.8 Hz, 2H), 1.93-1.81 (m, 4H), 1.12-0.93 (m, 6H).

Example 169

[2-[5-(2-fluoroethoxy)pyrimidin-2-yl]phenyl]-[(1R, 2R,4S,5R)-2-methyl-5-[[5-(trifluoromethyl)-2-pyridyl]oxy]-3-azabicyclo[2.2.1]heptan-3-yl]methanone

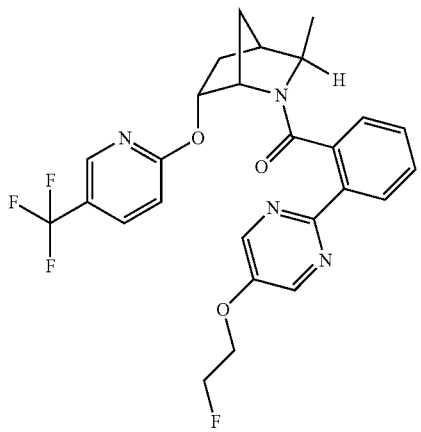 [SMILES: CC1C2CC(Oc3ccc(C(F)(F)F)cn3)C(C2)N1C(=O)c1ccccc1-c1ncc(OCCF)cn1]

Step A: 2-chloro-5-(2-fluoroethoxy)pyrimidine. To a vial charged with 2-chloropyrimidin-5-ol (300 mg, 2.23 mmol) and Cs₂CO₃ (0.97 g, 3.0 mmol), was added 1-fluoro-2-iodoethane (480 mg, 2.76 mmol) in DMF (5 mL). The mixture was stirred vigorously at rt for 3, then diluted with water, extracted with EtOAc, washed with brine. The organic layers were dried and concentrated. The residue was purified on a silica gel chromatography to afford 2-chloro-5-(2-fluoroethoxy)pyrimidine (111 mg, Yield 27%). MS (ESI): mass calcd. for C₆H₆ClFN₂O, 176.0; m/z found, 177.0 [M+H]⁺. ¹H NMR (400 MHz, d-chloroform) δ 8.31-8.24 (s, 2H), 4.80-4.74 (m, 1H), 4.70-4.64 (m, 1H), 4.31-4.20 (m, 2H).

Step B: tert-butyl 2-(5-(2-fluoroethoxy)pyrimidin-2-yl)benzoate. To a microwave reaction vial charged with PdCl₂(dppf) (41 mg, 0.06 mmol) and K₂CO₃ (234 mg, 1.7 mmol), were added title compound in step A (100 mg, 0.57 mmol) and (2-(tert-butoxycarbonyl)phenyl)boronic acid (165 mg, 0.74 mmol). The vial was sealed and purged with nitrogen. Dioxane/Water (5:1, 5 mL) was added via a syringe. The reaction mixture was heated to 110° C. for 3 hours. The mixture was diluted with water, extracted with EtOAc. The combined organic layers was washed with brine, dried, and concentrated. The residue was purified on a silica gel chromatography to afford the title product was a colorless oil (170 mg, Yield 94%) MS (ESI): mass calcd. for C₁₇H₁₉ClFN₂O₃, 318.1; m/z found, 319.1 [M+H]⁺. ¹H NMR (400 MHz, d-chloroform) δ 8.47-8.39 (s, 2H), 7.84-7.77 (m, 1H), 7.65-7.58 (m, 1H), 7.50-7.34 (dtd, J=25.7, 7.5, 1.4 Hz, 2H), 4.84-4.77 (m, 1H), 4.72-4.65 (m, 1H), 4.38-4.24 (m, 2H), 1.42-1.36 (s, 9H).

Step C: 2-(5-(2-fluoroethoxy)pyrimidin-2-yl)benzoic acid. The title compound was obtained by treating title compound in Step B with hydrochloric acid (4M, dioxane) at rt. Quantitative yield. MS (ESI): mass calcd. for C₁₃H₁₁FN₂O₃, 263.1. m/z found, 264.0 [M+H]⁺. ¹H NMR (400 MHz, CD₃CN) δ 8.61-8.53 (s, 2H), 7.99-7.91 (ddd, J=7.8, 1.4, 0.6 Hz, 1H), 7.81-7.74 (ddd, J=7.6, 1.5, 0.6 Hz, 1H), 7.69-7.51 (dtd, J=32.5, 7.5, 1.4 Hz, 2H), 4.91-4.84 (m, 1H), 4.79-4.72 (m, 1H), 4.52-4.45 (m, 1H), 4.44-4.38 (m, 1H).

Step D: [2-[5-(2-fluoroethoxy)pyrimidin-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone. The title compound was prepared analogous to Example 12 title compound of Step C, intermediate B-14A and 2-fluoro-3-trifluoromethylpyridine. MS (ESI): mass calcd. for C₂₆H₂₄F₄N₄O₃, 516.2. m/z found, 517.2 [M+H]⁺. ¹H NMR (400 MHz, CD3CN) δ 8.61-8.53 (s, 2H), 8.05 (s, 1H), 7.97-7.89 (dd, J=7.8, 1.4 Hz, 1H), 7.81-7.74 (dd, J=7.6, 1.5 Hz, 1H), 7.26-7.30 (m, 1H), 7.06-7.09 (d, J=7.8 Hz, 1H), 6.92-6.85 (m, 2H), 4.92-4.84 (m, 2H), 4.79-4.72 (m, 1H), 4.52-4.45 (m, 1H), 4.44-4.38 (m, 1H), 3.90-3.78 (2H), 1.33-1.24 (m, 4H), 0.92-0.87 (s, 1H).

Example 170

[2-(5-fluoropyrazin-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone

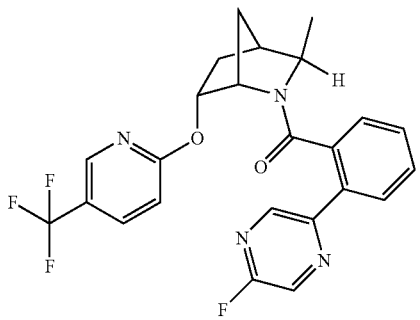 [SMILES: CC1C2CC(Oc3ccc(C(F)(F)F)cn3)C(C2)N1C(=O)c1ccccc1-c1cnc(F)cn1]

Step A: (2-(5-chloropyrazin-2-yl)phenyl)((1S,3R,4R,6R)-3-methyl-6-((5-(trifluoromethyl)pyridin-2-yl)oxy)-2-azabicyclo[2.2.1]heptan-2-yl)methanone. The title compound was prepared analogous to Example 169 step B, C and D using 2-bromo-5-chloropyrazine. MS (ESI): mass calcd. for $C_{24}H_{20}ClF_3N_4O_2$, 488.12. m/z found, 489.1 $[M+H]^+$.

Step B: [2-(5-fluoropyrazin-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone. To a vial charged with (2-(5-chloropyrazin-2-yl)phenyl)((1S,3R,4R,6R)-3-methyl-6-((5-(trifluoromethyl)pyridin-2-yl)oxy)-2-azabicyclo[2.2.1]heptan-2-yl)methanone (11 mg, 0.0225 mmol) in DMSO (0.25 mL), was added CsF (100 mg, 0.675 mmol). The vial was sealed and heated to 95° C. for 3 hours. The reaction mixture was diluted with water and purified by HPLC to afford the title compound (3 mg, Yield 28%) MS (ESI): mass calcd. for $C_{24}H_{20}F_4N_4O_2$, 472.2. m/z found, 473.0 $[M+H]^+$. $^1$H NMR (400 MHz, $CD_3CN$) δ 8.65-8.58 (dd, J=8.3, 1.4 Hz, 1H), 8.43-8.38 (t, J=1.5 Hz, 1H), 8.09-8.04 (d, J=2.4 Hz, 1H), 7.93-7.88 (s, 1H), 7.57-7.50 (m, 1H), 7.40-7.31 (td, J=7.6, 1.4 Hz, 1H), 7.17-7.09 (ddd, J=7.7, 1.3, 0.5 Hz, 1H), 7.02-6.88 (m, 2H), 4.98-4.91 (d, J=9.9 Hz, 1H), 3.83-3.75 (m, 2H), 2.23-2.11 (m, 2H), 1.37-1.18 (m, 2H), 1.15-1.09 (d, J=6.3 Hz, 3H), 0.95-0.83 (d, J=10.8 Hz, 1H).

Example 171

[2-(6-fluoro-3-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone

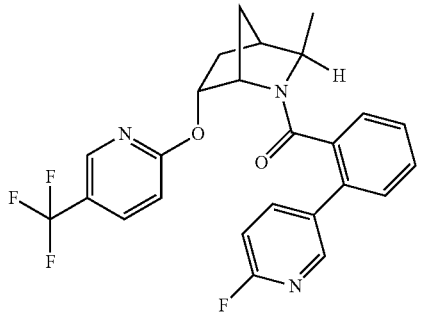 [SMILES: CC1C2CC(Oc3ccc(C(F)(F)F)cn3)C(C2)N1C(=O)c1ccccc1-c1ccc(F)nc1]

The title compound was prepared analogous to Example 169 step B using (6-fluoropyridin-3-yl)boronic acid and (2-iodophenyl)((1S,3R,4R,6R)-3-methyl-6-((5-(trifluoromethyl)pyridin-2-yl)oxy)-2-azabicyclo[2.2.1]heptan-2-yl)methanone. MS (ESI): mass calcd. for $C_{25}H_{21}F_4N_3O_2$, 471.2. m/z found, 472.1 $[M+H]^+$. $^1$H NMR (400 MHz, $CD_3CN$) δ 8.40-8.19 (m, 1H), 8.14-8.05 (m, 1H), 8.04-7.84 (m, 2H), 7.38-7.26 (m, 2H), 7.20-7.06 (m, 2H), 7.01-6.87 (m, 2H), 5.07-4.86 (m, 1H), 3.86-3.61 (m, 2H), 2.26-2.07 (m, 2H), 1.35-1.18 (m, 2H), 1.09-1.01 (d, J=6.3 Hz, 3H), 0.93-0.78 (s, 1H).

Example 172

[2-(2-fluoro-4-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone

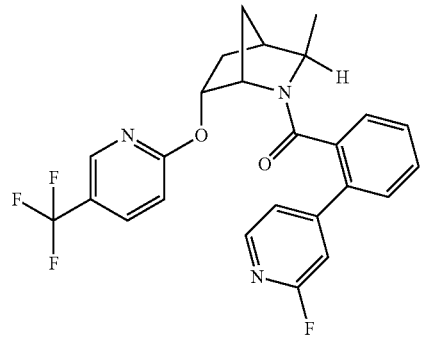 [SMILES: CC1C2CC(Oc3ccc(C(F)(F)F)cn3)C(C2)N1C(=O)c1ccccc1-c1cccc(F)n1]

The title compound was prepared analogous to Example 169 step B using (2-fluoropyridin-4-yl)boronic acid and (2-iodophenyl)((1S,3R,4R,6R)-3-methyl-6-((5-(trifluoromethyl)pyridin-2-yl)oxy)-2-azabicyclo[2.2.1]heptan-2-yl)methanone. MS (ESI): mass calcd. for $C_{25}H_{21}F_4N_3O_2$, 471.2. m/z found, 472.1 $[M+H]^+$. $^1$H NMR (400 MHz, $CD_3CN$) δ 8.32-8.25 (dt, J=5.1, 0.7 Hz, 1H), 8.13-8.07 (dq, J=2.7, 0.9 Hz, 1H), 7.94-7.86 (ddd, J=8.6, 2.5, 0.7 Hz, 1H), 7.43-7.30 (m, 3H), 7.18-7.07 (m, 2H), 7.03-6.89 (m, 2H), 4.99-4.90 (dt, J=10.1, 3.3 Hz, 1H), 3.79-3.71 (m, 2H), 2.22-2.07 (m, 2H), 1.34-1.22 (m, 2H), 1.12-1.05 (d, J=6.3 Hz, 3H), 0.91-0.83 (d, J=10.5 Hz, 1H).

Example 173

[2-(6-fluoro-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone

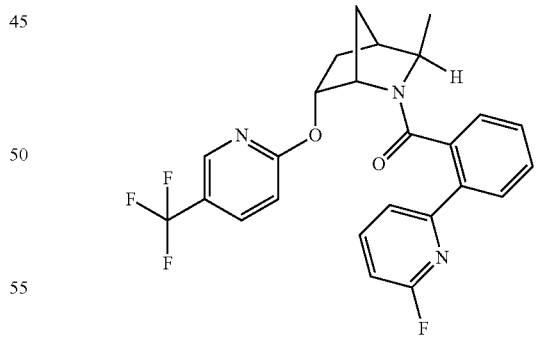

The title compound was prepared analogous to Example 169 step B using (2-fluoropyridin-2-yl)boronic acid and (2-iodophenyl)((1S,3R,4R,6R)-3-methyl-6-((5-(trifluoromethyl)pyridin-2-yl)oxy)-2-azabicyclo[2.2.1]heptan-2-yl)methanone. MS (ESI): mass calcd. for $C_{25}H_{21}F_4N_3O_2$, 471.2. m/z found, 472.1 $[M+H]^+$. $^1$H NMR (400 MHz, $CD_3CN$) δ 8.08-7.98 (dt, J=2.2, 1.1 Hz, 1H), 7.98-7.80 (m, 2H), 7.51-7.37 (m, 2H), 7.30-7.22 (td, J=7.6, 1.4 Hz, 1H), 7.09-6.96 (m, 2H), 6.92-6.79 (m, 2H), 4.98-4.78 (dt, J=10.1, 3.3 Hz, 1H), 3.83-3.66 (m, 2H), 2.16-2.02 (m, 2H), 1.30-1.16 (m, 2H), 1.12-0.99 (d, J=6.3 Hz, 3H), 0.91-0.76 (m, 1H).

Example 174

[(1R,2R,4S,5R)-2-methyl-5-[[5-(trifluoromethyl)-2-pyridyl]oxy]-3-azabicyclo[2.2.1]heptan-3-yl]-[2-(6-nitro-2-pyridyl)phenyl]methanone

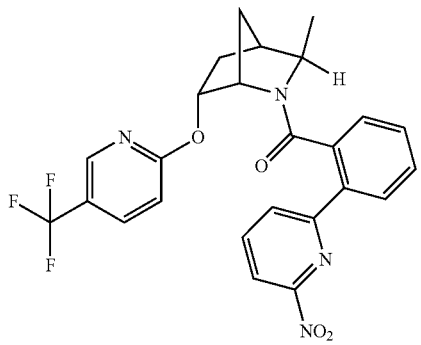 [SMILES: CC1C2CC(Oc3ccc(C(F)(F)F)cn3)C(C2)N1C(=O)c1ccccc1-c1cccc([N+](=O)[O-])n1]

The title compound was prepared analogous to Example 169 step B, C and D using 2-chloro-6-nitropyridine. MS (ESI): mass calcd. for $C_{25}H_{21}F_3N_4O_4$, 498.2. m/z found, 499.2 [M+H]$^+$. $^1$H NMR (400 MHz, CD$_3$CN) δ 8.34-8.12 (m, 2H), 8.08-8.01 (m, 1H), 7.99-7.81 (dd, J=7.6 Hz, 2H), 7.60-7.49 (ddd, J=7.7, 1.3 Hz, 1H), 7.43-7.28 (td, J=7.6, 1.4 Hz, 2H), 7.14-7.04 (m, 1H), 7.03-6.80 (m, 2H), 4.99-4.83 (d, J=10.1 Hz, 1H), 3.89-3.65 (m, 2H), 2.47-2.38 (s, 2H), 1.36-1.13 (m, 2H), 1.04-0.92 (d, J=6.3 Hz, 3H), 0.79-0.64 (d, J=10.8 Hz, 1H).

Example 175

[2-(6-bromo-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone

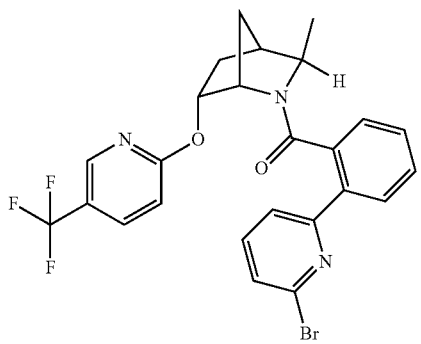 [SMILES: CC1C2CC(Oc3ccc(C(F)(F)F)cn3)C(C2)N1C(=O)c1ccccc1-c1cccc(Br)n1]

The title compound was prepared analogous to Example 169 step B, C and D using 2,6-dibromopyridine and intermediate B-14A. MS (ESI): mass calcd. for $C_{25}H_{21}BrF_3N_3O_2$, 531.1; m/z found, 532.2 [M+H]$^+$. $^1$H NMR (400 MHz, CD$_3$CN) δ 8.09-8.03 (s, 1H), 7.95-7.83 (d, J=8.7 Hz, 1H), 7.79-7.70 (m, 1H), 7.63-7.58 (m, 1H), 7.55-7.42 (m, 2H), 7.37-7.26 (m, 1H), 7.07-7.02 (m, 1H), 6.97-6.86 (m, 2H), 5.01-4.88 (d, J=10.1 Hz, 1H), 3.93-3.81 (s, 2H), 3.80-3.70 (d, J=6.3 Hz, 1H), 2.24-2.06 (s, 2H), 1.34-1.23 (m, 2H), 1.16-1.07 (d, J=6.3 Hz, 3H), 0.94-0.82 (d, J=10.7 Hz, 1H).

Example 176

[(1R,2S,4S,5R)-2-(hydroxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone

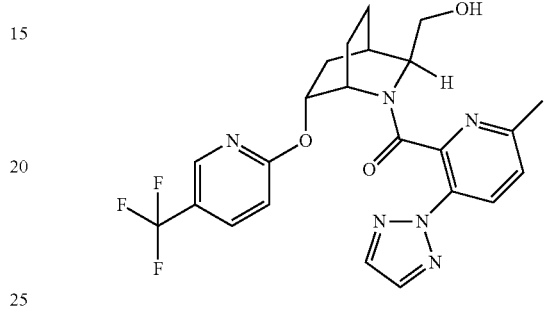

Step A: (1S,3S,4R,6R)-tert-butyl 3-((methoxymethoxy)methyl)-6-((5-(trifluoromethyl)pyridin-2-yl)oxy)-2-azabicyclo[2.2.2]octane-2-carboxylate. To intermediate B-36 (1S,3S,4R,6R)-tert-butyl 6-hydroxy-3-((methoxymethoxy)methyl)-2-azabicyclo[2.2.2]octane-2-carboxylate (130 mg) dissolved in DMF (3 mL) was added NaH (28 mg, 0.7 mmol, 60% dispersion in mineral oil). After 5 minutes 2-chloro-5-(trifluoromethyl)pyridine (102 mg, 0.56 mmol) was added and the reaction left to stir at room temperature. After stirring for 5 h, the mixture was carefully quenched with H$_2$O, and the aqueous layer extracted with EtOAc (3×). The combined organics were washed with, brine, dried with MgSO$_4$, filtered and concentrated. Purification via silica gel chromatography (0-20% EtOAc in hexanes) gave the title compound (70 mg). MS (ESI) mass calcd. for $C_{21}H_{29}F_3N_2O_5$, 446.47. m/z found 347.1 [M+2H-tBu]$^+$.

Step B: ((1S,3S,4R,6R)-6-((5-(trifluoromethyl)pyridin-2-yl)oxy)-2-azabicyclo[2.2.2]octan-3-yl)methanol.xHCl. To the title compound of step A (70 mg, 0.16 mmol) in DCM (3 mL) was added 4M HCl in dioxane (1 mL) and the reaction mixture was stirred for 3 h at room temperature after which the reaction was concentrated to give the title compound of step B (80 mg), which was used without further purification. MS (ESI) mass calcd. for $C_{14}H_{17}F_3N_2O2$, 302.3. m/z found 303.1 [M+H]$^+$.

Step C: ((1S,3S,4R,6R)-3-(hydroxymethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone. To the title compound of step B (80 mg) and intermediate A-26 (104 mg, 0.51 mmol) in DCM (3 mL) was added DIPEA (0.15 mL, 0.85 mmol), EDCI (98 mg, 0.51 mmol), and HOBt (69 mg, 0.51 mmol). The reaction mixture was stirred at rt overnight. Upon completion, the reaction was diluted with DCM, washed with H$_2$O, concentrated, and purified via silica gel chromatography (0-100% EtOAc in hexanes) to give the title compound (46 mg). MS (ESI): mass calcd. for $C_{23}H_{23}F_3N_6O_3$, 488.2; m/z found, 489.2 [M+H]$^+$. Analytical HPLC was obtained on a Agilent 1100 Series using an Inertsil ODS-3 column (3 mm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.33 min (major rotamer) at 254 nm $^1$H NMR (500 MHz, CDCl$_3$) δ 8.46-8.37 (m, 1H), 8.24-8.19 (m, 1H), 7.92-7.87 (m, 1H), 7.86-7.82 (m, 1H), 7.37-7.30 (m, 1H), 7.13-6.65 (m, 2H), 5.32-5.25 (m, 1H), 5.00-4.88 (m, 1H), 4.60-4.25 (m, 2H), 4.21-4.06 (m, 1H), 3.98-3.87 (m, 1H), 3.66-3.56 (m, 1H), 2.62 (s, 3H), 2.14-2.02 (m, 2H), 2.02-1.85 (m, 2H), 1.56-1.42 (m, 2H).

Example 177

[2-fluoro-6-(triazol-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone

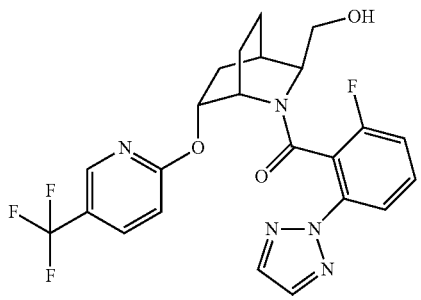 [SMILES: O=C(c1c(F)cccc1-n1nccn1)N1C(CO)C2CCC1C(Oc1ccc(C(F)(F)F)cn1)C2]

The title compound was prepared analogous to Example 176 substituting intermediate A-26 with intermediate A-11. MS (ESI): mass calcd. for $C_{23}H_{21}F_4N_5O_3$, 491.2. m/z found, 492.0 [M+H]$^+$. Analytical HPLC was obtained on a Agilent 1100 Series using an Inertsil ODS-3 column (3 mm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.05 min at 254 nm $^1$H NMR (500 MHz, CDCl$_3$) δ 8.40-8.34 (m, 1H), 7.97-7.86 (m, 1H), 7.86-7.78 (m, 2H), 7.51-7.50 (m, 1H), 7.19-7.08 (m, 2H), 6.91-6.83 (m, 1H), 5.36-5.24 (m, 1H), 5.12-5.00 (m, 1H), 4.91-4.81 (m, 1H), 4.67-4.52 (m, 1H), 3.73-3.52 (m, 1H), 2.56-2.47 (m, 1H), 2.18-1.85 (m, 3H), 1.81-1.42 (m, 4H).

Example 178

[5-fluoro-2-(5-fluoropyrimidin-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone

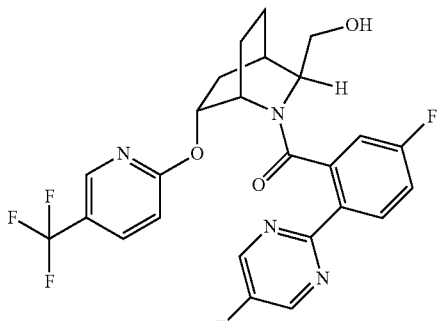

The title compound was prepared analogous to Example 176 substituting intermediate A-26 with intermediate A-22. MS (ESI): mass calcd. for $C_{25}H_{21}F_5N_4O_3$, 520.2. m/z found, 522.0 [M+H]$^+$. Analytical HPLC was obtained on a Agilent 1100 Series using an Inertsil ODS-3 column (3 mm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.44 min at 254 nm. $^1$H NMR (400 MHz, CDCl$_3$) δ 8.70-8.49 (m, 2H), 8.44-8.27 (m, 2H), 7.92-7.80 (m, 1H), 7.26-7.18 (m, 1H), 7.08-7.00 (m, 1H), 6.96-6.89 (m, 1H), 5.39-5.02 (m, 2H), 4.66-4.49 (m, 1H), 4.12-3.79 (m, 2H), 3.74-3.53 (m, 1H), 2.60-2.47 (m, 1H), 1.98-1.77 (m, 2H), 1.77-1.37 (m, 4H).

Example 179

[(1R,2S,4S,5R)-2-(methoxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone

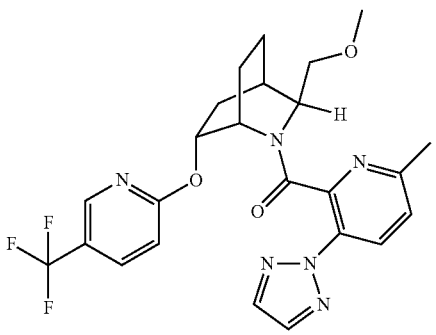 [SMILES: COCC1C2CCC(C(Oc3ccc(C(F)(F)F)cn3)C2)N1C(=O)c1nc(C)ccc1-n1nccn1]

Step A: (1S,3S,4R,6R)-tert-butyl 3-(methoxymethyl)-6-((5-(trifluoromethyl)pyridin-2-yl)oxy)-2-azabicyclo[2.2.2]octane-2-carboxylate. Product of step A was prepared analogous to (1S,3S,4R,6R)-tert-butyl 3-((methoxymethoxy)methyl)-6-((5-(trifluoromethyl)pyridin-2-yl)oxy)-2-azabicyclo[2.2.2]octane-2-carboxylate. Substituting (1S,3S,4R,6R)-tert-butyl 6-hydroxy-3-((methoxymethoxy)methyl)-2-azabicyclo[2.2.2]octane-2-carboxylate for (1S,3S,4R,6R)-tert-butyl 6-hydroxy-3-(methoxymethyl)-2-azabicyclo[2.2.2]octane-2-carboxylate. MS (ESI) mass calcd. for $C_{20}H_{22}F_3NO_4$, 416.44. m/z found 317.0 [M+2H—CO$_2$tBu]$^+$.

Step B: (1S,3S,4R,6R)-3-(methoxymethyl)-6-((5-(trifluoromethyl)pyridin-2-yl)oxy)-2-azabicyclo[2.2.2]octane.x-HCl. Product of step B was prepared analogous to ((1S,3S,4R,6R)-6-((5-(trifluoromethyl)pyridin-2-yl)oxy)-2-azabicyclo[2.2.2]octan-3-yl)methanol.xHCl. Substituting (1S,3S,4R,6R)-tert-butyl 3-((methoxymethoxy)methyl)-6-((5-(trifluoromethyl)pyridin-2-yl)oxy)-2-azabicyclo[2.2.2]octane-2-carboxylate for product from Step A. MS (ESI) mass calcd. for $C_{15}H_{19}F_3N_2O_2$, 316.32. m/z found 317.2 [M+H]$^+$.

Step C: ((1S,3S,4R,6R)-3-(methoxymethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone. Product of step C was prepared analogous to ((1S,3S,4R,6R)-3-(hydroxymethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanon. Substituting ((1S,3S,4R,6R)-6-((5-(trifluoromethyl)pyridin-2-yl)oxy)-2-azabicyclo[2.2.2]octan-3-yl)methanol.xHCl for product from Step B. MS (ESI): mass calcd. for $C_{24}H_{25}F_3N_6O_3$, 502.2. m/z found, 502.9 [M+H]. $^1$H NMR (500 MHz, CDCl$_3$) δ 8.50-8.23 (m, 1H), 8.23-8.06 (m, 1H), 7.88-7.83 (m, 1H), 7.73-7.68 (m, 1H), 7.44-7.27 (m, 1H), 7.07-6.88

(m, 1H), 6.86-6.72 (m, 1H), 4.88-4.67 (m, 1H), 4.47-4.36 (m, 1H), 4.28-4.17 (m, 1H), 3.49-3.42 (m, 3H), 2.70-2.53 (m, 2H), 2.39-2.18 (m, 3H), 2.15-1.99 (m, 1H), 1.82-1.63 (m, 3H), 1.57-1.42 (m, 1H), 1.39-1.29 (m, 1H), 1.08-0.87 (m, 1H).

Example 180

[(1R,2S,4S,5R)-2-(methoxymethyl)-5-[[5-(trifluoromethyl)-2-pyridyl]oxy]-3-azabicyclo[2.2.2]octan-3-yl]-(6-methyl-3-pyrimidin-2-yl-2-pyridyl)methanone

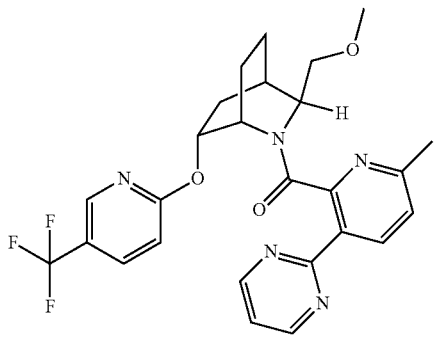 [SMILES: COCC1C2CCC(C(Oc3ccc(C(F)(F)F)cn3)C2)N1C(=O)c1nc(C)ccc1-c1ncccn1]

The title compound was prepared analogous to Example 179 substituting intermediate A-26 with intermediate A-27. MS (ESI): mass calcd. for $C_{26}H_{26}F_3N_5O_3$, 513.2. m/z found, 513.9 [M+H]$^+$. Analytical HPLC was obtained on a Agilent 1100 Series using an Inertsil ODS-3 column (3 mm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.43 min at 254 nm $^1$H NMR (500 MHz, CDCl$_3$) δ 9.14-8.35 (m, 3H), 8.28-7.93 (m, 1H), 7.91-7.56 (ddd, J=59.1, 8.7, 2.5 Hz, 1H), 7.44-7.27 (m, 1H), 7.25-7.07 (m, 1H), 7.06-6.71 (m, 1H), 5.59-5.33 (s, 1H), 4.92-4.67 (m, 1H), 4.52-4.21 (m, 2H), 3.51-3.38 (m, 3H), 2.66-2.55 (d, J=22.3 Hz, 2H), 2.45-2.17 (s, 3H), 1.93-1.40 (m, 5H), 1.40-1.24 (d, J=10.3 Hz, 1H).

Example 181

[(1R,2S,4S,5R)-2-(methoxymethyl)-5-[[5-(trifluoromethyl)-2-pyridyl]oxy]-3-azabicyclo[2.2.2]octan-3-yl]-(2-pyrimidin-2-ylphenyl)methanone

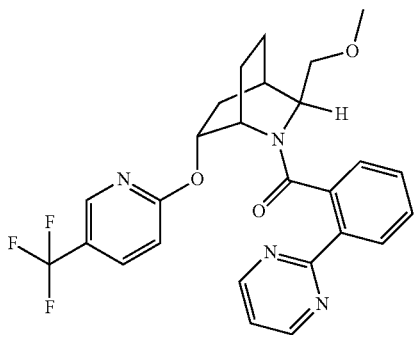 [SMILES: COCC1C2CCC(C(Oc3ccc(C(F)(F)F)cn3)C2)N1C(=O)c1ccccc1-c1ncccn1]

The title compound was prepared analogous to Example 179 substituting intermediate A-26 with intermediate A-28. MS (ESI): mass calcd. for $C_{26}H_{25}F_3N_4O_3$, 498.2. m/z found, 499.0 [M+H]$^+$. Analytical HPLC was obtained on a Agilent 1100 Series using an Inertsil ODS-3 column (3 mm, 50×3 mm), mobile phase of 5-99% ACN in 0.05% TFA over 1.6 min and then hold at 99% ACN for 0.4 min, at a flow rate of 2.2 mL/min (Temperature=50° C.). $R_t$=1.52 min at 254 nm $^1$H NMR (500 MHz, CDCl$_3$) δ 9.10-8.71 (m, 1H), 8.65-8.29 (m, 1H), 8.29-7.92 (m, 1H), 7.89-7.57 (m, 2H), 7.57-7.33 (m, 2H), 7.26-7.13 (m, 2H), 7.06-6.68 (m, 1H), 5.45-5.18 (s, 1H), 4.88-4.39 (m, 1H), 4.38-4.04 (s, 1H), 3.84-3.60 (m, 2H), 3.54-3.34 (m, 3H), 2.67-2.48 (m, 1H), 2.11-1.84 (s, 2H), 1.82-1.41 (s, 3H), 1.41-1.20 (s, 1H).

Example 182

[(1R,2R,4S,5R)-5-[[5-(difluoromethyl)-2-pyridyl]oxy]-2-methyl-3-azabicyclo[2.2.1]heptan-3-yl]-(6-methyl-3-pyrimidin-2-yl-2-pyridyl)methanone

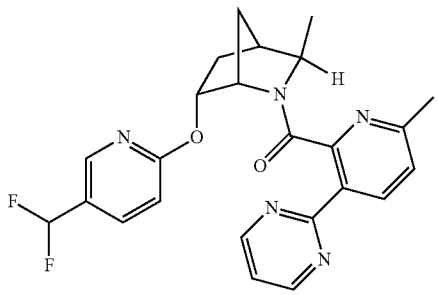 [SMILES: Cc1ccc(-c2ncccn2)c(C(=O)N2C(C)C3CC(Oc4ccc(C(F)F)cn4)C2C3)n1]

The title compound was prepared analogous to Example 28 substituting intermediate A-12 with intermediate A-27 and 2-chloro-5-(trifluoromethyl)pyridine with 2-chloro-5-(difluoromethyl)pyridine. MS (ESI): mass calcd. for $C_{24}H_{23}F_2N_5O_2$, 451.2. m/z found, 452.1 [M+H]$^+$. $^1$H NMR (500 MHz, CDCl$_3$) δ 8.86-8.78 (d, J=4.9 Hz, 2H), 8.17-8.11 (d, J=8.0 Hz, 1H), 7.91-7.87 (m, 1H), 7.67-7.62 (m, 1H), 7.26-7.23 (m, 1H), 7.05-7.01 (m, 1H), 6.98-6.93 (m, 1H), 6.69-6.44 (t, J=56.1 Hz, 1H), 4.94-4.86 (m, 1H), 4.20-4.13 (m, 1H), 4.02-3.91 (q, J=6.3 Hz, 1H), 2.31-2.27 (s, 3H), 2.21-2.13 (m, 2H), 1.41-1.37 (d, J=6.3 Hz, 3H), 1.37-1.24 (m, 2H).

Example 183

(6-methyl-3-(2H-1,2,3-triazol-2-yl)pyridin-2-yl) ((1S*,3R*,4R*,6R*)-3-methyl-6-(quinoxalin-2-yloxy)-2-azabicyclo[2.2.1]heptan-2-yl)methanone

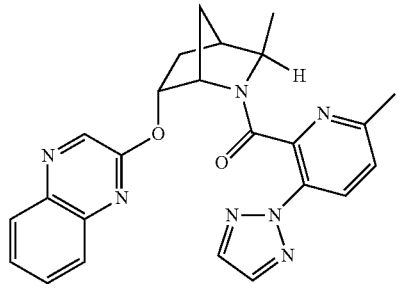 [SMILES: Cc1ccc(-n2nccn2)c(C(=O)N2C(C)C3CC(Oc4cnc5ccccc5n4)C2C3)n1]

The title compound was prepared analogous to Example 28 substituting intermediate A-12 with intermediate A-26 and 2-chloro-5-(trifluoromethyl)pyridine with 2-chloroquinoxaline. MS (ESI): mass calcd. for C$_{24}$H$_{23}$N$_{7}$O$_{2}$, 441.2. m/z found, 442.1 [M+H]$^+$. $^1$H NMR (500 MHz, CDCl$_3$) δ 8.51 (s, 1H), 7.99-7.94 (m, 1H), 7.87 (s, 2H), 7.64-7.58 (m, 2H), 7.57-7.49 (m, 2H), 6.50 (d, J=8.3, 0.6 Hz, 1H), 5.07-4.98 (m, 1H), 4.38-4.32 (m, 1H), 4.01 (q, J=6.3 Hz, 1H), 2.31-2.21 (m, 2H), 2.08 (s, 3H), 1.59-1.47 (m, 2H), 1.44-1.40 (m, 1H), 1.38 (d, J=6.3 Hz, 3H).

Example 184

(3-fluoro-2-(2H-1,2,3-triazol-2-yl)phenyl)((1S*,3R*,4R*,6R*)-3-methyl-6-(quinoxalin-2-yloxy)-2-azabicyclo[2.2.1]heptan-2-yl)methanone

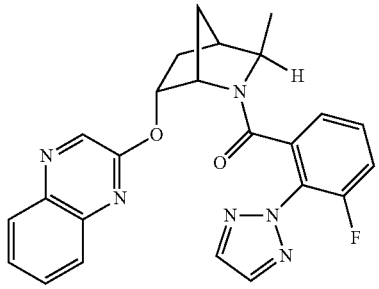 [SMILES: CC1C2CC(Oc3cnc4ccccc4n3)C(C2)N1C(=O)c1cccc(F)c1-n1nccn1]

The title compound was prepared analogous to Example 28 substituting intermediate A-12 with intermediate A-16 and 2-chloro-5-(trifluoromethyl)pyridine with 2-chloroquinoxaline. MS (ESI): mass calcd. for C$_{24}$H$_{21}$FN$_{6}$O$_{2}$, 444.2. m/z found, 445.0 [M+H]$^+$. $^1$H NMR (500 MHz, CDCl$_3$) δ 8.46 (s, 1H), 8.05-7.99 (m, 1H), 7.92 (s, 2H), 7.66-7.56 (m, 3H), 6.98-6.92 (m, 1H), 6.62-6.51 (m, 2H), 5.08 (dt, J=10.2, 3.3 Hz, 1H), 4.26-4.19 (m, 1H), 3.87 (q, J=6.3 Hz, 1H), 2.29-2.21 (m, 1H), 2.19-2.13 (m, 1H), 1.44-1.35 (m, 2H), 1.24-1.20 (m, 1H), 1.10 (d, J=6.3 Hz, 3H).

Example 185

(6-methyl-3-(2H-1,2,3-triazol-2-yl)pyridin-2-yl)((1S*,3R*,4R*,6R*)-3-methyl-6-(quinolin-3-yloxy)-2-azabicyclo[2.2.1]heptan-2-yl)methanone

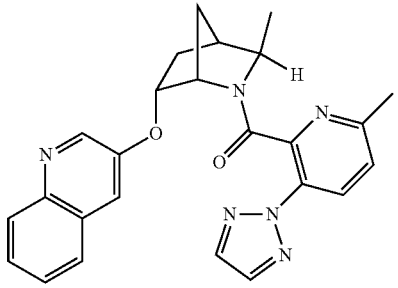 [SMILES: Cc1ccc(-n2nccn2)c(C(=O)N2C(C)C3CC(Oc4cnc5ccccc5c4)C2C3)n1]

The title compound was prepared analogous to Example 28 substituting intermediate A-12 with intermediate A-26 and 2-chloro-5-(trifluoromethyl)pyridine with 2-chloroquinoline. MS (ESI): mass calcd. for C$_{25}$H$_{24}$N$_{6}$O$_{2}$, 440.2. m/z found, 441.1 [M+H]$^+$. $^1$H NMR (500 MHz, CDCl$_3$) δ 7.90-7.84 (m, 3H), 7.68-7.63 (m, 2H), 7.56-7.49 (m, 2H), 7.35 (ddd, J=8.0, 6.2, 2.0 Hz, 1H), 6.96 (d, J=8.8 Hz, 1H), 6.54 (dd, J=8.2, 0.6 Hz, 1H), 5.03 (dt, J=10.0, 3.2 Hz, 1H), 4.31 (t, J=2.4 Hz, 1H), 3.98 (q, J=6.3 Hz, 1H), 2.28-2.17 (m, 2H), 2.09 (s, 3H), 1.48-1.41 (m, 2H), 1.41-1.38 (m, 1H), 1.36 (d, J=6.3 Hz, 3H).

Example 186

((1S*,3R*,4R*,6R*)-6-((6-fluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone

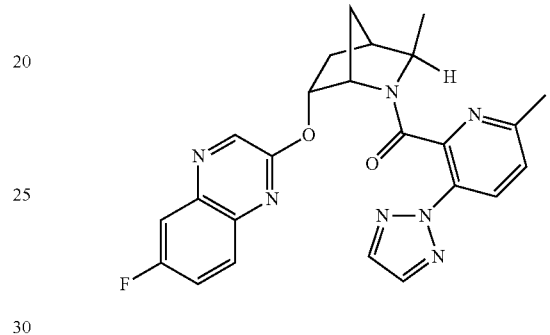

The title compound was prepared analogous to Example 28 substituting intermediate A-12 with intermediate A-26 and 2-chloro-5-(trifluoromethyl)pyridine with 2-chloro-6-fluoroquinoxaline. MS (ESI): mass calcd. for C$_{24}$H$_{22}$FN$_{7}$O$_{2}$, 459.2. m/z found, 460.1 [M+H]$^+$. $^1$H NMR (500 MHz, CDCl$_3$) δ 8.53 (s, 1H), 7.87 (s, 2H), 7.66-7.60 (m, 2H), 7.51 (dd, J=9.1, 5.6 Hz, 1H), 7.38 (ddt, J=9.1, 8.1, 2.9 Hz, 1H), 6.59 (dd, J=8.2, 0.6 Hz, 1H), 5.05-4.98 (m, 1H), 4.33 (t, J=2.4 Hz, 1H), 4.01 (q, J=6.2 Hz, 1H), 2.27-2.21 (m, 2H), 2.11 (s, 3H), 1.56 (ddt, J=10.7, 3.8, 1.8 Hz, 1H), 1.53-1.46 (m, 1H), 1.44-1.39 (m, 1H), 1.37 (d, J=6.3 Hz, 3H). Major rotamer reported.

Example 187

(3-fluoro-2-(2H-1,2,3-triazol-2-yl)phenyl)((1S*,3R*,4R*,6R*)-6-((6-fluoroquinoxalin-2-yl)oxy)-3-methyl-2-azabicyclo[2.2.1]heptan-2-yl)methanone

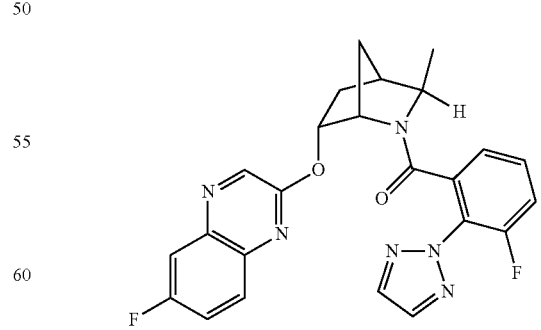

The title compound was prepared analogous to Example 28 substituting intermediate A-12 with intermediate A-16 and 2-chloro-5-(trifluoromethyl)pyridine with 2-chloro-6-fluoroquinoxaline. MS (ESI): mass calcd. for C₂₄H₂₀F₂N₆O₂, 462.2. m/z found, 463.1 [M+H]⁺. ¹H NMR (500 MHz, CDCl₃) δ 8.47 (s, 1H), 7.92 (s, 2H), 7.67 (dd, J=9.0, 2.8 Hz, 1H), 7.58 (dd, J=9.1, 5.6 Hz, 1H), 7.42 (ddd, J=9.1, 8.1, 2.8 Hz, 1H), 6.95 (dt, J=7.7, 1.2 Hz, 1H), 6.66 (ddd, J=9.8, 8.4, 1.5 Hz, 1H), 6.63-6.57 (m, 1H), 5.04 (dt, J=10.2, 3.3 Hz, 1H), 4.20 (t, J=2.4 Hz, 1H), 3.86 (q, J=6.3 Hz, 1H), 2.24 (ddd, J=13.5, 10.2, 4.6 Hz, 1H), 2.18-2.13 (m, 1H), 1.44-1.35 (m, 2H), 1.28-1.21 (m, 1H), 1.10 (d, J=6.3 Hz, 3H). Major rotamer reported.

Example 188

(2-(2H-1,2,3-triazol-2-yl)phenyl)((1S*,3R*,4R*,6R*)-6-(((6-fluoroquinoxalin-2-yl)oxy)-3-methyl-2-azabicyclo[2.2.1]heptan-2-yl)methanone

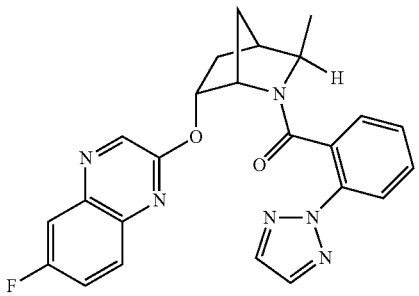 [SMILES: CC1C2CC(Oc3cnc4cc(F)ccc4n3)C(C2)N1C(=O)c1ccccc1-n1nccn1]

The title compound was prepared analogous to Example 28 substituting intermediate A-12 with intermediate A-1 and 2-chloro-5-(trifluoromethyl)pyridine with 2-chloro-6-fluoroquinoxaline. MS (ESI): mass calcd. for C₂₄H₂₁FN₆O₂, 444.2. m/z found, 445.1 [M+H]⁺. ¹H NMR (500 MHz, CDCl₃) δ 8.45 (s, 1H), 7.85 (s, 2H), 7.66 (dd, J=9.0, 2.8 Hz, 1H), 7.52-7.45 (m, 2H), 7.38 (ddd, J=9.1, 8.1, 2.9 Hz, 1H), 7.15 (dd, J=7.7, 1.5 Hz, 1H), 6.76 (ddd, J=8.3, 7.5, 1.5 Hz, 1H), 6.50 (t, J=7.5 Hz, 1H), 5.02-4.95 (m, 1H), 4.01-3.91 (m, 2H), 2.27-2.17 (m, 2H), 1.44 (dt, J=13.2, 3.0 Hz, 1H), 1.34 (d, J=6.3 Hz, 3H), 1.30-1.23 (m, 2H). Major rotamer reported.

Example 189

((1S*,3R*,4R*,6R*)-6-((6,7-difluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone

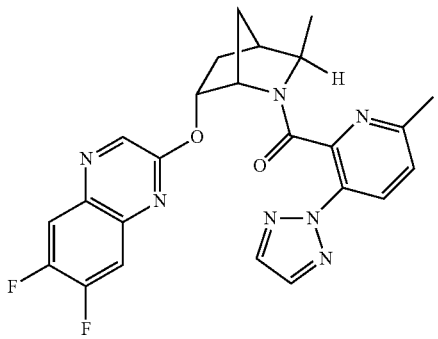 [SMILES: Cc1ccc(-n2nccn2)c(C(=O)N2C(C)C3CC(Oc4cnc5cc(F)c(F)cc5n4)C2C3)n1]

The title compound was prepared analogous to Example 28 substituting intermediate A-12 with intermediate A-26 and 2-chloro-5-(trifluoromethyl)pyridine with 2-chloro-6,7-difluoro-quinoxaline. MS (ESI): mass calcd. for C₂₄H₂₁F₂N₇O₂, 477.2. m/z found, 478.1 [M+H]⁺. ¹H NMR (500 MHz, CDCl₃) δ 8.51 (s, 1H), 7.87 (s, 2H), 7.76-7.67 (m, 2H), 7.32-7.26 (m, 1H), 6.70 (d, J=8.3 Hz, 1H), 5.05-4.97 (m, 1H), 4.28 (t, J=2.4 Hz, 1H), 4.00 (q, J=6.3 Hz, 1H), 2.29-2.21 (m, 2H), 2.15 (s, 3H), 1.57 (ddd, J=10.7, 3.9, 1.9 Hz, 1H), 1.53-1.45 (m, 1H), 1.44-1.39 (m, 1H), 1.37 (d, J=6.3 Hz, 3H).

Example 190

((1S*,3R*,4R*,6R*)-6-((6,7-difluoroquinoxalin-2-yl)oxy)-3-methyl-2-azabicyclo[2.2.1]heptan-2-yl)(3-fluoro-2-(2H-1,2,3-triazol-2-yl)phenyl)methanone

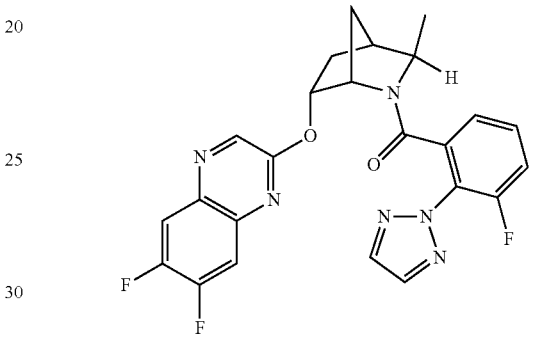

The title compound was prepared analogous to Example 28 substituting intermediate A-12 with intermediate A-16 and 2-chloro-5-(trifluoromethyl)pyridine with 2-chloro-6,7-difluoro-quinoxaline. MS (ESI): mass calcd. for C₂₄H₁₉F₃N₆O₂, 480.2. m/z found, 481.1 [M+H]⁺. ¹H NMR (500 MHz, CDCl₃) δ 8.44 (s, 1H), 7.92 (s, 2H), 7.78 (dd, J=10.3, 8.2 Hz, 1H), 7.37 (dd, J=10.8, 7.9 Hz, 1H), 7.01 (dt, J=7.7, 1.2 Hz, 1H), 6.78 (ddd, J=9.7, 8.4, 1.4 Hz, 1H), 6.70 (td, J=8.0, 4.8 Hz, 1H), 5.05 (dt, J=10.1, 3.3 Hz, 1H), 4.15 (s, 1H), 3.86 (q, J=6.3 Hz, 1H), 2.29-2.20 (m, 1H), 2.20-2.14 (m, 1H), 1.43-1.33 (m, 2H), 1.29-1.22 (m, 1H), 1.09 (d, J=6.3 Hz, 3H).

Example 191

(2-(2H-1,2,3-triazol-2-yl)phenyl)((1S*,3R*,4R*,6R*)-6-(((6,7-difluoroquinoxalin-2-yl)oxy)-3-methyl-2-azabicyclo[2.2.1]heptan-2-yl)methanone

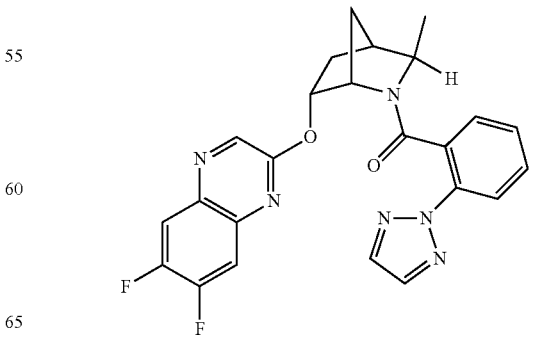

The title compound was prepared analogous to Example 28 substituting intermediate A-12 with intermediate A-1 and 2-chloro-5-(trifluoromethyl)pyridine with 2-chloro-6,7-difluoro-quinoxaline. MS (ESI): mass calcd. for $C_{24}H_{20}F_2N_6O_2$, 462.2. m/z found, 463.0 [M+H]$^+$. $^1$H NMR (500 MHz, CDCl$_3$) δ 8.41 (s, 1H), 7.86 (s, 2H), 7.77 (dd, J=10.4, 8.2 Hz, 1H), 7.52 (d, J=8.1 Hz, 1H), 7.31-7.23 (m, 1H), 7.17 (dd, J=7.7, 1.5 Hz, 1H), 6.85 (ddd, J=9.3, 7.7, 1.6 Hz, 1H), 6.53 (t, J=7.6 Hz, 1H), 5.01-4.93 (m, 1H), 3.94 (q, J=6.4, 6.0 Hz, 2H), 2.27-2.17 (m, 2H), 1.48-1.39 (m, 1H), 1.34 (d, J=6.3 Hz, 3H), 1.29 (s, 2H).

Example 192 ethyl (1R,2S,4S,5R)-3-[6-methyl-3-(triazol-2-yl)pyridine-2-carbonyl]-5-[[5-(trifluoromethyl)-2-pyridyl]oxy]-3-azabicyclo[2.2.1]heptane-2-carboxylate

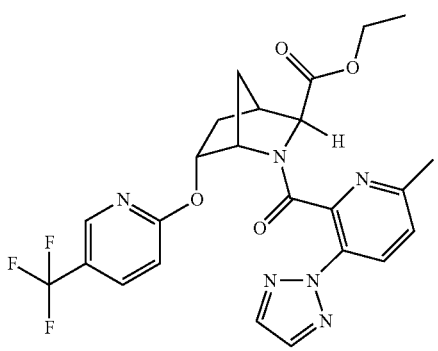 [SMILES: CCOC(=O)C1C2CC(Oc3ccc(C(F)(F)F)cn3)C(C2)N1C(=O)c1nc(C)ccc1-n1nccn1]

The title compound was prepared analogous to Example 28 substituting (1S,3S,4R,6S)-2-tert-butyl 3-ethyl 6-hydroxy-2-azabicyclo[2.2.1]heptane-2,3-dicarboxylate (CAS 501431-08-0) for intermediate B-12 in the synthesis of intermediate B-13 and intermediate A-12 with intermediate A-26. MS (ESI): mass calcd. for $C_{24}H_{23}F_3N_6O_4$, 516.2. m/z found, 517.1 [M+H]$^+$. $^1$H NMR (500 MHz, CDCl$_3$) δ 8.11 (d, J=8.4 Hz, 1H), 8.05-8.01 (m, 1H), 7.82 (s, 2H), 7.75-7.72 (m, 1H), 7.12-7.09 (m, 1H), 7.02-6.98 (m, 1H), 5.04 (dt, J=10.3, 3.3 Hz, 1H), 4.63 (dd, J=3.6, 1.7 Hz, 1H), 4.38-4.34 (m, 1H), 4.33-4.31 (m, 1H), 4.29-4.22 (m, 1H), 2.95 (t, J=4.0 Hz, 1H), 2.20 (s, 3H), 2.16-2.09 (m, 1H), 1.78-1.71 (m, 2H), 1.62-1.59 (m, 1H), 1.34 (t, J=7.1 Hz, 3H).

Example 193

[(1R,2R,4S,5R)-5-[(5-chloro-2-pyridyl)oxy]-2-methyl-3-azabicyclo[2.2.1]heptan-3-yl]-[6-methyl-2-(triazol-2-yl)-3-pyridyl]methanone

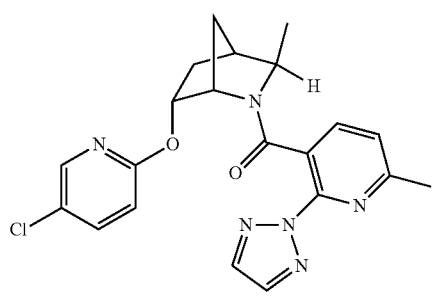 [SMILES: Cc1ccc(C(=O)N2C(C)C3CC(Oc4ccc(Cl)cn4)C2C3)c(-n2nccn2)n1]

The title compound was prepared analogous to Example 121 substituting intermediate A-1 with intermediate A-3. MS (ESI): mass calcd. for $C_{21}H_{21}ClN_6O_2$, 424.1. m/z found, 425.0 [M+H]$^+$. $^1$H NMR (500 MHz, Chloroform-d) δ 7.89 (s, 2H), 7.69 (dd, J=2.7, 0.7 Hz, 1H), 7.50 (dd, J=8.8, 2.7 Hz, 1H), 7.47 (d, J=7.8 Hz, 1H), 6.70 (d, J=7.8, 1H), 6.64 (dd, J=8.8, 0.7 Hz, 1H), 4.80-4.74 (m, 1H), 3.88 (q, J=6.3 Hz, 1H), 3.86-3.82 (m, 1H), 2.60 (s, 3H), 2.18-2.09 (m, 2H), 1.33 (d, J=6.3 Hz, 3H), 1.35-1.20 (m, 3H).

Example 194

[(1R,2R,4S,5R)-5-[(5-chloro-2-pyridyl)oxy]-2-methyl-3-azabicyclo[2.2.1]heptan-3-yl]-[5-methyl-2-(triazol-2-yl)-3-pyridyl]methanone

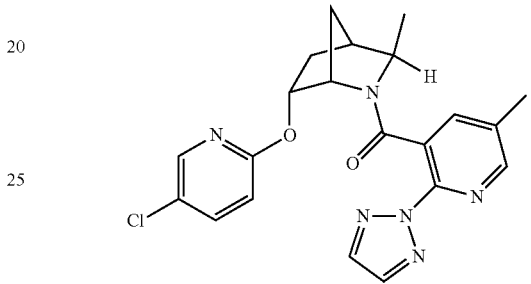

The title compound was prepared analogous to Example 121 substituting intermediate A-1 with intermediate A-25. MS (ESI): mass calcd. for $C_{21}H_{21}ClN_6O_2$, 424.1. m/z found, 425.0 [M+H]$^+$. $^1$H NMR (500 MHz, Chloroform-d) δ 8.27 (dd, J=2.3, 0.8 Hz, 1H), 7.89 (s, 2H), 7.72 (dd, J=2.6, 0.7 Hz, 1H), 7.51 (dd, J=8.7, 2.7 Hz, 1H), 7.43 (dt, J=2.4, 0.8 Hz, 1H), 6.64 (dd, J=8.7, 0.7 Hz, 1H), 4.82-4.76 (m, 1H), 3.89 (q, J=6.3 Hz, 1H), 3.88-3.85 (m, 1H), 2.18-2.09 (m, 5H), 1.35 (d, J=6.3 Hz, 3H), 1.34-1.28 (m, 2H), 1.27-1.22 (m, 1H).

Example 195

[(1R,3R,4S,6R)-3-[(5-chloro-2-pyridyl)oxy]-2,2-dideuterio-6-methyl-5-azabicyclo[2.2.1]heptan-5-yl]-[2-(triazol-2-yl)phenyl]methanone

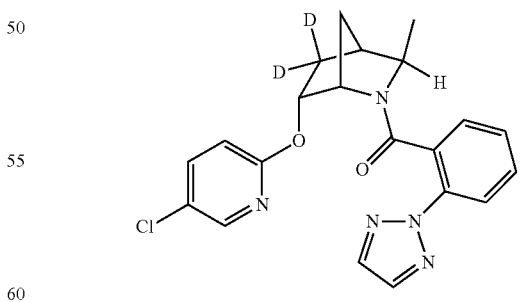

Step A: tert-butyl (1S,3R,4R)-3-methyl-6-oxo-2-azabicyclo[2.2.1]heptane-2-carboxylate-5,5-d2. Sodium metal (26 mg, 1.13 mmol) was added portion wise to MeOD (10 mL). Upon complete dissolution of the sodium metal Intermediate B-13A (216 mg, 0.96 mmol) was added and the reaction mixture was left to stir at room temperature. After 20.5 h the reaction mixture was concentrated, diluted with D₂O/DCM, and the layers separated. The aqueous layer was extracted with additional EtOAc and the combined organics were then dried with MgSO₄, filtered, and concentrated to provide the title compound as a colourless oil (200 mg) which was used without further purification. MS (ESI) mass calcd. for $C_{12}H_{12}D_2NO_3$, 227.1. m/z found 172.1 [M+2H-tBu]⁺. ¹H NMR (500 MHz, Chloroform-d) δ 4.25-3.92 (m, 1H), 3.62-3.29 (m, 1H), 2.44 (s, 1H), 2.14-2.00 (m, 1H), 1.59-1.54 (m, 1H), 1.44 (s, 9H), 1.30 (d, J=6.4 Hz, 3H).

Step B: tert-butyl (1S,3R,4R)-6-hydroxy-3-methyl-2-azabicyclo[2.2.1]heptane-2-carboxylate-5,5-d2. To the title compound of step A (200 mg) in DCM (6 mL) and MeOD (2 mL) was added NaBH₄ (80 mg, 2.12 mmol) in a single portion. After 6.25 h the reaction was diluted with H₂O and the aqueous layer extracted with DCM (×3). The combined organics were then dried with MgSO₄, filtered, and concentrated to provide the title compound as a light blue oil (197 mg) which was used without further purification. MS (ESI) mass calcd. for $C_{12}H_{19}D_2NO$, 229.2; m/z found 174.1 [M+2H-tBu]⁺.

Step C: tert-butyl (1S,3R,4R)-6-((5-chloropyridin-2-yl)oxy)-3-methyl-2-azabicyclo[2.2.1]heptane-2-carboxylate-5,5-d2. To the title compound of step B (98 mg) and 5-chloro-2-fluoropyridine (84 mg, 0.64 mmol) dissolved in DMF (5 mL) was added NaH (26 mg, 0.65 mmol, 60% dispersion in mineral oil) and the reaction mixture left to stir at room temperature. After stirring for 4.75 h, the mixture was carefully quenched with H₂O, and the aqueous layer extracted with EtOAc (3×). The combined organics were washed with 5% LiCl solution, brine, dried with MgSO₄, filtered and concentrated. Purification via silica gel chromatography (0-20% EtOAc in hexanes) gave the title compound (93 mg). MS (ESI) mass calcd. for $C_{17}H_{21}D_2ClN_2O_3$, 340.2. m/z found 341.2 [M+H]⁺.

Step D: (1S,3R,4R)-6-((5-chloropyridin-2-yl)oxy)-3-methyl-2-azabicyclo[2.2.1]heptane-5,5-d2.xHCl. To the title compound of step C (93 mg) in EtOAc (3 mL) was added 4M HCl in dioxane (6 mL). After 21 h the reaction was concentrated to give the title compound as an off-white solid (80 mg) which was used without further purification. MS (ESI) mass calcd. for $C_{12}H_{13}D_2ClN_2O$, 240.1. m/z found 241.0 [M+H]⁺.

Step E: [(1R,3R,4S,6R)-3-[(5-chloro-2-pyridyl)oxy]-2,2-dideuterio-6-methyl-5-azabicyclo[2.2.1]heptan-5-yl]-[2-(triazol-2-yl)phenyl]methanone. To the title compound of step D (26 mg) and intermediate A-1 (20 mg, 0.11 mmol) in DMF (0.85 mL) was added DIPEA (0.05 mL, 0.3 mmol) and HATU (39 mg, 0.10 mmol). Upon completion, the reaction was diluted with MeOH, filtered, and purified using Agilent Prep Method X to give the title compound (21 mg). MS (ESI): mass calcd. for $C_{21}H_{18}ClD_2N_5O_2$, 411.1. m/z found, 412.1 [M+H]⁺. ¹H NMR (500 MHz, Chloroform-d) δ 7.84 (s, 2H), 7.69-7.65 (m, 2H), 7.50 (dd, J=8.8, 2.7 Hz, 1H), 7.36 (ddd, J=8.1, 7.5, 1.5 Hz, 1H), 7.24 (dd, J=7.7, 1.5 Hz, 1H), 6.95 (td, J=7.6, 1.2 Hz, 1H), 6.67 (dd, J=8.8, 0.7 Hz, 1H), 4.80 (d, J=2.8 Hz, 1H), 3.87 (q, J=6.3 Hz, 1H), 3.82 (br. s, 1H), 2.14-2.10 (m, 1H), 1.30 (d, J=6.3 Hz, 3H), 1.25-1.17 (m, 2H).

Example 196

[(1R,3R,4S,6R)-3-[(5-chloro-2-pyridyl)oxy]-2,2-dideuterio-6-methyl-5-azabicyclo[2.2.1]heptan-5-yl]-[6-methyl-3-(triazol-2-yl)-2-pyridyl]methanone

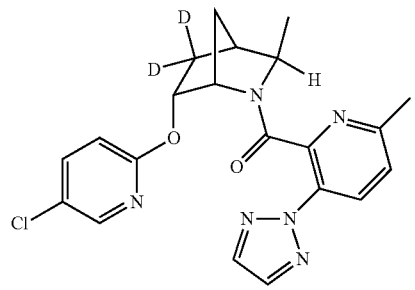 [SMILES: [2H]C1([2H])C2CC(C1Oc1ccc(Cl)cn1)N(C(=O)c1nc(C)ccc1-n1nccn1)C2C]

The title compound was prepared analogous to Example 195 substituting intermediate A-1 with intermediate A-26. MS (ESI): mass calcd. for $C_2H_{19}ClD_2N_6O_2$, 426.2. m/z found, 427.0 [M+H]⁺. ¹H NMR (500 MHz, Chloroform-d) δ 7.87 (d, J=8.3 Hz, 1H), 7.85 (s, 2H), 7.67 (dd, J=2.7, 0.7 Hz, 1H), 7.44 (dd, J=8.8, 2.7 Hz, 1H), 7.13 (d, J=8.3 Hz, 1H), 6.80 (dd, J=8.8, 0.7 Hz, 1H), 4.78 (d, J=2.7 Hz, 1H), 4.07-4.04 (m, 1H), 3.93 (q, J=6.2 Hz, 1H), 2.35 (s, 3H), 2.16-2.13 (m, 1H), 1.40 (dt, J=10.6, 2.0 Hz, 1H), 1.33 (d, J=6.3 Hz, 3H), 1.30-1.26 (m, 1H).

Example 197

[(1R,3R,4S,6R)-3-[(5-chloro-2-pyridyl)oxy]-2,2-dideuterio-6-methyl-5-azabicyclo[2.2.1]heptan-5-yl]-[3-fluoro-2-(triazol-2-yl)phenyl]methanone

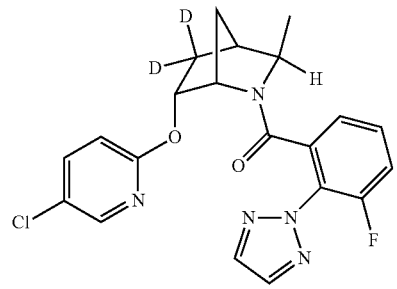 [SMILES: [2H]C1([2H])C2CC(C1Oc1ccc(Cl)cn1)N(C(=O)c1cccc(F)c1-n1nccn1)C2C]

The title compound was prepared analogous to Example 195 substituting intermediate A-1 with intermediate A-16. MS (ESI): mass calcd. for $C_2H_{17}ClD_2FN_5O_2$, 429.1. m/z found, 430.0 [M+H]⁺. ¹H NMR (500 MHz, Chloroform-d) δ 7.90 (s, 2H), 7.76 (dd, J=2.7, 0.7 Hz, 1H), 7.52 (dd, J=8.8, 2.7 Hz, 1H), 7.17 (ddd, J=9.7, 6.2, 3.5 Hz, 1H), 7.09-7.01 (m, 2H), 6.69 (dd, J=8.7, 0.7 Hz, 1H), 4.87 (d, J=2.8 Hz, 1H), 4.01 (dq, J=2.7, 1.1 Hz, 1H), 3.78 (q, J=6.3 Hz, 1H), 2.08 (q, J=1.4 Hz, 1H), 1.28 (ddt, J=10.8, 2.0, 1.1 Hz, 1H), 1.20 (dt, J=10.8, 2.0 Hz, 1H), 1.04 (d, J=6.3 Hz, 3H).

Example 198

[(1R,3R,4S,6R)-2,2-dideuterio-6-methyl-3-[[5-(trifluoromethyl)-2-pyridyl]oxy]-5-azabicyclo[2.2.1]heptan-5-yl]-[6-methyl-3-(triazol-2-yl)-2-pyridyl]methanone

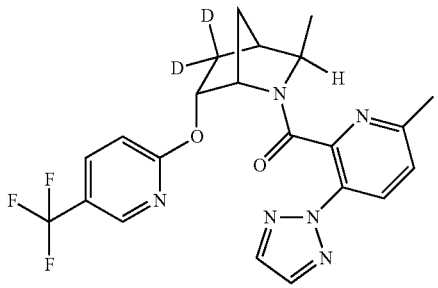 [SMILES: [2H]C1([2H])C2CC(C1Oc1ccc(C(F)(F)F)cn1)N(C(=O)c1nc(C)ccc1-n1nccn1)C2C]

Step A: tert-butyl (1S,3R,4R)-3-methyl-6-oxo-2-azabicyclo[2.2.1]heptane-2-carboxylate-5,5-d2. The title compound was prepared analogous to Example 205 Step A. MS (ESI) mass calcd. for $C_{12}H_{12}D_2NO_3$, 227.1. m/z found 172.1 [M+2H-tBu]$^+$.

Step B: tert-butyl (1S,3R,4R)-6-hydroxy-3-methyl-2-azabicyclo[2.2.1]heptane-2-carboxylate-5,5-d2. The title compound was prepared analogous to Example 205 Step A. MS (ESI) mass calcd. for $C_{12}H_{19}D_2NO$, 229.2. m/z found 174.1 [M+2H-tBu]$^+$.

Step C: tert-butyl (1S,3R,4R)-3-methyl-6-((5-(trifluoromethyl)pyridin-2-yl)oxy)-2-azabicyclo[2.2.1]heptane-2-carboxylate-5,5-d2. To the title compound of step B (116 mg) and 2-chloro-5-(trifluoromethyl)pyridine (138 mg, 0.76 mmol) dissolved in DMF (5 mL) was added NaH (30 mg, 0.75 mmol, 60% dispersion in mineral oil) and the reaction mixture left to stir at room temperature. After stirring for 2.25 h, the mixture was carefully quenched with H$_2$O, and the aqueous layer extracted with EtOAc (3×). The combined organics were washed with 5% LiCl solution, brine, dried with MgSO$_4$, filtered and concentrated. Purification via silica gel chromatography (0-20% EtOAc in hexanes) gave the title compound (133 mg). MS (ESI) mass calcd. for $C_{12}H_{21}D_2F_3N_2O_3$, 374.2. m/z found 375.0 [M+H]$^+$.

Step D: (1S,3R,4R)-3-methyl-6-((5-(trifluoromethyl)pyridin-2-yl)oxy)-2-azabicyclo[2.2.1]heptane-5,5-d2.xHCl. To the title compound of step C (133 mg, 0.36 mmol) in EtOAc (3 mL) was added 4M HCl in dioxane (6 mL). After 6 h the reaction was concentrated to give the title compound as an off-white solid (113 mg) which was used without further purification. MS (ESI) mass calcd. for $C_{13}H_{13}D_2F_3N_2O$, 274.1. m/z found 275.0 [M+H]$^+$.

Step E: [(1R,3R,4S,6R)-2,2-dideuterio-6-methyl-3-[[5-(trifluoromethyl)-2-pyridyl]oxy]-5-azabicyclo[2.2.1]heptan-5-yl]-[6-methyl-3-(triazol-2-yl)-2-pyridyl]methanone. To the title compound of step D (28 mg) and intermediate A-26 (20 mg, 0.098 mmol) in DMF (0.7 mL) was added DIPEA (0.05 mL, 0.3 mmol) and HATU (38 mg, 0.10 mmol). Upon completion, the reaction was diluted with MeOH, filtered, and purified using Agilent Prep Method X to give the title compound (27 mg). MS (ESI) mass calcd. for $C_{22}H_{19}D_2F_3N_6O_2$, 460.2. m/z found, 461.0 [M+H]$^+$. $^1$H NMR (500 MHz, Chloroform-d) δ 8.06-8.02 (m, 1H), 7.86 (d, J=8.3 Hz, 1H), 7.86 (s, 2H), 7.69 (dd, J=8.7, 2.6, Hz, 1H), 7.08 (d, J=8.3 Hz, 1H), 6.94-6.91 (m, 1H), 4.90 (d, J=2.8 Hz, 1H), 4.12-4.08 (m, 1H), 3.95 (q, J=6.3 Hz, 1H), 2.31 (s, 3H), 2.19-2.17 (m, 1H), 1.46 (dt, J=10.7, 2.0 Hz, 1H), 1.35 (d, J=6.3 Hz, 3H), 1.35-1.30 (m, 1H).

Example 199

[(1R,3R,4S,6R)-2,2-dideuterio-6-methyl-3-[[5-(trifluoromethyl)-2-pyridyl]oxy]-5-azabicyclo[2.2.1]heptan-5-yl]-[3-fluoro-2-(triazol-2-yl)phenyl]methanone

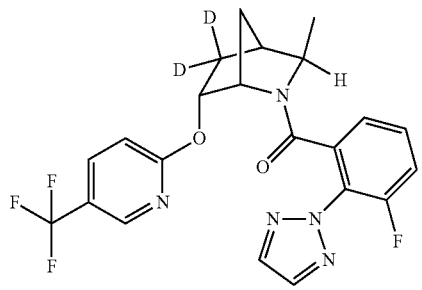

The title compound was prepared analogous to Example 198 substituting intermediate A-26 with intermediate A-16. MS (ESI): mass calcd. for $C_{22}H_{17}D_2F_4N_5O_2$, 463.2. m/z found, 463.9 [M+H]$^+$. $^1$H NMR (500 MHz, Chloroform-d) δ 8.11-8.08 (m, 1H), 7.91 (s, 2H), 7.77 (dd, J=8.8, 2.5 Hz, 1H), 7.13 (ddd, J=9.7, 8.0, 1.7 Hz, 1H), 7.01-6.93 (m, 2H), 6.84-6.80 (m, 1H), 4.97 (d, J=2.8 Hz, 1H), 4.07-4.03 (m, 1H), 3.80 (q, J=6.3 Hz, 1H), 2.12-2.09 (m, 1H), 1.33-1.28 (m, 1H), 1.20 (dt, J=10.9, 2.0 Hz, 1H), 1.05 (d, J=6.3 Hz, 3H).

Example 200

[(1R,3R,4S,6R)-2,2-dideuterio-6-methyl-3-[[5-(trifluoromethyl)-2-pyridyl]oxy]-5-azabicyclo[2.2.1]heptan-5-yl]-[5-methyl-3-(triazol-2-yl)-2-pyridyl]methanone

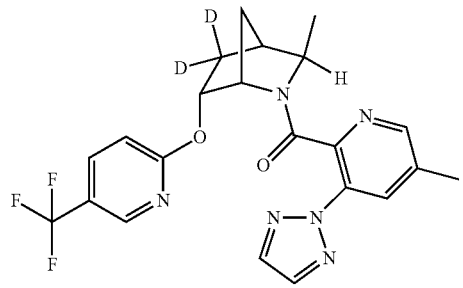 [SMILES: [2H]C1([2H])C2CC(C1Oc1ccc(C(F)(F)F)cn1)N(C(=O)c1ncc(C)cc1-n1nccn1)C2C]

The title compound was prepared analogous to Example 198 substituting intermediate A-26 with intermediate A-19. MS (ESI): mass calcd. for $C_{22}H_{19}D_2F_3N_6O_2$, 460.2. m/z found, 461.0 [M+H]$^+$. $^1$H NMR (500 MHz, Chloroform-d) δ 7.97-7.94 (m, 1H), 7.85 (s, 2H), 7.82-7.80 (m, 1H), 7.77-7.75 (m, 1H), 7.70 (dd, J=8.7, 2.5 Hz, 1H), 6.94-6.90 (m, 1H), 4.93 (d, J=2.7 Hz, 1H), 4.11-4.07 (m, 1H), 3.98 (q, J=6.3 Hz, 1H), 2.28 (s, 3H), 2.22-2.18 (m, 1H), 1.52 (dt, J=10.7, 2.0 Hz, 1H), 1.37 (d, J=6.3 Hz, 3H), 1.37-1.32 (m, 1H).

Example 201

[(1R,3R,4S,6R)-2,2-dideuterio-6-methyl-3-[[5-(trifluoromethyl)-2-pyridyl]oxy]-5-azabicyclo[2.2.1]heptan-5-yl]-[2-(triazol-2-yl)phenyl]methanone

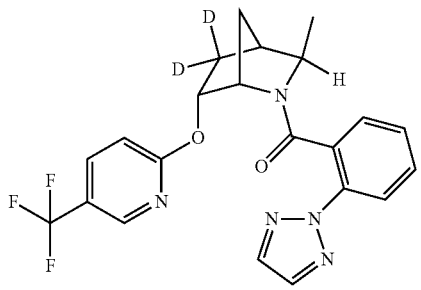 [SMILES: [2H]C1([2H])C2CC(C1Oc1ccc(C(F)(F)F)cn1)N(C(=O)c1ccccc1-n1nccn1)C2C]

The title compound was prepared analogous to Example 198 substituting intermediate A-26 with intermediate A-1. MS (ESI): mass calcd. for $C_{22}H_{18}D_2F_3N_5O_2$, 445.2. m/z found, 445.9 [M+H]$^+$. $^1$H NMR (500 MHz, Chloroform-d) δ 8.00 (s, 1H), 7.84 (s, 2H), 7.75 (dd, J=8.7, 2.5 Hz, 1H), 7.66 (d, J=8.1 Hz 1H), 7.32-7.28 (m, 1H), 7.18 (dd, J=7.7, 1.5 Hz, 1H), 6.86-6.81 (m, 1H), 6.79 (d, J=8.7 Hz, 1H), 4.89 (d, J=2.8 Hz, 1H), 3.92-3.83 (m, 2H), 2.14 (s, 1H), 1.31 (d, J=6.3 Hz, 3H), 1.26-1.19 (m, 2H).

Example 202

[4-(2-fluoroethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone

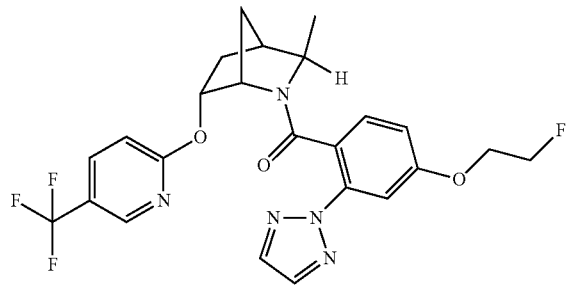 [SMILES: CC1C2CC(Oc3ccc(C(F)(F)F)cn3)C(C2)N1C(=O)c1ccc(OCCF)cc1-n1nccn1]

The title compound was prepared analogous to Example 28 substituting intermediate A-12 with intermediate A-33. MS (ESI): mass calcd. for $C_{24}H_{23}F_4N_5O_3$, 505.2. m/z found, 505.9 [M+H]$^+$. $^1$H NMR (400 MHz, Chloroform-d) δ 8.09-8.05 (m, 1H), 7.83 (s, 2H), 7.75 (dd, J=8.5, 2.4 Hz 1H), 7.23 (d, J=2.5 Hz, 1H), 7.14 (d, J=8.5 Hz, 1H), 6.79 (d, J=8.7 Hz, 1H), 6.43 (dd, J=8.6, 2.5 Hz, 1H), 4.95-4.89 (dt, J=10.7, 3.5 Hz, 1H), 4.81-4.77 (m, 1H), 4.70-4.65 (m, 1H), 4.23-4.19 (m, 1H), 4.17-4.12 (m, 1H), 3.88 (q, J=6.4 Hz, 1H), 3.87-3.83 (m, 1H), 2.19-2.10 (m, 2H), 1.36-1.28 (m, 1H), 1.31 (d, J=6.3 Hz, 3H), 1.27-1.18 (s, 2H).

Example 203

[2-(2-hydroxyethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone

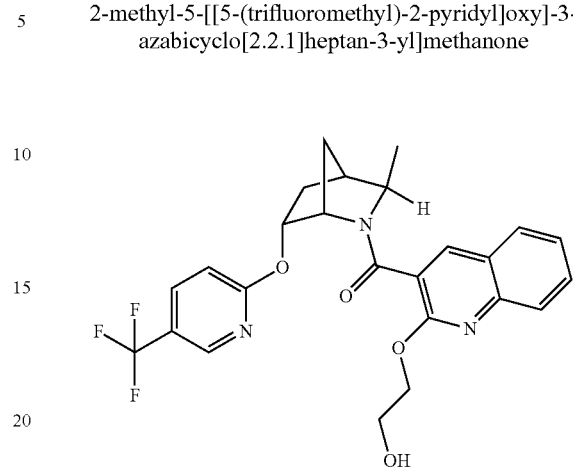

The title compound was prepared analogous to Example 28 substituting intermediate A-12 with intermediate A-34. MS (ESI): mass calcd. for $C_{25}H_{24}F_3N_3O_4$, 487.2. m/z found, 487.9 [M+H]$^+$. $^1$H NMR (400 MHz, Chloroform-d) δ 7.91-7.85 (m, 1H), 7.67 (s, 1H), 7.55-7.49 (m, 2H), 7.32 (d, J=8.7 Hz, 1H), 7.23 (dd, J=7.9, 1.6 Hz, 1H), 7.18-7.12 (m, 1H), 6.74 (d, J=8.7 Hz, 1H), 5.09-5.03 (m, 1H), 4.63-4.51 (m, 2H), 4.48-4.40 (m, 1H), 4.07-3.96 (m, 3H), 2.63 (t, J=5.4 Hz, 1H), 2.35-2.19 (m, 3H), 1.65-1.59 (m, 1H), 1.48-1.41 (m, 4H).

Example 204

[5-(2-bromoethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone

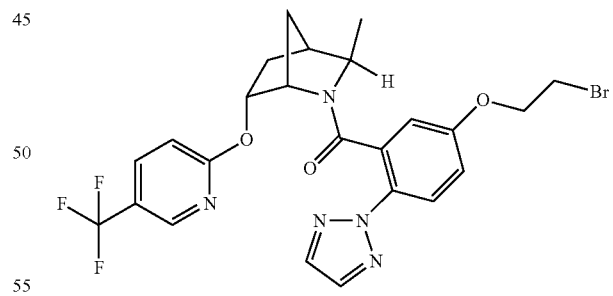

The title compound was prepared analogous to Example 28 substituting intermediate A-12 with intermediate A-36. MS (ESI): mass calcd. for $C_{24}H_{23}BrF_3N_5O_3$, 565.1. m/z found, 565.8 [M+H]$^+$. $^1$H NMR (400 MHz, Chloroform-d) δ 8.13-8.08 (m, 1H), 7.74-7.67 (m, 1H), 7.61 (s, 2H), 7.32-7.26 (m, 1H), 6.83-6.76 (m, 1H), 6.69 (d, J=3.1 Hz, 1H), 6.59 (dd, J=8.8, 3.1 Hz, 1H), 5.10-5.03 (m, 1H), 4.73 (t, J=5.7 Hz, 2H), 4.32-4.15 (m, 3H), 3.94 (q, J=6.3 Hz, 1H), 2.36-2.26 (m, 2H), 2.19-2.12 (m, 1H), 1.63-1.56 (m, 1H), 1.44 (d, J=6.3 Hz, 3H), 1.40-1.32 (m, 1H).

Example 205

[2-(2-fluoroethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone

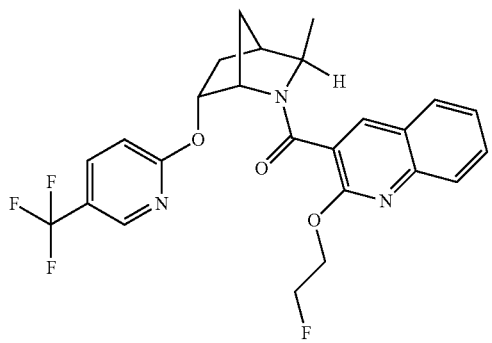 [SMILES: CC1C2CC(Oc3ccc(C(F)(F)F)cn3)C(C2)N1C(=O)c1cc2ccccc2nc1OCCF]

To a solution of example 213 (11.5 mg, 0.024 mmol) dissolved in DCM (2 mL) was added bis(2-methoxyethyl) aminosulfur trifluoride (0.055 mL, 0.54 M in DCM) dropwise. After 16.5 h tetrabutylammonium difluorotriphenylsilicate (13 mg, 0.024 mmol) was added. After an additional 66 h the reaction mixture was diluted with saturated NaHCO$_3$ solution and the aqueous layer was extracted with DCM (×4). The organics were combined, dried with MgSO$_4$, filtered, and concentrated. The residual was dissolved in MeOH, filtered, and purified using Agilent Prep Method X to give the title compound (4.1 mg). MS (ESI): mass calcd. for C$_{25}$H$_{23}$F$_4$N$_3$O$_3$, 489.2; m/z found, 490.2 [M+H]$^+$. $^1$H NMR (400 MHz, Chloroform-d) δ 7.90-7.84 (m, 1H), 7.66 (s, 1H), 7.56-4.76 (m, 2H), 7.45-7.38 (m, 1H), 7.24-7.18 (m, 1H), 7.17-7.10 (m, 1H), 6.77-6.70 (m, 1H), 5.10-5.02 (m, 1H), 4.92-4.84 (m, 1H), 4.79-4.73 (m, 1H), 4.72-4.47 (m, 3H), 4.05-3.96 (m, 1H), 2.37-2.19 (m, 3H), 1.63 (d, J=7.3 Hz, 3H), 1.51-1.41 (m, 4H). Analytical HPLC was obtained on a Phenomenex using a XBridge C18 column (5 μm, 100×4 6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.13 min at 254 nm.

Example 206

(7-(2-fluoroethoxy)quinolin-8-yl)((1S,3R,4R,6R)-3-methyl-6-((5-(trifluoromethyl)pyridin-2-yl)oxy)-2-azabicyclo[2.2.1]heptan-2-yl)methanone

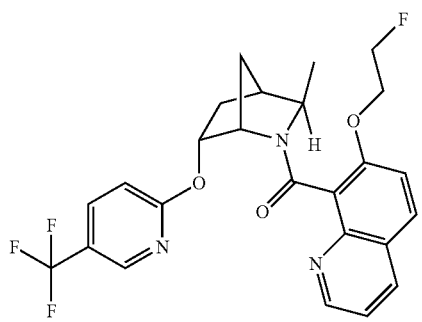 [SMILES: CC1C2CC(Oc3ccc(C(F)(F)F)cn3)C(C2)N1C(=O)c1c(OCCF)ccc2cccnc12]

The title compound was prepared analogous to Example 28 substituting intermediate A-12 with intermediate A-35. MS (ESI): mass calcd. for C$_{25}$H$_{23}$F$_4$N$_3$O$_3$, 489.2. m/z found, 490.2 [M+H]$^+$. Analytical HPLC was obtained on a Phenomenex using a XBridge C18 column (5 nm, 100×4 6 mm), mobile phase of 10-100% ACN in 20 mM NH$_4$OH over 2 min and then hold at 100% ACN for 2 min, at a flow rate of 2.5 mL/min (Temperature=45° C.). R$_t$=2.05 min at 254 nm NOTE: Compound exists as a mixture of rotamers, major rotamer reported.

Example 207

(R/S)-[2-isobutyl-5-[[5-(trifluoromethyl)-2-pyridyl]oxy]-3-azabicyclo[2.2.1]heptan-3-yl]-[2-(triazol-2-yl)phenyl]methanone

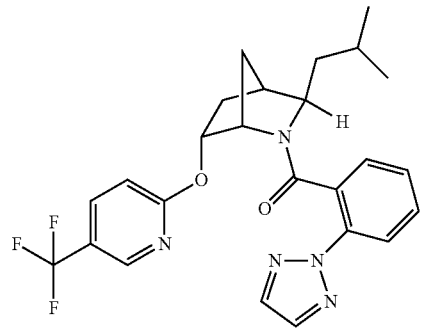 [SMILES: CC(C)CC1C2CC(Oc3ccc(C(F)(F)F)cn3)C(C2)N1C(=O)c1ccccc1-n1nccn1]

The title compound was prepared analogous to Example 12 substituting 3-methylbutanal for acetaldehyde in the preparation of intermediate B-9 and intermediate A-30 with intermediate A-1. MS (ESI): mass calcd. for C$_{25}$H$_{26}$F$_3$N$_5$O$_2$, 485.2. m/z found, 486.0 [M+H]$^+$. MP=163° C.

Example 208

(R/S)-[2-isobutyl-5-[[5-(trifluoromethyl)-2-pyridyl]oxy]-3-azabicyclo[2.2.1]heptan-3-yl]-[5-methyl-3-(triazol-2-yl)-2-pyridyl]methanone

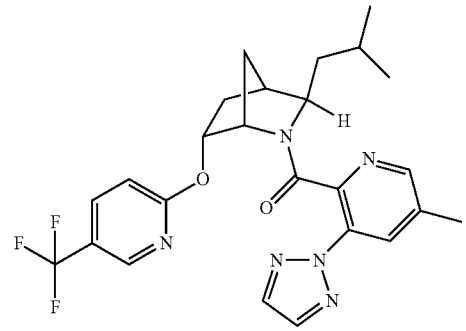 [SMILES: Cc1cnc(C(=O)N2C(CC(C)C)C3CC(Oc4ccc(C(F)(F)F)cn4)C2C3)c(-n2nccn2)c1]

The title compound was prepared analogous to Example 207 substituting intermediate A-1 with intermediate A-29. MS (ESI): mass calcd. for $C_{25}H_{27}F_3N_6O_2$, 500.2. m/z found, 501.0 [M+H]+.

Example 209

(R/S)-[2-isobutyl-5-[[5-(trifluoromethyl)-2-pyridyl]oxy]-3-azabicyclo[2.2.1]heptan-3-yl]-(2-pyrimidin-2-ylphenyl)methanone

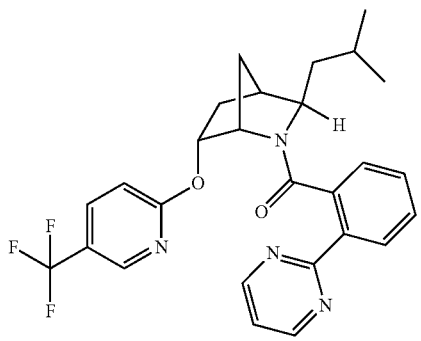 [SMILES: CC(C)CC1C2CC(Oc3ccc(C(F)(F)F)cn3)C(C2)N1C(=O)c1ccccc1-c1ncccn1]

The title compound was prepared analogous to Example 207 substituting intermediate A-1 with intermediate A-24. MS (ESI): mass calcd. for $C_{27}H_{27}F_3N_4O_2$, 496.2. m/z found, 497.0 [M+H]$^+$.

Example 210

(R/S)-[2-isobutyl-5-[[5-(trifluoromethyl)-2-pyridyl]oxy]-3-azabicyclo[2.2.1]heptan-3-yl]-[6-methyl-3-(triazol-2-yl)-2-pyridyl]methanone

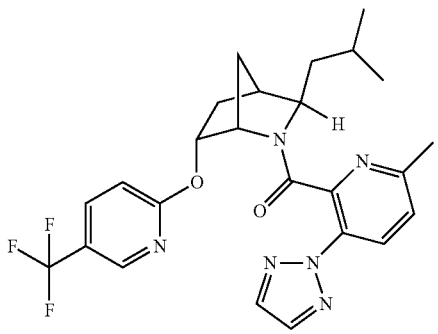 [SMILES: Cc1ccc(-n2nccn2)c(C(=O)N2C(CC(C)C)C3CC(Oc4ccc(C(F)(F)F)cn4)C2C3)n1]

The title compound was prepared analogous to Example 207 substituting intermediate A-1 with intermediate A-26. MS (ESI): mass calcd. for $C_{25}H_{27}F_3N_6O_2$, 500.2. m/z found, 501.0 [M+H]$^+$.

Example 211

(R/S)-(3-fluoro-2-pyrimidin-2-yl-phenyl)-[2-isobutyl-5-[[5-(trifluoromethyl)-2-pyridyl]oxy]-3-azabicyclo[2.2.1]heptan-3-yl]methanone

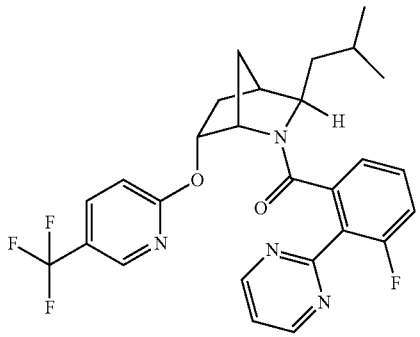 [SMILES: CC(C)CC1C2CC(Oc3ccc(C(F)(F)F)cn3)C(C2)N1C(=O)c1cccc(F)c1-c1ncccn1]

The title compound was prepared analogous to Example 207 substituting intermediate A-1 with intermediate A-2. MS (ESI): mass calcd. for $C_{27}H_{26}F_4N_4O_2$, 514.2. m/z found, 515.0 [M+H]$^+$.

Example 212

(R/S)-[2-(5-fluoropyrimidin-2-yl)phenyl]-[2-isobutyl-5-[[5-(trifluoromethyl)-2-pyridyl]oxy]-3-azabicyclo[2.2.1]heptan-3-yl]methanone

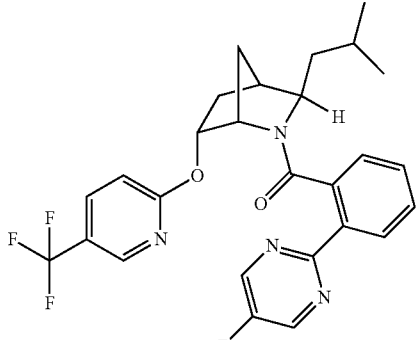

The title compound was prepared analogous to Example 207 substituting intermediate A-1 with intermediate A-20. MS (ESI): mass calcd. for $C_{27}H_{26}F_4N_4O_2$, 514.2. m/z found, 515.0 [M+H]$^+$.

Example 213

(R/S)-[2-ethyl-5-[[5-(trifluoromethyl)-2-pyridyl]oxy]-3-azabicyclo[2.2.1]heptan-3-yl]-[2-(triazol-2-yl)phenyl]methanone

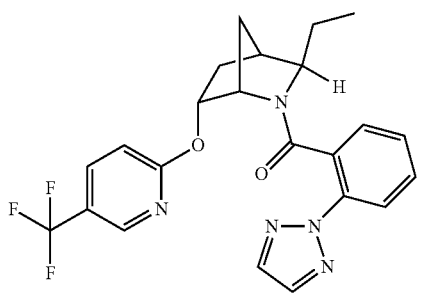 [SMILES: CCC1C2CC(Oc3ccc(C(F)(F)F)cn3)C(C2)N1C(=O)c1ccccc1-n1nccn1]

The title compound was prepared analogous to Example 12 substituting propionaldehyde for acetaldehyde in the preparation of intermediate B-9 and intermediate A-30 with intermediate A-1. MS (ESI): mass calcd. for $C_{23}H_{22}F_3N_5O_2$, 457.2. m/z found, 458.0 [M+H]$^+$.

Example 214

(R/S)-[2-ethyl-5-[[5-(trifluoromethyl)-2-pyridyl]oxy]-3-azabicyclo[2.2.1]heptan-3-yl]-(2-pyrimidin-2-ylphenyl)methanone

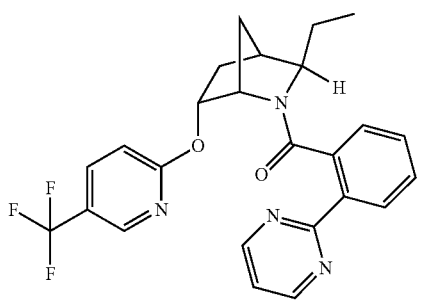 [SMILES: CCC1C2CC(Oc3ccc(C(F)(F)F)cn3)C(C2)N1C(=O)c1ccccc1-c1ncccn1]

The title compound was prepared analogous to Example 213 substituting intermediate A-1 with intermediate A-24. MS (ESI): mass calcd. for $C_{25}H_{23}F_3N_4O_2$, 468.2. m/z found, 469.0 [M+H]$^+$.

Example 215

(R/S)-[2-ethyl-5-[[5-(trifluoromethyl)-2-pyridyl]oxy]-3-azabicyclo[2.2.1]heptan-3-yl]-[6-methyl-3-(triazol-2-yl)-2-pyridyl]methanone

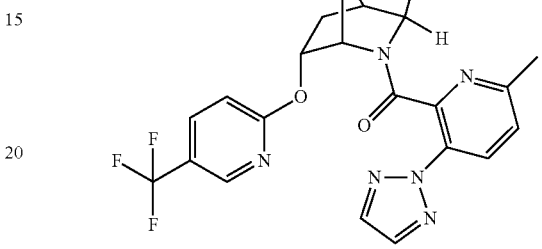

The title compound was prepared analogous to Example 213 substituting intermediate A-1 with intermediate A-26. MS (ESI): mass calcd. for $C_{23}H_{23}F_3N_6O_2$, 472.2. m/z found, 473.0 [M+H]$^+$.

Example 216

(R/S)-[2-ethyl-5-[[5-(trifluoromethyl)-2-pyridyl]oxy]-3-azabicyclo[2.2.1]heptan-3-yl]-[5-methyl-3-(triazol-2-yl)-2-pyridyl]methanone

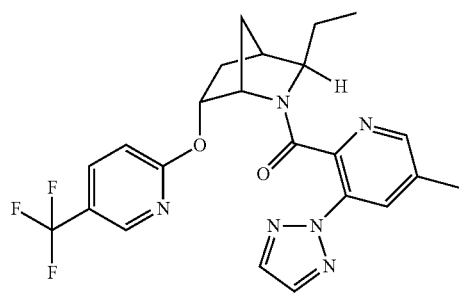 [SMILES: CCC1C2CC(Oc3ccc(C(F)(F)F)cn3)C(C2)N1C(=O)c1ncc(C)cc1-n1nccn1]

The title compound was prepared analogous to Example 213 substituting intermediate A-1 with intermediate A-19. MS (ESI): mass calcd. for $C_{23}H_{23}F_3N_6O_2$, 472.2. m/z found, 473.0 [M+H]$^+$.

Example 217

(R/S)-[2-ethyl-5-[[5-(trifluoromethyl)-2-pyridyl]oxy]-3-azabicyclo[2.2.1]heptan-3-yl]-(3-fluoro-2-pyrimidin-2-yl-phenyl)methanone

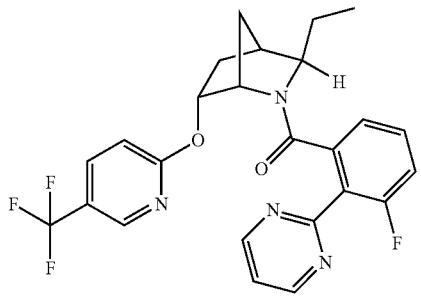 [SMILES: CCC1C2CC(Oc3ccc(C(F)(F)F)cn3)C(C2)N1C(=O)c1cccc(F)c1-c1ncccn1]

The title compound was prepared analogous to Example 213 substituting intermediate A-1 with intermediate A-2. MS (ESI): mass calcd. for $C_{25}H_{22}F_4N_4O_2$, 486.2. m/z found, 487.0 [M+H]$^+$.

Example 218

(R/S)-[2-ethyl-5-[[5-(trifluoromethyl)-2-pyridyl]oxy]-3-azabicyclo[2.2.1]heptan-3-yl]-[2-(5-fluoropyrimidin-2-yl)phenyl]methanone

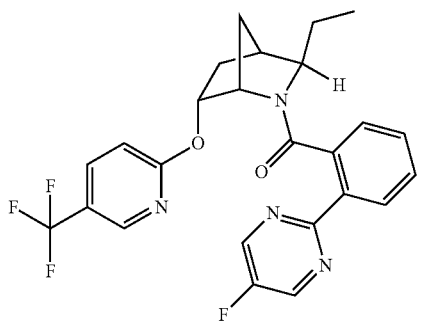 [SMILES: CCC1C2CC(Oc3ccc(C(F)(F)F)cn3)C(C2)N1C(=O)c1ccccc1-c1ncc(F)cn1]

The title compound was prepared analogous to Example 213 substituting intermediate A-1 with intermediate A-20. MS (ESI): mass calcd. for $C_{25}H_{22}F_4N_4O_2$, 486.2. m/z found, 487.0 [M+H]+.

Example 219

(2-(pyrimidin-2-yl)phenyl)((1S,3R,4R,6R)-3-methyl-6-((6-fluoro-5-(trifluoromethyl)pyridin-2-yl)oxy)-2-azabicyclo[2.2.1]heptan-2-yl)methanone

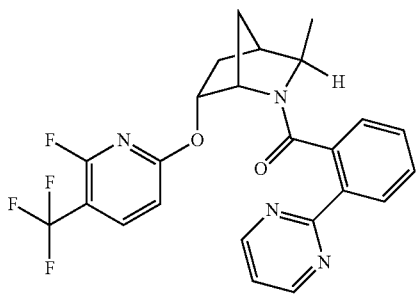 [SMILES: CC1C2CC(Oc3ccc(C(F)(F)F)c(F)n3)C(C2)N1C(=O)c1ccccc1-c1ncccn1]

The title compound was prepared analogous to Example 15, using 2,6-difluoro-3-trifluoromethylpyridine, intermediate B-14A, intermediate C-1,2-iodobenzoic acid. MS (ESI): mass calcd. for $C_{24}H_{20}F_4N_4O_2$, 472.15. m/z found, 473.2 [M+H]$^+$. $^1$H NMR (400 MHz, CD$_3$CN) δ 8.95-8.84 (d, J=4.9 Hz, 2H), 8.05-7.94 (m, 1H), 7.94-7.81 (dd, J=7.8, 1.3 Hz, 1H), 7.45-7.38 (t, J=4.9 Hz, 1H), 7.38-7.26 (td, J=7.6, 1.4 Hz, 1H), 7.09-6.98 (dd, J=7.6, 1.3 Hz, 1H), 6.98-6.86 (td, J=7.5, 1.3 Hz, 1H), 6.86-6.73 (m, 1H), 4.86-4.70 (s, 1H), 3.99-3.84 (s, 1H), 3.84-3.72 (d, J=6.3 Hz, 1H), 2.24-2.08 (m, 2H), 1.40-1.26 (m, 2H), 1.26-1.20 (d, J=6.3 Hz, 3H), 1.01-0.81 (s, 1H).

Examples 220-229, shown below in Table 5, are also contemplated within the scope of embodiments presented herein and may be prepared using the procedures described above.

TABLE 5

| Ex. No. | Compound | Chemical Name |
|---|---|---|
| 220 | | ((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone |

TABLE 5-continued

| Ex. No. | Compound | Chemical Name |
|---|---|---|
| 221 | | ((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone |
| 222 | | (5-fluoro-2-(5-fluoropyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |
| 223 | | (5-fluoro-2-(pyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |
| 224 | | (1S,3R,4R,6R)-6-((6-fluoro-5-(trifluoromethyl)pyridin-2-yl)oxy)-3-methyl-2-azabicyclo[2.2.1]heptan-2-yl)(2-(pyrimidin-2-yl)phenyl)methanone |
| 225 | | (3-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |

TABLE 5-continued

| Ex. No. | Compound | Chemical Name |
|---|---|---|
| 226 | | (3-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |
| 227 | | (4-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |
| 228 | | (5-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone |
| 229 | | (3-(2-fluoroethoxy)isoquinolin-4-yl)((1S,3R,4R,6R)-3-methyl-6-((5-(trifluoromethyl)pyridin-2-yl)oxy)-2-azabicyclo[2.2.1]heptan-2-yl)methanone |

Assays:

The in vitro affinity of the compounds of the invention for the rat/human orexin 1 and human orexin 2 receptors was determined by competitive radioligand binding using [$^3$H] (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Langmead et al., 2004) and [$^3$H]EMPA (n-ethyl-2[96-methoxy-pyridin-3-yl)-(toluene-2-sulfonyl)-amino]-N-pyridin-3-ylmethyl acetamide), respectively (Langmead et al., 2004, British Journal of Pharmacology 141:340-346; Malherbe et al., 2004, British Journal of Pharmacology 156:1326-41).

The in vitro functional antagonism of the compounds on the human orexin 1 and orexin 2 receptors was determined using fluorometric imaging plate reader (FLIPR) based calcium assays.

Data are analyzed using pc-Sandy macro and graphed on Graphpad Prism 5. For analysis, each concentration point is averaged from triplicate values and the averaged values are plotted on Graphpad Prism. The IC50 was determined by applying the following equation (GraphPad Prism 5.0, San Diego) for one site competition where X=log (concentration) and Y=specific binding. Top denotes the total [$^3$H]—(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)- methanone) binding, bottom denotes the nonspecific [$^3$H]—(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) binding. Graphpad Prism calculates Ki value from IC$_{50}$ and the pre-determined Kd values for [$^3$H]—(1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) and [$^3$H]-EMPA. The Ki for each compound is then uploaded into 3DX. Each run comprises individual compounds in triplicate. The data in Table 1 and Table 2 represent averages from between 2-20 runs Rat and Human Orexin 1 Receptor Radioligand Binding Studies Human Embryonic Kidney 293 cells (HEK293) stably expressing rat orexin 1 receptor (Genebank accession number NM_001525) or Chinese ovary cells (CHO) stably expressing human orexin 1 receptor (Genebank accession number NM_001526) were grown to confluency in DMEM (Hyclone, cat # SH30022), 10% FBS, 1× Pen/Strep, 1× sodium pyruvate, 10 mM HEPES, 600 μg/mL G418 and DMEM/F12 (Gibco, Cat #11039), 10% FBS, 1× Pen/Strep, 600 μg/mL G418 media, respectively on 150 cm$^2$ tissue culture plates, washed with 5 mM EDTA in PBS (HyClone Dulbecco's Phosphate Buffered Saline 1× with Calcium and Magnesium, Cat # SH30264.01, hereafter referred to simply as PBS) and scraped into 50 ml tubes. After centrifugation (2K×G, 5 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [$^3$H]— (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Moraveck Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [$^3$H]— (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

IC$_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d$=4 nM for rat orexin 1 receptor and 6 nM for human orexin 1 receptor.

Human Orexin 2 Receptor Radioligand Binding Studies

HEK293 stably expressing human orexin 2 receptor (Genebank accession number NM_001526) were grown to confluency in DMEM (Hyclone, cat # SH30022), 10% FBS, 1× Pen/Strep, 1× NaPyruvate, 10 mM HEPES, 600 μg/ml G418 media on 150 cm$^2$ tissue culture plates, washed with 5 mM EDTA in PBS (HyClone Dulbecco's Phosphate Buffered Saline 1× with Calcium and Magnesium, Cat # SH30264.01, hereafter referred to simply as PBS) and scraped into 50 ml tubes. After centrifugation (2K×G, 5 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and homogenized for 45 sec just prior to addition to the reactions. Competition binding experiments in 96 well polypropylene plates were performed using [$^3$H]-EMPA (Moraveck Corporation, specific activity=29.6 Ci/mmol), diluted to a 5 nM concentration in PBS (2 nM final concentration). Compounds were solubilized in 100% DMSO (Acros Organics, Cat. #61042-1000) and tested over a range of 7 concentration (from 0.1 nM to 10 μM). The final concentration of DMSO in the reactions is equal to or less than 0.1%. Total and nonspecific binding was determined in the absence and presence of 10 μM almorexant. The total volume of each reaction is 200 μL (20 μL of diluted compounds, 80 μL of [$^3$H]-EMPA diluted in PBS and 100 μL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

IC$_{50}$ values (i.e. concentration of unlabelled compound required to compete for 50% of specific binding to the radioligand) was calculated using the GraphPad Prism software (GraphPad Prism Software Inc., San Diego, Calif.) with a fit to a sigmoidal dose-response curve. Apparent Ki values were calculated as $K_i=IC_{50}/(1+C/K_d)$, where C is concentration of radioligand and $K_d$=2 nM.

Human Orexin 1 Receptor Ca$^{2+}$ Mobilization Assay

CHO cells stably transfected with the human orexin 1 receptor (Genebank accession number NM_001526) were grown to confluency in DMEM/F12, 10% FBS, 1× pen-strep, 400 μg/ml G418. Cells were seeded on to 384-well Packard viewplates at a density of 10,000 cells/well and incubated overnight at 37° C., 5% CO2. The cells were dye-loaded with BD Calcium Assay kit (BD, cat #640178) in HBSS (Gibco, cat#14025-092) with 2.5 mM probenecid and incubated at 37° C., 5% CO$_2$ for 45 min. Cells were pre-incubated with compounds (diluted in DMEM/F-12) for 15-30 minutes before agonist (orexin A, 10 nM) stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent $pK_B$ values using a modified Cheng-Prusoff correction. Apparent $pK_B = -\log IC_{50}/1+[\text{conc agonist}/EC_{50}]$.

Human Orexin 2 Receptor $Ca^{2+}$ Mobilization Assay

PFSK-1 cells endogenously expressing the human orexin 2 receptor were grown to confluency in RPMI1640 (Hyclone, cat#30027.02), 10% FBS, 1× pen-strep. Cells were seeded on to 384-well Packard viewplates at a density of 5,000 cells/well and incubated overnight at 37° C., 5% CO2. The cells were dye-loaded with BD Calcium Assay kit (BD, cat #640178) in HBSS (Gibco, cat#14025-092) with 2.5 mM probenecid and incubated at 37° C., 5% $CO_2$ for 45 min. Cells were pre-incubated with compounds (diluted in DMEM/F-12) for 15-30 minutes before agonist (orexin B, 100 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent $pK_B$ values using a modified Cheng-Prusoff correction. Apparent $pK_B = -\log IC_{50}/1+[\text{conc agonist}/EC_{50}]$.

Preferred compounds of the invention are set forth in the table below. Orexin receptor activity of certain compounds of the Formula I is set forth in Table 6 below.

TABLE 6

| Ex. No. | rOX1 $K_i$ (nM) | hOX1 $K_i$ (nM) | hOX2 $K_i$ (nM) |
|---|---|---|---|
| 1 | 24 | 84 | 5200 |
| 2 | 17 | 22 | 668 |
| 2A | 7101 | NT | >10000 |
| 2B | 27 | 54 | 975 |
| 3 | 21 | 20 | 649 |
| 3A | 11 | 14 | 426 |
| 3B | 351 | NT | >10000 |
| 4 | 56 | 59 | 637 |
| 5 | 20 | 11 | 278 |
| 5A | 5100 | NT | >10000 |
| 5B | 11 | 12 | 146 |
| 6 | 90 | 83 | 664 |
| 6A | 6299 | NT | >10000 |
| 6B | 22 | 36 | 154 |
| 7 | 125 | 144 | 1200 |
| 8 | 11 | 16 | 1100 |
| 9 | 15 | 15 | 3700 |
| 10 | 14 | 23 | >10000 |
| 11 | 14 | 15 | 2100 |
| 12 | 8 | 8 | 1100 |
| 13 | 62 | 64 | 1600 |
| 14 | 11 | 13 | 3700 |
| 15 | 12 | 11 | 1200 |
| 16 | 20 | 38 | 1200 |
| 16A | 1736 | NT | >10000 |
| 16B | 7 | 6 | 635 |
| 17 | 11 | 11 | 1100 |
| 17A | 339 | NT | >10000 |
| 17B | 4 | 4 | 947 |
| 18 | 7 | 8 | 1600 |
| 18A | 142 | 167 | >10000 |
| 18B | 3 | 5 | 879 |
| 19 | 10 | 29 | 2200 |
| 19A | 746 | NT | >10000 |
| 19B | 5 | 6 | 1960 |
| 20 | 12 | 15 | 3100 |
| 20A | 115 | 136 | >10000 |

TABLE 6-continued

| Ex. No. | rOX1 $K_i$ (nM) | hOX1 $K_i$ (nM) | hOX2 $K_i$ (nM) |
|---|---|---|---|
| 20B | 4 | 6 | 1893 |
| 21 | 4 | 4 | 619 |
| 21A | 182 | 259 | >10000 |
| 21B | 4 | 3 | 518 |
| 22 | 9 | 5 | 861 |
| 22A | 1240 | NT | >10000 |
| 22B | 5 | 6 | 567 |
| 23 | 14 | 14 | 2398 |
| 24 | 6 | 15 | 1500 |
| 25 | 7 | 9 | 8100 |
| 26 | 6 | 6 | 4300 |
| 27 | 5 | 8 | 595 |
| 28 | 6 | 5 | 1300 |
| 29 | 5 | 14 | 836 |
| 30 | 4 | 6 | 689 |
| 31 | 6 | 6 | 2300 |
| 32 | 6 | 8 | 1900 |
| 33 | 4 | 3 | 602 |
| 34 | 11 | 14 | 6299 |
| 35 | 4 | 7 | 4100 |
| 36 | 845 | NT | >10000 |
| 37 | 3716 | NT | >10000 |
| 38 | 216 | 283 | 4900 |
| 39 | 90 | 123 | 3600 |
| 40 | 544 | NT | >10000 |
| 41 | 300 | NT | >10000 |
| 42 | 55 | 45 | >10000 |
| 43 | 22 | 13 | 5700 |
| 44 | 71 | 55 | 7700 |
| 45 | 15 | 18 | 6899 |
| 46 | 24 | 29 | 4298 |
| 47 | 68 | 151 | >10000 |
| 48 | 29 | 55 | >10000 |
| 49 | 26 | 25 | >10000 |
| 50 | 23 | 30 | >10000 |
| 51 | 15 | 24 | 2136 |
| 52 | 18 | 14 | 2550 |
| 53 | 22 | 31 | 7600 |
| 54 | 26 | 18 | 3400 |
| 55 | 24 | 20 | 3200 |
| 56 | 145 | 314 | 7000 |
| 57 | 15 | 10 | >10000 |
| 58 | 11 | 14 | 236 |
| 59 | 20 | 53 | 4100 |
| 60 | 16 | 19 | 349 |
| 61 | 11 | 23 | 585 |
| 62 | 5 | 4 | 360 |
| 63 | 3 | 4 | 78 |
| 64 | 4 | 4 | 324 |
| 65 | 3 | 3 | 183 |
| 66 | 7 | 5 | 317 |
| 67 | 16 | 21 | 567 |
| 68 | 11 | 6 | 625 |
| 68A | 233 | 308 | >10000 |
| 68B | 4 | 5 | 259 |
| 69 | 19 | 11 | 345 |
| 69A | >10000 | NT | >10000 |
| 69B | 7 | 5 | 236 |
| 70 | 21 | 30 | 2000 |
| 71 | 32 | 29 | 1500 |
| 72 | 22 | 22 | >10000 |
| 73 | 17 | 21 | 2000 |
| 74 | 48 | 35 | 3764 |
| 75 | 92 | 66 | >10000 |
| 76 | 36 | 46 | >10000 |
| 77 | 13 | 20 | 4779 |
| 78 | 122 | 102 | >10000 |
| 79 | 49 | 46 | >10000 |
| 80 | 43 | 35 | 4170 |
| 110 | 7 | 5 | 146 |
| 121 | 3 | 3 | 423 |
| 122 | 3 | 3 | 452 |
| 148 | 12 | 14 | 2400 |
| 156 | 6 | 10 | 1100 |
| 157 | 29 | 129 | 5999 |
| 158 | 35 | 138 | 2700 |
| 159 | 14 | 41 | 2800 |

TABLE 6-continued

| Ex. No. | rOX1 $K_i$ (nM) | hOX1 $K_i$ (nM) | hOX2 $K_i$ (nM) |
|---|---|---|---|
| 160 | 8 | 11 | 872 |
| 161 | 4 | 8 | 5000 |
| 162 | 236 | 106 | >10000 |
| 163 | 2 | NT | 398 |
| 164 | 5 | NT | 565 |
| 165 | 8 | NT | 841 |
| 166 | 4 | NT | 1100 |
| 167 | 4.8 | NT | 767 |
| 168 | 14 | 20 | 1385 |
| 169 | 52 | NT | 3935 |
| 170 | 9 | NT | 1600 |
| 171 | 23 | 17 | 1600 |
| 172 | 66 | 67 | >10000 |
| 173 | 3 | 5 | 343 |
| 174 | 8 | 9 | 3935 |
| 175 | 13 | 15 | 837 |
| 176 | 33 | 35 | 8100 |
| 177 | 1150 | NT | >10000 |
| 178 | 1100 | NT | >10000 |
| 179 | 15 | NT | 2100 |
| 180 | 32 | NT | 1700 |
| 181 | 87 | NT | >10000 |
| 182 | 11 | NT | 95 |
| 183 | 5 | 5 | 195 |
| 184 | 4 | 2 | 208 |
| 185 | 2 | 3 | 61 |
| 186 | 18 | 12 | 125 |
| 187 | 7 | 6 | 136 |
| 188 | 6 | 7 | 107 |
| 189 | 41 | 42 | 109 |
| 190 | 10 | 8 | 123 |
| 191 | 10 | 10 | 72 |
| 192 | 53 | NT | 795 |
| 193 | 8 | 8 | 4700 |
| 194 | 5 | 5 | 2900 |
| 195 | 8 | 4 | 523 |
| 196 | 4 | 2 | 208 |
| 197 | 4 | 3 | 481 |
| 198 | 5 | 5 | 538 |
| 199 | 5 | 5 | 556 |
| 200 | 7 | 7 | 1200 |
| 201 | 4 | 4 | 691 |
| 202 | 196 | NT | >10000 |
| 203 | 60 | NT | >10000 |
| 204 | 71 | NT | 236 |
| 205 | 22 | NT | 5400 |
| 206 | 7.4 | NT | 286 |
| 207 | 51 | 45 | 3900 |
| 208 | 177 | 170 | 418 |
| 209 | 44 | 24 | 3000 |
| 210 | 76 | 73 | 1500 |
| 211 | 38 | 30 | 3300 |
| 212 | 100 | 55 | 3800 |
| 213 | 4 | 2 | 208 |
| 214 | 7 | 10 | 316 |
| 215 | 7 | 9 | 517 |
| 216 | 11 | 11 | 1500 |
| 217 | 13 | 9 | 243 |
| 218 | 9 | 9 | 526 |
| 219 | 4 | NT | 1014 |

*NT means not tested

All patents, patent applications, publications and presentations referred to herein are incorporated by reference in their entirety. Any conflict between any reference cited herein and the teaching of this specification is to be resolved in favor of the latter.

While the foregoing specification teaches the principles of the present invention, and specific embodiments of the invention have been described for the purposes of illustration, and examples have been provided for the purposes of illustration, it will be understood that various modifications may be made without deviating from the spirit and scope of the invention as come within the scope of the following claims and their equivalents.

What is claimed:

1. A compound of Formula I:

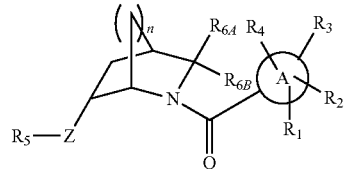

or an enantiomer or diastereomer thereof;
or a pharmaceutically acceptable salt thereof;
wherein
ring A is phenyl or a heteroaryl ring selected from pyridyl, thiazolyl, or isoquinolinyl;
wherein when ring A is thiazolyl, ring A is optionally substituted with up to 3 substituents selected from $R_1$, $R_2$, $R_3$ or $R_4$, and wherein when ring A is phenyl, pyridyl, or isoquinolinyl, ring A is optionally substituted with up to 4 substituents selected from $R_1$, $R_2$, $R_3$ or $R_4$;
$R_1$ is H, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo or alkyl;
$R_2$ is H, alkyl, alkoxy, or halo;
Z is NH, N—$CH_3$, N—$CH_2CH_3$, N—$CH_2$-cyclopropyl, N—C(=O)$CH_3$, N—$CH_2CH_2OCH_3$ or O;
$R_3$ is H, alkyl, alkoxy, halo, triazolyl, thiazolyl, pyridazinyl, pyrimidinyl, pyrazinyl, oxazolyl, isoxazolyl, oxadiazolyl, pyridyl, phenyl, or pyrazolyl, wherein triazolyl, thiazolyl, pyridazinyl, pyrimidinyl, pyrazinyl, oxazolyl, isoxazolyl, oxadiazolyl, pyridyl, phenyl or pyrazolyl is optionally substituted with up to two substituents selected from halo, alkyl, $NO_2$, or hydroxy-alkoxy;
$R_4$ is H or alkyl;
or $R_3$ and $R_4$, together with the atoms to which they are attached, form a 6-membered aryl ring or a 5- or 6-membered heteroaryl ring;
$R_5$ is pyridyl, pyrazinyl, benzoxazolyl, pyridazinyl, naphthyridinyl, pyrimidinyl, quinoxalinyl, quinolinyl, or phenyl, wherein the pyridyl, pyrazinyl, benzoxazolyl, pyridazinyl, naphthyridinyl pyrimidinyl, quinoxalinyl, quinolinyl, or phenyl is optionally substituted with up to two substituents selected from halo, alkoxy, hydroxymethyl or alkyl;
$R_{6A}$ and $R_{6B}$ are independently selected from H, alkyl, hydroxyalkyl, -alkyl-alkoxy, alkyl-alkoxy-alkoxy, or —$CO_2$-alkyl;
wherein one or both of $R_{6A}$ and $R_{6B}$ is other than H; and
n is 1 or 2.

2. The compound of claim 1, wherein one of $R_{6A}$ or $R_{6B}$ is H and the other is alkyl, $CH_2$-halo, $CH_2$—OH, or $CH_2$-alkoxy.

3. The compound of claim 1, wherein one of $R_{6A}$ or $R_{6B}$ is H and the other is methyl, ethyl, $CH_2$—F, $CH_2$—OH, or $CH_2$—$OCH_3$.

4. The compound of claim 1, wherein one of $R_{6A}$ or $R_{6B}$ is H and the other is $CH_3$, $CH_2$—$CH_3$, $CH_2$—$CH(CH_3)_2$, $CH_2$—F, $CH_2$—OH, $CH_2$—$OCH_3$, and $CH_2$—$OCH_2$—$OCH_3$.

5. The compound of claim 1, wherein one of $R_{6A}$ or $R_{6B}$ is H and the other is $CH_3$, $CH_2$—F, $CH_2$—OH, and $CH_2$—$OCH_3$.

6. A compound selected from the group consisting of
(R/S)-(3-fluoro-2-(pyrimidin-2-yl)phenyl)(–3-methyl-6-((5-(trifluoromethyl)pyridin-2-yl)oxy)-2-azabicyclo[2.2.1]heptan-2-yl)methanone;
(R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone;
(2-(2H-1,2,3-triazol-2-yl)phenyl)((1R*,3R*,4S*,6S*)-3-methyl-6-((5-(trifluoromethyl)pyridin-2-yl)oxy)-2-azabicyclo[2.2.1]heptan-2-yl)methanone;
(2-(2H-1,2,3-triazol-2-yl)phenyl)((1S*,3S*,4R*,6R*)-3-methyl-6-((5-(trifluoromethyl)pyridin-2-yl)oxy)-2-azabicyclo[2.2.1]heptan-2-yl)methanone;
(R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone;
(6-methyl-3-(2H-1,2,3-triazol-2-yl)pyridin-2-yl)((1R*,3R*,4S*,6S*)-3-methyl-6-((5-(trifluoromethyl)pyridin-2-yl)oxy)-2-azabicyclo[2.2.1]heptan-2-yl)methanone;
(6-methyl-3-(2H-1,2,3-triazol-2-yl)pyridin-2-yl)((1S*,3S*,4R*,6R*)-3-methyl-6-((5-(trifluoromethyl)pyridin-2-yl)oxy)-2-azabicyclo[2.2.1]heptan-2-yl)methanone;
(R/S)-(3-fluoro-2-(pyrimidin-2-yl)phenyl)(3-methyl-6-((5-(trifluoromethyl)pyrazin-2-yl)amino)-2-azabicyclo[2.2.1]heptan-2-yl)methanone;
(R/S)-(2-(2H-1,2,3-triazol-2-yl)phenyl)(3-methyl-6-((5-(trifluoromethyl)pyrazin-2-yl)amino)-2-azabicyclo[2.2.1]heptan-2-yl)methanone;
(2-(2H-1,2,3-triazol-2-yl)phenyl)((1R*,3R*,4R*,6S*)-3-methyl-6-((5-(trifluoromethyl)pyrazin-2-yl)amino)-2-azabicyclo[2.2.1]heptan-2-yl)methanone;
(2-(2H-1,2,3-triazol-2-yl)phenyl)((1S*,3S*,4S*,6R*)-3-methyl-6-((5-(trifluoromethyl)pyrazin-2-yl)amino)-2-azabicyclo[2.2.1]heptan-2-yl)methanone;
(R/S)-(6-methyl-3-(2H-1,2,3-triazol-2-yl)pyridin-2-yl)(3-methyl-6-((5-(trifluoromethyl)pyrazin-2-yl)amino)-2-azabicyclo[2.2.1]heptan-2-yl)methanone;
(6-methyl-3-(2H-1,2,3-triazol-2-yl)pyridin-2-yl)((1R*,3R*,4R*,6S*)-3-methyl-6-((5-(trifluoromethyl)pyrazin-2-yl)amino)-2-azabicyclo[2.2.1]heptan-2-yl)methanone;
(6-methyl-3-(2H-1,2,3-triazol-2-yl)pyridin-2-yl)((1S*,3S*,4S*,6R*)-3-methyl-6-((5-(trifluoromethyl)pyrazin-2-yl)amino)-2-azabicyclo[2.2.1]heptan-2-yl)methanone;
(R/S)-(3-bromo-6-methylpyridin-2-yl)(3-methyl-6-((5-(trifluoromethyl)pyrazin-2-yl)amino)-2-azabicyclo[2.2.1]heptan-2-yl)methanone;
(R/S)-(3-fluoro-2-(pyrimidin-2-yl)phenyl)(3-methyl-6-((5-(trifluoromethyl)pyridin-2-yl)oxy)-2-azabicyclo[2.2.1]heptan-2-yl)methanone;
(R/S)-(3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone;
(R/S)-(6-methyl-2-(2H-1,2,3-triazol-2-yl)pyridin-3-yl)(3-methyl-6-((5-(trifluoromethyl)pyridin-2-yl)oxy)-2-azabicyclo[2.2.1]heptan-2-yl)methanone;
(R/S)-(5-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone;
(R/S)-(3-fluoro-2-(oxazol-2-yl)phenyl)(3-methyl-6-((5-(trifluoromethyl)pyridin-2-yl)oxy)-2-azabicyclo[2.2.1]heptan-2-yl)methanone;
(R/S)-(3-ethoxy-6-methylpyridin-2-yl)(3-methyl-6-((5-(trifluoromethyl)pyridin-2-yl)oxy)-2-azabicyclo[2.2.1]heptan-2-yl)methanone;
(R/S)-3-methyl-6-((5-(trifluoromethyl)pyridin-2-yl)oxy)-2-azabicyclo[2.2.1]heptan-2-yl)(3-(pyrimidin-2-yl)pyridin-2-yl)methanone;
(R/S)-(3-methyl-6-((5-(trifluoromethyl)pyridin-2-yl)oxy)-2-azabicyclo[2.2.1]heptan-2-yl)(2-(pyrimidin-2-yl)phenyl)methanone;
(R/S)-(6-methyl-3-(pyrimidin-2-yl)pyridin-2-yl)(3-methyl-6-((5-(trifluoromethyl)pyridin-2-yl)oxy)-2-azabicyclo[2.2.1]heptan-2-yl)methanone;
(6-methyl-3-(pyrimidin-2-yl)pyridin-2-yl)((1R*,3S*,4S*,6 S*)-3-methyl-6-((5-(trifluoromethyl)pyridin-2-yl)oxy)-2-azabicyclo[2.2.1]heptan-2-yl)methanone;
(6-methyl-3-(pyrimidin-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone;
(R/S)-(4-fluoro-2-(pyrimidin-2-yl)phenyl)(–3-methyl-6-((5-(trifluoromethyl)pyridin-2-yl)oxy)-2-azabicyclo[2.2.1]heptan-2-yl)methanone;
(4-fluoro-2-(pyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone;
(4-fluoro-2-(pyrimidin-2-yl)phenyl)((1S*,3S*,4R*,6R*)-3-methyl-6-((5-(trifluoromethyl)pyridin-2-yl)oxy)-2-azabicyclo[2.2.1]heptan-2-yl)methanone;
(R/S)-(5-fluoro-2-(pyrimidin-2-yl)phenyl)(–3-methyl-6-((5-(trifluoromethyl)pyridin-2-yl)oxy)-2-azabicyclo[2.2.1]heptan-2-yl)methanone;
(5-fluoro-2-(pyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone;
(5-fluoro-2-(pyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(R/S)-(2-(5-fluoropyrimidin-2-yl)phenyl)(3-methyl-6-((5-(trifluoromethyl)pyridin-2-yl)oxy)-2-azabicyclo[2.2.1]heptan-2-yl)methanone;
(2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone;
(2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(R/S)-(3-fluoro-2-(5-fluoropyrimidin-2-yl)phenyl)(3-methyl-6-((5-(trifluoromethyl)pyridin-2-yl)oxy)-2-azabicyclo[2.2.1]heptan-2-yl)methanone;
(3-fluoro-2-(5-fluoropyrimidin-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone;
(3-fluoro-2-(5-fluoropyrimidin-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(R/S)-(2-(2H-1,2,3-triazol-2-yl)phenyl)(3-methyl-6-((5-(trifluoromethyl)pyridin-2-yl)oxy)-2-azabicyclo[2.2.1]heptan-2-yl)methanone;
(2-(2H-1,2,3-triazol-2-yl)phenyl)((1R*,3S*,4S*,6S*)-3-methyl-6-((5-(trifluoromethyl)pyridin-2-yl)oxy)-2-azabicyclo[2.2.1]heptan-2-yl)methanone;
(2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;

(R/S)-(6-methyl-3-(2H-1,2,3-triazol-2-yl)pyridin-2-yl)(3-methyl-6-((5-(trifluoromethyl)pyridin-2-yl)oxy)-2-azabicyclo[2.2.1]heptan-2-yl)methanone;
(6-methyl-3-(2H-1,2,3-triazol-2-yl)pyridin-2-yl)((1R*,3S*,4S*,6S*)-3-methyl-6-((5-(trifluoromethyl)pyridin-2-yl)oxy)-2-azabicyclo[2.2.1]heptan-2-yl)methanone;
(6-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone;
(3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone;
(5-methyl-3-(2H-1,2,3-triazol-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone;
(6-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone;
(5-methyl-2-(2H-1,2,3-triazol-2-yl)pyridin-3-yl)((1S*,3R*,4R*,6R*)-3-methyl-6-((5-(trifluoromethyl)pyridin-2-yl)oxy)-2-azabicyclo[2.2.1]heptan-2-yl)methanone;
(3-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(4-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(5-fluoro-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(2-fluoro-6-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
(4-methoxy-2-(2H-1,2,3-triazol-2-yl)phenyl)((1S*,3R*,4R*,6R*)-3-methyl-6-((5-(trifluoromethyl)pyridin-2-yl)oxy)-2-azabicyclo[2.2.1]heptan-2-yl)methanone;
((1S*,3R*,4R*,6R*)-3-methyl-6-((5-(trifluoromethyl)pyridin-2-yl)oxy)-2-azabicyclo[2.2.1]heptan-2-yl)(3-(pyrimidin-2-yl)pyridin-2-yl)methanone;
((1S*,3R*,4R*,6R*)-3-methyl-6-((5-(trifluoromethyl)pyridin-2-yl)oxy)-2-azabicyclo[2.2.1]heptan-2-yl)(2-(pyrimidin-2-yl)phenyl)methanone;
(3-fluoro-5'-methyl-[2,3'-bipyridin]-2'-yl)((1S*,3R*,4R*,6R*)-3-methyl-6-((5-(trifluoromethyl)pyridin-2-yl)oxy)-2-azabicyclo[2.2.1]heptan-2-yl)methanone;
(5-methyl-3-(pyrimidin-2-yl)pyridin-2-yl)((1S*,3R*,4R*,6R*)-3-methyl-6-((5-(trifluoromethyl)pyridin-2-yl)oxy)-2-azabicyclo[2.2.1]heptan-2-yl)methanone;
(4'-fluoro-[1,1'-biphenyl]-3-yl)((1S,3R,4R,6R)-3-methyl-6-((5-(trifluoromethyl)pyridin-2-yl)oxy)-2-azabicyclo[2.2.1]heptan-2-yl)methanone;
(3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone;
(3-fluoro-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone;
(3-methyl-2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone;
(6-methyl-3-(2H-1,2,3-triazol-2-yl)pyridin-2-yl)((1S*,3R*,4R*,6R*)-3-methyl-6-((6-(trifluoromethyl)pyridin-3-yl)oxy)-2-azabicyclo[2.2.1]heptan-2-yl)methanone;
(2-(2H-1,2,3-triazol-2-yl)phenyl)((1S*,3R*,4R*,6R*)-3-methyl-6-((6-(trifluoromethyl)pyridin-3-yl)oxy)-2-azabicyclo[2.2.1]heptan-2-yl)methanone;
(R/S)-(6-methyl-3-(2H-1,2,3-triazol-2-yl)pyridin-2-yl)(3-methyl-6-((5-(trifluoromethyl)pyrazin-2-yl)oxy)-2-azabicyclo[2.2.1]heptan-2-yl)methanone;
(R/S)-(2-(2H-1,2,3-triazol-2-yl)phenyl)(3-methyl-6-((5-(trifluoromethyl)pyrazin-2-yl)oxy)-2-azabicyclo[2.2.1]heptan-2-yl)methanone;
(R/S)-(6-methyl-3-(pyrimidin-2-yl)pyridin-2-yl)(3-methyl-6-((5-(trifluoromethyl)pyrazin-2-yl)oxy)-2-azabicyclo[2.2.1]heptan-2-yl)methanone;
(R/S)-3-methyl-6-((5-(trifluoromethyl)pyrazin-2-yl)oxy)-2-azabicyclo[2.2.1]heptan-2-yl)(2-(pyrimidin-2-yl)phenyl)methanone;
(6-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone;
(3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone;
(5-methyl-3-(2H-1,2,3-triazol-2-yl)pyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone;
(6-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone;
(5-methyl-2-(2H-1,2,3-triazol-2-yl)pyridin-3-yl)((1S*,3R*,4R*,6R*)-3-methyl-6-((5-(trifluoromethyl)pyrazin-2-yl)oxy)-2-azabicyclo[2.2.1]heptan-2-yl)methanone;
(2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
(3-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
(4-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
5-fluoro-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
(2-fluoro-6-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
(3-ethoxy-6-methylpyridin-2-yl)((1S*,3R*,4R*,6R*)-3-methyl-6-((5-(trifluoromethyl)pyrazin-2-yl)oxy)-2-azabicyclo[2.2.1]heptan-2-yl)methanone;
4-methoxy-2-(2H-1,2,3-triazol-2-yl)phenyl)((1S*,3R*,4R*,6R*)-3-methyl-6-((5-(trifluoromethyl)pyrazin-2-yl)oxy)-2-azabicyclo[2.2.1]heptan-2-yl)methanone;
(R/S)-(6-methyl-3-(2H-1,2,3-triazol-2-yl)pyridin-2-yl)(3-methyl-6-((5-(trifluoromethyl)pyridin-2-yl)amino)-2-azabicyclo[2.2.1]heptan-2-yl)methanone;
(R/S)-(5-methyl-3-(pyrimidin-2-yl)pyridin-2-yl)(3-methyl-6-((5-(trifluoromethyl)pyridin-2-yl)amino)-2-azabicyclo[2.2.1]heptan-2-yl)methanone;

(6-methyl-3-(pyrimidin-2-yl)pyridin-2-yl)((1S,3R,4
S,6R)-3-methyl-6-((5-(trifluoromethyl)pyridin-2-yl)
amino)-2-azabicyclo[2.2.1]heptan-2-yl)methanone;
(R/S)-(5-methyl-3-(2H-1,2,3-triazol-2-yl)pyridin-2-yl)(3-
methyl-6-((5-(trifluoromethyl)pyridin-2-yl)amino)-2-
azabicyclo[2.2.1]heptan-2-yl)methanone;
((1S*,3R*,4S*,6R*)-3-methyl-6-((5-(trifluoromethyl)
pyridin-2-yl)amino)-2-azabicyclo[2.2.1]heptan-2-yl)
(3-(pyrimidin-2-yl)pyridin-2-yl)methanone;
(6-methyl-3-(2H-1,2,3-triazol-2-yl)pyridin-2-yl)((1S*,
3R*,4S*,6R*)-3-methyl-6-((5-(trifluoromethyl)pyri-
din-2-yl)amino)-2-azabicyclo[2.2.1]heptan-2-yl)
methanone;
(3-(2H-1,2,3-triazol-2-yl)pyridin-2-yl)((1S*,3R*,4S*,
6R*)-3-methyl-6-((5-(trifluoromethyl)pyridin-2-yl)
amino)-2-azabicyclo[2.2.1]heptan-2-yl)methanone;
(3-fluoro-2-(2H-1,2,3-triazol-2-yl)phenyl)((1S*,3R*,
4S*,6R*)-3-methyl-6-((5-(trifluoromethyl)pyridin-2-
yl)amino)-2-azabicyclo[2.2.1]heptan-2-yl)methanone;
(5-methyl-3-(2H-1,2,3-triazol-2-yl)pyridin-2-yl)((1S*,
3R*,4S*,6R*)-3-methyl-6-((5-(trifluoromethyl)pyri-
din-2-yl)amino)-2-azabicyclo[2.2.1]heptan-2-yl)
methanone;
(R/S)-(3-fluoro-2-(pyrimidin-2-yl)phenyl)(3-methyl-6-
((5-(trifluoromethyl)pyrazin-2-yl)amino)-2-azabicyclo
[2.2.1]heptan-2-yl)methanone;
(R/S)-(2-(2H-1,2,3-triazol-2-yl)phenyl)(3-methyl-6-((5-
(trifluoromethyl)pyrazin-2-yl)amino)-2-azabicyclo
[2.2.1]heptan-2-yl)methanone;
(2-(2H-1,2,3-triazol-2-yl)phenyl)((1R*,3S*,4R*,6S*)-3-
methyl-6-((5-(trifluoromethyl)pyrazin-2-yl)amino)-2-
azabicyclo[2.2.1]heptan-2-yl)methanone;
(2-(2H-1,2,3-triazol-2-yl)phenyl)((1S*,3R*,4S*,6R*)-3-
methyl-6-((5-(trifluoromethyl)pyrazin-2-yl)amino)-2-
azabicyclo[2.2.1]heptan-2-yl)methanone;
(R/S)-(6-methyl-3-(2H-1,2,3-triazol-2-yl)pyridin-2-yl)(3-
methyl-6-((5-(trifluoromethyl)pyrazin-2-yl)amino)-2-
azabicyclo[2.2.1]heptan-2-yl)methanone;
(6-methyl-3-(2H-1,2,3-triazol-2-yl)pyridin-2-yl)((1R*,
3S*,4R*,6 S*)-3-methyl-6-((5-(trifluoromethyl)
pyrazin-2-yl)amino)-2-azabicyclo[2.2.1]heptan-2-yl)
methanone;
(6-methyl-3-(2H-1,2,3-triazol-2-yl)pyridin-2-yl)((1S*,
3R*,4S*,6R*)-3-methyl-6-((5-(trifluoromethyl)
pyrazin-2-yl)amino)-2-azabicyclo[2.2.1]heptan-2-yl)
methanone;
(R/S)-3-(fluoromethyl)-6-((5-(trifluoromethyl)pyridin-2-
yl)oxy)-2-azabicyclo[2.2.1]heptan-2-yl)(6-methyl-3-
(2H-1,2,3-triazol-2-yl)pyridin-2-yl)methanone;
(R/S)-(2-fluoro-6-(oxazol-2-yl)phenyl)-3-(fluoromethyl)-
6-((5-(trifluoromethyl)pyridin-2-yl)oxy)-2-azabicyclo
[2.2.1]heptan-2-yl)methanone;
(R/S)-3-(fluoromethyl)-6-((5-(trifluoromethyl)pyridin-2-
yl)oxy)-2-azabicyclo[2.2.1]heptan-2-yl)(5-methyl-2-
(2H-1,2,3-triazol-2-yl)pyridin-3-yl)methanone;
(R/S)-(2-(2H-1,2,3-triazol-2-yl)phenyl)(3-(fluorom-
ethyl)-6-((5-(trifluoromethyl)pyridin-2-yl)oxy)-2-
azabicyclo[2.2.1]heptan-2-yl)methanone;
((1S,3 S,4R,6R)-3-(fluoromethyl)-6-((5-(trifluoromethyl)
pyridin-2-yl)oxy)-2-azabicyclo[2.2.2]octan-2-yl)(6-
methyl-3-(pyrimidin-2-yl)pyridin-2-yl)methanone;
((1S,3 S,4R,6R)-3-(fluoromethyl)-6-((5-(trifluoromethyl)
pyridin-2-yl)oxy)-2-azabicyclo[2.2.2]octan-2-yl)(2-
(pyrimidin-2-yl)phenyl)methanone;
(5-fluoro-2-(pyrimidin-2-yl)phenyl)((1S,3 S,4R,6R)-3-
(fluoromethyl)-6-((5-(trifluoromethyl)pyridin-2-yl)
oxy)-2-azabicyclo[2.2.2]octan-2-yl)methanone;

((1S,3 S,4R,6R)-3-(fluoromethyl)-6-((5-(trifluoromethyl)
pyridin-2-yl)oxy)-2-azabicyclo[2.2.2]octan-2-yl)(6-
methyl-3-(2H-1,2,3-triazol-2-yl)pyridin-2-yl)metha-
none;
(5-fluoro-2-(2H-1,2,3-triazol-2-yl)phenyl)((1S,3 S,4R,
6R)-3-(fluoromethyl)-6-((5-(trifluoromethyl)pyridin-
2-yl)oxy)-2-azabicyclo[2.2.2]octan-2-yl)methanone;
(3-fluoro-2-(pyrimidin-2-yl)phenyl)((1S,3 S,4R,6R)-3-
(fluoromethyl)-6-((5-(trifluoromethyl)pyridin-2-yl)
oxy)-2-azabicyclo[2.2.2]octan-2-yl)methanone;
(5-fluoro-2-(5-fluoropyrimidin-2-yl)phenyl)((1S,3 S,4R,
6R)-3-(fluoromethyl)-6-((5-(trifluoromethyl)pyridin-
2-yl)oxy)-2-azabicyclo[2.2.2]octan-2-yl)methanone;
and pharmaceutically acceptable salts thereof.
7. A compound selected from the group consisting of
((1S,3R,4R,6R)-3-ethyl-6-((5-(trifluoromethyl)pyridin-2-
yl)oxy)-2-azabicyclo[2.2.1]heptan-2-yl)(2-(pyrimidin-2-yl)
phenyl)methanone;
((1S,3R,4R,6R)-3-ethyl-6-((5-(trifluoromethyl)pyridin-2-
yl)oxy)-2-azabicyclo[2.2.1]heptan-2-yl)(3-fluoro-2-
(pyrimidin-2-yl)phenyl)methanone;
((1S,3R,4R,6R)-3-ethyl-6-((5-(trifluoromethyl)pyridin-2-
yl)oxy)-2-azabicyclo[2.2.1]heptan-2-yl)(2-(5-fluoro-
pyrimidin-2-yl)phenyl)methanone;
((1S,3R,4S,6R)-3-ethyl-6-((5-(trifluoromethyl)pyridin-2-
yl)amino)-2-azabicyclo[2.2.1]heptan-2-yl)(2-(pyrimi-
din-2-yl)phenyl)methanone;
(2-(2H-1,2,3-triazol-2-yl)phenyl)((1S,3R,4S,6R)-3-ethyl-
6-((5-(trifluoromethyl)pyridin-2-yl)amino)-2-azabicy-
clo[2.2.1]heptan-2-yl)methanone;
((1S,3R,4S,6R)-3-ethyl-6-((5-(trifluoromethyl)pyridin-2-
yl)amino)-2-azabicyclo[2.2.1]heptan-2-yl)(6-methyl-
3-(2H-1,2,3-triazol-2-yl)pyridin-2-yl)methanone;
((1S,3R,4S,6R)-3-ethyl-6-((5-(trifluoromethyl)pyridin-2-
yl)amino)-2-azabicyclo[2.2.1]heptan-2-yl)(6-methyl-
3-(2H-1,2,3-triazol-2-yl)pyridin-2-yl)methanone;
(2-(2H-1,2,3-triazol-2-yl)phenyl)((1S,3R,4R,6R)-3-
ethyl-6-((5-(trifluoromethyl)pyridin-2-yl)oxy)-2-
azabicyclo[2.2.1]heptan-2-yl)methanone;
((1S,3R,4R,6R)-3-ethyl-6-((5-(trifluoromethyl)pyridin-2-
yl)oxy)-2-azabicyclo[2.2.1]heptan-2-yl)(6-methyl-3-
(2H-1,2,3-triazol-2-yl)pyridin-2-yl)methanone;
((1S,3R,4R,6R)-3-ethyl-6-((5-(trifluoromethyl)pyridin-2-
yl)oxy)-2-azabicyclo[2.2.1]heptan-2-yl)(5-methyl-3-
(2H-1,2,3-triazol-2-yl)pyridin-2-yl)methanone;
((1S,3R,4S,6R)-3-ethyl-6-((5-(trifluoromethyl)pyrazin-2-
yl)amino)-2-azabicyclo[2.2.1]heptan-2-yl)(2-(pyrimi-
din-2-yl)phenyl)methanone;
(2-(2H-1,2,3-triazol-2-yl)phenyl)((1S,3R,4S,6R)-3-ethyl-
6-((5-(trifluoromethyl)pyrazin-2-yl)amino)-2-azabicy-
clo[2.2.1]heptan-2-yl)methanone;
((1S,3R,4S,6R)-3-ethyl-6-((5-(trifluoromethyl)pyrazin-2-
yl)amino)-2-azabicyclo[2.2.1]heptan-2-yl)(6-methyl-
3-(2H-1,2,3-triazol-2-yl)pyridin-2-yl)methanone;
((1S,3R,4R,6R)-3-isobutyl-6-((5-(trifluoromethyl)pyri-
din-2-yl)oxy)-2-azabicyclo[2.2.1]heptan-2-yl)(2-(py-
rimidin-2-yl)phenyl)methanone;
(3-fluoro-2-(pyrimidin-2-yl)phenyl)((1S,3R,4R,6R)-3-
isobutyl-6-((5-(trifluoromethyl)pyridin-2-yl)oxy)-2-
azabicyclo[2.2.1]heptan-2-yl)methanone;
(2-(5-fluoropyrimidin-2-yl)phenyl)((1S,3R,4R,6R)-3-
isobutyl-6-((5-(trifluoromethyl)pyridin-2-yl)oxy)-2-
azabicyclo[2.2.1]heptan-2-yl)methanone;
((1S,3R,4R,6R)-6-((5-(fluoromethyl)pyridin-2-yl)oxy)-
3-methyl-2-azabicyclo[2.2.1]heptan-2-yl)(2-(pyrimi-
din-2-yl)phenyl)methanone;

(2-(2H-1,2,3-triazol-2-yl)phenyl)((1S,3R,4R,6R)-6-((5-(fluoromethyl)pyridin-2-yl)oxy)-3-methyl-2-azabicyclo[2.2.1]heptan-2-yl)methanone;
((1S,3R,4R,6R)-6-((5-(fluoromethyl)pyridin-2-yl)oxy)-3-methyl-2-azabicyclo[2.2.1]heptan-2-yl)(6-methyl-3-(2H-1,2,3-triazol-2-yl)pyridin-2-yl)methanone;
(2-(2H-1,2,3-triazol-2-yl)phenyl)((1S,3R,4R,6R)-3-isobutyl-6-((5-(trifluoromethyl)pyridin-2-yl)oxy)-2-azabicyclo[2.2.1]heptan-2-yl)methanone;
((1S,3R,4R,6R)-3-isobutyl-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone;
((1S,3R,4R,6R)-3-isobutyl-6-((5-(trifluoromethyl)pyridin-2-yl)oxy)-2-azabicyclo[2.2.1]heptan-2-yl)(5-methyl-3-(2H-1,2,3-triazol-2-yl)pyridin-2-yl)methanone;
((1S,3 S,4R,6R)-3-(methoxymethyl)-6-((5-(trifluoromethyl)pyridin-2-yl)oxy)-2-azabicyclo[2.2.1]heptan-2-yl)(2-(pyrimidin-2-yl)phenyl)methanone;
(2-(2H-1,2,3-triazol-2-yl)phenyl)((1S,3 S,4R,6R)-3-(methoxymethyl)-6-((5-(trifluoromethyl)pyridin-2-yl)oxy)-2-azabicyclo[2.2.1]heptan-2-yl)methanone;
((1S,3 S,4R,6R)-3-(methoxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone;
((1S,3R,4R,6R)-3-methyl-6-((5-(trifluoromethyl)pyridin-2-yl)oxy)-2-azabicyclo[2.2.1]heptan-2-yl)(2-(pyridazin-3-yl)phenyl)methanone;
(5-(4-fluorophenyl)-2-methylthiazol-4-yl)((1S,3R,4R,6R)-3-methyl-6-((5-(trifluoromethyl)pyridin-2-yl)oxy)-2-azabicyclo[2.2.1]heptan-2-yl)methanone;
((1S,3R,4R,6R)-6-((5-(difluoromethyl)pyridin-2-yl)oxy)-3-methyl-2-azabicyclo[2.2.1]heptan-2-yl)(2-(pyrimidin-2-yl)phenyl)methanone;
(2-(2H-1,2,3-triazol-2-yl)phenyl)((1S,3R,4R,6R)-6-((5-(difluoromethyl)pyridin-2-yl)oxy)-3-methyl-2-azabicyclo[2.2.1]heptan-2-yl)methanone;
((1S,3R,4R,6R)-6-((5-(difluoromethyl)pyridin-2-yl)oxy)-3-methyl-2-azabicyclo[2.2.1]heptan-2-yl)(6-methyl-3-(2H-1,2,3-triazol-2-yl)pyridin-2-yl)methanone;
((1S,3 S,4R,6R)-3-(1-methoxyethyl)-6-((5-(trifluoromethyl)pyridin-2-yl)oxy)-2-azabicyclo[2.2.1]heptan-2-yl)(2-(pyrimidin-2-yl)phenyl)methanone;
(2-(2H-1,2,3-triazol-2-yl)phenyl)((1S,3 S,4R,6R)-3-(1-methoxyethyl)-6-((5-(trifluoromethyl)pyridin-2-yl)oxy)-2-azabicyclo[2.2.1]heptan-2-yl)methanone;
((1S,3 S,4R,6R)-3-(1-methoxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone;
((1S,3R,4R,6R)-3-methyl-6-((5-methylpyridin-2-yl)oxy)-2-azabicyclo[2.2.1]heptan-2-yl)(2-(pyrimidin-2-yl)phenyl)methanone;
(2-(2H-1,2,3-triazol-2-yl)phenyl)((1S,3R,4R,6R)-3-methyl-6-((5-methylpyridin-2-yl)oxy)-2-azabicyclo[2.2.1]heptan-2-yl)methanone;
(6-methyl-3-(2H-1,2,3-triazol-2-yl)pyridin-2-yl)((1S,3R,4R,6R)-3-methyl-6-((5-methylpyridin-2-yl)oxy)-2-azabicyclo[2.2.1]heptan-2-yl)methanone;
((1S,3 S,4R,6R)-3-(hydroxymethyl)-6-((5-(trifluoromethyl)pyridin-2-yl)oxy)-2-azabicyclo[2.2.1]heptan-2-yl)(2-(pyrimidin-2-yl)phenyl)methanone;
(2-(2H-1,2,3-triazol-2-yl)phenyl)((1S,3 S,4R,6R)-3-(hydroxymethyl)-6-((5-(trifluoromethyl)pyridin-2-yl)oxy)-2-azabicyclo[2.2.1]heptan-2-yl)methanone;
((1S,3 S,4R,6R)-3-(hydroxymethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone;
((1S,3R,4R,6R)-6-((5-chloropyridin-2-yl)oxy)-3-methyl-2-azabicyclo[2.2.1]heptan-2-yl)(2-(pyrimidin-2-yl)phenyl)methanone;
(2-(2H-1,2,3-triazol-2-yl)phenyl)((1S,3R,4R,6R)-6-((5-chloropyridin-2-yl)oxy)-3-methyl-2-azabicyclo[2.2.1]heptan-2-yl)methanone;
((1S,3R,4R,6R)-6-((5-chloropyridin-2-yl)oxy)-3-methyl-2-azabicyclo[2.2.1]heptan-2-yl)(6-methyl-3-(2H-1,2,3-triazol-2-yl)pyridin-2-yl)methanone;
((1S,3 S,4R,6R)-3-(1-hydroxyethyl)-6-((5-(trifluoromethyl)pyridin-2-yl)oxy)-2-azabicyclo[2.2.1]heptan-2-yl)(2-(pyrimidin-2-yl)phenyl)methanone;
(2-(2H-1,2,3-triazol-2-yl)phenyl)((1S,3 S,4R,6R)-3-(1-hydroxyethyl)-6-((5-(trifluoromethyl)pyridin-2-yl)oxy)-2-azabicyclo[2.2.1]heptan-2-yl)methanone;
((1S,3 S,4R,6R)-3-(1-hydroxyethyl)-6-((5-(trifluoromethyl)pyridin-2-yl)oxy)-2-azabicyclo[2.2.1]heptan-2-yl)(6-methyl-3-(2H-1,2,3-triazol-2-yl)pyridin-2-yl)methanone;
((1S,3R,4S,6R)-6-((3-fluoro-5-(trifluoromethyl)pyridin-2-yl)amino)-3-methyl-2-azabicyclo[2.2.1]heptan-2-yl)(2-(pyrimidin-2-yl)phenyl)methanone;
(2-(2H-1,2,3-triazol-2-yl)phenyl)((1S,3R,4 S,6R)-6-((3-fluoro-5-(trifluoromethyl)pyridin-2-yl)amino)-3-methyl-2-azabicyclo[2.2.1]heptan-2-yl)methanone;
((1S,3R,4S,6R)-6-((3-fluoro-5-(trifluoromethyl)pyridin-2-yl)amino)-3-methyl-2-azabicyclo[2.2.1]heptan-2-yl)(6-methyl-3-(2H-1,2,3-triazol-2-yl)pyridin-2-yl)methanone;
((1S,3R,4S,6R)-6-(benzo[d]oxazol-2-ylamino)-3-methyl-2-azabicyclo[2.2.1]heptan-2-yl)(2-(pyrimidin-2-yl)phenyl)methanone;
(2-(2H-1,2,3-triazol-2-yl)phenyl)((1S,3R,4S,6R)-6-(benzo[d]oxazol-2-ylamino)-3-methyl-2-azabicyclo[2.2.1]heptan-2-yl)methanone;
((1S,3R,4S,6R)-6-(benzo[d]oxazol-2-ylamino)-3-methyl-2-azabicyclo[2.2.1]heptan-2-yl)(6-methyl-3-(2H-1,2,3-triazol-2-yl)pyridin-2-yl)methanone;
((1S,3R,4S,6R)-3-methyl-6-((5-(trifluoromethyl)pyrimidin-2-yl)amino)-2-azabicyclo[2.2.1]heptan-2-yl)(2-(pyrimidin-2-yl)phenyl)methanone;
(2-(2H-1,2,3-triazol-2-yl)phenyl)((1S,3R,4S,6R)-3-methyl-6-((5-(trifluoromethyl)pyrimidin-2-yl)amino)-2-azabicyclo[2.2.1]heptan-2-yl)methanone;
(6-methyl-3-(2H-1,2,3-triazol-2-yl)pyridin-2-yl)((1S,3R,4S,6R)-3-methyl-6-((5-(trifluoromethyl)pyrimidin-2-yl)amino)-2-azabicyclo[2.2.1]heptan-2-yl)methanone;
((1S,3R,4R,6R)-6-((5-bromopyridin-2-yl)oxy)-3-methyl-2-azabicyclo[2.2.1]heptan-2-yl)(2-(pyrimidin-2-yl)phenyl)methanone;
(2-(2H-1,2,3-triazol-2-yl)phenyl)((1S,3R,4R,6R)-6-((5-bromopyridin-2-yl)oxy)-3-methyl-2-azabicyclo[2.2.1]heptan-2-yl)methanone;
((1S,3R,4R,6R)-6-((5-bromopyridin-2-yl)oxy)-3-methyl-2-azabicyclo[2.2.1]heptan-2-yl)(6-methyl-3-(2H-1,2,3-triazol-2-yl)pyridin-2-yl)methanone;
((1S,3 S,4R,6R)-3-(fluoromethyl)-6-((5-(trifluoromethyl)pyridin-2-yl)oxy)-2-azabicyclo[2.2.2]octan-2-yl)(2-methoxy-6-(pyrimidin-2-yl)phenyl)methanone;
((1S,3 S,4R,6R)-3-(fluoromethyl)-6-((5-(trifluoromethyl)pyridin-2-yl)oxy)-2-azabicyclo[2.2.2]octan-2-yl)(4-methyl-2-(2H-1,2,3-triazol-2-yl)phenyl)methanone;

((1S,3 S,4R,6R)-3-(fluoromethyl)-6-((5-(trifluoromethyl)pyridin-2-yl)oxy)-2-azabicyclo[2.2.2]octan-2-yl)(2-methyl-6-(2H-1,2,3-triazol-2-yl)phenyl)methanone;
(2-fluoro-6-(pyrimidin-2-yl)phenyl)((1S,3 S,4R,6R)-3-(fluoromethyl)-6-((5-(trifluoromethyl)pyridin-2-yl)oxy)-2-azabicyclo[2.2.2]octan-2-yl)methanone;
(2-(2H-1,2,3-triazol-2-yl)phenyl)((1S,3 S,4R,6R)-3-(fluoromethyl)-6-((5-(trifluoromethyl)pyridin-2-yl)oxy)-2-azabicyclo[2.2.2]octan-2-yl)methanone;
((1S,3 S,4R,6R)-3-(fluoromethyl)-6-((5-(trifluoromethyl)pyridin-2-yl)oxy)-2-azabicyclo[2.2.2]octan-2-yl)(3-methyl-2-(oxazol-2-yl)phenyl)methanone;
((1S,3 S,4R,6R)-3-(fluoromethyl)-6-((5-(trifluoromethyl)pyridin-2-yl)oxy)-2-azabicyclo[2.2.2]octan-2-yl)(3-methyl-2-(pyridin-2-yl)phenyl)methanone;
((1S,3 S,4R,6R)-3-(fluoromethyl)-6-((5-(trifluoromethyl)pyridin-2-yl)oxy)-2-azabicyclo[2.2.2]octan-2-yl)(2-(5-fluoropyrimidin-2-yl)phenyl)methanone;
((1S,3 S,4R,6R)-3-(fluoromethyl)-6-((5-(trifluoromethyl)pyridin-2-yl)oxy)-2-azabicyclo[2.2.2]octan-2-yl)(5-methyl-3-(2H-1,2,3-triazol-2-yl)pyridin-2-yl)methanone;
(2-bromo-3-fluorophenyl)((1S,3 S,4R,6R)-3-(fluoromethyl)-6-((5-(trifluoromethyl)pyridin-2-yl)oxy)-2-azabicyclo[2.2.2]octan-2-yl)methanone;
(3-fluoro-2-(pyrimidin-2-yl)phenyl)((1S,3R,4R,6R)-3-methyl-6-((5-(trifluoromethyl)pyridin-2-yl)oxy)-2-azabicyclo[2.2.2]octan-2-yl)methanone;
(3-fluoro-2-(pyrimidin-2-yl)phenyl)((1S,3 S,4R,6R)-3-(hydroxymethyl)-6-((5-(trifluoromethyl)pyridin-2-yl)oxy)-2-azabicyclo[2.2.2]octan-2-yl)methanone;
(3-fluoro-2-(pyrimidin-2-yl)phenyl)((1S,3 S,4R,6R)-3-(methoxymethyl)-6-((5-(trifluoromethyl)pyridin-2-yl)oxy)-2-azabicyclo[2.2.2]octan-2-yl)methanone;
(3-fluoro-2-(2H-1,2,3-triazol-2-yl)phenyl)((1S,3R,4R,6R)-3-methyl-6-((5-(trifluoromethyl)pyridin-2-yl)oxy)-2-azabicyclo[2.2.2]octan-2-yl)methanone;
(3-fluoro-2-(2H-1,2,3-triazol-2-yl)phenyl)((1S,3 S,4R,6R)-3-(hydroxymethyl)-6-((5-(trifluoromethyl)pyridin-2-yl)oxy)-2-azabicyclo[2.2.2]octan-2-yl)methanone;
(3-fluoro-2-(2H-1,2,3-triazol-2-yl)phenyl)((1S,3 S,4R,6R)-3-(methoxymethyl)-6-((5-(trifluoromethyl)pyridin-2-yl)oxy)-2-azabicyclo[2.2.2]octan-2-yl)methanone;
(3-fluoro-2-(pyrimidin-2-yl)phenyl)((1S,3 S,4R,6R)-3-((methoxymethoxy)methyl)-6-((5-(trifluoromethyl)pyridin-2-yl)oxy)-2-azabicyclo[2.2.2]octan-2-yl)methanone;
(3-fluoro-2-(2H-1,2,3-triazol-2-yl)phenyl)((1S,3 S,4R,6R)-3-((methoxymethoxy)methyl)-6-((5-(trifluoromethyl)pyridin-2-yl)oxy)-2-azabicyclo[2.2.2]octan-2-yl)methanone;
and pharmaceutically acceptable salts thereof.

8. A compound selected from the group consisting of
((1S,3 S,4R,6R)-3-(fluoromethyl)-6-((5-(trifluoromethyl)pyridin-2-yl)oxy)-2-azabicyclo[2.2.2]octan-2-yl)(6-methyl-3-(2H-1,2,3-triazol-2-yl)pyridin-2-yl)methanone;
[(1R,2R,4S,5R)-5-[[5-(difluoromethyl)-2-pyridyl]oxy]-2-methyl-3-azabicyclo[2.2.1]heptan-3-yl]-[6-methyl-3-(triazol-2-yl)-2-pyridyl]methanone;
[(1R,2R,4S,5R)-5-[(5-chloro-2-pyridyl)oxy]-2-methyl-3-azabicyclo[2.2.1]heptan-3-yl]-[2-(triazol-2-yl)phenyl]methanone;
[(1R,2R,4S,5R)-5-[(5-chloro-2-pyridyl)oxy]-2-methyl-3-azabicyclo[2.2.1]heptan-3-yl]-[6-methyl-3-(triazol-2-yl)-2-pyridyl]methanone;
(3-fluoro-2-pyrimidin-2-yl-phenyl)-[(1R,2R,4S,5R)-2-methyl-5-[[5-(trifluoromethyl)-2-pyridyl]oxy]-3-azabicyclo[2.2.2]octan-3-yl]methanone;
[6-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone;
[(1R,2R,4S,5R)-2-methyl-5-[[5-(trifluoromethyl)-2-pyridyl]oxy]-3-azabicyclo[2.2.2]octan-3-yl]-[2-(triazol-2-yl)phenyl]methanone;
[6-methyl-3-pyrimidin-2-yl-2-pyridyl]-[(1R,2R,4S,5R)-2-methyl-5-[[5-(trifluoromethyl)-2-pyridyl]oxy]-3-azabicyclo[2.2.2]octan-3-yl]methanone;
[(1R,2R,4S,5R)-2-methyl-5-[[5-(trifluoromethyl)-2-pyridyl]oxy]-3-azabicyclo[2.2.2]octan-3-yl]-[3-(triazol-2-yl)-2-pyridyl]methanone;
[5-methyl-3-(triazol-2-yl)-2-pyridyl]-[(1R,2R,4S,5R)-2-methyl-5-[[5-(trifluoromethyl)-2-pyridyl]oxy]-3-azabicyclo[2.2.2]octan-3-yl]methanone;
(5-methyl-3-pyrimidin-2-yl-2-pyridyl)-[(1R,2R,4S,5R)-2-methyl-5-[[5-(trifluoromethyl)-2-pyridyl]oxy]-3-azabicyclo[2.2.2]octan-3-yl]methanone;
(3-fluoro-2-pyrimidin-2-yl-phenyl)-[(1R,2R,4S,5S)-2-methyl-5-[[5-(trifluoromethyl)-2-pyridyl]oxy]-3-azabicyclo[2.2.2]octan-3-yl]methanone;
[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[2-(triazol-2-yl)phenyl]methanone;
[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[3-fluoro-2-(triazol-2-yl)phenyl]methanone;
[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[6-methyl-3-(triazol-2-yl)-2-pyridyl]methanone;
[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-[5-methyl-3-(triazol-2-yl)-2-pyridyl]methanone;
[(1R,2R,4S,5R)-2-deuterio-2-(trideuteriomethyl)-5-[[5-(trifluoromethyl)-2-pyridyl]oxy]-3-azabicyclo[2.2.1]heptan-3-yl]-(5-fluoro-2-pyrimidin-2-yl-phenyl)methanone;
[2-[4-(3-fluoropropyl)triazol-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone;
[2-[5-(2-fluoroethoxy)pyrimidin-2-yl]phenyl]-[(1R,2R,4S,5R)-2-methyl-5-[[5-(trifluoromethyl)-2-pyridyl]oxy]-3-azabicyclo[2.2.1]heptan-3-yl]methanone;
[2-(5-fluoropyrazin-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone;
[2-(6-fluoro-3-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone;
[2-(2-fluoro-4-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone;
[2-(6-fluoro-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone;
[(1R,2R,4S,5R)-2-methyl-5-[[5-(trifluoromethyl)-2-pyridyl]oxy]-3-azabicyclo[2.2.1]heptan-3-yl]-[2-(6-nitro-2-pyridyl)phenyl]methanone;

[2-(6-bromo-2-pyridyl)phenyl]-[(1R,2R,4S,5R)-2-methyl-5-[[5-(trifluoromethyl)-2-pyridyl]oxy]-3-azabicyclo[2.2.1]heptan-3-yl]methanone;

[(1R,2S,4S,5R)-2-(hydroxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone;

[2-fluoro-6-(triazol-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone;

[5-fluoro-2-(5-fluoropyrimidin-2-yl)phenyl]-[(1R,2S,4S,5R)-2-(hydroxymethyl)-5-[[5-(trifluoromethyl)-2-pyridyl]oxy]-3-azabicyclo[2.2.2]octan-3-yl]methanone;

[(1R,2S,4S,5R)-2-(methoxymethyl)-5-[[5-(trifluoromethyl)-2-pyridyl]oxy]-3-azabicyclo[2.2.2]octan-3-yl]-[6-methyl-3-(triazol-2-yl)-2-pyridyl]methanone;

[(1R,2S,4S,5R)-2-(methoxymethyl)-5-[[5-(trifluoromethyl)-2-pyridyl]oxy]-3-azabicyclo[2.2.2]octan-3-yl]-(6-methyl-3-pyrimidin-2-yl-2-pyridyl)methanone;

[(1R,2S,4S,5R)-2-(methoxymethyl)-5-[[5-(trifluoromethyl)-2-pyridyl]oxy]-3-azabicyclo[2.2.2]octan-3-yl]-(2-pyrimidin-2-ylphenyl)methanone;

[(1R,2R,4S,5R)-5-[[5-(difluoromethyl)-2-pyridyl]oxy]-2-methyl-3-azabicyclo[2.2.1]heptan-3-yl]-(6-methyl-3-pyrimidin-2-yl-2-pyridyl)methanone;

(6-methyl-3-(2H-1,2,3-triazol-2-yl)pyridin-2-yl)((1S*,3R*,4R*,6R*)-3-methyl-6-(quinoxalin-2-yloxy)-2-azabicyclo[2.2.1]heptan-2-yl)methanone;

(3-fluoro-2-(2H-1,2,3-triazol-2-yl)phenyl)((1S*,3R*,4R*,6R*)-3-methyl-6-(quinoxalin-2-yloxy)-2-azabicyclo[2.2.1]heptan-2-yl)methanone;

(6-methyl-3-(2H-1,2,3-triazol-2-yl)pyridin-2-yl)((1S*,3R,4R,6R*)-3-methyl-6-(quinolin-3-yloxy)-2-azabicyclo[2.2.1]heptan-2-yl)methanone;

((1S*,3R*,4R*,6R*)-6-((6-fluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone;

(3-fluoro-2-(2H-1,2,3-triazol-2-yl)phenyl)((1S*,3R*,4R*,6R*)-6-((6-fluoroquinoxalin-2-yl)oxy)-3-methyl-2-azabicyclo[2.2.1]heptan-2-yl)methanone;

(2-(2H-1,2,3-triazol-2-yl)phenyl)((1S*,3R*,4R*,6R*)-6-((6-fluoroquinoxalin-2-yl)oxy)-3-methyl-2-azabicyclo[2.2.1]heptan-2-yl)methanone;

((1S*,3R*,4R*,6R*)-6-((6,7-difluoroquinoxalin-2-yl)oxy)-3-methyl-2-azabicyclo[2.2.1]heptan-2-yl)(6-methyl-3-(2H-1,2,3-triazol-2-yl)pyridin-2-yl)methanone;

((1S*,3R*,4R*,6R*)-6-((6,7-difluoroquinoxalin-2-yl)oxy)-3-methyl-2-azabicyclo[2.2.1]heptan-2-yl)(3-fluoro-2-(2H-1,2,3-triazol-2-yl)phenyl)methanone;

(2-(2H-1,2,3-triazol-2-yl)phenyl)((1S*,3R*,4R*,6R*)-6-((6,7-difluoroquinoxalin-2-yl)oxy)-3-methyl-2-azabicyclo[2.2.1]heptan-2-yl)methanone;

ethyl (1R,2S,4S,5R)-3-[6-methyl-3-(triazol-2-yl)pyridine-2-carbonyl]-5-[[5-(trifluoromethyl)-2-pyridyl]oxy]-3-azabicyclo[2.2.1]heptane-2-carboxylate;

[(1R,2R,4S,5R)-5-[(5-chloro-2-pyridyl)oxy]-2-methyl-3-azabicyclo[2.2.1]heptan-3-yl]-[6-methyl-2-(triazol-2-yl)-3-pyridyl]methanone;

[(1R,2R,4S,5R)-5-[(5-chloro-2-pyridyl)oxy]-2-methyl-3-azabicyclo[2.2.1]heptan-3-yl]-[5-methyl-2-(triazol-2-yl)-3-pyridyl]methanone;

[(1R,3R,4S,6R)-3-[(5-chloro-2-pyridyl)oxy]-2,2-dideuterio-6-methyl-5-azabicyclo[2.2.1]heptan-5-yl]-[2-(triazol-2-yl)phenyl]methanone;

[(1R,3R,4S,6R)-3-[(5-chloro-2-pyridyl)oxy]-2,2-dideuterio-6-methyl-5-azabicyclo[2.2.1]heptan-5-yl]-[6-methyl-3-(triazol-2-yl)-2-pyridyl]methanone;

[(1R,3R,4S,6R)-3-[(5-chloro-2-pyridyl)oxy]-2,2-dideuterio-6-methyl-5-azabicyclo[2.2.1]heptan-5-yl]-[3-fluoro-2-(triazol-2-yl)phenyl]methanone;

[(1R,3R,4S,6R)-2,2-dideuterio-6-methyl-3-[[5-(trifluoromethyl)-2-pyridyl]oxy]-5-azabicyclo[2.2.1]heptan-5-yl]-[6-methyl-3-(triazol-2-yl)-2-pyridyl]methanone;

[(1R,3R,4S,6R)-2,2-dideuterio-6-methyl-3-[[5-(trifluoromethyl)-2-pyridyl]oxy]-5-azabicyclo[2.2.1]heptan-5-yl]-[3-fluoro-2-(triazol-2-yl)phenyl]methanone;

[(1R,3R,4S,6R)-2,2-dideuterio-6-methyl-3-[[5-(trifluoromethyl)-2-pyridyl]oxy]-5-azabicyclo[2.2.1]heptan-5-yl]-[5-methyl-3-(triazol-2-yl)-2-pyridyl]methanone;

[(1R,3R,4S,6R)-2,2-dideuterio-6-methyl-3-[[5-(trifluoromethyl)-2-pyridyl]oxy]-5-azabicyclo[2.2.1]heptan-5-yl]-[2-(triazol-2-yl)phenyl]methanone;

[4-(2-fluoroethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone;

[2-(2-hydroxyethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone;

[5-(2-bromoethoxy)-2-(triazol-2-yl)phenyl]-[(1R,2R,4S,5R)-2-methyl-5-[[5-(trifluoromethyl)-2-pyridyl]oxy]-3-azabicyclo[2.2.1]heptan-3-yl]methanone;

[2-(2-fluoroethoxy)-3-quinolyl]-[(1R,2R,4S,5R)-2-methyl-5-[[5-(trifluoromethyl)-2-pyridyl]oxy]-3-azabicyclo[2.2.1]heptan-3-yl]methanone;

(7-(2-fluoroethoxy)quinolin-8-yl)((1S,3R,4R,6R)-3-methyl-6-((5-(trifluoromethyl)pyridin-2-yl)oxy)-2-azabicyclo[2.2.1]heptan-2-yl)methanone;

(R/S)-[2-isobutyl-5-[[5-(trifluoromethyl)-2-pyridyl]oxy]-3-azabicyclo[2.2.1]heptan-3-yl]-[2-(triazol-2-yl)phenyl]methanone;

(R/S)-[2-isobutyl-5-[[5-(trifluoromethyl)-2-pyridyl]oxy]-3-azabicyclo[2.2.1]heptan-3-yl]-[5-methyl-3-(triazol-2-yl)-2-pyridyl]methanone;

(R/S)-[2-isobutyl-5-[[5-(trifluoromethyl)-2-pyridyl]oxy]-3-azabicyclo[2.2.1]heptan-3-yl]-(2-pyrimidin-2-ylphenyl)methanone;

(R/S)-[2-isobutyl-5-[[5-(trifluoromethyl)-2-pyridyl]oxy]-3-azabicyclo[2.2.1]heptan-3-yl]-[6-methyl-3-(triazol-2-yl)-2-pyridyl]methanone;

(R/S)-(3-fluoro-2-pyrimidin-2-yl-phenyl)-[2-isobutyl-5-[[5-(trifluoromethyl)-2-pyridyl]oxy]-3-azabicyclo[2.2.1]heptan-3-yl]methanone;

(R/S)-[2-(5-fluoropyrimidin-2-yl)phenyl]-[2-isobutyl-5-[[5-(trifluoromethyl)-2-pyridyl]oxy]-3-azabicyclo[2.2.1]heptan-3-yl]methanone;

(R/S)-[2-ethyl-5-[[5-(trifluoromethyl)-2-pyridyl]oxy]-3-azabicyclo[2.2.1]heptan-3-yl]-[2-(triazol-2-yl)phenyl]methanone;

(R/S)-[2-ethyl-5-[[5-(trifluoromethyl)-2-pyridyl]oxy]-3-azabicyclo[2.2.1]heptan-3-yl]-(2-pyrimidin-2-ylphenyl)methanone;

(R/S)-[2-ethyl-5-[[5-(trifluoromethyl)-2-pyridyl]oxy]-3-azabicyclo[2.2.1]heptan-3-yl]-[6-methyl-3-(triazol-2-yl)-2-pyridyl]methanone;

(R/S)-[2-ethyl-5-[[5-(trifluoromethyl)-2-pyridyl]oxy]-3-azabicyclo[2.2.1]heptan-3-yl]-[5-methyl-3-(triazol-2-yl)-2-pyridyl]methanone;

(R/S)-[2-ethyl-5-[[5-(trifluoromethyl)-2-pyridyl]oxy]-3-azabicyclo[2.2.1]heptan-3-yl]-(3-fluoro-2-pyrimidin-2-yl-phenyl)methanone;

(R/S)-[2-ethyl-5-[[5-(trifluoromethyl)-2-pyridyl]oxy]-3-azabicyclo[2.2.1]heptan-3-yl]-[2-(5-fluoropyrimidin-2-yl)phenyl]methanone;
(2-(pyrimidin-2-yl)phenyl)((1S,3R,4R,6R)-3-methyl-6-((6-fluoro-5-(trifluoromethyl)pyridin-2-yl)oxy)-2-azabicyclo[2.2.1]heptan-2-yl)methanone;
and pharmaceutically acceptable salts thereof.

9. A compound selected from the group consisting of
((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone;
((1S,3R,4R,6R)-6-((6-fluoro-5-(trifluoromethyl)pyridin-2-yl)oxy)-3-methyl-2-azabicyclo[2.2.1]heptan-2-yl)(2-(5-fluoropyrimidin-2-yl)phenyl)methanone;
(5-fluoro-2-(5-fluoropyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
(5-fluoro-2-(pyrimidin-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
((1S,3R,4R,6R)-6-((6-fluoro-5-(trifluoromethyl)pyridin-2-yl)oxy)-3-methyl-2-azabicyclo[2.2.1]heptan-2-yl)(2-(pyrimidin-2-yl)phenyl)methanone;
(3-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
(3-fluoro-2-(1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
(4-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
(5-fluoro-2-(2H-1,2,3-triazol-2-yl)phenyl)((1S,3R,4R,6R)-6-((6-fluoro-5-(trifluoromethyl)pyridin-2-yl)oxy)-3-methyl-2-azabicyclo[2.2.1]heptan-2-yl)methanone;
(3-(2-fluoroethoxy)isoquinolin-4-yl)((1S,3R,4R,6R)-3-methyl-6-((5-(trifluoromethyl)pyridin-2-yl)oxy)-2-azabicyclo[2.2.1]heptan-2-yl)methanone;
and pharmaceutically acceptable salts thereof.

10. A pharmaceutical composition comprising a therapeutically effective amount of a compound according to claim 1 and at least one pharmaceutically acceptable excipient.

11. A method of treating a disease, disorder, or medical condition selected from the group consisting of anxiety, anxious depression, post-traumatic stress disorder, panic disorder, attention deficit disorder, and substance abuse, comprising administering to a subject an effective amount of a compound of claim 1.

12. A compound of Formula I:

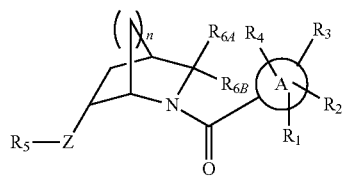

wherein
ring A is phenyl or a heteroaryl ring selected from pyridyl, thiazolyl, or isoquinolinyl; wherein when ring A is thiazolyl, ring A is optionally substituted with up to 3 substituents selected from $R_1$, $R_2$, $R_3$ or $R_4$, and wherein when ring A is phenyl, pyridyl, or isoquinolinyl, ring A is optionally substituted with up to 4 substituents selected from $R_1$, $R_2$, $R_3$ or $R_4$;

Z is NH, N—$CH_3$, N—$CH_2CH_3$, N—$CH_2$-cyclopropyl, N—C(=O)$CH_3$, N—$CH_2CH_2OCH_3$ or O;

$R_1$ is H, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo, or alkyl;

$R_2$ is H, alkyl, alkoxy, or halo;

$R_3$ is H, alkyl, alkoxy, halo, triazolyl, thiazolyl, pyridazinyl, pyrimidinyl, oxazolyl, isoxazolyl, oxadiazolyl, pyridyl, phenyl, or pyrazolyl, wherein triazolyl, thiazolyl, pyridazinyl, pyrimidinyl, oxazolyl, isoxazolyl, oxadiazolyl, pyridyl, phenyl or pyrazolyl is optionally substituted with up to two substituents selected from halo or alkyl;

$R_4$ is H or alkyl;

or $R_3$ and $R_4$, together with the atoms to which they are attached, form a 6-membered aryl ring or a 5- or 6-membered heteroaryl ring;

$R_5$ is pyridyl, pyrazinyl, benzoxazolyl, pyridazinyl, naphthyridinyl or pyrimidinyl, wherein the pyridyl, pyrazinyl, benzoxazolyl, pyridazinyl, naphthyridinyl or pyrimidinyl is optionally substituted with up to two substituents selected from halo, alkoxy, hydroxymethyl, or alkyl; and $R_{6A}$ and $R_{6B}$ are independently selected from H, alkyl, hydroxyalkyl, alkyl-alkoxy or alkyl-alkoxy-alkoxyl;

wherein one or both of $R_{6a}$ and $R_{6b}$ is other than H; and
n is 1 or 2.

13. A pharmaceutical composition comprising a therapeutically effective amount of a compound according to claim 12 and at least one pharmaceutically acceptable excipient.

14. A method of treating a disease, disorder, or medical condition selected from the group consisting of anxiety, anxious depression, post-traumatic stress disorder, panic disorder, attention deficit disorder, and substance abuse, comprising administering to a subject an effective amount of a compound according to claim 12.

15. A compound of Formula II:

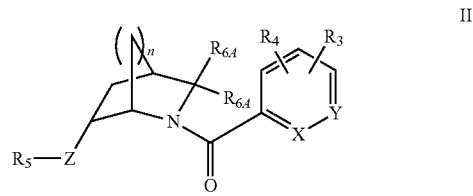

or an enantiomer or diastereomer thereof;
or a pharmaceutically acceptable salt thereof;
wherein:
X is N or $CR_1$;
Y is N or $CR_2$; provided that X and Y are not both N;
$R_1$ is H, halo, triazolyl, pyridazinyl, pyrimidinyl, oxazolyl, or pyridyl, wherein triazolyl, pyridazinyl, pyrimidinyl, oxazolyl, or pyridyl are optionally substituted with up to two substituents selected from halo, or alkyl;
$R_2$ is H, alkyl, alkoxy, or halo;
Z is NH, or O;

$R_3$ is H, alkyl, alkoxy, halo, triazolyl, pyrimidinyl, pyridyl, or phenyl, wherein triazolyl, pyrimidinyl, pyridyl, or phenyl is optionally substituted with up to two substituents selected from halo or alkyl;

$R_4$ is H or alkyl;

$R_5$ is pyridyl, pyrazinyl, or benzoxazolyl, wherein the pyridyl, pyrazinyl, or benzoxazolyl is optionally substituted with up to two groups selected from halo, alkoxy, hydroxymethyl or alkyl;

$R_{6A}$ and $R_{6B}$ are independently selected from H, alkyl, hydroxyalkyl, alkyl-alkoxy or alkyl-alkoxy-alkoxy;

wherein one or both of $R_{6A}$ and $R_{6B}$ is other than H; and n is 1 or 2.

16. The compound of claim 15, wherein

X is $CR_1$;

Y is $CR_2$;

$R_1$ is triazolyl, pyrimidinyl, or pyridyl, wherein pyrimidinyl and pyridyl are optionally substituted with F;

$R_2$ is H;

$R_3$ is H, or $CH_3$; and $R_4$ is H.

17. A pharmaceutical composition comprising a therapeutically effective amount of a compound according to claim 15 and at least one pharmaceutically acceptable excipient.

18. A method of treating a disease, disorder, or medical condition selected from the group consisting of anxiety, anxious depression, post-traumatic stress disorder, panic disorder, attention deficit disorder, and substance abuse, comprising administering to a subject an effective amount of a compound of claim 15.

* * * * *